(12) United States Patent
Agrez

(10) Patent No.: US 12,134,663 B2
(45) Date of Patent: Nov. 5, 2024

(54) CATIONIC PEPTIDES FOR ACTIVATING LCK

(71) Applicant: Interk Peptide Therapeutics Limited, New South Wales (AU)

(72) Inventor: Michael Valentine Agrez, New South Wales (AU)

(73) Assignee: Interk Peptide Therapeutics Limited, New South Wales (AU)

( * ) Notice: Subject to any disclaimer, the term of this patent is extended or adjusted under 35 U.S.C. 154(b) by 827 days.

(21) Appl. No.: 17/055,250

(22) PCT Filed: May 15, 2019

(86) PCT No.: PCT/AU2019/050462
§ 371 (c)(1),
(2) Date: Nov. 13, 2020

(87) PCT Pub. No.: WO2019/218015
PCT Pub. Date: Nov. 21, 2019

(65) Prior Publication Data
US 2021/0380639 A1    Dec. 9, 2021

(30) Foreign Application Priority Data
May 15, 2018   (AU) ............................... 2018901672

(51) Int. Cl.
| C07K 7/08 | (2006.01) |
| A61K 38/00 | (2006.01) |
| A61P 35/00 | (2006.01) |
| A61P 35/04 | (2006.01) |
| C07K 7/06 | (2006.01) |

(52) U.S. Cl.
CPC ................ *C07K 7/08* (2013.01); *A61P 35/00* (2018.01); *A61P 35/04* (2018.01); *C07K 7/06* (2013.01); *A61K 38/00* (2013.01); *C07K 2319/00* (2013.01)

(58) Field of Classification Search
None
See application file for complete search history.

(56) References Cited

U.S. PATENT DOCUMENTS

2015/0110744 A1 * 4/2015 Agrez .............. C07K 14/70546 435/375
2017/0327543 A1 * 11/2017 Viscidi ................. C07K 14/005

FOREIGN PATENT DOCUMENTS

| CN | 110997693 A | 4/2020 | |
| EP | 353565 A * | 2/1990 | .............. A61P 37/04 |
| JP | H02088595 A | 3/1990 | |
| JP | 2007522094 A | 8/2007 | |
| JP | 2011520436 A | 7/2011 | |
| JP | 2012518602 A | 8/2012 | |
| WO | 2009021137 A2 | 2/2009 | |
| WO | 2009038026 A1 | 3/2009 | |
| WO | 2010068692 A1 | 6/2010 | |
| WO | 2012174412 A2 | 12/2012 | |
| WO | 2013110120 A1 | 8/2013 | |
| WO | WO-2018226992 A1 * | 12/2018 | ......... C07K 14/4711 |

OTHER PUBLICATIONS

Boulikas, Teni. "Putative nuclear localization signals (NLS) in protein transcription factors." Journal of cellular biochemistry 55.1 (1994): 32-58. (Year: 1994).*
"European Search Opinion in EP19803532.1, Jul. 30, 2021, 5 pages".
"Extended European Search Report in EP19803532.1, Feb. 28, 2022, 1 page".
"Supplementary European Search Report in EP19803532, dated Feb. 14, 2022, 3 pages".
Grasis, Juris A., et al., "In Vivo Significance of ITK-SLP-76 Interaction in Cytokine Production", Molecular and Cellular Biology, vol. 30, No. 14, Jul. 15, 2010 (Jul. 15, 2010), pp. 3596-3609, XP055873256, US ISSN: 0270-7306, DOI: 10.1128/MCB.01657-09 Retrieved from the Internet: URL:https://journals.asm.org/doi/pdf/10.1128/MCB.01657-09>.
Mitsui, H. , et al., "Intradermal injections of polyarginine-containing immunogenic antigens preferentially elicit Tc1 and Th1 activation and antitumour immunity", British Journal of Dermatology, John Wiley, Hoboken, USA, vol. 162, No. 1, Oct. 26, 2009 (Oct. 26, 2009), pp. 29-41, XP071134444, ISSN: 0007-0963, DOI: 10.1111/J.1365-2133.2009.09490.X.
Simeoni, Luca , "Lck activation: puzzling the pieces together", Oncotarget, vol. 8, No. 61, Nov. 7, 2017 (Nov. 7, 2017), pp. 102761-102762, XP055885438, United States ISSN: 1949-2553, DOI:10.18632/oncotarget.22309.
PCT International Search Report and Written Opinion in PCT/AU2019/050462 dated Jul. 17, 2019, 12 pages.

* cited by examiner

*Primary Examiner* — Bethany P Barham
*Assistant Examiner* — Peter Anthopolos

(57) ABSTRACT

The present invention related to compositions and methods for activating Lck, including in vivo, in vitro and ex vivo uses.

1 Claim, 44 Drawing Sheets
Specification includes a Sequence Listing.

FIG. 1

| Peptide | Lck Activity above control (1µM) |
|---|---|
| RRRR (SEQ ID NO: 1, IK00400) | 0% |
| RRRRR (SEQ ID NO: 2, IK00500) | 0% |
| RRRRRR (SEQ ID NO: 3, IK00600) | 0% |
| RRRRRRRR (SEQ ID NO: 4, IK00800) | 126% |
| rrrrrrrr (SEQ ID NO: 5, IKD00800) | 80% |
| RRRRRRRRR (SEQ ID NO: 6, IK00900) | 325% |
| RRRRRRRRRR (SEQ ID NO: 7, IK00100) | 389% |
| RRRRRRRRRRRR (SEQ ID NO: 8, IK01200) | 401% |
| RRRRRRRRRRRRRR (SEQ ID NO: 9, IK01400) | 351% |
| rrrrrrrrrrrrrr (SEQ ID NO: 10, IKD01400) | 228% |
| RRRRRRRRRRRRRR-OH (SEQ ID NO: 11, IK014OH) | 156% |
| RRRRRRRRRRRRRRRRRRRR (SEQ ID NO: 12, IK00200) | 279% |
| KKKKKKKKKK (SEQ ID NO: 13, 10Lys) | 161% |
| HHHHHHHHHH (SEQ ID NO: 14, 10His) | 0% |
| OrnOrnOrnOrnOrnOrnOrnOrnOrnOrn (SEQ ID NO: 15, 10 Orn) | 13% |
| HHH-RRRRRRRRR-HHH (SEQ ID NO: 16, IK03930) | 386% |
| HHHHH-RRRRRRRRR-HHHHH (SEQ ID NO: 17, IK05950) | 286% |
| KKKKKKKK-HHHHHHHHHH (SEQ ID NO: 18, IK00K10) | 70% |
| RRRRRRRR-HHHHHHHHHH (SEQ ID NO: 19, IK00810) | 259% |
| RRRRRRRRR-HHHHHHHHHH (SEQ ID NO: 20, IK00910) | 348% |
| DDDDDDDDD-NH$_2$ (SEQ ID NO: 21, IKD9) | 0% |
| DSEAENPLY-DDDDDDDDD-NH$_2$ (SEQ ID NO: 23, IKDE800) | 0% |
| RSKAKNPLY-RRRRRRRRR-NH$_2$ (SEQ ID NO: 24, IK14800) | 377% |
| RSKAKNPLYR-RRRRRRRR-(2Adod)$_4$-NH$_2$ (SEQ ID NO: 65, IK14804) | 468% |
| RVKVKVVVR-RRRRRRRR-(2Adod)$_4$-NH$_2$ (SEQ ID NO: 66, IK15804) | 335% |

FIG. 2

| Peptide | Lck Activity above control (1 μM) | | | | | | | |
|---|---|---|---|---|---|---|---|---|
| | Blk | cSRC | Fgr | Fyn | Hck | Lck | Lyn | Yes |
| IK00800 | 0% | 0% | % | 0% | 0% | 126% | 0% | 0% |
| IK00100 | 0% | 0% | 0% | 0% | 0% | 389% | 0% | 0% |
| 10Lys | 0% | 0% | 0% | 0% | 0% | 161% | 0% | 0% |
| 10His | 0% | 0% | 0% | 0% | 0% | 0% | 0% | 0% |
| IK14800 | 0% | 0% | 0% | 0% | 0% | 578% | 0% | 0% |
| IKD14800 | 0% | 0% | 0% | 0% | 0% | 490% | 0% | 0% |
| IK15800 | 0% | 0% | 0% | 0% | 0% | 593% | 0% | 0% |

FIG. 4

| Peptide | Lck Activity above control (1 μM) |
|---|---|
| RSKAK (SEQ ID NO: 25, IK5000) | 5% |
| RSKAK-R (SEQ ID NO: 26, IK50100) | 0% |
| RSKAK-RR (SEQ ID NO: 27, IK50200) | 5% |
| RSKAK-RRR (SEQ ID NO: 28, IK50300) | 0% |
| RSKAK-RRRR (SEQ ID NO: 29, IK50400) | 0% |
| RSKAKNPLY (SEQ ID NO: 30, IK94000) | 0% |
| RSKAKNPLYR (SEQ ID NO: 31, IK14000) | 0% |
| RSKAKNPLY-RRRR (SEQ ID NO: 32, IK14300) | 0% |
| RSKAKNPLY-RRRRR (SEQ ID NO: 33, IK14400) | 85% |
| RSKAKNPLY-RRRRRR (SEQ ID NO: 34, IK14500) | 82% |
| r s k a k n p l y - r r r r r r (SEQ ID NO: 35, ID94600) | 60% |
| C-RSKAKNPLY-RRRRRR-C (Cyclised) (SEQ ID NO: 36, IK14500C) | 221% |
| RSKAK-RRRRRRRRR (SEQ ID NO: 37, IK50900) | 531% |
| RSKAKNPLY-RRRRRRRRR (SEQ ID NO: 24, IK14800) | 496% |
| r s k a k n p l y - r r r r r r r r r (SEQ ID NO: 129, IKD14800) | 490% |
| r r r r r r r r r - y l p n k a k s r (SEQ ID NO: 39, IKR81400) | 616% |
| IAGQ-RSKAKNPLY-RRRRRRRRR (SEQ ID NO: 40, IKM14800) | 454% |
| RSKAKNPLY-RRRRRRRRR-GPLG (SEQ ID NO: 41, IK148MP9) | 320% |
| RRRRRRRRR-SKAKNPLYR (SEQ ID NO: 42, IK9R94S) | 542% |
| RRRRRRRRR-YLPNKAKSR (SEQ ID NO: 43, IK9R94Y) | 630% |
| RSKAKNPLY-KKKKKKKKK (SEQ ID NO: 44, IK94K90) | 49% |
| RSKAKNPLY-RHHHHHHHHH (SEQ ID NO: 45, IK14010) | 30% |

FIG. 5

| Peptide | Lck Activity above control (1 μM) |
|---|---|
| RSKAKNPLY-RRRRRRRRR-HHHHH (SEQ ID NO: 46, IK14510) | 524% |
| RSKAKNPLY-RRRRRRRRR-HHHHHHHHH (SEQ ID NO: 47, IK14810) | 899% |
| Branched < RSKAKNPLY-RRRRRRRRR-HHHHHHHHH (SEQ ID NO: 48, Br IK14810) | 596% |
| RSKAKNPLY-RRRRRRRRR-HHHHHHHHHH (SEQ ID NO: 49, IK14820) | 556% |
| HHHHH-RSKAKNPLY-RRRRRRRRR (SEQ ID NO: 50, IK11480) | 883% |
| HHHHH-RRRRRRRRR-HHHHH-RSKAKNPLYR (SEQ ID NO: 51, IK59514) | 441% |
| RRRRRRRR-HHHHHHHHH-RSKAKNPLYR (SEQ ID NO: 52, IK81140) | 567% |
| HHHHH-RSKAKNPLY-RRRRRRRRR-HHHHH (SEQ ID NO: 53, IK51455) | 685% |
| RSKAKNPLY-RKRKRKRKRK (SEQ ID NO: 54, IK94RK0) | 456% |
| RVKVKVVVV (SEQ ID NO: 55, IK95000) | 518% |
| RVKVKVVVV-RRRRR (SEQ ID NO: 56, IK15400) | 382% |
| RVKVKVVVV-RRRRRRRR (SEQ ID NO: 57, IK15700) | 512% |
| RVKVKVVVV-RRRRRRRRR (SEQ ID NO: 58, IK15800) | 479% |
| RRRRRRRR-RVKVKVVVV-R (SEQ ID NO: 59, IK80150) | 520% |
| RVKVKVVVV-RRRRRRRRR-HHHHHHHHH (SEQ ID NO: 60, IK50810) | 778% |
| RVKVKVVVV-RHRHRHRHRHRHRHRH-HH (SEQ ID NO: 61, IK52820) | 408% |
| KEKLKNPLFK-RRRRRRRR-HHHHHHHHH (SEQ ID NO: 62, IK50810) | 778% |
| RVKVKVVVV-RHRHRHRHRHRHRHRH (SEQ ID NO: 63, IK52820) | 408% |
| KEKLKNPLFK-RRRRRRRR-HHHHHHHHH (SEQ ID NO: 64, IKB2810) | 379% |

RRRRRRRR-NH$_2$

IK00900 v Lck(h)

DDDDDDDD-NH$_2$

IKD9 v Lck(h)

CATIONIC PEPTIDES FOR ACTIVATING LCK

CROSS-REFERENCE TO RELATED APPLICATIONS

This application is the national stage entry of PCT/AU2019/050462, filed on May 15, 2019, which claims priority from Australian Patent Application number 2018901672 filed May 15, 2018, the disclosures of which are hereby incorporated by reference in their entirety.

CROSS-REFERENCE TO SEQUENCE LISTING

The Sequence Listing identified as "Replacement Sequence Listing.txt" (33100 bytes), created Apr. 29, 2024, is hereby incorporated by reference.

FIELD OF THE INVENTION

The present invention relates to the stimulation of Lck (lymphocyte-specific protein tyrosine kinase) activity and to Lck activators for use in the prophylaxis or treatment of various diseases or conditions.

BACKGROUND OF THE INVENTION

In molecular biology, CD4 (cluster of differentiation 4) is a glycoprotein found on the surface of immune cells such as T helper cells, monocytes, macrophages and dendritic cells. CD4+ T helper cells are white blood cells that are an essential part of the immune system and which send signals to other immune cells such as CD8 killer cells to destroy infectious particles. A T cell is activated when the T Cell Receptor (TCR) and the co-receptor bind the antigen peptide:major histocompatibility complex (MHC), which causes the TCR complexes to cluster and triggers an intracellular cascade. In T cell activation the binding of the co-receptors CD4 and CD8 to class II or class I MHC molecules, respectively, increases the sensitivity of T cells to antigen.

Lck is a member of the Src family kinases and is essential for the development of T-cell-effector potential, i.e., proliferation and differentiation of both developing thymocytes and mature T cells together with effective cytokine transcription (Lovatt M et al, Mol & Cell Biology, 2006, 26 (22): 8655-8665).

Phosphorylation of the TCR by Lck initiates downstream signalling by creating binding sites that recruit the cytosolic kinase ZAP70 (Zeta-chain-associated protein kinase 70) to the cell membrane (Iwashima M et al, Science, 1994, 263: 1136-1139). More particularly, Lck is regulated by the C-terminal Src kinase (Csk) which phosphorylates Tyr 505 resulting in inactivation of Lck, trans-auto-phosphorylation of the Lck activation loop Tyr 394 which activates the kinase activity of Lck via re-arrangement of the active site, and de-phosphorylation by phosphatases (Fulop T et al, Longevity & Healthspan, 2012, 1: 6).

Upon TCR stimulation, the CD4/CD8-associated Lck is brought into proximity with TCR/CD3 complexes and phosphorylates the immune-receptor tyrosine-based activation motifs (ITAMs) of the CD3 molecules. ZAP70 kinase is then recruited to the phosphorylated ITAMs and is subsequently activated by Lck. This results in the activation of multiple pathways that eventually lead to T cell activation and IL-2 production (Wang G et al, BioMed Research International, 2014, doi.org/10.1155/2014/682010).

In addition, dendritic cell (DC)-mediated activation of Lck leads to "TCR licensing", a process that dramatically increases the sensitivity and magnitude of the TCR response to cognate peptide-MHC class II antigen complexes (Meraner P et al, 2007, J Immunol, 178(4): 2262-2271). Such intra-epithelial DETC cells (dendritic epidermal T cells) or gamma/delta T cells play a pivotal role in homeostasis, tissue repair, inflammation and protection from malignancy (Witherden D A & Havran W L, J Leukoc Biol, 2013, 94(1): 69-76).

SUMMARY OF THE INVENTION

In one embodiment, the present invention provides a peptide for activating Lck, wherein the peptide comprises a Lck-activating cationic amino acid sequence having more than 6 contiguous cationic amino acids. In another embodiment, the cationic amino acid sequence comprises from 8 to 10 contiguous cationic amino acids.

In another embodiment, the cationic amino acids are independently selected from the group consisting of arginine, lysine, and ornithine. In another embodiment, the cationic amino acid sequence is selected from the group consisting of RRRRRRRR (SEQ ID NO: 4), rrrrrrrr (SEQ ID NO: 5), RRRRRRRRR (SEQ ID NO: 6), and rrrrrrrrr (SEQ ID NO: 114).

In another embodiment, the peptide consists of the cationic amino acid sequence.

In another embodiment, the peptide further comprises a Lck activating polypeptide moiety of Formula I or an inverted sequence thereof:

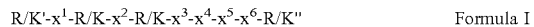

$$R/K'\text{-}x^1\text{-}R/K\text{-}x^2\text{-}R/K\text{-}x^3\text{-}x^4\text{-}x^5\text{-}x^6\text{-}R/K''$$  Formula I wherein:
each R/K is independently an arginine or lysine amino acid residue;
R/K' is an arginine or lysine amino acid residue and is present or absent;
R/K" is an arginine or lysine amino acid residue and is present or absent;
$x^1$ to $x^6$ are each independently an amino acid; and
wherein amino acids $x^3$ to $x^6$ are collectively present or absent, and R/K" is absent when amino acids $x^3$ to $x^6$ are absent.

In another embodiment, one or more of amino acids $x^1$ to $x^6$ are hydrophobic amino acids.

In another embodiment, the Lck activating polypeptide moiety is coupled to the N-terminal or C-terminal end of the cationic amino acid sequence.

In another embodiment, the peptide amino acid sequence comprises L amino acid residues. In another embodiment, the peptide amino acid sequence comprises D amino acid residues.

In another embodiment, the peptide amino acid sequence is selected from the group consisting of RSKAKNPLYRRRRRRRRR (SEQ ID NO: 24), rskaknplyrrrrrrrrr (SEQ ID NO: 129), RVKVKVVVVRRRRRRRRR (SEQ ID NO: 58), and rvkvkvvvvrrrrrrrrr (SEQ ID NO: 111), RSKAK-RRRRRRRRR (SEQ ID NO: 37), r r r r r r r r r-y l p n k a k s r (SEQ ID NO: 39), IAGQ-RSKAKNPLY-RRRRRRRRR (SEQ ID NO: 40), RSKAKNPLY-RRRRRRRRR-GPLG (SEQ ID NO: 41), RRRRRRRRR-SKAKNPLYR (SEQ ID NO: 42), RRRRRRRRR-YLPNKAKSR (SEQ ID NO: 43), RSKAKNPLY (SEQ ID NO: 30), RRRRRRRRR-HHHHH (SEQ ID NO: 112), RSKAKNPLY-RRRRRRRRR-HHHHHHHHHH (SEQ ID NO: 47), Branched<RSKAKNPLY-RRRRRRRRR- HHHHHHHHHH (SEQ ID NO: 48), RSKAKNPLY-RRRRRRRRR-HHHHHHHHHH (SEQ ID NO: 49), HHHHH-RSKAKNPLY-RRRRRRRRR (SEQ ID NO: 50), HHHHH-RRRRRRRRR-HHHHH-RSKAKNPLYR (SEQ ID NO: 51), RRRRRRRR-HHHHHHHHHH-RSKAKN-PLYR (SEQ ID NO: 52), HHHHH-RSKAKNPLY-RRRRRRRRR-HHHHH (SEQ ID NO: 53), RSKAKNPLY-RKRKRKRKRK (SEQ ID NO: 54), RVKVKVVVV-RRRRR (SEQ ID NO: 56), RVKVKVVVV-RRRRRRRR (SEQ ID NO: 57), RRRRRRRR-RVKVKVVVV-R (SEQ ID NO: 59), RVKVKVVVV-RRRRRRRRR-HHHHHHHHHH (SEQ ID NO: 60), RVKVKVVVV-RHRHRHRHRHRHRHRH-HH (SEQ ID NO: 61), KEKLKNPLFK-RRRRRRRR-HHHHHHHHHH (SEQ ID NO: 62), RVKVKVVVV-RHRHRHRHRHRHRHRH (SEQ ID NO: 63), and KEKLKNPLFK-RRRRRRRR-HHHHHHHHHH (SEQ ID NO: 64).

In another embodiment, the peptide comprises the amino acid sequence RSKAKNPLY-RRRRR (SEQ ID NO: 33) or RSKAKNPLY-RRRRRR (SEQ ID NO: 34).

In another embodiment, the amino acid sequence is amidated at the C-terminal end of the peptide.

In another embodiment, the peptide for activating Lck further comprises a compound of Formula II coupled to the N-terminal or C-terminal end of the cationic amino acid sequence;

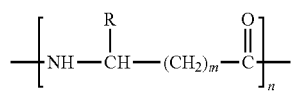

Formula II wherein:
n is the number of monomer units of the compound and is an integer of from 1 to 5;
each m is independently an integer of from 0 to 18; and
each R group is independently H or a $C_1$ to $C_{18}$ side chain.

In another embodiment, the R group of each monomer unit is independently a $C_1$ to $C_{18}$ side chain. In another embodiment, each R group is independently 18–m carbon atoms in length wherein m has a value of from 0 to 17.

In another embodiment, the peptide for activating Lck further comprises a compound coupled to the N-terminal or C-terminal end of the cationic amino acid sequence, wherein the compound is at least one fatty acid. In another embodiment, at least four fatty acids are coupled to the C-terminal end of the cationic amino acid sequence.

In another embodiment, the distal most fatty acid is amidated.

In another embodiment, the coupling of more than one fatty acids is linear. In another embodiment, the coupling of more than one fatty acids is branched.

In another embodiment, the fatty acid is saturated.

In another embodiment, the fatty acid is selected from the group consisting of caproic acid, caprylic acid, capric acid (decanoic acid), and lauric acid (dodecanoic acid).

In another embodiment, the present invention provides a peptide comprising an amino acid sequence selected from the group consisting of RSKAKNPLYRRRRRRRRR (SEQ ID NO: 24), rskaknplyrrrrrrrrr (SEQ ID NO: 129), RVKVKVVVVRRRRRRRRR (SEQ ID NO: 58), and rvkvkvvvvrrrrrrrrr (SEQ ID NO: 111).

In another embodiment, the present invention provides a peptide consisting of an amino acid sequence selected from the group consisting of RSKAKNPLYRRRRRRRRR (SEQ ID NO: 24), rskaknplyrrrrrrrrr (SEQ ID NO: 129), RVKVKVVVVRRRRRRRRR (SEQ ID NO: 58), and rvkvkvvvvrrrrrrrrr (SEQ ID NO: 111).

In another embodiment, the present invention provides a pharmaceutical composition comprising as an active ingredient a peptide for activating Lck as described herein and a pharmaceutically acceptable diluent or carrier.

In another embodiment, the present invention provides a method of increasing an activity of Lck kinase, the method comprising contacting a Lck kinase with a composition comprising a peptide for activating Lck as described herein or a pharmaceutical composition comprising a peptide for activating Lck as described herein.

In another embodiment, the present invention provides a method of increasing Y394 phosphorylation of Lck kinase, the method comprising contacting a Lck kinase with a composition comprising a peptide for activating Lck as described herein or a pharmaceutical composition comprising a peptide for activating Lck as described herein.

In another embodiment, the present invention provides a method of increasing IL-2 secretion from a cell or a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-2Ra (CD25) expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-2RB (CD122) expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-2 responsiveness of a cell or in population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing CD28 expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-12 secretion from a cell or a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-12R expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the IL-12R is IL-12RB1 and/or IL-12RB2.

In another embodiment, the present invention provides a method of increasing IL-12 responsiveness of a cell or in population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-21 secretion from a cell or a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-15 secretion from a cell or a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-15R expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-15 responsiveness of a cell or in population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-18R expression on a cell or in a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing IL-18 responsiveness of a cell or in population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing cytokine secretion from a cell or a population of cells, the method comprising contacting a cell or a population of cells with a composition comprising a peptide for activating Lck as described herein or a pharmaceutical composition comprising a peptide for activating Lck as described herein.

In another embodiment, the cytokine is IFNg.

In another embodiment, the present invention provides a method of inducing proliferation of a cell or a population of cells, the method comprising contacting a cell or a population of cells with a composition comprising a peptide for activating Lck as described herein or a pharmaceutical composition comprising a peptide for activating Lck as described herein.

In another embodiment, the present invention provides a method of increasing proliferation of a population of cells, the method comprising contacting a population of cells with a composition comprising a peptide for activating Lck as described herein or a pharmaceutical composition comprising a peptide for activating Lck as described herein.

In another embodiment, the present invention provides a method as described herein wherein the cell is, or the population of cells comprises, a cell selected from the group consisting of a CD4+ T cell, a CD8+ T cell, a NK cell, or a dendritic cell.

In another embodiment, the cell is, or the population of cells comprises, a naive cell.

In another embodiment, the present invention provides a method of enhancing a T cell function, the method comprising contacting a T cell or a population of T cells with a composition comprising a peptide for activating Lck as described herein or a pharmaceutical composition comprising a peptide for activating Lck as described herein.

In another embodiment, the present invention provides a method of enhancing a cytotoxic cell function, the method comprising contacting a cytotoxic cell or a population of cytotoxic cells with a composition comprising a peptide for activating Lck as described herein or a pharmaceutical composition comprising a peptide for activating Lck as described herein.

In another embodiment, the present invention provides a method of reducing exhaustion of a T cell or a population of T cells, the method comprising contacting a T cell or a population of T cells with a composition comprising a peptide for activating Lck as described herein or a pharmaceutical composition comprising a peptide for activating Lck as described herein.

In another embodiment, the present invention provides a method of treating oxidative damage the method comprising contacting a cell or a population of cells with a composition comprising a peptide for activating Lck as described herein or a pharmaceutical composition comprising a peptide for activating Lck as described herein.

In another embodiment, the present invention provides a method of decreasing the proportion of Treg cells in a cell population, the method comprising contacting a Treg containing cell population with a composition comprising a peptide for activating Lck as described herein or a pharmaceutical composition comprising a peptide for activating Lck as described herein.

In another embodiment, the Treg cells are Foxp3+ Treg cells.

In another embodiment, the present invention provides a method of increasing CD25 expression in the presence of a checkpoint inhibitor, the method comprising contacting a cell or a population of cells with a composition comprising a peptide for activating Lck as described herein or a pharmaceutical composition comprising a peptide for activating Lck as described herein.

In another embodiment, the contacting is performed in vivo or in vitro.

In another embodiment, the method is performed ex vivo.

In another embodiment, the present invention provides a cell or a population of cells derived from a cell or a population of cells obtained by contacting a cell or a population of cells with a composition comprising a peptide for activating Lck as described herein or a pharmaceutical composition comprising a peptide for activating Lck as described herein.

In another embodiment, the present invention provides a method as described herein wherein the peptide or pharmaceutical composition is administered to a subject to increase an activity of Lck in vivo.

In another embodiment, the present invention provides a method of increasing an activity of Lck in a subject, comprising administering to the subject a composition comprising a peptide for activating Lck as described herein or a pharmaceutical composition comprising a peptide for activating Lck as described herein.

In another embodiment, the present invention provides a method of inducing an immune response in a subject, comprising administering to the subject a composition comprising a peptide for activating Lck as described herein or a pharmaceutical composition comprising a peptide for activating Lck as described herein.

In another embodiment, the present invention provides a method of treating and/or preventing at least one symptom associated with a disease or condition characterised by inhibition or down-regulation of Lck or Lck activity, comprising administering to a subject a composition comprising a peptide for activating Lck as described herein or a pharmaceutical composition comprising a peptide for activating Lck as described herein.

In another embodiment, the present invention provides a method described herein wherein the disease or condition characterised by inhibition or down-regulation of Lck or Lck activity is selected from the group consisting of pathogenic infections, sepsis (e.g., chronic sepsis) from pathogenic infections, immune deficiency disorders, reduced immune response, lowered T cell count, T cell abnormalities, T-cell exhaustion, and T cell checkpoint blockade In another embodiment, the present invention provides a method as described herein, wherein the disease or condition is cancer.

In another embodiment, the present invention provides a method of vaccinating a subject in need thereof, the method comprising administering to a subject a composition comprising a peptide for activating Lck as described herein or a pharmaceutical composition comprising a peptide for activating Lck as described herein.

In another embodiment, the present invention provides a method of treating and/or preventing cancer in a subject in need thereof, the method comprising administering to a subject a composition comprising a peptide for activating Lck as described herein or a pharmaceutical composition comprising a peptide for activating Lck as described herein.

In another embodiment, the present invention provides a method of decreasing immunosuppression in a subject, the method comprising administering to the subject a composition comprising a peptide for activating Lck as described herein or a pharmaceutical composition comprising a peptide for activating Lck as described herein.

In another embodiment, the present invention provides a method of treating and/or preventing age related immune dysfunction in a subject, the method comprising administering to the subject a composition comprising a peptide for activating Lck as described herein or a pharmaceutical composition comprising a peptide for activating Lck as described herein.

In another embodiment, the present invention provides a method of inducing a Th1 response in a subject, the method comprising administering to the subject a composition comprising a peptide for activating Lck as described herein or a pharmaceutical composition comprising a peptide for activating Lck as described herein..

In another embodiment, the present invention provides a dosage unit form for the treatment and/or prevention of at least one symptom associated with a disease or condition characterised by inhibition or down-regulation of Lck or Lck activity comprising a peptide as described herein.

In another embodiment, the present invention provides a dosage unit form for the treatment of prophylaxis of cancer comprising a peptide as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers, integers or steps.

BRIEF DESCRIPTION OF THE ACCOMPANYING DRAWINGS

FIG. 1 shows Lck activation by polypeptides in vitro.

FIG. 2 shows selective activation of Lck compared to other SFKs.

A: Photograph of a developed Western blot showing the result of probing with the anti-phospho tyrosine antibody 4G10. The level of phosphorylation of Lck enzyme increased with increasing concentrations of the peptide actives RRRRRRRR (SEQ ID NO: 4, "8Arg"; lane 8 (10 µM) compared to lane 7 (1 µM)) and RRRRRRRRRR (SEQ ID NO: 7, "10Arg"; lane 6 (10 µM) compared to lane 5 (1 µM)). B: Photograph of a developed Western blot showing auto-phosphorylation of Lck at tyrosine Y394 induced by the 8Arg and 10Arg peptides following probing with anti-pY394 antibody. Increased auto-phosphorylation was associated with increasing concentration of the 8Arg (lanes 7-8) and 10Arg (lanes 5-6) polypeptides.

FIG. 4 shows Lck activation by polypeptides in vitro.

FIG. 5 shows Lck activation by polypeptides in vitro.

Figure 6:
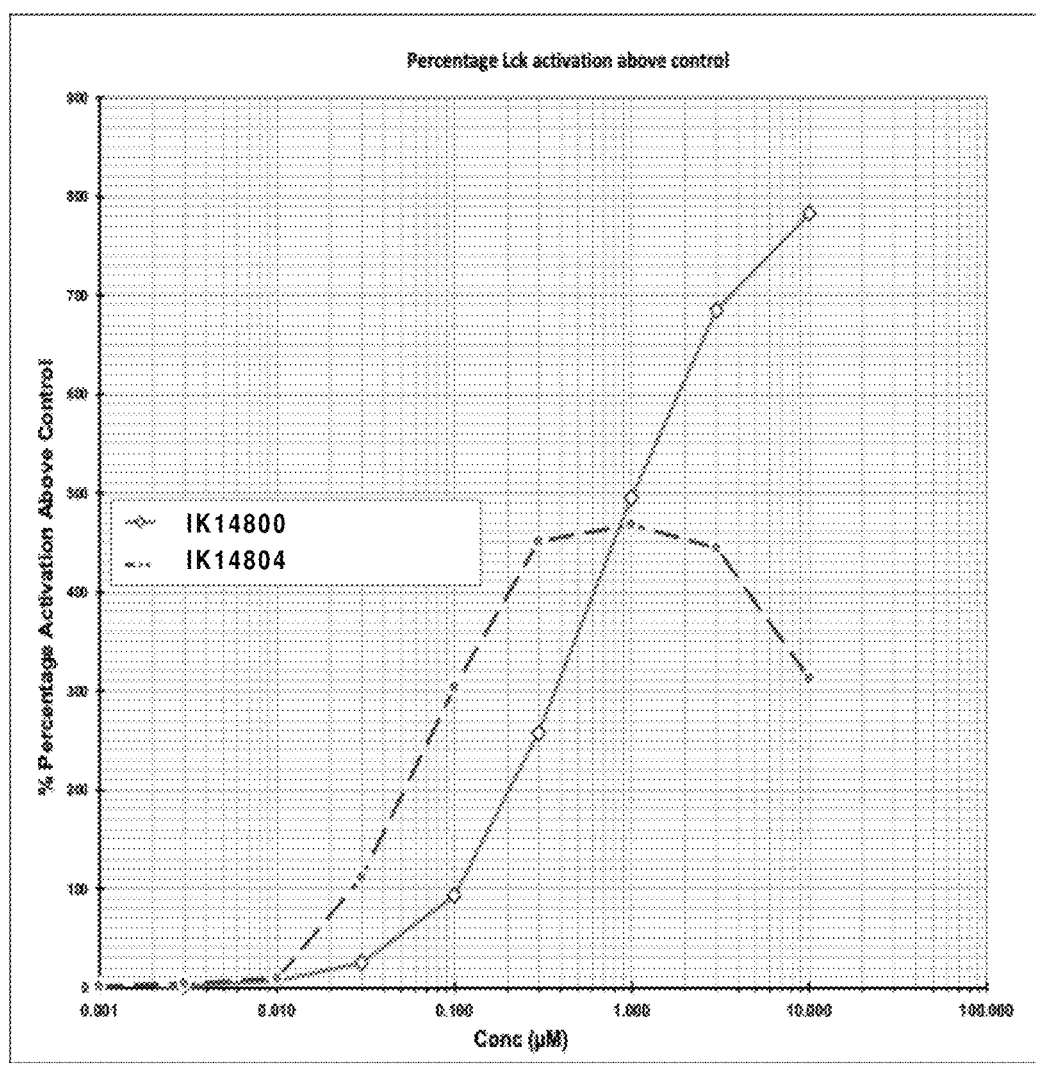

FIG. 6 shows dose dependent activation of Lck activity when Lck is contacted with the polypeptides RSKAKNPLY-RRRRRRRRR (SEQ ID NO: 24, "IK14800") and RSKAKNPLY-RRRRRRRRR-(2Adod)$_4$-NH$_2$ (SEQ ID NO: 65, "IK14804").

FIG. 7 shows the Lck activating polypeptides RRRRRRRRR (SEQ ID NO: 6, "IK00900") induces IL-2 secretion relative to control in wild-type Jurkat cells. A: Wild-type Jurkat cells (am immortalised line of human T lymphocyte cells) were stimulated by exposure to biotinylated anti-CD3 antibody in the presence of anti-CD28 antibody and avidin. During the culture period (48 hours or 72 hours) cells were exposed to test polypeptides. Cell supernatant was assayed for IL-2 at the end of 48 or 72 hours using a standard commercially available ELISA kit as described above. B: The Lck activating polypeptide RSKAKNPLY-RRRRRRRRR (SEQ ID NO: 24, "IK14800") induces IL-2 secretion relative to control in wild-type Jurkat cells following 72 h exposure.

Figure 8A:
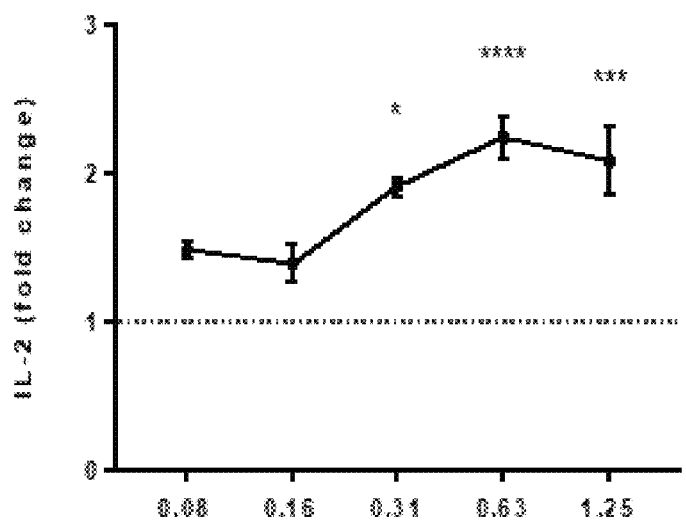
Figure 8B:
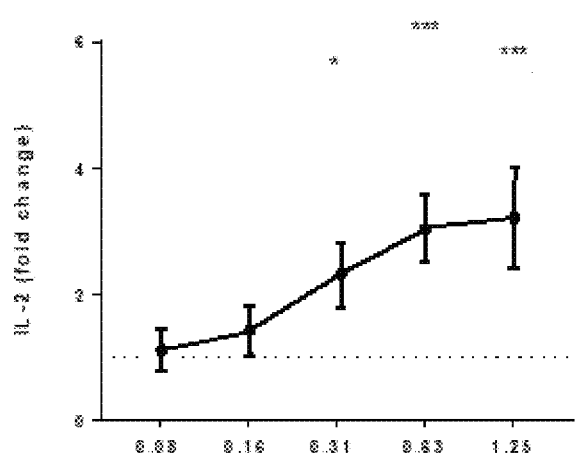

FIG. 8 shows the Lck activating fusion polypeptide RSKAKNPLY-RRRRRRRRR (SEQ ID NO: 24, "IK14800") induces IL-2 secretion relative to control in isolated human CD4+ and CD8+ T cells. Effect of Lck activating peptides on IL-2 production from isolated CD4+ and CD8+ T cells (immunomagnetic separation from healthy human PBMCs) following anti-CD3 and anti-CD28 stimulation for 48 hrs. Data are presented as mean +/−SEM from 3 donors each normalised to vehicle control. Statistical comparisons were made using two-way ANOVA with Dunnett's post-test comparing each concentration of test peptide to 0.08 μM (*p<0.05, *p<0.001, **p<0.0001). Dotted line indicates vehicle control values for normalised data.

Figure 9A:
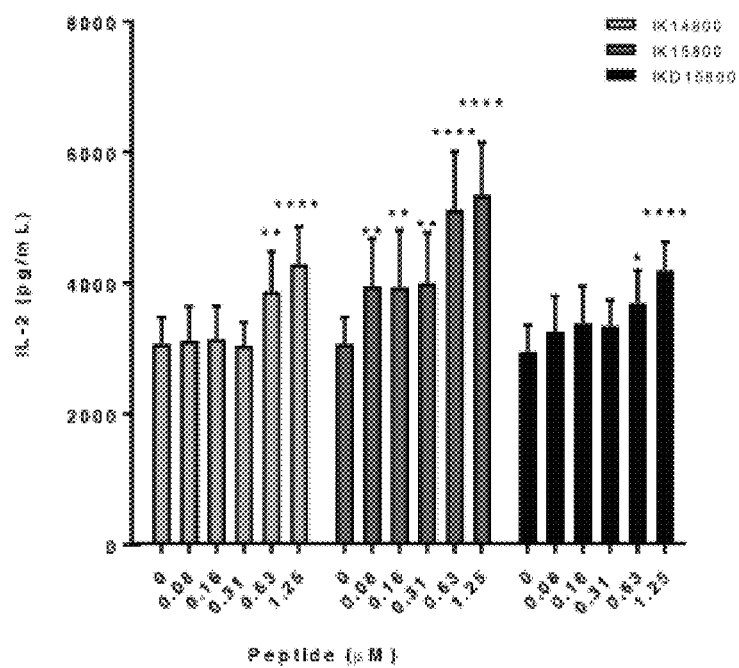
Figure 9B:
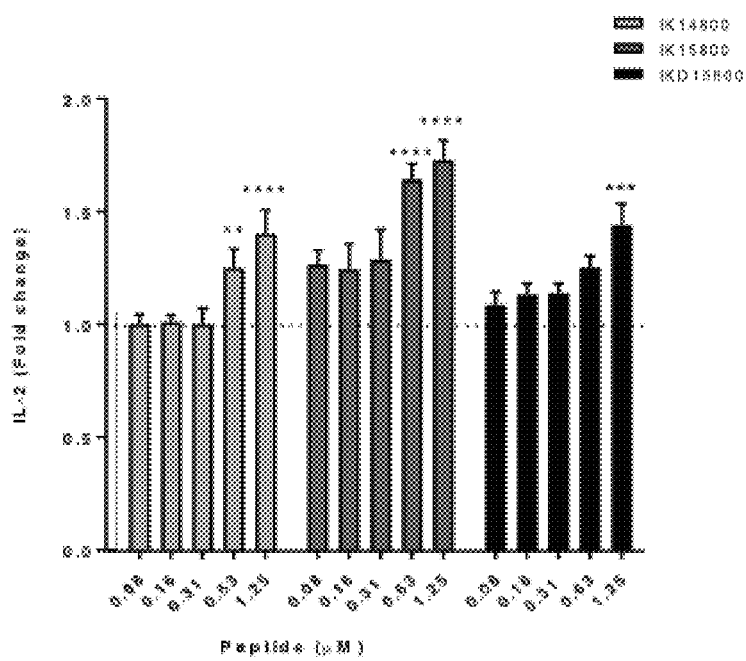

FIG. 9 shows Lck activating polypeptides RSKAKNPLY-RRRRRRRRR (SEQ ID NO: 24, "IK14800"), RVKVKVVVV-RRRRRRRRR (SEQ ID NO: 58, "IK15800"), and RVKVKVVVV-RRRRRRRRR (SEQ ID NO: 58) comprising only D amino acids (i.e. rvkvkvvvv-rrrrrrrrr; SEQ ID NO: 111, "IKD15800"), induce IL-2 secretion relative to control in isolated human T cells. In brief, isolated T cells (CD3+) were stimulated with anti-CD3 anti-CD28 Dynabeads™ and cultured together the Lck activating polypeptide RSKAKNPLY-RRRRRRRRR (SEQ ID NO: 24, "IK14800"), RVKVKVVVV-RRRRRRRRR (SEQ ID NO: 58, "IK15800"), and RVKVKVVVV-RRRRRRRRR (SEQ ID NO: 58) comprising only D amino acids (SEQ ID NO: 111, "IKD15800"), over a 5-concentration range plus vehicle control (0-1.25 μM) for 72 hours after which supernatants were collected and assessed for IL-2 by ELISA. Data presented shows the mean IL-2 pg/ml and fold change (normalised to vehicle)+/− SEM, n=4. Data were analysed by RM two-way ANOVA with Dunnett's post-test comparing each peptide concentration with vehicle or where normalised test concentration was compared to lowest test concentration, *p<0.05, p<0.01, *p<0.001, ****p<0.0001. Dotted line indicates vehicle control values for normalised data (right).

Figure 10:
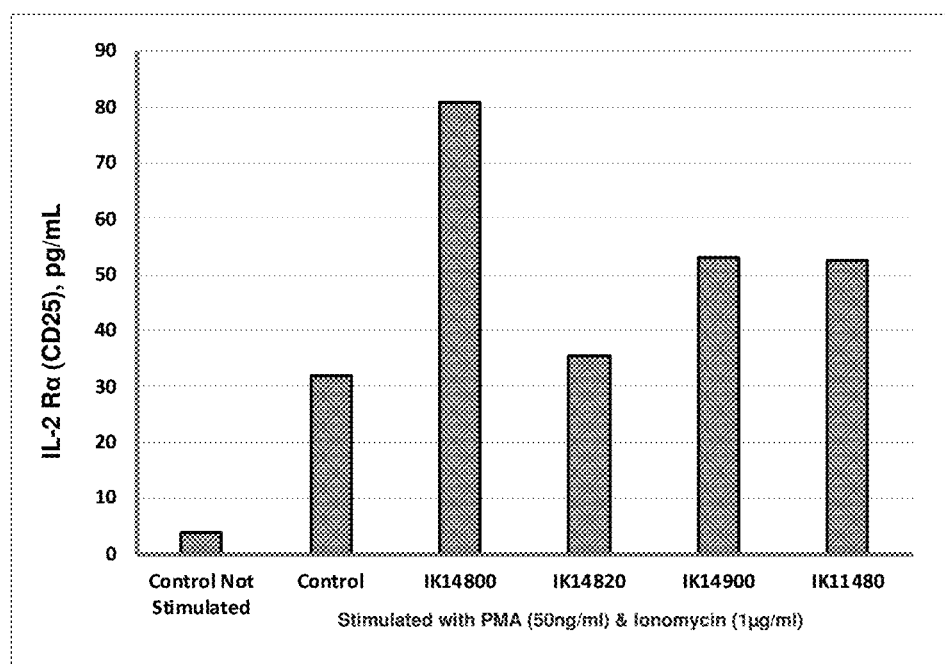
Figure 11A:
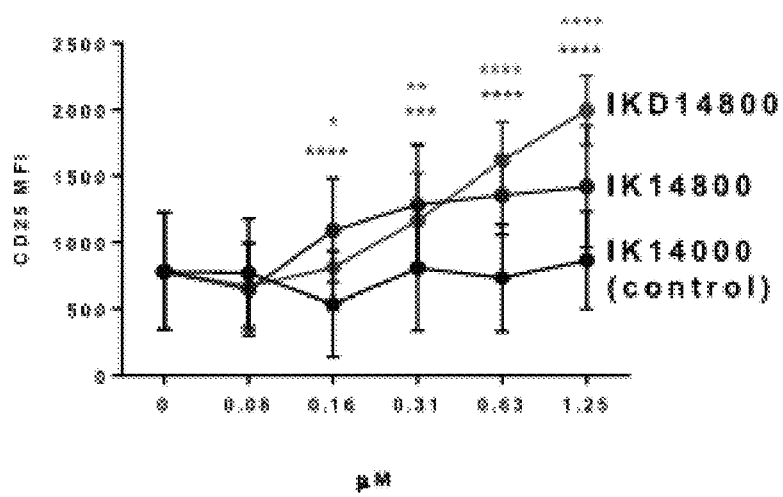
Figure 11B:
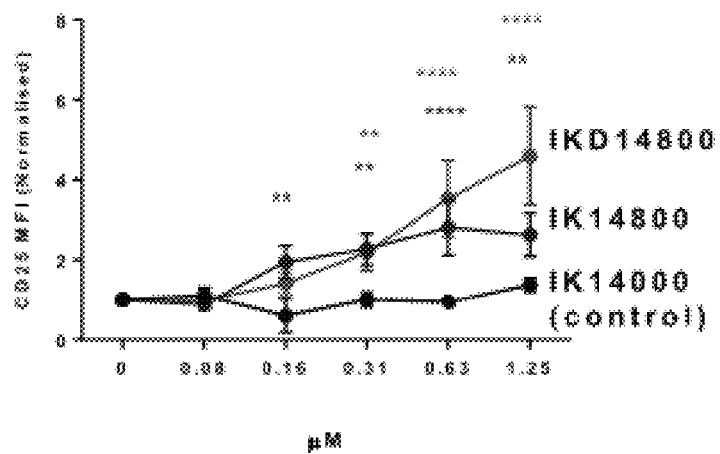
Figure 11C:
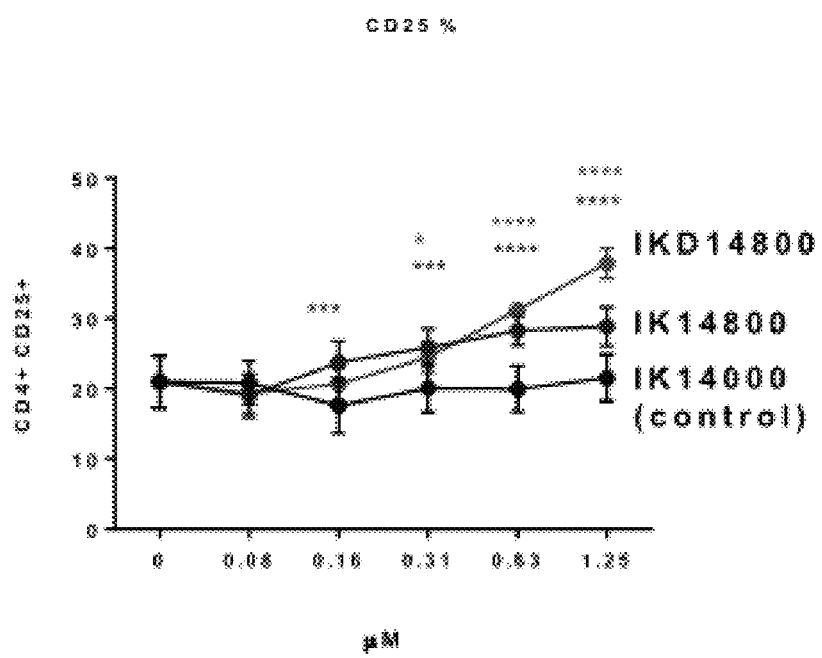
Figure 11D:
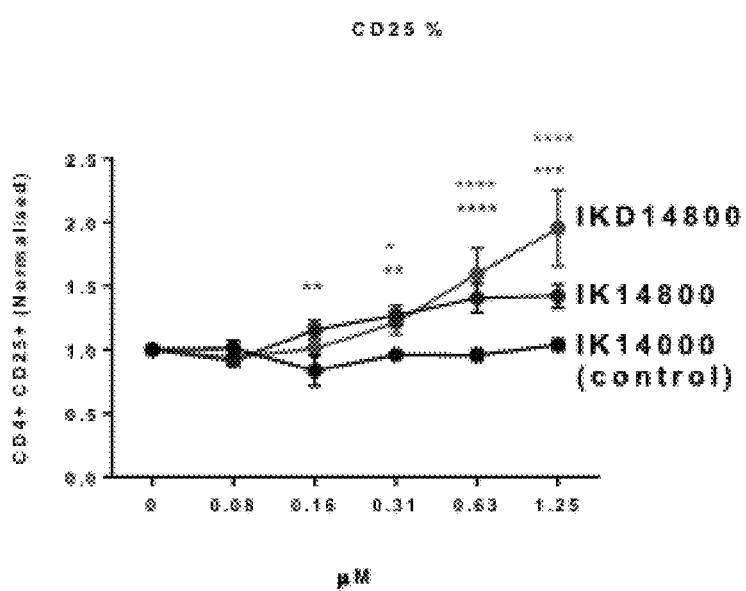

FIG. 10 shows IL-2R alpha (CD25) expression was increased when stimulated cells were exposed to peptides RSKAKNPLY-RRRRRRRRR (SEQ ID NO: 115, "IK14900"), HHHHH-RSKAKNPLY-RRRRRRRRR (SEQ ID NO: 50, "IK11480"), RSKAKNPLY-RRRRRRRRR-HHHHHHHHHHHH (SEQ ID NO: 49, "IK14820") and in particular, the peptide RSKAKNPLY-RRRRRRRRR (SEQ ID NO: 24, "IK14800"). Cells were seeded at 1 million cells per well (12 well plate, 2 mL volume) and stimulated with PMA (50 ng/mL) and Ionomycin (1 μg/mL). The cells were then treated with peptides as indicated, and then incubated for 48 hours at 37° C. The supernatant (100 uL, n=3), was then analyzed for IL-12Rα content.

FIG. 11 shows expression of CD25 is increased in exhausted CD4+ T cells upon restimulation with the Lck activating fusion polypeptides IK14800 (RSKAKNPLY-RRRRRRRRR, SEQ ID NO: 24) and IKD14800 (rskaknply-rrrrrrrrr, SEQ ID NO: 129), relative to IK14000 (SEQ ID NO: 31, control). Cells were stained for flow cytometry after 72 hrs in culture to assess CD25 (MFI, top, to indicate level of expression and frequency, bottom). From within the viable population, cells were gated to focus on CD4+ cells which were then gated on CD25+ populations. Data are presented as mean +/− sem from 4 biological replicates as absolute values, left and normalised to vehicle, right. *P<0.05, P<0.01, *P<0.001, ****P<0.0001. Two-way ANOVA with Dunnetts post test was used to compare each peptide to control peptide (IK14000, SEQ ID NO: 31) at each test concentration.

Figure 12:
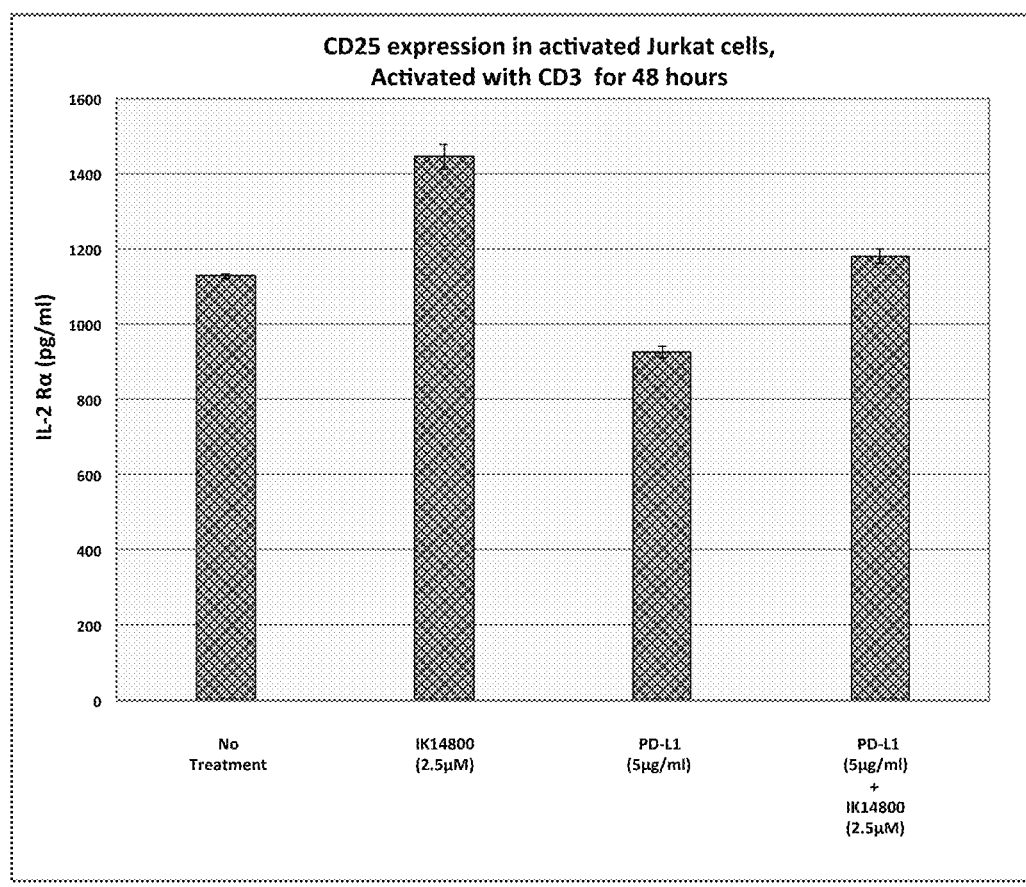

FIG. 12 shows the addition of RSKAKNPLY-RRRRRRRRR-NH$_2$ (SEQ ID NO: 24, IK14800) rescued suppression of IL-2Ralpha induced by the PD-1/PD-L1 interaction. In brief, Jurkat cells were activated by means of exposure to culture dish adhered anti-CD3 antibody to induce cell surface expression of programmed cell death receptor 1 (PD-1), and were cultured for 48 hours in the absence of additives or with the peptide RSKAKNPLY-RRRRRRRRR-NH$_2$ (SEQ ID NO: 24, IK14800 at 2.5 μM) alone, 5 μg/ml recombinant PD-L1 (the ligand for PD-1) alone to induce checkpoint blockade in the cells, or with the IK14800 peptide (SEQ ID NO: 31) plus recombinant PD-L1. IL-2Ralpha (CD25) was measured in cell lysates by means of a standard commercially available ELISA kit as described above.

Figure 13:
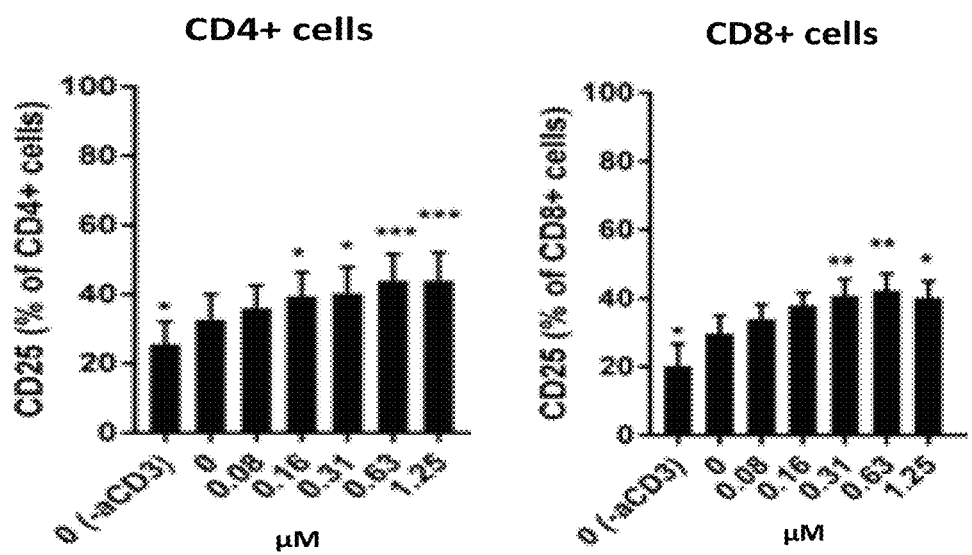

FIG. 13 shows expression of IL2Ra (CD25) is increased in CD4+ and CD8+ T cells when stimulated with anti-CD3. CD25 expression in CD4+ (left) and CD8+ (right) cells from stimulated PBMCs. Freshly isolated PBMCs were stimulated with or without (− aCD3) anti-CD3 (1 pg/mL) for 24 hrs in the presence of test peptide IK14800 at indicated concentrations (μM). Data are presented as mean +/− SEM from 4 donors. *p<0.05, p<0.01, *p<0.001, two way ANOVA with Dunnett's post-test was used to compare concentrations of each peptide (or unstimulated cells) to vehicle (0).

Figure 14A:
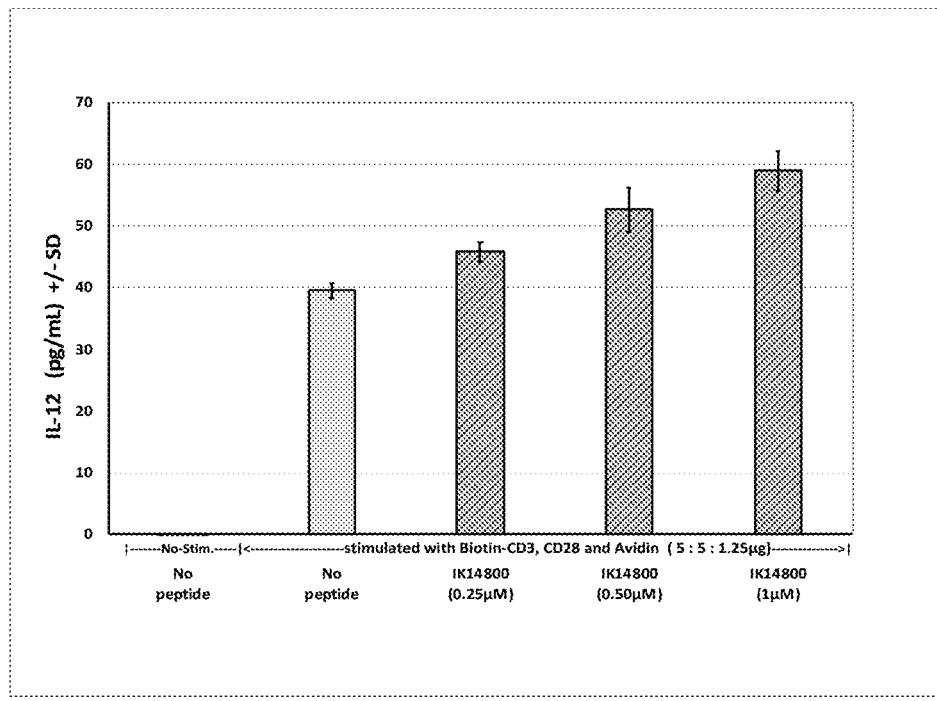
Figure 14B:
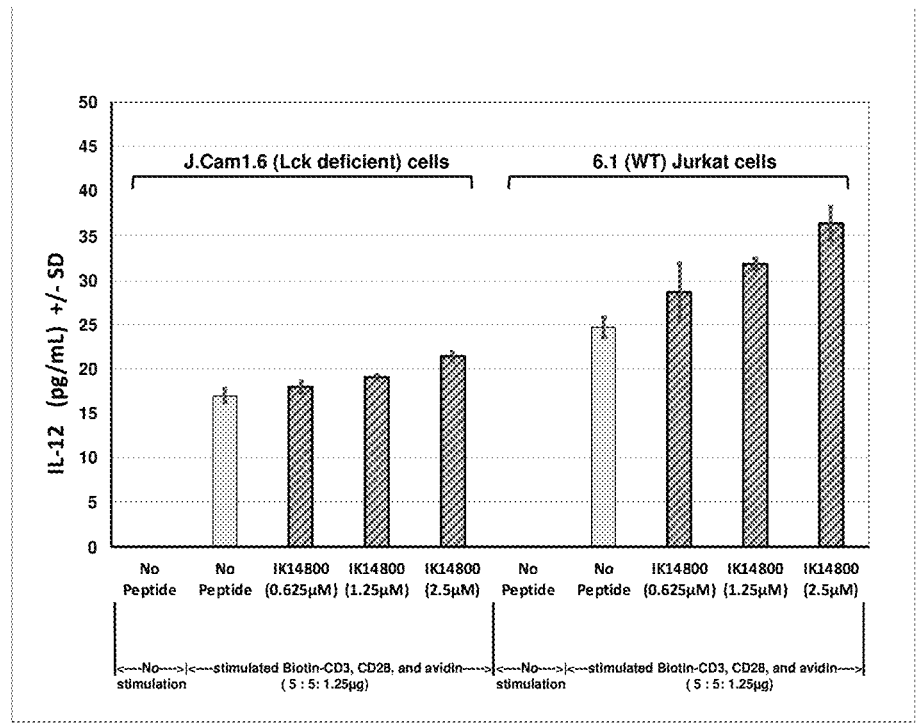
Figure 15A:
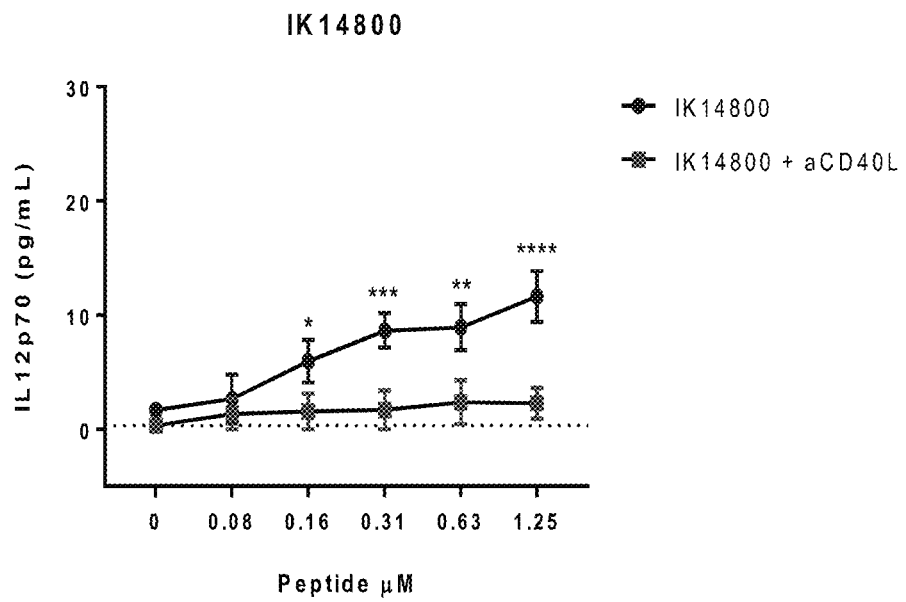
Figure 15B:
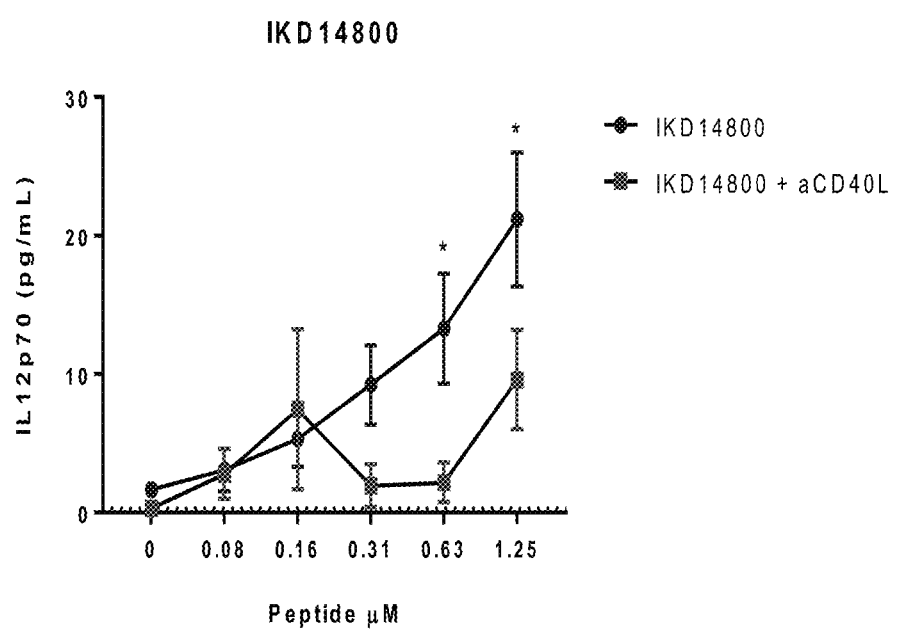
Figure 15C:
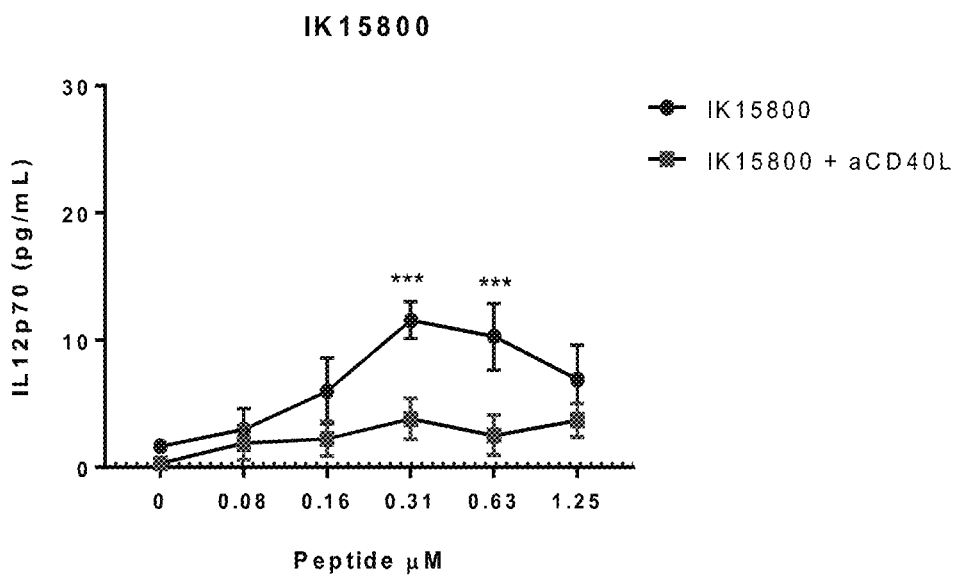
Figure 15D:
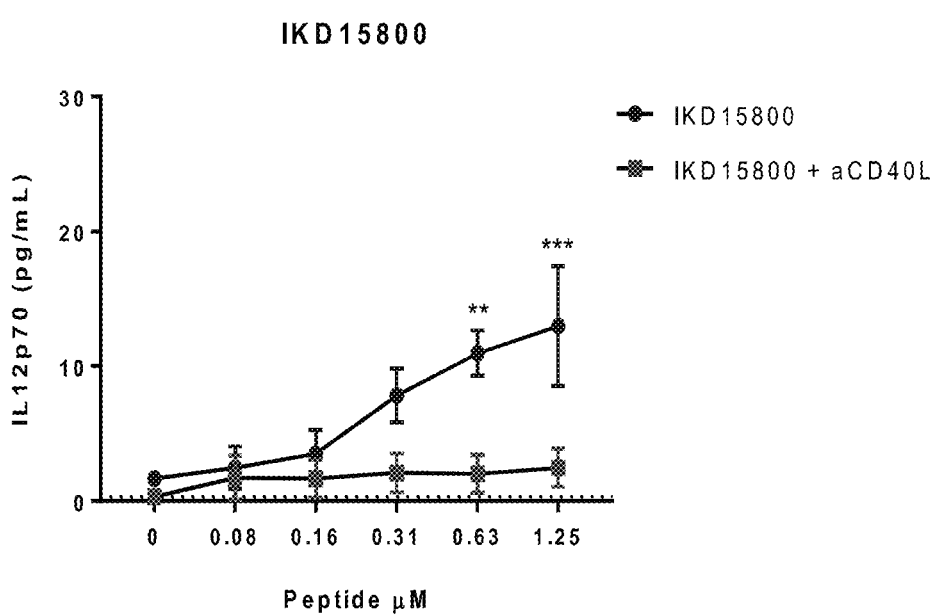

FIG. 14 shows Lck activating polypeptides increase IL-12 secretion in a human T lymphocyte (Jurkat) cell line. A. Cells seeded at 1 million cells per well (12 well plate, 2 mL volume) and stimulated with Biotin-CD3, CD28, and avidin (5:5:1.25 μg). The cells were then treated with peptide IK14800, and then incubated for 48 hours at 37° C. The supernatant (100 ul, n=3), was then analyzed for IL12 content. FIG. 14B shows that the ability of the Lck activating polypeptide RSKAKNPLY-RRRRRRRRR (SEQ ID NO: 24, IK14800) to induce IL-12 secretion in Jurkat cells relative to control, is dependent on Lck. This data demonstrates that IL-12 secretion in a human T cell line by the Lck activating fusion polypeptide RSKAKNPLY-RRRRRRRRR (SEQ ID NO: 24, IK14800) is dependent on Lck. Cells seeded at 1 million cells per well (12 well plate, 2 mL volume) and stimulated with Biotin-CD3, CD28, and avidin (5:5:1.25 μg). The cells were then treated with peptide IK14800, and then incubated for 48 hours at 37° C. The supernatant (100 ul, n=3), was then analyzed for IL-12 content.

FIG. 15 shows that the Lck activating polypeptides RVKVKVVVV-RRRRRRRRR (SEQ ID NO: 58), RSKAKNPLY-RRRRRRRRR (SEQ ID NO: 24) and RSKAKNPLY-RRRRRRRRR (SEQ ID NO: 24) comprising only D amino acids (rskaknply-rrrrrrrrr, SEQ ID NO: 129) induce IL-12 secretion in anti-CD3 stimulated PBMCs, relative to anti-CD3 stimulated PBMCs in the presence of anti-CD40L blocking antibody, which inhibits the production of IL-12. The Lck activating polyarginine polypeptide RRRRRRRRR also induced IL-12 secretion in anti-CD3 stimulated PBMCs, relative to anti-CD3 stimulated PBMCs in the presence of anti-CD40L blocking antibody. Anti-CD3 stimulated PBMCs were cultured together with IK14800, IKD14800, IK15800 and IKD15800 in the presence and absence of anti-CD40L blocking antibody for 24 hrs. Supernatants were assessed for IL-12p70 levels by ELISA. Data shown indicates mean IL-12p70 pg/mL values +/− SEM, n=4. Data were analysed by two-way ANOVA with Sidak's post-test comparing peptide treatment alone with peptide+anti-CD40L, *p<0.05, p<0.01, *p<0.001, ****p<0.0001. Dotted line indicates average vehicle control.

Figure 16:
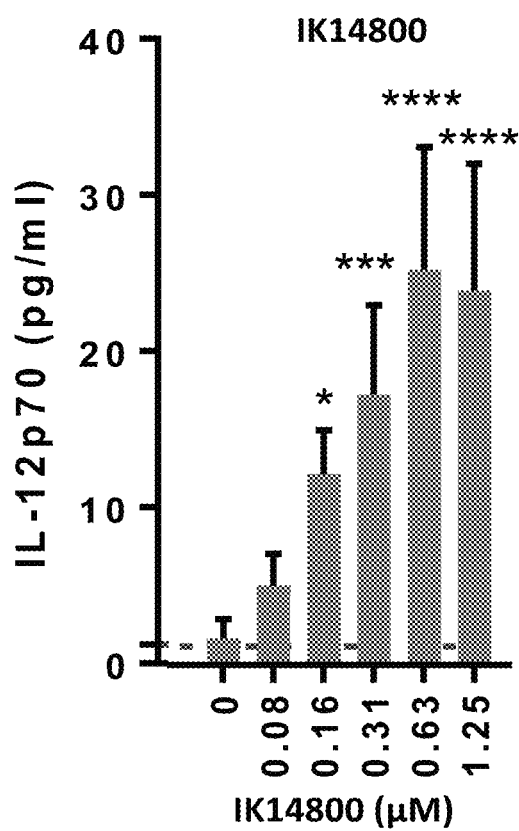

FIG. 16 shows that the Lck activating polypeptide RSKAKNPLY-RRRRRRRRR (SEQ ID NO: 24, IK14800) induces IL-12p70 secretion relative to control at 24 hours. PBMCs were cultured together with anti-CD3 (1 μg/ml) stimulation and peptides over a 5-concentration range (0-1.25 μM) for 24 hrs after which supernatants were collected and analysed for IL-12p70 by ELISA. Data presented indicates the mean cytokine production (pg/mL) in response to peptide treatment, +/− SEM, n=4. Data were analysed by two-way ANOVA with Dunnett's post-test, *P<0.05, *P<0.001, **P<0.0001. Dotted line indicates mean unstimulated PBMC expression.

Figure 17:
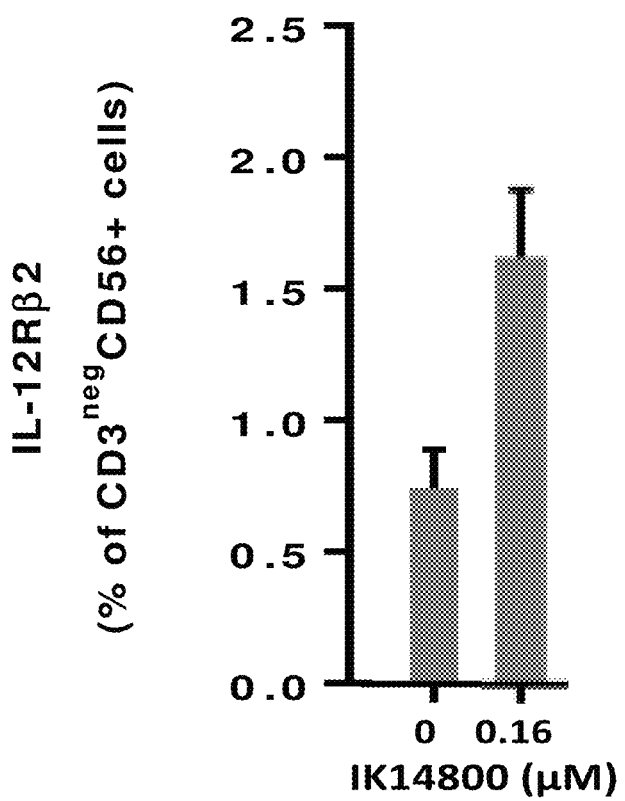

FIG. 17 shows the Lck activating polypeptide RSKAKN-PLY-RRRRRRRRR (SEQ ID NO: 24, IK14800) induces IL-12Rβ2 expression in a population of NK cells (CD3$^{neg}$CD56+ cells). Anti-CD3 stimulated PBMCs were cultured together with IK14800 at 0.16 μM plus vehicle control (0) for 72 hrs after which CD3$^{NEG}$CD56+ NK cells were assessed for IL-12Rβ2 expression by flow cytometry. Data presented indicate the mean respective IL-12Rβ2 expression (percentage of CD3$^{NEG}$CD56+ NK cells) in response to peptide treatment.

Figure 18:
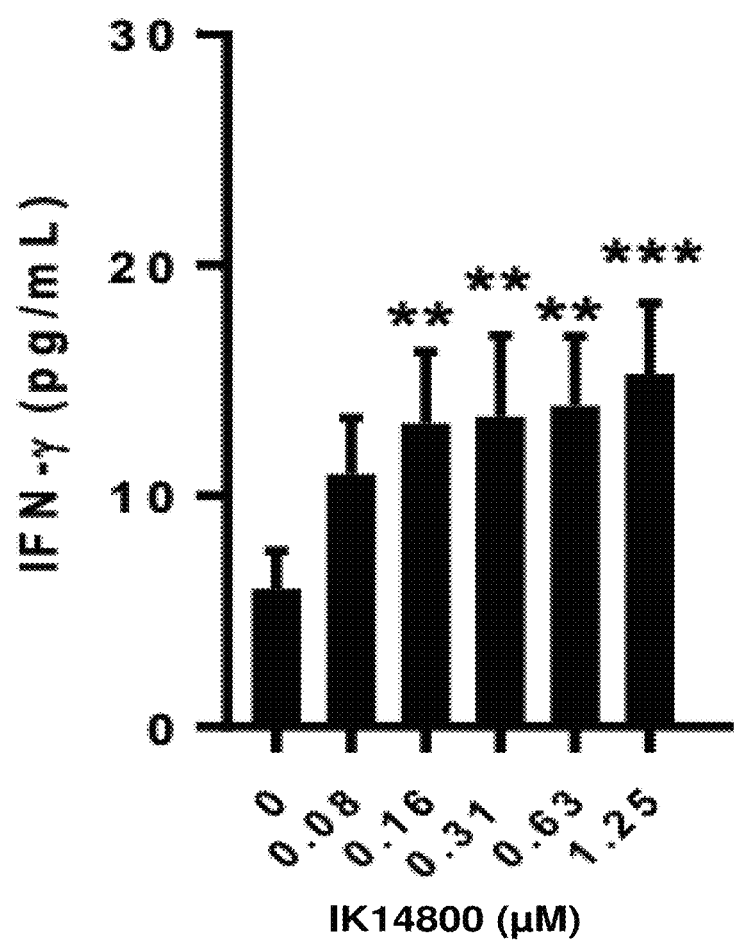

FIG. 18 shows that the Lck activating polypeptide RSKAKNPLY-RRRRRRRRR (SEQ ID NO: 24, IK14800) induces IFN-γ secretion relative to unstimulated CD4+ T cells. Isolated CD4+ T cells were stimulated with anti-CD3 anti-CD28 Dynabeads™ and cultured together with IK14800 (SEQ ID NO: 24) over a 5-concentration range plus vehicle control (0-1.25 μM) for 24 hrs after which supernatants were assessed for IFN-γ by ELISA. Data presented indicates the mean respective IFN-γ (pg/ml values as normalised to vehicle) in response to peptide treatment, +/− SEM, n=4. Data were analysed by RM two-way ANOVA with Dunnett's post-test comparing IK14800 (SEQ ID NO: 24) concentration with vehicle or where normalised to lowest peptide concentration, p<0.01, *p<0.001.

Figure 19A:
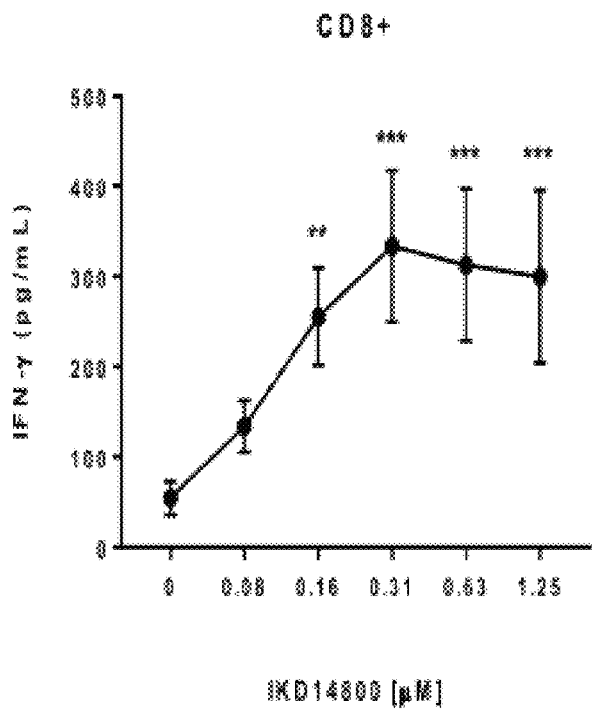
Figure 19B:
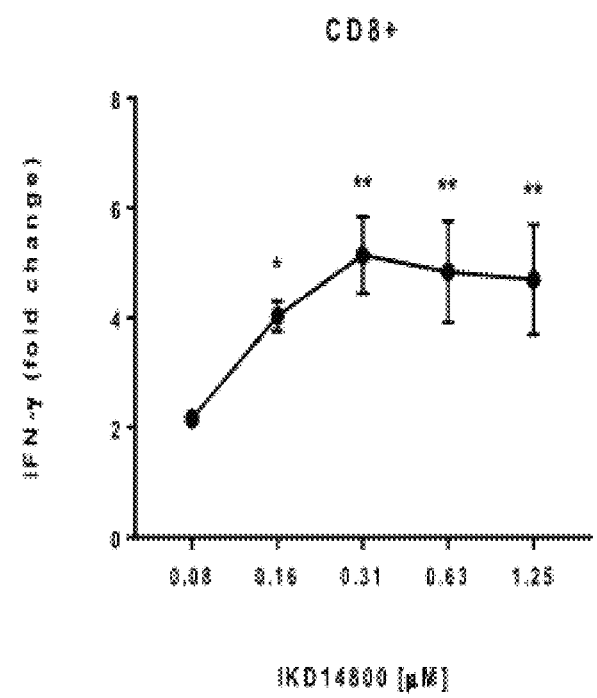

FIG. 19 shows that the Lck activating polypeptide RSKAKNPLY-RRRRRRRRR (SEQ ID NO: 24), comprising only D amino acids (SEQ ID NO: 129, IKD14800), induces IFN-γ secretion by stimulated human CD8+ T cells, relative to unstimulated CD8+ T cells. Isolated CD8+ T cells were cultured together with anti-CD3 anti-CD28 coated dynabeads (4:1 cell to bead ratio) stimulation in the presence of IKD14800 (SEQ ID NO: 24) over a 5-concentration range (0-1.25 μM). After 24 hrs supernatants were sampled and assessed for IFN-γ by ELISA. Data presented indicates the mean IFN-γ production (pg/mL) in CD8+ T cell populations +/− SEM, n=4. Data were also normalised to vehicle control and expressed as mean fold change, n=3. Data were analysed by RM one-way ANOVA with Dunnett's post-test, *p<0.05, p<0.01, *p<0.001. Significant differences indicate comparisons made between respective peptide concentration and vehicle control or where data is normalised to lowest peptide concentration (0.08 μM).

Figure 20:
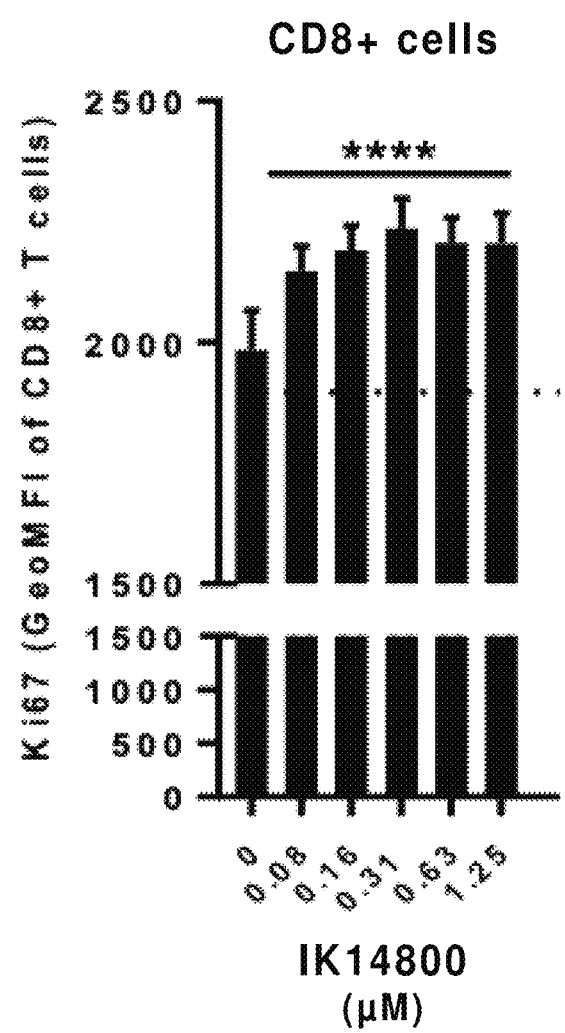

FIG. 20 shows that the Lck activating polypeptide RSKAKNPLY-RRRRRRRRR (SEQ ID NO: 24) increases the proliferating population of human CD8+ T cells. Isolated CD8+ T cells were stimulated with anti-CD3 anti-CD28 Dynabeads™ and cultured together with IK14800 (SEQ ID NO: 24), over a 5-concentration range plus vehicle control (0-1.25 μM) for 24 hrs after which CD8+ T cells were assessed for Ki67 expression by flow cytometry. Data presented indicates the mean respective Ki67 (MFI) in response to peptide treatment, +/− SEM, n=4. Data were analysed by RM two-way ANOVA with Dunnett's post-test comparing peptide concentration with vehicle, ****p<0.0001. Dotted line indicates mean unstimulated control values.

Figure 21:
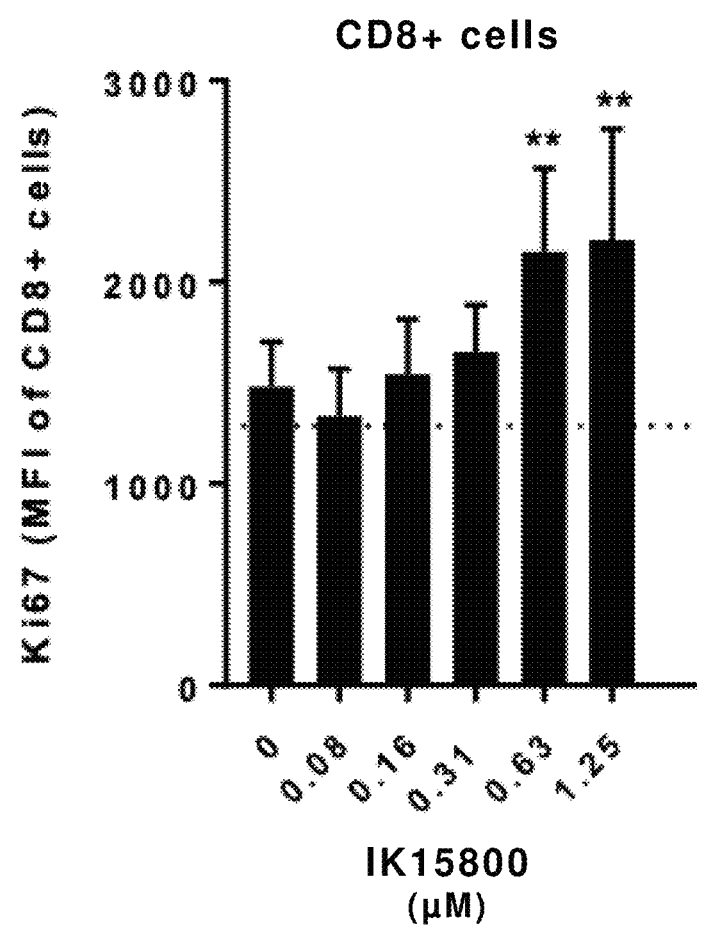

FIG. 21 shows that the Lck activating polypeptide RVKVKVVVV-RRRRRRRRR (SEQ ID NO: 58, IK15800) increases the proliferating population of human CD8+ T cells. Ki67 (proliferation) expression in CD8+ T cells in response to IK15800 (SEQ ID NO: 58) in a stimulated PBMC assay. Anti-CD3 stimulated PBMCs were cultured together with IKD15800 (SEQ ID NO: 58) over a 5-concentration range plus vehicle control (0-1.25 μM) for 72 hrs after which CD8+ T cells were assessed for Ki67 expression by flow cytometry. Data presented indicates the mean respective expression (MFI) in response to peptide treatment, +/− SEM, n=3. Data were analysed by RM two-way ANOVA with Dunnett's post-test comparing each peptide concentration with vehicle, **P<0.01. Dotted line indicates unstimulated control values.

FIG. 22 shows that the Lck activating polypeptides RVKVKVVVV-RRRRRRRRR (SEQ ID NO: 58, IK15800) and RSKAKNPLY-RRRRRRRRR (SEQ ID NO: 24, IK14800) induce CD28 expression in CD4+ and CD8+ T cells relative to no peptide control. A. PBMCs were cultured together with anti-CD3 (1 μg/ml) stimulation and IK14800 and tested over a 5-concentration range (0-1.25 μM) for 72 hrs after which cells were assessed for expression of CD28 by flow cytometry. Data indicate the mean respective expression in CD8+ T cell populations in response to peptide treatment, +/− SEM, n=4. Data was analysed by two-way ANOVA with Dunnett's post-test. *p<0.05, *P<0.001. Dotted line indicates unstimulated cells. B. PBMCs were cultured together with anti-CD3 (1 μg/ml) stimulation and test peptides and tested over a 5-concentration range (0-1.25 μM) for 72 hrs after which cells were assessed for expression of CD28 by flow cytometry. Data presented indicates the mean respective expression in CD4+ T cell populations in response to peptide treatment, +/− SEM, n=4. Data was analysed by two-way ANOVA with Dunnett's post-test P<0.01, *P<0.001 **p<0.0001. Dotted line indicates unstimulated cells.

Figure 23A:
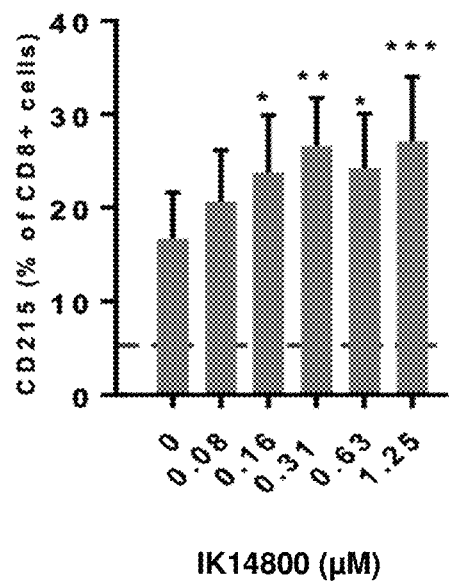
Figure 23B:
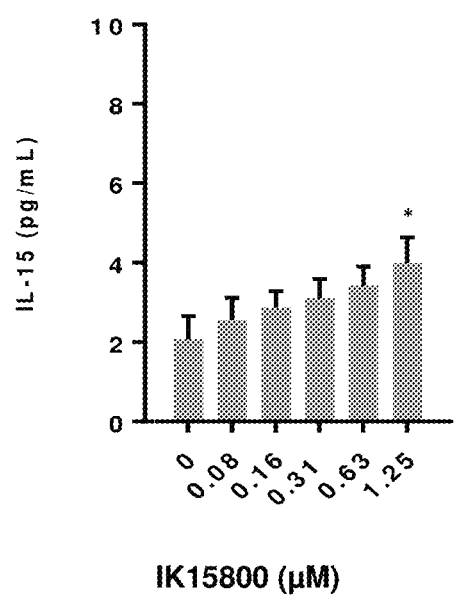
Figure 23C:
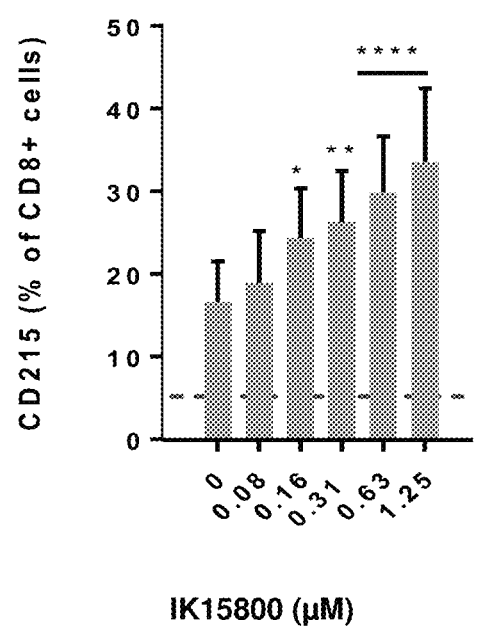

FIG. 23A shows Lck activating polypeptides increase IL-15R expression on and IL-15 secretion from human stimulated CD8+ T cells. A. PBMCs were cultured together with anti-CD3 (1 μg/ml) stimulation and RSKAKNPLY-RRRRRRRRR (SEQ ID NO: 24, IK14800) over a 5-concentration range (0-1.25 μM) for 72 hrs after which cells were assessed for expression of CD215 (IL-15R) by flow cytometry. Data presented indicates the mean respective expression in CD8+ T cell populations in response to no peptide treatment, +/− SEM, n=4. Data were analysed by two-way ANOVA with Dunnett's post-test, *P<0.05, P<0.01, *P<0.001. Dotted line indicates unstimulated PBMC expression. FIG. 23B. PBMCs were cultured together with anti-CD3 (1 μg/ml) stimulation and RVKVKVVVV-RRRRRRRRR (SEQ ID NO: 58, IK15800) over a 5-concentration range (0-1.25 μM). Supernatants were collected and assessed for IL-15 by ELISA, n=3+/− SEM. Dotted line indicates unstimulated PBMC expression. *p<0.05, 1.25 μM compared with 0 peptide, by T test. FIG. 23C. PBMCs were cultured together with anti-CD3 (1 μg/ml) stimulation and RVKVKVVVV-RRRRRRRRR (SEQ ID NO: 58, IK15800) over a 5-concentration range (0-1.25 μM) for 72 hrs after which cells were assessed for expression of CD215 (IL-15R) by flow cytometry. Data presented indicates the mean respective expression in CD8+ T cell populations in response to no peptide treatment, +/− SEM, n=4. Data were analysed by two-way ANOVA with Dunnett's post-test, *P<0.05, P<0.01, **P<0.0001. Dotted line indicates unstimulated PBMC expression.

Figure 24:
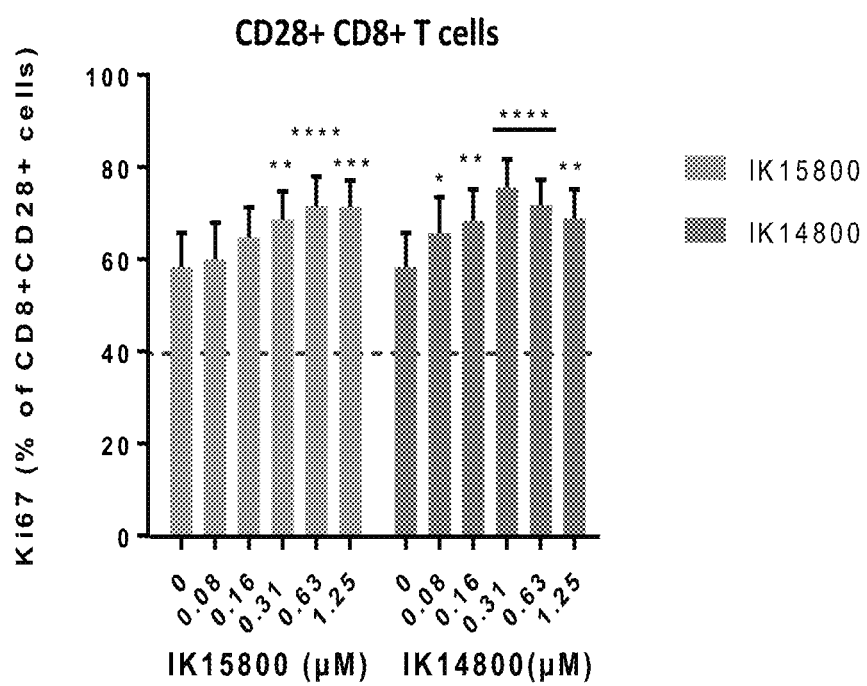

FIG. 24 shows that the Lck activating polypeptides RVKVKVVVV-RRRRRRRRR (SEQ ID NO: 58, IK15800) and RSKAKNPLY-RRRRRRRRR (SEQ ID NO: 24, IK4800) increase the proliferating population of human CD28+/CD8+ T cells. PBMCs were cultured together with anti-CD3 (1 μg/ml) stimulation and peptides IK15800 and IK14800 tested over a 5-concentration range (0-1.25 μM) for 72 hrs after which cells were assessed for Ki67 by flow cytometry. Data presented indicates mean Ki67 (indicator of proliferation) expression in CD28+ subpopulation of CD8+ T cells in response to peptide treatment, +/− SEM, n=4. Data was analysed by two-way ANOVA with Dunnett's post-test. *p<0.05, P<0.01, *P<0.001, ****P<0.0001. Dotted line indicates unstimulated cells.

Figure 25:
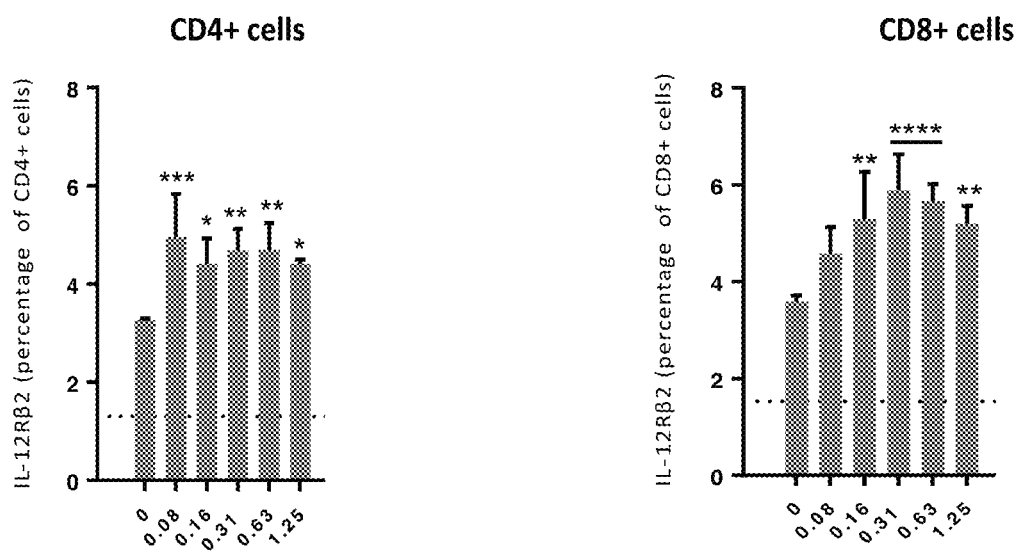

FIG. 25 shows the Lck activating polypeptide RVKVKVVVV-RRRRRRRRR (SEQ ID NO: 58, IK15800) induces IL-12Rβ2 expression in CD4+ and CD8+ T cells. Isolated T cells (CD3+) were stimulated with anti-CD3 anti-CD28 Dynabeads™ and cultured together with IK15800 (SEQ ID NO: 58) over a 5-concentration range plus vehicle control (0-1.25 µM) for 72 hrs after which CD4+ and CD8+ T cells were assessed for IL-12Rβ2 expression by flow cytometry. Data presented indicates the mean IL-12Rβ2 expression (% of CD4+ or CD8+ T cells) in response to peptide treatment, +/− SEM, n=4. Data were analysed by RM two-way ANOVA with Dunnett's post-test comparing each peptide concentration with vehicle, *p<0.05, p<0.01, *p<0.001, ****p<0.0001. Dotted line indicates mean unstimulated control values.

Figure 26A:
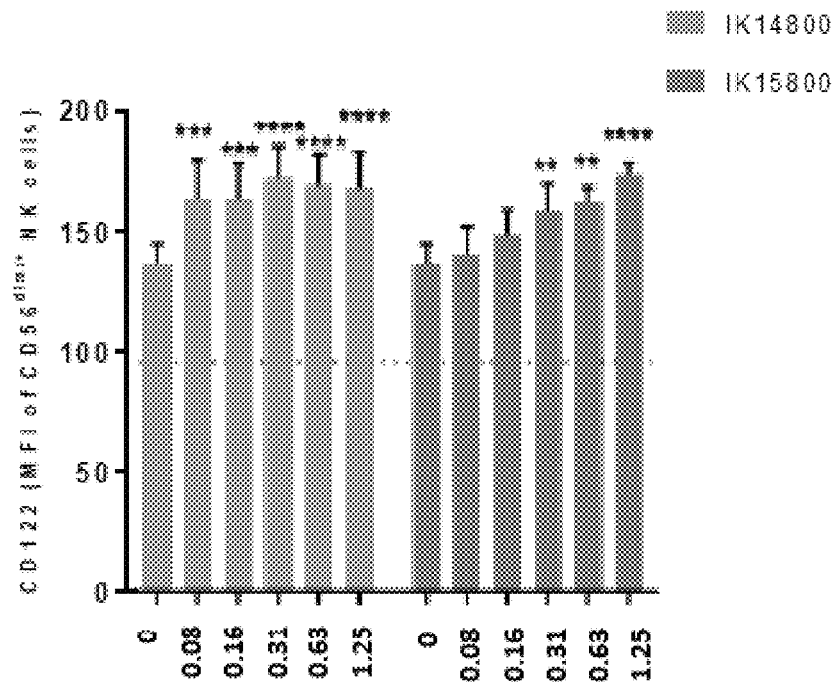
Figure 26B:
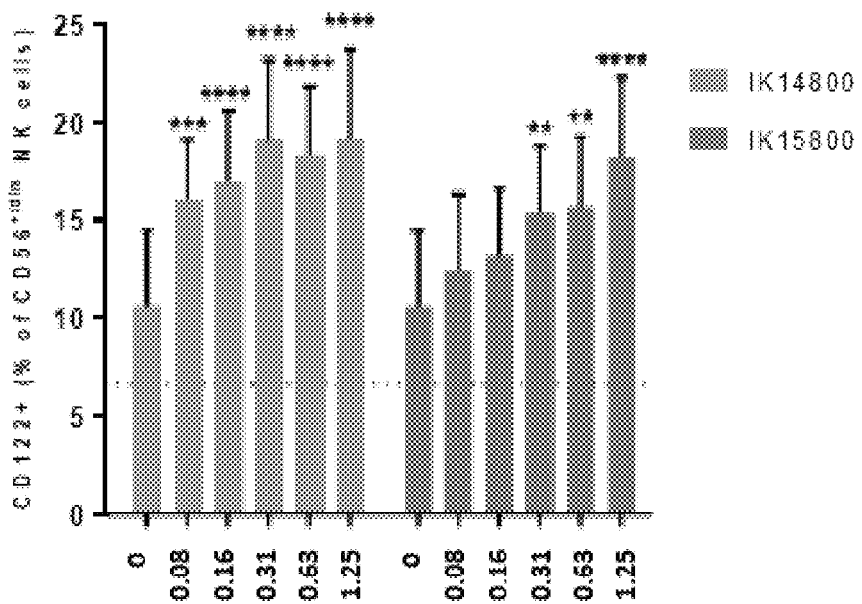

FIG. 26 shows the Lck activating polypeptides RVKVKVVVV-RRRRRRRRR (SEQ ID NO: 58, IK15800) and RSKAKNPLY-RRRRRRRRR (SEQ ID NO: 24, IK14800) induce IL-2Rβ expression in CD3negCD56+/dim NK cells. PBMCs from healthy donors were stimulated with anti-CD3 (1 µg/mL) for 72 hrs in the presence of test peptides (0.08-1.25 µM) or vehicle control. At the end of the culture period, cells were collected and assessed for IL-2Rβ (CD122) expression within $CD3^{neg}CD56^{+/dim}$ NK cells by flow cytometry. Data shown as mean IL-2Rβ (CD122) expression (% positive cells or MFI)+/− SEM, n=4. Data were analysed using repeated measures two-way ANOVA with Holm-Sidak's multiple comparisons post-test comparing test substance to vehicle control, p<0.01, *p<0.001, ****p<0.0001. Blue dotted line indicates mean expression in unstimulated samples.

Figure 27:
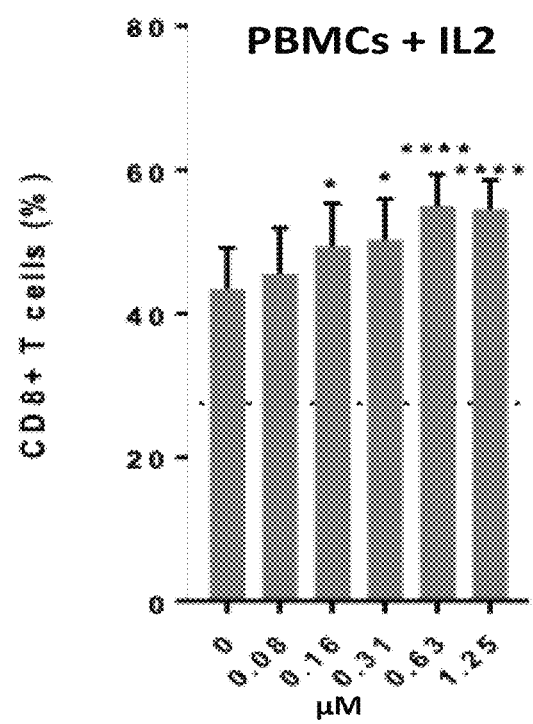

FIG. 27 shows the Lck activating polypeptide RVKVKVVVV-RRRRRRRRR (SEQ ID NO: 58, IK15800) induces expansion of CD8+ cell populations within PBMCs. PBMCs from healthy donors were stimulated via TCR+IL-2 for 10 days in the presence of IK15800 (SEQ ID NO: 58, 0.08-1.25 µM) or vehicle control. At the end of the culture period, cells were collected and assessed for CD8+ cell proportions by flow cytometry. Data show as mean percentage expression +/− SEM, n=4. Data were analysed using repeated measures two-way ANOVA with Holm-Sidak's multiple comparisons post-test comparing test substance to vehicle control, *p<0.05, ****p<0.0001. Dotted line indicates mean expression in unstimulated samples.

Figure 28A:
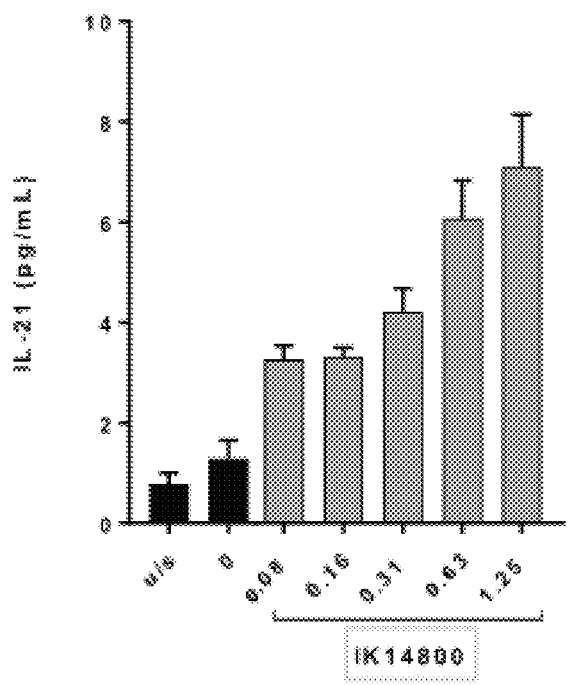
Figure 28B:
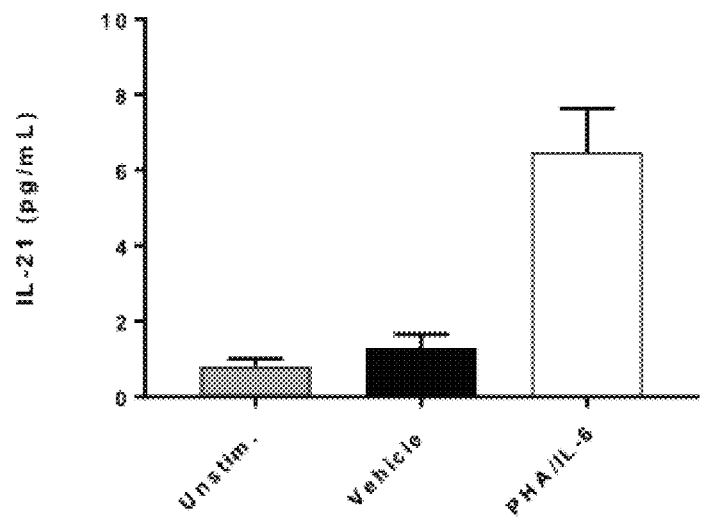

FIG. 28 shows the Lck activating polypeptide RSKAKN-PLY-RRRRRRRRR (SEQ ID NO: 24, IK14800) induces IL-21 production by CD4+ T-cells. CD4+ T cells were isolated and cultured in the presence of anti-CD3 anti-CD28 stimulation and IK14800 (SEQ ID NO: 24) for 48 hr. At the end of culture, supernatants were assessed for IL-21 by ELISA. Data shown represents IL-21 production (pg/mL) after 48 hr culture (left) +/− SEM, n=1. Cytokine was only detected in supernatants from one donor (hence no statistical calculation). Control (right) shows IL-6 boost to IL-21 secretion.

Figure 29:
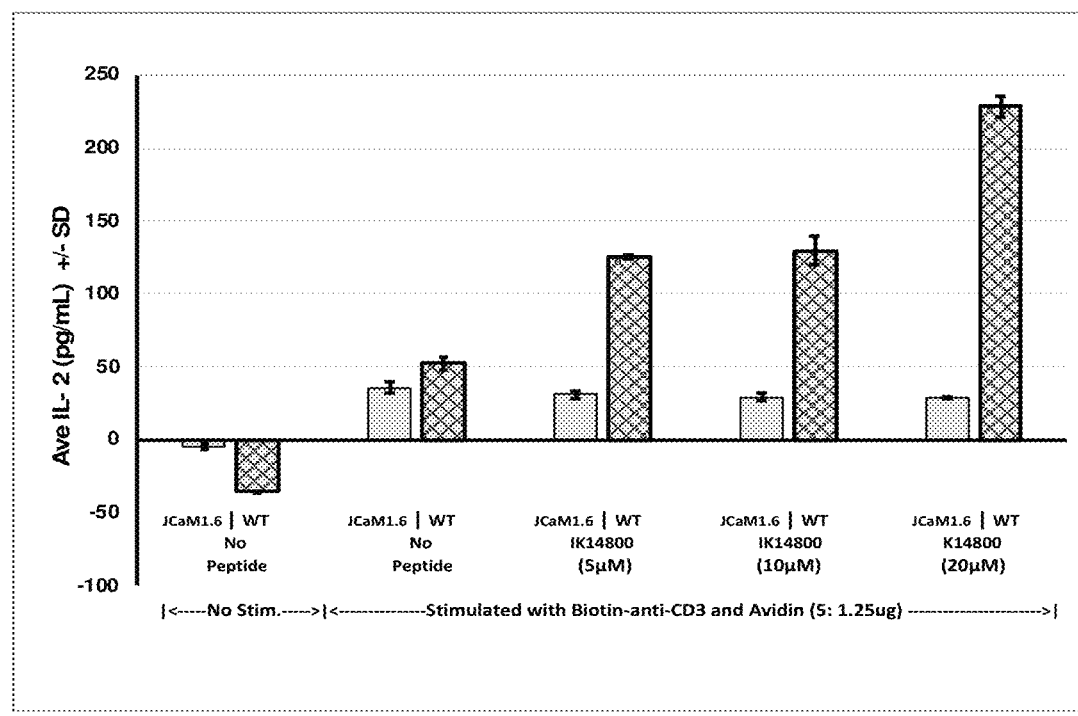

FIG. 29 shows the Lck activating polypeptide RSKAKN-PLY-RRRRRRRRR (SEQ ID NO: 24, IK14800) increases IL-2 production by a human T cell line upon subsequent antigenic stimulation, when administered prior to antigenic stimulation. 5 million cells seeded in T25 flasks and treated with varying concentrations of 14800 (SEQ ID NO: 24) as indicated in the above table for 1 hour, after which the cell suspensions were centrifuged and washed twice with fresh media. A mixture of Biotin-anti-CD3 and Avidin (5:1.25 ug) in 500 uL of media was added into the wells of a 12 well plate. After 10 minutes the cells were seeded at 1 million per well and the cell suspension made up to 2 mL volume with media. The samples were subsequently further stimulated with aniti-CD28 (5 ug/mL), incubated for 48 hours at 37° C. and the supernatant (100 uL, n=3), was then analyzed for IL2 content.

Figure 30:
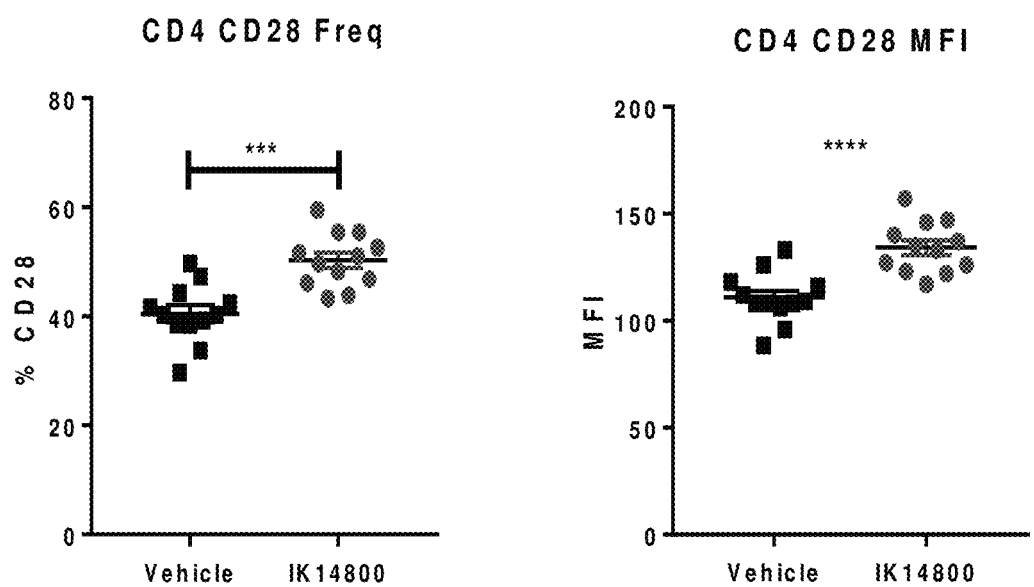
Figure 31:
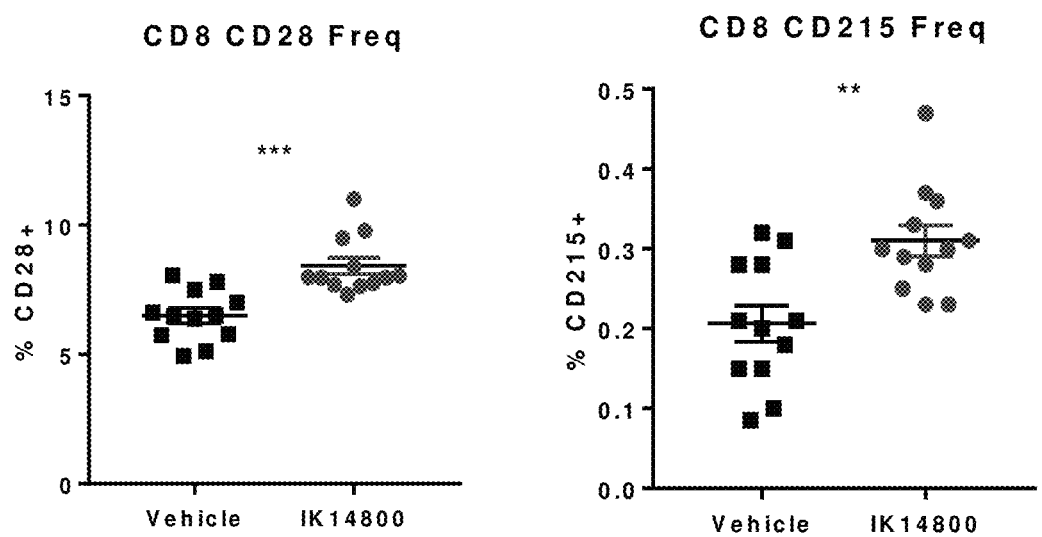
Figure 32:
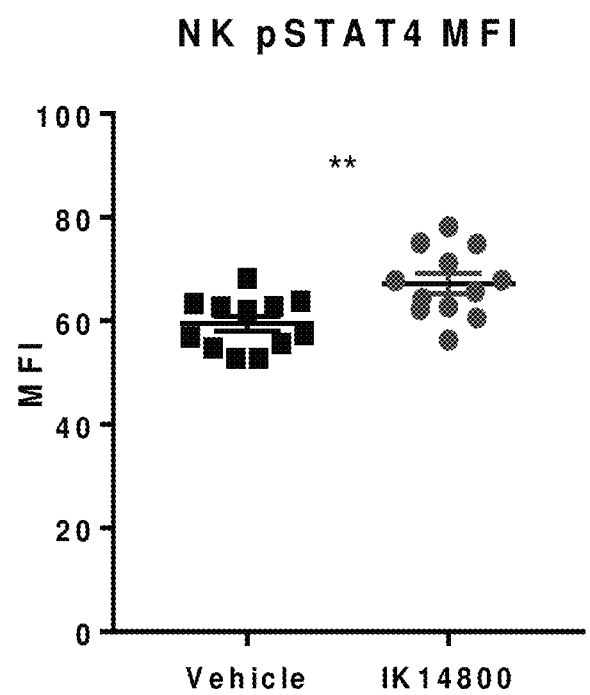

FIG. 30 shows the Lck activating polypeptide RSKAKN-PLY-RRRRRRRRR (SEQ ID NO: 24, IK14800) increases the percentage of CD4+ T cells expressing CD28, and relative expression of CD28 on CD4+ T Cells in splenocytes in Lewis Lung Cancer mice. Data show the proportion of CD4+ T cells determined to be positive for CD28 (left) and the geometric mean of CD28 on CD4+ T cells (right) as measured by flow cytometry compared to control sample (vehicle). *p<0.001, p<0.0001 as determined by a two tailed t-test FIG. 31 shows the Lck activating polypeptide RSKAKN-PLY-RRRRRRRRR (SEQ ID NO: 24, IK14800) increases the percentage of CD8+ T cells expressing CD28 and CD215 in splenocytes in Lewis Lung Cancer mice. p<0.01, *p<0.001 as determined by a two tailed t-test FIG. 32 shows the Lck activating polypeptide RSKAKN-PLY-RRRRRRRRR (SEQ ID NO: 24, IK14800) increases the expression of pSTAT4 on NK Cells in splenocytes from Lewis Lung Cancer mice. The data show the geometric mean of pSTAT4 on NK cells as measured by flow cytometry as determined by two-tailed t-test (p<0.01).

Figure 33A:
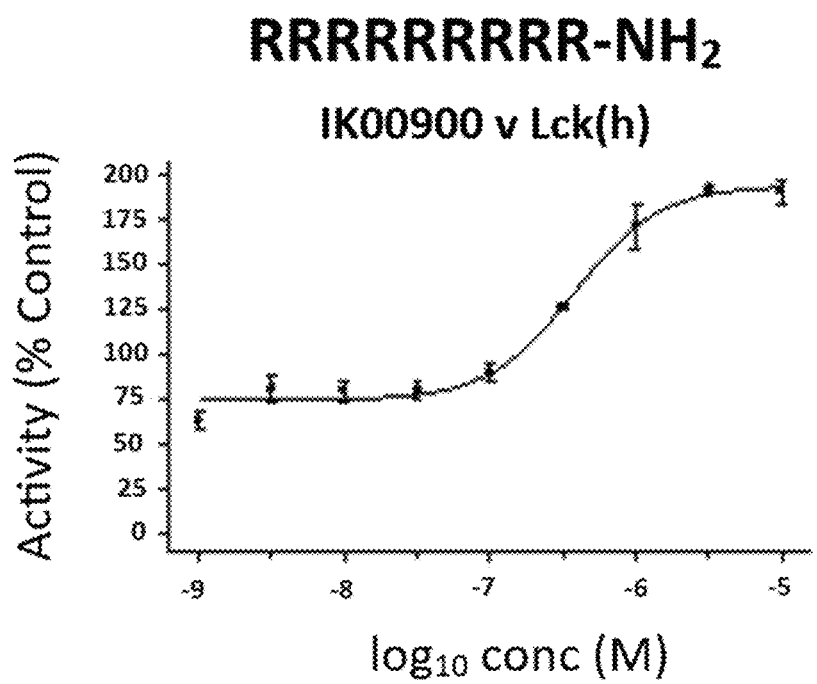
Figure 33B:
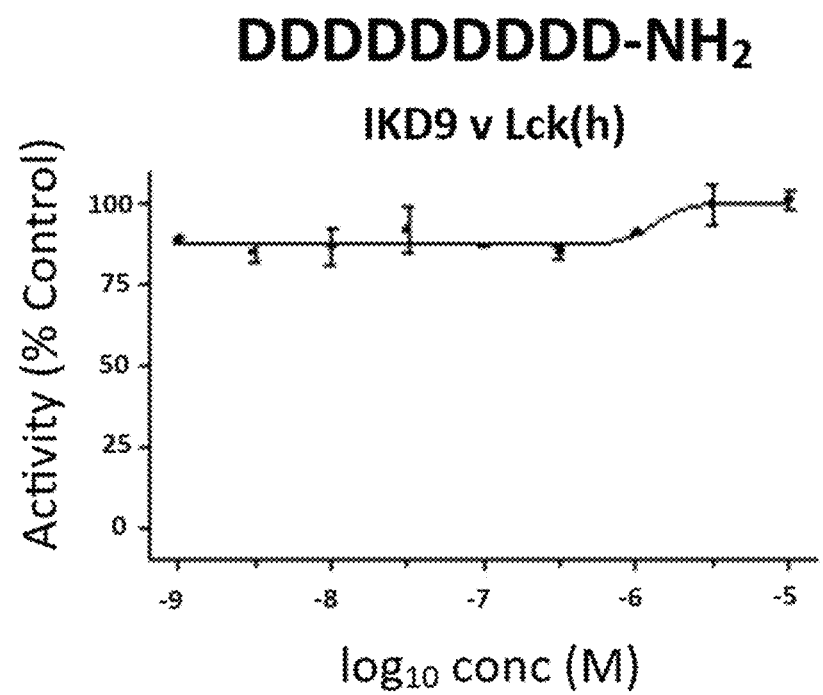

FIG. 33 shows the polypeptide DDDDDDDDD (SEQ ID NO: 21) does not increase the activity of Lck.

Figure 34:
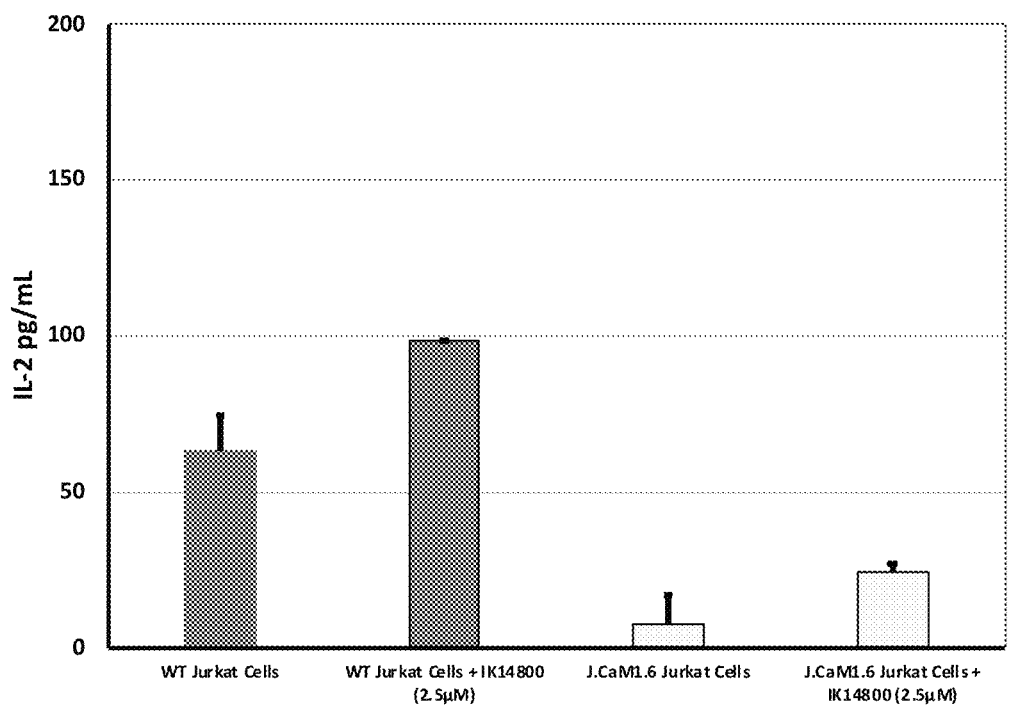

FIG. 34 shows that the ability of the Lck activating polypeptide RSKAKNPLY-RRRRRRRRR (SEQ ID NO: 24) to induce IL-2 secretion in Jurkat cells relative to control, is dependent on Lck. This data demonstrates that IL-2 secretion in a human T cell line by the Lck activating fusion polypeptide RSKAKNPLY-RRRRRRRRR (SEQ ID NO: 24) is dependent on Lck. Jurkat cells (WT and Lck Deficient) were stimulated with 200 uL of CD3/CD28 (5 ug/ml of each) made in PBS for 1 hour at 37° C. Cells were seeded at 1 million per well and treated with IK14800 (SEQ ID NO: 24).

Figure 35:
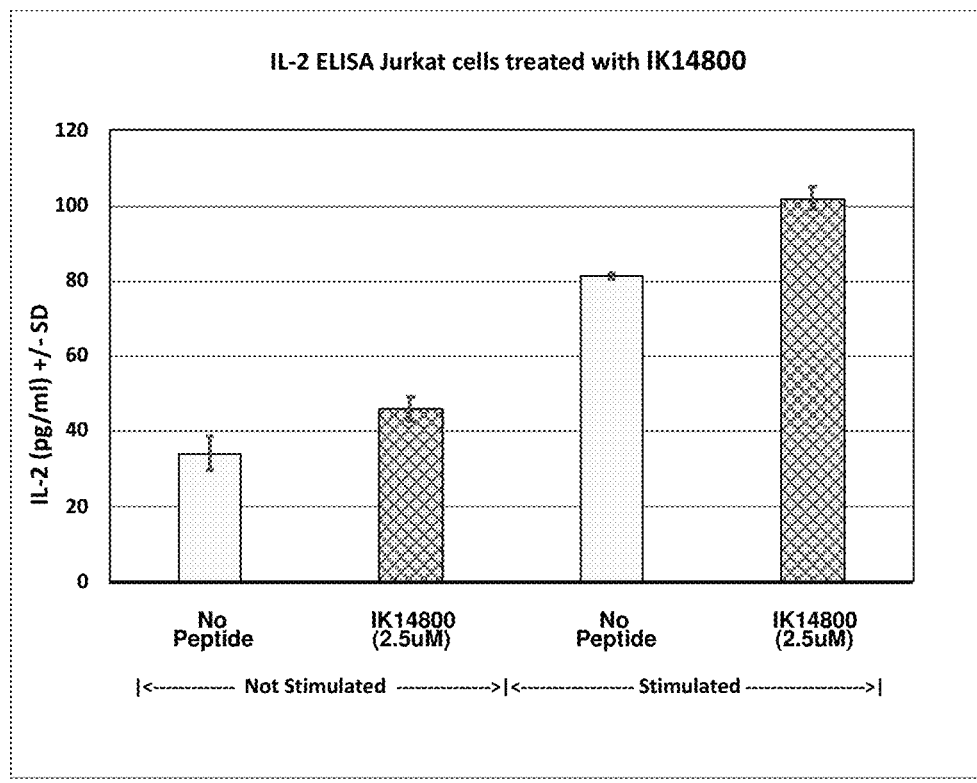

FIG. 35 shows the increase in IL-2 production by treatment with Lck activating polypeptide RSKAKNPLY-RRRRRRRRR (SEQ ID NO: 24, IK14800) does not occur in the absence of antigenic stimulation. In brief, 12 well plates were coated with anti-CD3 (5 µg/mL) solution made up in PBS (200 µL) and incubated at 37° C. overnight. The anti-CD3 solution was then aspirated and wells gently washed twice with media (1 mL, 10 minutes). Jurkat cells were seeded at 1 million per well, further stimulated with anti-CD28 (5 µg/mL) and then treated with RSKAKNPLY-RRRRRRRRR (SEQ ID NO: 24, IK14800) (2.5 µM) at time zero. Cells were incubated for 72 hours and the supernatants were then analysed for IL-2 by ELISA.

Figure 36:
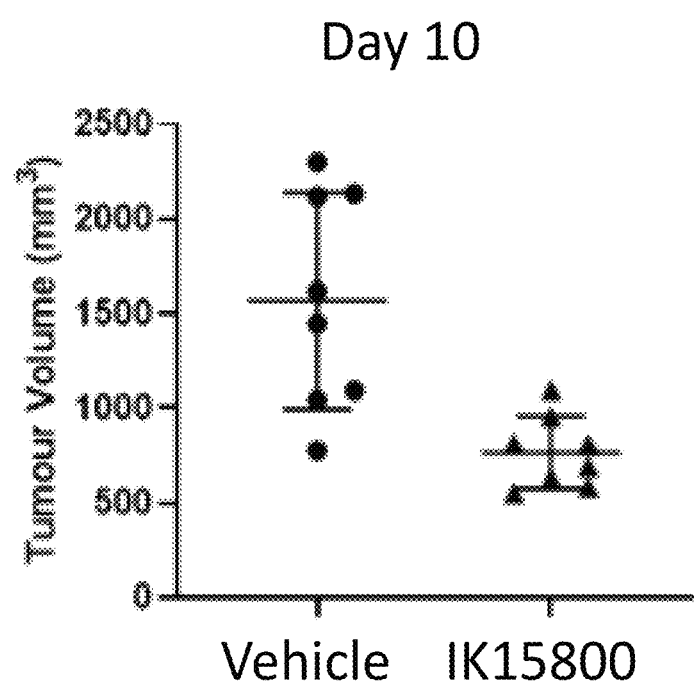

FIG. 36 shows intraperitoneal administration of RVKVKVVVV-RRRRRRRRR (SEQ ID NO: 58, IK15800) reduces tumour area in a Lewis Lung Cancer (LCC) model. RVKVKVVVV-RRRRRRRRR (SEQ ID NO: 58) was administered intraperitoneally (200 µg) twice per week for two weeks in female C57 black mice commencing at day 10 after inoculation ($1 \times 10^6$ cells), n=8 per cohort after which H&E sections were assessed for evidence of tumour infiltration and tumour mass was calculated as percentage of healthy lung tissue. Data points show the mean area of tumour mass per sample. **p<0.005 unpaired t-test.

Figure 37:
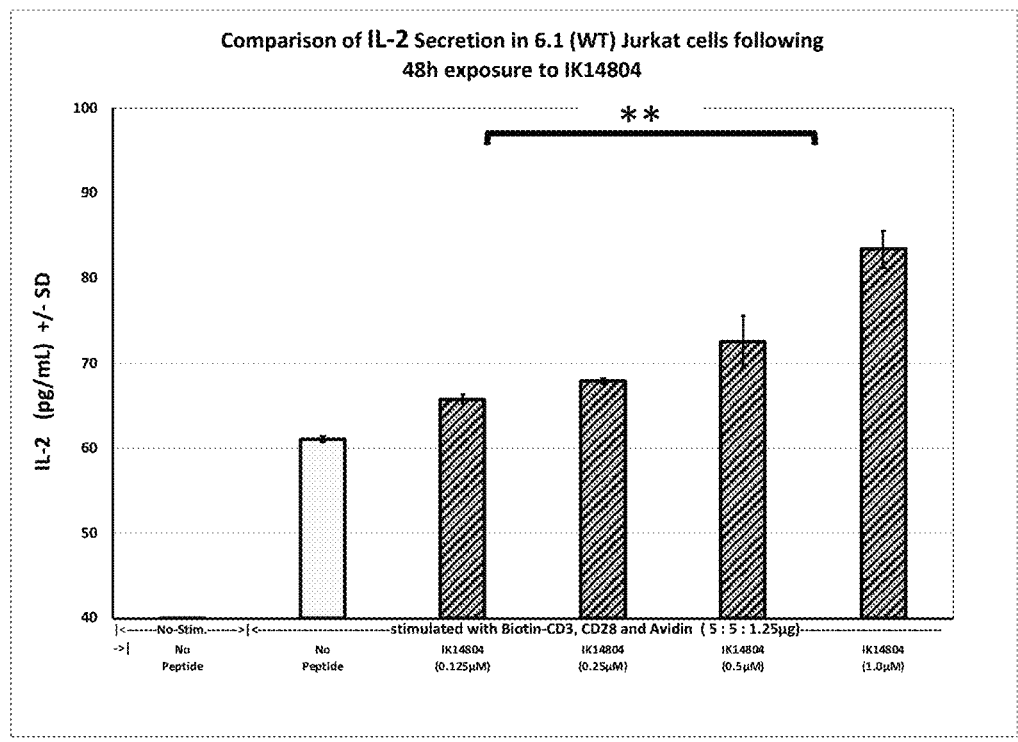

FIG. 37 shows a Lck activating polypeptide coupled to fatty acids increases IL-2 secretion in a human T lymphocyte (Jurkat) cell line. Cells were seeded at 1 million cells per well (12 well plate, 2 mL volume) and stimulated with Biotin-CD3, CD28, and avidin (5:5:1.25 µg). The cells were then treated with RSKAKNPLY-RRRRRRRRR-(2Adod)$_4$-NH$_2$ (SEQ ID NO: 65, IK14804), and then incubated for 48 hours at 37° C. The supernatant (100 uL, n=3), was then analyzed for IL-2 content.

Figure 38:
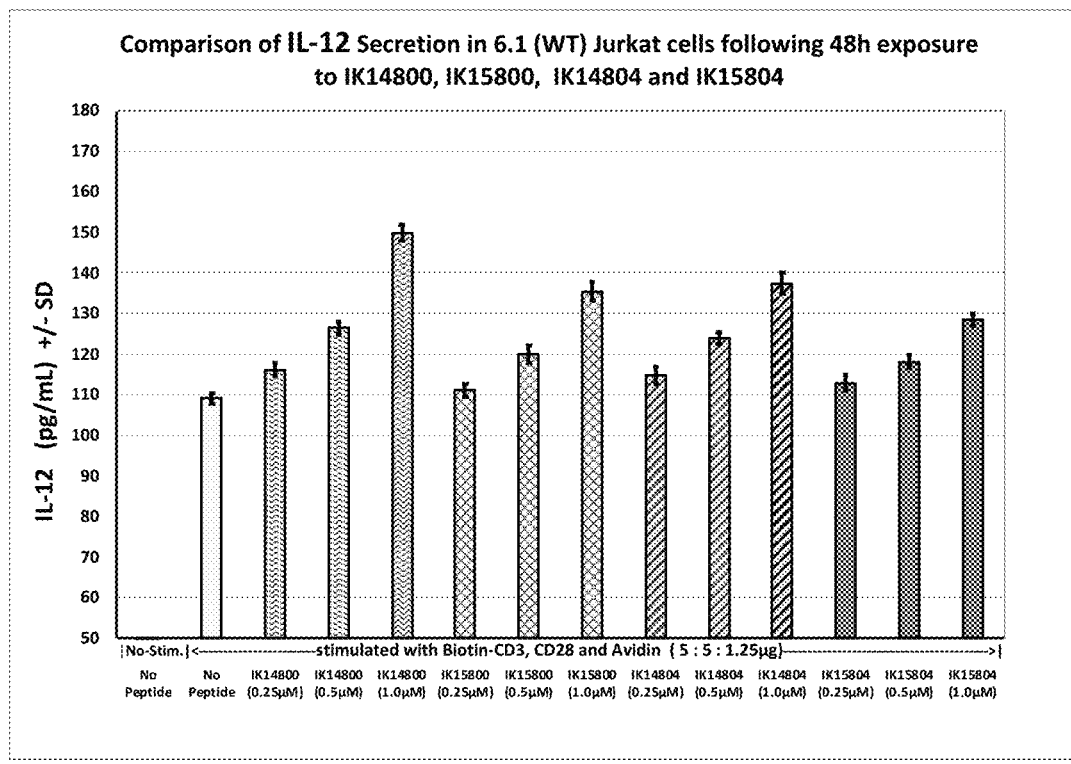

FIG. 38 shows Lck activating polypeptides coupled to fatty acids increase IL-12 secretion in a human T lymphocyte (Jurkat) cell line. Cells were seeded at 1 million cells per well (12 well plate, 2 mL volume) and stimulated with Biotin-CD3, CD28, and avidin (5:5:1.25 µg). The cells were then treated with RSKAKNPLY-RRRRRRRRR (SEQ ID NO: 24, IK14800), RVKVKVVVV-RRRRRRRRR (SEQ ID NO: 58, IK15800), RSKAKNPLY-RRRRRRRRR-(2Adod)$_4$-NH$_2$ (SEQ ID NO: 65, IK14804) and RVKVKVVVV-RRRRRRRRR-(2Adod)$_4$-NH$_2$ (SEQ ID NO: 66, IK15804). The cells were then incubated for 48 hours at 37° C. The supernatants (100 uL, n=3), were then analyzed for IL-12 content.

Figure 39:
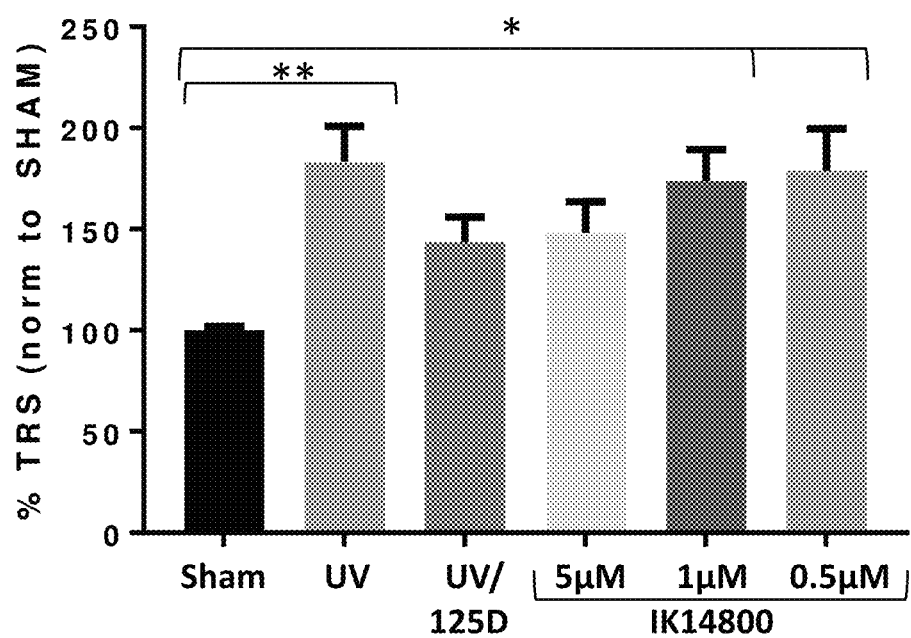

FIG. 39 shows Lck activating polypeptides inhibit lipid peroxidation in cell membranes. [#=Thiol Redox State]. One-way Anova with Tukey's multiple comparisons test, *p<0.05, **p<0.01. The significance difference in TRS between Sham and UV irradiation in the absence of treatment is not seen in the presence of either 125D or RSKAKNPLY-RRRRRRRRR (SEQ ID NO: 24, IK14800) at the highest concentration (5 µM) compared with lower RSKAKNPLY-RRRRRRRRR (SEQ ID NO: 24, IK14800) doses.

Figure 40:
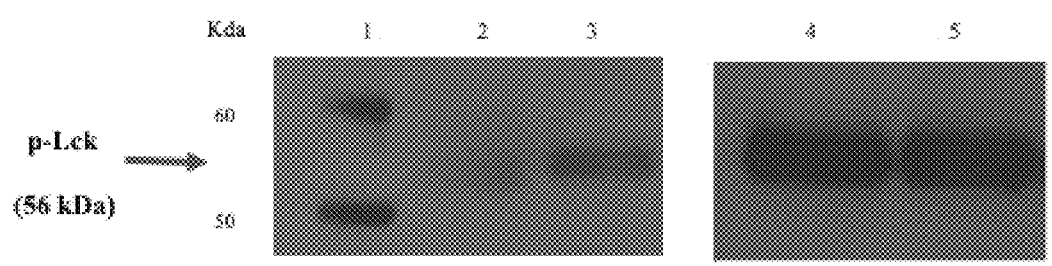

FIG. 40 shows RSKAKNPLY-RRRRRRRRR (SEQ ID NO: 24, IK14800) increases phosphorylation of Lck at Y394 detected by the anti-pY394 antibody, relative to no peptide control, while levels of total Lck remained unchanged.

Figure 41A:
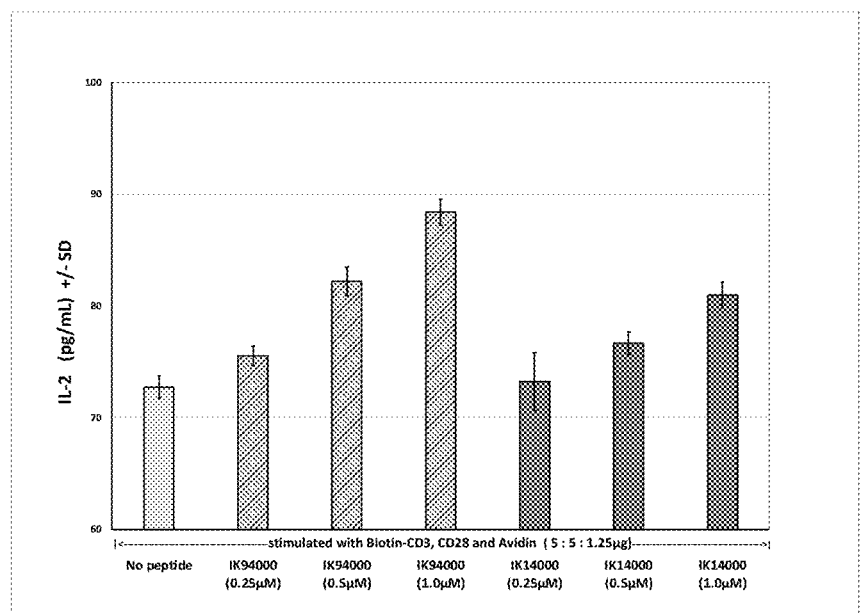
Figure 41B:
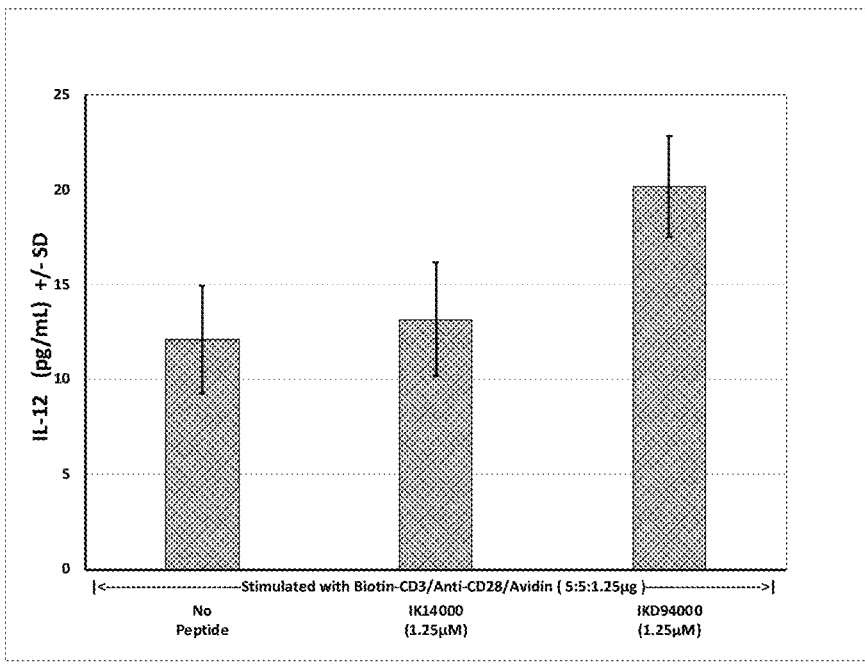

FIG. 41A shows the polypeptides RSKAKNPLYR (SEQ ID NO: 31, "IK14000") and RSKAKNPLY (SEQ ID NO: 30, "IK94000") increase IL-2 secretion in a human T lymphocyte (Jurkat) cell line. FIG. 41B shows rskaknply (SEQ ID NO: 117, "IKD94000", but not RSKAKNPLYR (SEQ ID NO: 31, "IK14000"), increase IL-12 secretion in a human T lymphocyte (Jurkat) cell line.

DETAILED DESCRIPTION

Members of the non-receptor Src kinase family (SKF) include the following eight kinases in mammals: Src, Fyn, Yes, Fgr, Lyn, Hck, Lck, and Blk, and a selective Lck activator has never been identified (Bae O-N et al, Journal of Neuroscience, 2012, 32(21): 7278-7286).

The present invention relates in part to the finding that polycationic peptides comprising more than 6 or more contiguous cationic amino acids as described herein can stimulate the activity of Lck. In at least some embodiments of a Lck activator in accordance with the invention may stimulate activation of only Lck amongst the SKF members. The need for Lck activators and particularly specific Lck activators is relevant to a broad range of conditions that may be either age or non-age-related.

Accordingly, in one embodiment, the present invention provides a peptide for activating Lck, wherein the peptide comprises a Lck-activating cationic amino acid sequence having more than 6 contiguous cationic amino acids.

As used herein, the term "activating" generally refers to increasing an activity of at least one target protein. In the specific context of a kinase this activation leads to increased phosphorylation of at least one target substrate or site. This activation can be caused by any means including (but not limited to) increasing the probability that a complex forms between a protein kinase and a binding partner of the protein kinase, or increasing the activity of the kinase once bound to its target. Such activation may take place either in vivo or in vitro.

As used herein "a peptide for activating Lck" is used interchangeably with "a Lck activating polypeptide" or "a Lck activator".

Lck is also referred to as: LCK proto-oncogene, Leukocyte C-terminal Src kinase; Lymphocyte cell-specific protein-tyrosine kinase; Protein YT16; Proto-oncogene Lck; T cell-specific protein-tyrosine kinase; and p56-LCK.

Gene and protein sequences for Lck in humans can be derived from the HUGO Gene Nomenclature Committee (HGNC) (http://www.genenames.org/). The HGNC reference numbers for Src (and splice variants) in humans are listed in Table 1 below, together with GenBank Accession numbers and GeneIDs.

TABLE 1

| HGNC Gene Number | GenBank Accession Number (amino acid) | GenBank Accession Number (nucleotide) | UniProt Reference | GeneID |
|---|---|---|---|---|
| HGNC: 6524 | NP_001036236.1 (isoform a/variant 1) | NM_001042771.2 (isoform a/variant 1) | P06239 | HGNC: 6524 |
| | NP_005347.3 (isoform a/variant 2) | NM_005356.5 (isoform a/variant 2) | | |
| | NP_001317397.1 (isoform b) | NM_001330468.1 (isoform b) | | |

Lck has a number of activities. Lck autophosphorylates at its positive regulatory site Tyr 394, and phosphorylates a number of proteins, including the CD3 receptor, CEACAM1, ZAP-70, SLP-76, the IL-2 receptor, Protein kinase C, ITK, PLC, SHC, RasGAP, CbI, Vav1, and PI3K. Lck has been shown to interact with ADAM15, CD2, CD44, CD4, COUP-TFII, DLG1, NOTCH1, PIK3CA, PTPN6, PTPRC, UNC119, SYK, UBE3A, and ZAP70.

The present inventors have demonstrated that the activators described herein can increase the activity of Lck, including phosphorylation of Lck at Y394, and increased production of IL-2.

Accordingly, as used herein the term "an activity of Lck" includes phosphorylation of Lck at Y394, production of IL-2, phosphorylation of CD3 receptor, CEACAM1, ZAP-70, SLP-76, the IL-2 receptor, Protein kinase C, ITK, PLC, SHC, RasGAP, CbI, Vav1, and/or PI3K; interact with ADAM15, CD2, CD44, CD4, COUP-TFII, DLG1, NOTCH1, PIK3CA, PTPN6, PTPRC, UNC119, SYK, UBE3A, and/or ZAP70, and/or phosphorylation of a TCR.

Typically, the polycationic peptide is from 7 to about 35 amino acids in length. Thus the polycationic peptide may, for example, be 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length. Typically, the polycationic peptide is up to about 25 amino acids in length and more typically, is up to about 24, 23, 22, 21, 20, 19, 18 17, or 16 amino acids in length.

Typically, all of the amino acids of the polycationic peptide are cationic amino acid residues. However, polycationic peptides comprising cationic amino acid that are contiguous with one another as described above and one or more non-cationic amino acids residues are also expressly provide for by the invention. Typically in such embodiments, at least 50% or greater, 55% or greater, 60% or greater, 65% or greater, 70% or greater, 75% or greater, 80% or greater, 85% or greater, 90% or greater, or 95% or greater of the amino acids comprising the polycationic peptide are cationic peptides. Examples of such polycationic peptides may comprise cationic amino acids interspersed by one or more non-cationic amino acids, and/or e.g., include a respective N-terminal and/or C-terminal non-cationic amino acid or amino acid sequence, and all such polycationic peptides are expressly encompassed herein.

A polycationic peptide (PP) as described herein typically comprises at least 7 contiguous cationic amino acids and more usually, at least 8, 9 or 10 contiguous cationic amino acids.

In particularly preferred embodiments the polycationic peptide typically comprises from 8 to 16 contiguous cationic amino acids, more typically from 8 to 12 contiguous cationic amino acids and most typically, from 8 to 10 contiguous cationic amino acids.

The cationic amino acids comprising the polycationic peptide may be independently selected from the group consisting of arginine (R), lysine (K), histidine (H) and ornithine amino acid residues.

Various sequence combinations of the cationic amino acid residues may be employed. For example, the polycationic peptide may comprise a linear amino sequence of arginine amino acids (e.g., 7, 8, 9, 10, 11, 12 or more arginine residues) commencing from the N-terminal end of the polycationic peptide followed by a sequence of non-arginine cationic amino acids (e.g., histidine or lysine residues), or vice versa. In such embodiments, the sequence of non-arginine amino acids is typically up to about 16 amino acids in length (i.e., 1, 2, 3, 4, 5, 6, 7, 8, 9, 10, 11, 12, 13, 14, 15 or 16 amino acids), and the use of all such polycationic peptides is expressly encompassed herein.

In other embodiments, the cationic amino acids may be arranged in an alternating series of "couplets" or triplets of the cationic peptides such as a couplet or triplet of an arginine and a non-arginine amino acid (e.g., couplets of RH) or alternatively, couplets or triplets in which the positions of the amino acids in the couplets are reversed (e.g., couplets of HR). Likewise, the polycationic peptide may comprise a combination of a series of couplets or triplets of different ones of the cationic amino acids (e.g., couplets of RH or HR) followed and/or preceded by a respective further cationic amino acid or cationic amino acid sequence (e.g., a histidine or polyhistidine sequence), typically of up to about 16 amino acids (i.e., 1, 2, 3, 4, 5, 6, 7, 8, 9, 10, 11, 12, 13, 14, 15 or 16 amino acids). As will be understood, by the term "couplet" is meant two consecutive amino acids. Likewise, by the term "triplet" is meant three consecutive amino acids. In at least some polycationic peptides having repeating cationic amino acid couplets (e.g., RH or HR), the polycationic peptide may commence and/or terminate with at least one couplet or triplet of one or more further respective cationic amino acid residues (e.g., HH, RR, KK, HHH, RRR, KKK, HHHH (SEQ ID NO: 118), RRRR (SEQ ID NO: 119), KKKK (SEQ ID NO: 120) or the like).

The polycationic peptide of a Lck activator in accordance with the invention may, for instance, be selected from the following non-limiting examples: RRRRRRR (SEQ ID NO: 121, 7Arg), RRRRRRRR (SEQ ID NO: 4, 8Arg), RRRRRRRRR (SEQ ID NO: 6, 9Arg), RRRRRRRRRR (SEQ ID NO: 7, 10Arg), RRRRRRRRRRR (SEQ ID NO: 122, 11Arg), RRRRRRRRRRRR (SEQ ID NO: 8, 12Arg), RRRRRRRRRRRRR (SEQ ID NO: 123, 13Arg), RRRRRRRRRRRRRRR (SEQ ID NO: 124, 15Arg), RRRRRRRRRRRRRRRR (SEQ ID NO: 130, 16Arg), KKKKKK (SEQ ID NO: 131, 6Lys), RKKKKKKKKHHHHHHHHHH (SEQ ID NO: 132, R8K10His); RHHHHHHHHHH (SEQ ID NO: 127, R10His), RRRRRRRRHHHHHHHHHH (SEQ ID NO: 19, 8Arg10His), and RRRRRRRRRHHHHHHHHHH; (SEQ ID NO: 20, 9Arg10His) RRRRRRRR-RHHHHHHHHHHHHHH (SEQ ID NO: 133, 9Arg14His), RHRHRHRHRHRHRHRHRH (SEQ ID NO: 134, 9R/H-His), HRHRHRHRHRHRHRHRHH (SEQ ID NO: 135, 8H/R-2H).

In yet further embodiments, one or more of the arginine residues in a polycationic peptide exemplified above may be substituted for a respective lysine residue.

The use of inverted amino acid sequences of the foregoing polycationic peptides is also expressly encompassed herein. Various other amino acid sequence patterns may also be employed and all such sequence patterns are expressly encompassed herein. Whilst in preferred embodiments a polycationic peptide of a Lck activator utilised in a method in accordance with the invention is a linear peptide, embodiments may also be provided in which the polycationic peptide is a branched peptide. A branched polycationic peptide may, for example, be provided by coupling an amino acid or amino acid sequence to a lysine residue in the backbone of the polycationic peptide. An example of such a branched polycationic peptide is RK[8Arg]HHHHHHHHHH in which the 8Arg sequence (RRRRRRRR, SEQ ID NO: 4) is a side chain coupled to the lysine residue K. A side chain of a branched polycationic peptide as described herein may be up to 16 amino acids in length or more, e.g., 1, 2, 3, 4, 5, 6, 7, 8, 9, 10, 11, 12, 13, 14, 15 or 16 amino acids in length. Typically, a side chain of a polycationic peptide will be up to 10 amino acids in length, more typically up to about 9 amino acids in length and most typically, up to about 8 amino acids in length.

Typically, the cationic amino acids of the peptide active are selected from the group consisting of arginine (R), lysine (K), histidine (H) and ornithine and most typically, arginine (R), lysine (K) and histidine (H). Of these residues, contiguous arginine residues have been found to better stimulate Lck activity than a corresponding sequence of lysine or histidine residues. When the polycationic peptide comprises arginine and non-arginine amino residues (e.g., histidine), the polycationic peptide typically has a ratio of the non-arginine amino acid residues to arginine residues of about 1.2 or less, or about 1.1 or less, or about 1.0 or less, or about 0.9 or less, or about 0.8 or less, or even about 0.7 or less.

In at least some embodiments, the polycationic peptide comprises two or more couplets or triplets of a single cationic acid residue (e.g., arginine). The couplets or triplets can be side by side to one another (thereby forming a sequence of 4 or 6 contiguous residues of the cationic amino acid) or be spaced apart from one another by one or more of the other contiguous cationic amino acids (e.g., 1, 2, 3, 4, 5, 6, 7, 8, 9, 10 etc of the contiguous cationic amino acids) comprising the polycationic peptide.

Typically, at least a majority of the cationic amino acids of the polycationic peptide are arginine amino acids. Most typically, the contiguous cationic amino acids are all arginine amino acids.

In a preferred embodiment, the cationic amino acid sequence is selected from the group consisting of RRRRRRRR (SEQ ID NO: 4), rrrrrrrr (SEQ ID NO: 5), RRRRRRRRR (SEQ ID NO: 6), and rrrrrrrrr (SEQ ID NO: 114), wherein lowercase indicates dextrorotatory ("dextro") amino acids.

A Lck activator embodied by the invention can consist of the polycationic peptide or in other embodiments, comprise the polycationic peptide coupled to a further peptide moiety. The further peptide moiety may, for example, augment the Lck stimulatory activity of the polycationic peptide. In other embodiments, the polycationic peptide alone may not stimulate Lck activity, and the activity of Lck is only stimulated when the polycationic peptide is coupled to the further peptide moiety.

For convenience, the augmenting or other peptide moiety to which the polycationic peptide (PP) is coupled in at least some embodiments of the invention as described above is referred to in the following description as (AP/P).

In at least some embodiments, the augmenting or other peptide (AP/P) comprises an amino acid sequence of Formula I, or an inverted sequence thereof:

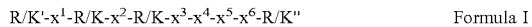 Formula I wherein:
each R/K is independently an arginine or lysine amino acid residue;
R/K' is an arginine or lysine amino acid residue and is present or absent;
R/K" is an arginine or lysine amino acid residue and is present or absent;
$x^1$ to $x^6$ are each independently an amino acid; and
wherein amino acids $x^3$ to $x^6$ are collectively present or absent, and R/K" is absent when amino acids $x^3$ to $x^6$ are present.

Typically, in an augmenting or other peptide (AP/P) of Formula I:
$x^1$, $x^3$ and $x^6$ are independently selected amino acids; and
$x^2$, $x^4$, and $x^5$ are each independently a hydrophobic amino acid.

In at least some embodiments $x^1$, $x^3$ and $x^6$ are hydrophilic amino acids, and $x^2$, $x^4$ and $x^5$ are hydrophobic amino acids.

In other embodiments $x^3$ and $x^6$ are hydrophilic amino acids, and $x^1$, $x^2$, $x^4$ and $x^5$ are hydrophobic amino acids.

In other embodiments $x^1$ and $x^3$ are hydrophilic amino acids, and $x^2$, $x^4$, $x^5$ and $x^6$ are hydrophobic amino acids.

In still other embodiments, amino acids $x^1$ to $x^6$ are all hydrophobic amino acids or at least a majority of amino acids $x^1$ to $x^6$ are hydrophobic amino acids.

The hydrophilic and hydrophobic amino acids of a polycationic peptide of a Lck activator as described herein may be encoded by the genetic code and/or comprise synthetic amino acids. Typically, the amino acids are encoded by the genetic code.

The hydrophilic amino acids of the polycationic peptide can be independently selected from polar, basic, and acidic amino acids.

The polar amino acids may, for example, be selected from the group consisting of serine (S), threonine (T), tyrosine (Y), asparagine (N), and glutamine (Q) amino acid residues.

The basic amino acids may, for example, be selected from the group consisting of lysine (K), arginine (R), histidine (H) and ornithine.

The acidic amino acids may, for example, be selected from glutamic acid (E) and aspartic acid (D).

Non-polar hydrophobic amino acids may, for example, be selected from the group consisting of alanine (A), valine (V), leucine (L), isoleucine (I), proline (P), cysteine (C), methionine (M), phenylalanine (F), tryptophan (W) and glycine (G). Typically, the hydrophobic amino acid(s) will be selected from alanine (A), valine (V) and phenylalanine (F).

Typically, in a peptide of Formula I at least one of R/K' and R/K" is present.

Most typically, amino acid residue R/K' of Formula I is present.

Typically, an augmenting or other peptide (AP/P) of Formula I comprises an amino acid sequence selected from the group consisting of:
(a) R-$x^1$-K-$x^2$-K-$x^3$-$x^4$-$x^5$-$x^6$-R/K";
(b) R-$x^1$-R-$x^2$-K-$x^3$-$x^4$-$x^5$-$x^6$-R/K"; and
(c) K-$x^1$-K-$x^2$-K-$x^3$-$x^4$-$x^5$-$x^6$-R/K".

Typically, in an augmenting or other peptide (AP/P) of Formula Ia:
$x^1$, $x^3$ and $x^6$ are hydrophilic amino acids; and
$x^2$, $x^4$, and $x^5$ are hydrophobic amino acids.

In at least some embodiments of an augmenting or other peptide (AP/P) of Formula Ia:
$x^1$, $x^3$ and $x^6$ are polar amino acids; and
$x^2$, $x^4$, and $x^5$ are non-polar amino acids.

Typically, in embodiments of Formula Ia:
$x^1$ is serine;
$x^2$ is alanine, leucine or valine;
$x^3$ is asparagine;
$x^4$ is proline, valine or alanine;
$x^5$ is leucine, valine or alanine; and
$x^6$ is tyrosine.

Most typically, in embodiments of Formula Ia, $x^2$ is alanine, $x^4$ is proline, and $x^5$ is leucine.

Typically, in an augmenting or other peptide (AP/P) of Formula Ib:
$x^3$ and $x^6$ are hydrophilic amino acids; and
$x^1$, $x^2$, $x^4$, and $x^5$ are hydrophobic amino acids.

In at least some embodiments of an augmenting or other peptide (AP/P) of Formula Ib:
$x^3$ and $x^6$ are polar amino acids; and
$x^1$, $x^2$, $x^4$, and $x^5$ are non-polar amino acids.

Typically, in embodiments of Formula Ib:
$x^1$ is alanine or glutamic acid;
$x^2$ is alanine, leucine or valine;
$x^3$ is asparagine;
$x^4$ is proline, valine or alanine;
$x^5$ is leucine, valine or alanine; and
$x^6$ is tyrosine.

Most typically, in embodiments of Formula Ib, $x^2$ is alanine, $x^4$ is proline, and $x^5$ is leucine.

Alternatively, in at least some embodiments of an augmenting or other peptide (AP/P) of Formula Ib:
$x^1$, $x^3$ and $x^6$ are hydrophilic amino acids; and
$x^2$, $x^4$ and $x^5$ are hydrophobic amino acids.

Typically, in such embodiments of Formula Ib:
$x^1$ is serine;
$x^2$ is alanine, leucine, or valine;
$x^3$ is asparagine;
$x^4$ is proline, valine or alanine;
$x^5$ is leucine, valine or alanine; and
$x^6$ is tyrosine.

Most typically, in such embodiments of Formula Ib, $x^2$ is alanine, $x^4$ is proline, and $x^5$ is leucine.

In at least some embodiments of an augmenting or other peptide (AP/P) of Formula Ic:
$x^1$ and $x^3$ are hydrophilic amino acids; and
$x^2$, $x^4$, $x^5$ and $x^6$ are hydrophobic amino acids.

Typically, in embodiments of Formula Ic:
$x^1$ is glutamic acid, valine or alanine;
$x^2$ is alanine, leucine or valine;
$x^3$ is asparagine;
$x^4$ is proline, valine or alanine;
$x^5$ is leucine, valine or alanine; and
$x^6$ is tyrosine.

In further embodiments, in an augmenting or other peptide (AP/P) of Formula I may comprise the following:
$x^1$ independently selected from valine, alanine, glutamic acid, and serine;
$x^2$ independently selected from valine, alanine, and leucine;
$x^3$ independently selected from valine, alanine and asparagine;
$x^4$ independently selected from valine, alanine and proline;
$x^5$ independently selected from valine, alanine and leucine;
$x^6$ independently selected from valine, alanine, phenylalanine and tyrosine.

In one embodiment, the peptide of Formula I is (the Lck activating polypeptide moiety) is coupled to the N-terminal or C-terminal end of the cationic amino acid sequence.

In at least some embodiments, the augmenting or other peptide (AP/P) of Formula I comprises the amino acid sequence R/K'-S-R/K-A-R/K-N-P-L-Y-R/K" (e.g., R/K-SKAKNPLY-R/K"), or an inverted sequence thereof.

In other embodiments, the augmenting or other peptide (AP/P) comprises, or consists of, a modified or variant sequence of R/K'-$x^1$-R/K-$x^2$-R/K-$x^3$-$x^4$-$x^5$-$x^6$-R/K" in which amino acids $x^1$ to $x^6$ have an overall amino acid sequence identity with the corresponding amino acids of peptide R/K'-S-R/K-A-R/K-N-P-L-Y-R/K" of greater than 30%, more usually 50% or greater, more usually greater than 65% and most usually, greater than 80%; or an inverted sequence of the modified or variant sequence. Examples of such peptides include KEKLKNPLFK (SEQ ID NO: 92) and RAKAKNPLF (SEQ ID NO: 95).

In further embodiments, the amino acids $x^1$ to $x^6$ of an augmenting or other peptide (AP/P) of the formula R/K'-$x^1$-R/K-$x^2$-R/K-$x^3$-$x^4$-$x^5$-$x^6$-R/K" may be independently selected from the group consisting of alanine (A), valine (V), serine (S), threonine (T), leucine (L), isoleucine (I) and glycine (G) residues. In at least some such embodiments, the peptide does not have a serine (S) or threonine (T) (both of which are polar amino acids) in position $x^1$. Typically, each of amino acids $x^1$ to $x^6$ are independently a non-polar amino acid and most typically, are selected from alanine, valine and serine. Typically, in this embodiment, each of amino acids $x^1$ to $x^6$ are independently selected from alanine (A) and valine (V). Examples of such peptides include R/K'-AKA-KAAAA-R/K" and R/K'-VKVKVVVV-R/K".

Typically, amino acid R/K" of an augmenting or other peptide of Formula I is absent. Examples of such peptides include RSKAKNPLY (SEQ ID NO: 30).

In at least some embodiments, amino acids $x^3$ to $x^6$ and R/K" are absent.

In at least some embodiments, amino acids $x^3$ to $x^6$ are present and R/K" is absent.

Typically, R/K' is present. Most typically, R/K' is arginine. Typically, each R/K is a respective lysine amino acid.

In at least some embodiments, amino acids $x^1$ to $x^6$ are hydrophobic amino acids.

In particularly preferred embodiments, amino acids $x^1$ to $x^6$ are the same.

In yet another embodiment, the augmenting or other peptide moiety of a Lck activator as described herein comprises a peptide of Formula I as follows, or an inverted sequence thereof:

R/K'-$x^1$-R/K-$x^2$-R/K      Formula I' wherein:
R/K' is an arginine or lysine amino acid residue;
each R/K is independently an arginine or lysine amino acid residue; and
$x^1$ and $x^2$ are each independently an amino acid as for Formula I and embodiments thereof as described above.

In at least some embodiment, a peptide of Formula I or Formula I' comprises R-$x^1$-K-$x^2$-K.

In particularly preferred embodiments, amino acids $x^1$ and $x^2$ of a peptide of Formula I or Ia are each independently a hydrophobic amino acid (e.g., valine (V) or alanine (A)) and typically, are the same.

Thus, from the above, an augmenting or other peptide (AP/P) may comprise or consist of a peptide of Formula I or I'. Hence, it will be understood that a peptide comprising a peptide of Formula I or I' may also include one or more additional amino acids that are contiguous with the peptide of Formula I or I'. For instance, the peptide may include one or more independently selected amino acids coupled to one or both ends (e.g., the N-terminal end and/or C-terminal end) of the peptide, respectively. As an example, in still further embodiments, an augmenting or other peptide (AP/P) comprising an amino acid sequence Formula I or I' may further include an amino acid moiety (AA) coupled to amino acid R/K' when present or to amino acid $x^1$ in embodiments in which amino acid R/K' is absent, as illustrated in Formula I" as follows:

AA-R/K'-$x^1$-R/K-$x^2$-R/K-$x^3$-$x^4$-$x^5$-$x^6$-R/K"      Formula I"

wherein AA is an amino acid or amino acid sequence, and each R/K, R/K', R/K" and amino acid residues $x^1$ to $x^6$ are as for Formula I above.

Likewise, embodiments may be provided in which the AA moiety is instead coupled to the other terminal end of the augmenting or other peptide (AP/P) of Formula I".

Typically, when present, the amino acid moiety AA consists of one or more independently selected cationic amino acids. Typically, the amino acids will be independently selected from arginine (R), histidine (H), lysine (K), and ornithine amino acid residues and most typically, will all be arginine (R) residues. In at least some embodiments the AA moiety, when present, consists of a cationic amino acid sequence of up to 30 cationic amino acids (e.g. 1, 2, 3, 4, 6, 7, 8, 9, 10, 11, 12, 13, 14, 15, 16, 17, 18, 19, 20, 21, 22, 23, 24, 25, 26, 27, 28, 29 or 30 cationic amino acid residue(s)).

In particularly preferred such embodiments, the AA moiety when present will comprise at least 2 cationic amino acids. Examples of such AA moieties include polyargine, polyhistidine and polylysine sequences (e.g., HH (2His), HHH (3 His), HHHH (SEQ ID NO 118, 4 His), HHHHH (SEQ ID NO 125, 5 His); RRRRRRRR (SEQ ID NO: 4, 8 Arg), and RRRRRRRRR (SEQ ID NO: 6, 9Arg)). In other embodiments, the AA moiety may comprise a peptide which terminates in 9, 8, 7, 6, 5, 4, 3, 2 or 1 cationic amino acids which is/are coupled to the R/K' amino acid of the augmenting peptide of Formula I' when present or to amino acid residue $x^1$ when the R/K' amino acid residue is absent.

The augmenting or other peptide (AP/P) when present in a Lck activator in accordance with the invention will typically have a length of up to about 40 amino acids. In at least some embodiments the augmenting or other peptide (AP/P) is at least 5 amino acids in length (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids). In at least some embodiments, the augmenting peptide will have a length of about 25 amino acids or less, or about 20, 15, 14, 13, 12, 11, or 10 amino acids less. In particularly preferred embodiments, the augmenting or other peptide (AP/P) will have a length of at least 9 amino acids. As will also be understood, all ranges of from 5 to e.g., 40 amino acids are also expressly provided for herein.

In one embodiment, the Lck activating polypeptide moiety is coupled to the N-terminal or C-terminal end of the cationic amino acid sequence.

By the term "inverted sequence" as used herein is meant the amino acid sequence is reversed. For example, the inverted sequence of RSKAKNPLY (SEQ ID NO: 30) is YLPNKAKSR (SEQ ID NO: 87). Thus, the amino acid sequence of the inverted sequence is in the reverse order whereby the N-terminal end of the original sequence becomes the C-terminal end of the inverted sequence and the C-terminal end of the original sequence becomes the N-terminal end of the inverted sequence. Typically, peptides utilised in accordance with embodiments of the invention are amidated or the like at least their carboxy end to protect against proteolytic degradation. However, any suitable N- or C-terminal modification for protecting against proteolytic degradation can also be employed (e.g., methylation).

As described further below, the amino acids of the augmenting or other peptide (A/P) can be L-amino acids and/or D-amino amino acids. Thus, the amino acids of an inverted sequence can be all L-amino acids or all D-amino acids, and the term "inverted sequence" extends to retro-inverso peptides in which all of the amino acids are D-amino acids but is not limited thereto.

In one embodiment, the peptide for activating Lck comprises an amino acid sequence is selected from the group consisting of RSKAKNPLYRRRRRRRRR (SEQ ID NO: 24), rskaknplyrrrrrrrr (SEQ ID NO: 129), RVKVKVVVVRRRRRRRRR (SEQ ID NO: 58), and rvkvkvvvvrrrrrrrr (SEQ ID NO: 111), RSKAK-RRRRRRRRR (SEQ ID NO: 37), r r r r r r r r r-y l p n k a k s r (SEQ ID NO: 39), IAGQ-RSKAKNPLY-RRRRRRRRR (SEQ ID NO: 40), RSKAKNPLY-RRRRRRRRR-GPLG (SEQ ID NO: 41), RRRRRRRRR-SKAKNPLYR (SEQ ID NO: 42), RRRRRRRRR-YLPNKAKSR (SEQ ID NO: 43), RSKAKNPLY (SEQ ID NO: 30), RRRRRRRRR-HHHHH (SEQ ID NO: 112), RSKAKNPLY-RRRRRRRRR-HHHHHHHHH (SEQ ID NO: 47), Branched<RSKAKNPLY-RRRRRRRRR-HHHHHHHHH (SEQ ID NO: 48), RSKAKNPLY-RRRRRRRRR-HHHHHHHHHHH (SEQ ID NO: 49), HHHHH-RSKAKNPLY-RRRRRRRRR (SEQ ID NO: 50), HHHHH-RRRRRRRRR-HHHHH-RSKAKNPLYR (SEQ ID NO: 51), RRRRRRRR-HHHHHHHHH-RSKAKN-PLYR (SEQ ID NO: 52), HHHHH-RSKAKNPLY-RRRRRRRRR-HHHHH (SEQ ID NO: 53), RSKAKNPLY-RKRKRKRKRK (SEQ ID NO: 54), RVKVKVVVV-RRRRR (SEQ ID NO: 56), RVKVKVVVV-RRRRRRRRR (SEQ ID NO: 57), RRRRRRRR-RVKVKVVVV-R (SEQ ID NO: 59), RVKVKVVVV-RRRRRRRRR-HHHHHHHHH (SEQ ID NO: 60), RVKVKVVVV-RHRHRHRHRHRHRHRH-HH (SEQ ID NO: 61), KEKLKNPLFK-RRRRRRRR-HHHHHHHHH (SEQ ID NO: 62), RVKVKVVVV-RHRHRHRHRHRHRHRHRH (SEQ ID NO: 63), and KEKLKNPLFK-RRRRRRRR-HHHHHHHHH (SEQ ID NO: 64).

In another embodiment, the peptide for activating Lck comprises the amino acid sequence RSKAKNPLY-RRRRR (SEQ ID NO: 33) or RSKAKNPLY-RRRRRR (SEQ ID NO: 34).

In one aspect the present invention provides a peptide comprising an amino acid sequence selected from the group consisting of RSKAKNPLYRRRRRRRRR (SEQ ID NO: 24), rskaknplyrrrrrrrr (SEQ ID NO: 129), RVKVKVVVVRRRRRRRRR (SEQ ID NO: 58), and rvkvkvvvvrrrrrrrr (SEQ ID NO: 111).

In another aspect the present invention provides a peptide consisting of an amino acid sequence selected from the group consisting of RSKAKNPLYRRRRRRRRR (SEQ ID NO: 24), rskaknplyrrrrrrrr (SEQ ID NO: 129), RVKVKVVVVRRRRRRRRR (SEQ ID NO: 58), and rvkvkvvvvrrrrrrrr (SEQ ID NO: 111).

TABLE 2

Table of Sequence Listings

| Sequence ID Number | Amino acid sequence* |
|---|---|
| SEQ ID NO: 1 | RRRR (IK00400) |
| SEQ ID NO: 2 | RRRRR (IK00500) |
| SEQ ID NO: 3 | RRRRRR (IK00600) |
| SEQ ID NO: 4 | RRRRRRRR (IK00800) |
| SEQ ID NO: 5 | r r r r r r r r (IKD00800) |
| SEQ ID NO: 6 | RRRRRRRRR (IK00900) |
| SEQ ID NO: 7 | RRRRRRRRRR (IK00100) |
| SEQ ID NO: 8 | RRRRRRRRRRRR (IK01200) |
| SEQ ID NO: 9 | RRRRRRRRRRRRRR (IK01400) |
| SEQ ID NO: 10 | r r r r r r r r r r r r r r (IKD01400) |
| SEQ ID NO: 11 | RRRRRRRRRRRRRR-OH (IK014OH) |
| SEQ ID NO: 12 | RRRRRRRRRRRRRRRRRRRR (IK00200) |

TABLE 2-continued

Table of Sequence Listings

| Sequence ID Number | Amino acid sequence* |
|---|---|
| SEQ ID NO: 13 | KKKKKKKKKK (10Lys) |
| SEQ ID NO: 14 | HHHHHHHHHH (10His) |
| SEQ ID NO: 15 | OrnOrnOrnOrnOrnOrnOrnOrnOrnOrn (10 Orn) |
| SEQ ID NO: 16 | HHH-RRRRRRRRR-HHH (IK03930) |
| SEQ ID NO: 17 | HHHHH-RRRRRRRRR-HHHHH (IK05950) |
| SEQ ID NO: 18 | KKKKKKKK-HHHHHHHHHH (IK00K10) |
| SEQ ID NO: 19 | RRRRRRRR-HHHHHHHHHH (IK00810) |
| SEQ ID NO: 20 | RRRRRRRRR-HHHHHHHHHH (IK00910) |
| SEQ ID NO: 21 | DDDDDDDD (IKD9) |
| SEQ ID NO: 22 | RRRRRRRR (IK00900) |
| SEQ ID NO: 23 | DSEAENPLY-DDDDDDDD (IKDE800) |
| SEQ ID NO: 24 | RSKAKNPLY-RRRRRRRRR-NH2 (IK14800) |
| SEQ ID NO: 25 | RSKAK (IK5000) |
| SEQ ID NO: 26 | RSKAK-R (IK50100) |
| SEQ ID NO: 27 | RSKAK-RR (IK50200) |
| SEQ ID NO: 28 | RSKAK-RRR (IK50300) |
| SEQ ID NO: 29 | RSKAK-RRRR (IK50400) |
| SEQ ID NO: 30 | RSKAKNPLY (IK94000) |
| SEQ ID NO: 31 | RSKAKNPLYR (IK14000) |
| SEQ ID NO: 32 | RSKAKNPLY-RRRR (IK14300) |
| SEQ ID NO: 33 | RSKAKNPLY-RRRRR (IK14400) |
| SEQ ID NO: 34 | RSKAKNPLY-RRRRRR (IK14500) |
| SEQ ID NO: 35 | r s k a k n p l y-r r r r r r (ID94600) |
| SEQ ID NO: 36 | C-RSKAKNPLY-RRRRRR-C (Cyclised) (IK14500C) |
| SEQ ID NO: 37 | RSKAK-RRRRRRRRR (IK50900) |
| SEQ ID NO: 38 | r s k a k n p l y-r r r r r r r r r |
| SEQ ID NO: 39 | r r r r r r r r-y l p n k a k s r (IKR81400) |
| SEQ ID NO: 40 | IAGQ-RSKAKNPLY-RRRRRRRRR (IKM14800) |
| SEQ ID NO: 41 | RSKAKNPLY-RRRRRRRRR-GPLG (IK148MP9) |
| SEQ ID NO: 42 | RRRRRRRRR-SKAKNPLYR (IK9R94S) |
| SEQ ID NO: 43 | RRRRRRRRR-YLPNKAKSR (IK9R94Y) |
| SEQ ID NO: 44 | RSKAKNPLY-KKKKKKKK (IK94K90) |
| SEQ ID NO: 45 | RSKAKNPLY-RHHHHHHHHH (IK14010) |
| SEQ ID NO: 46 | RSKAKNPLY-RRRRRRRRR-HHHHH (IK14510) |
| SEQ ID NO: 47 | RSKAKNPLY-RRRRRRRRR-HHHHHHHHH (IK14810) |
| SEQ ID NO: 48 | Branched < RSKAKNPLY-RRRRRRRRR-HHHHHHHHH (Br IK14810) |
| SEQ ID NO: 49 | RSKAKNPLY-RRRRRRRRR-HHHHHHHHHHH (IK14820) |

TABLE 2-continued

Table of Sequence Listings

| Sequence ID Number | Amino acid sequence* |
|---|---|
| SEQ ID NO: 50 | HHHHH-RSKAKNPLY-RRRRRRRR (IK11480) |
| SEQ ID NO: 51 | HHHHH-RRRRRRRR-HHHHH-RSKAKNPLYR (IK59514) |
| SEQ ID NO: 52 | RRRRRRRR-HHHHHHHHHH-RSKAKNPLYR (IK81140) |
| SEQ ID NO: 53 | HHHHH-RSKAKNPLY-RRRRRRRR-HHHHH (IK51455) |
| SEQ ID NO: 54 | RSKAKNPLY-RKRKRKRKRK (IK94RK0) |
| SEQ ID NO: 55 | RVKVKVVVV (IK95000) |
| SEQ ID NO: 56 | RVKVKVVVV-RRRRR (IK15400) |
| SEQ ID NO: 57 | RVKVKVVVV-RRRRRRRR (IK15700) |
| SEQ ID NO: 58 | RVKVKVVVV-RRRRRRRRR (IK15800) |
| SEQ ID NO: 59 | RRRRRRRR-RVKVKVVVV-R (IK80150) |
| SEQ ID NO: 60 | RVKVKVVVV-RRRRRRRR-HHHHHHHHHH (IK50810) |
| SEQ ID NO: 61 | RVKVKVVVV-RHRHRHRHRHRHRH-HH (IK52820) |
| SEQ ID NO: 62 | KEKLKNPLFK-RRRRRRRR-HHHHHHHHHH (IK50810) |
| SEQ ID NO: 63 | RVKVKVVVV-RHRHRHRHRHRHRHRH (IK52820) |
| SEQ ID NO: 64 | KEKLKNPLFK-RRRRRRRR-HHHHHHHHHH (IKB2810) |
| SEQ ID NO: 65 | RSKAKNPLYR-RRRRRRRR-(2Adod)4-NH2 (IK14804) |
| SEQ ID NO: 66 | RVKVKVVVVR-RRRRRRRR-(2Adod)4-NH2 (IK15804) |
| SEQ ID NO: 67 | KVEKIGEGTYGVVYK |
| SEQ ID NO: 68 | GFLGFK |
| SEQ ID NO: 69 | GPLGIAGQ |
| SEQ ID NO: 70 | PAGLLGC |
| SEQ ID NO: 71 | GPLGLWAQ |
| SEQ ID NO: 72 | VPNLRGDLQVLAQKVA |
| SEQ ID NO: 73 | KGISSQY |
| SEQ ID NO: 74 | SSKYQL |
| SEQ ID NO: 75 | GFLGFK |
| SEQ ID NO: 76 | KAAGFLGFK |
| SEQ ID NO: 77 | CAAGFLGFK |
| SEQ ID NO: 78 | GPLGIAGQ |
| SEQ ID NO: 79 | KAAGPLGIAGQ |
| SEQ ID NO: 80 | CAAGPLGGIAGQ |
| SEQ ID NO: 81 | PAGLLGC |
| SEQ ID NO: 82 | KAAPAGLLGC |
| SEQ ID NO: 83 | CAAPAGLLGC |
| SEQ ID NO: 84 | GPLGLWAQ |
| SEQ ID NO: 85 | KAAGPLGLWAQ |
| SEQ ID NO: 86 | CAAGPLGLWAQ |
| SEQ ID NO: 87 | YLPNKAKSR |

TABLE 2-continued

Table of Sequence Listings

| Sequence ID Number | Amino acid sequence* |
|---|---|
| SEQ ID NO: 88 | KAKSR |
| SEQ ID NO: 89 | RSRARNPLY |
| SEQ ID NO: 90 | RARAKNPLY |
| SEQ ID NO: 91 | KEKLKNPLF |
| SEQ ID NO: 92 | KEKLKNPLFK |
| SEQ ID NO: 93 | RVKVKVVVV |
| SEQ ID NO: 94 | RAKAKAAAA |
| SEQ ID NO: 95 | RAKAKNPLF |
| SEQ ID NO: 96 | RSKAK |
| SEQ ID NO: 97 | RAKAK |
| SEQ ID NO: 98 | RVKVK |
| SEQ ID NO: 99 | KVKVR |
| SEQ ID NO: 100 | RYLPNKAKSR |
| SEQ ID NO: 101 | YLPNRARSR |
| SEQ ID NO: 102 | YLPNKARAR |
| SEQ ID NO: 103 | FLPNKLKEK |
| SEQ ID NO: 104 | KFLPNKLKEK |
| SEQ ID NO: 105 | VVVVKVKVR |
| SEQ ID NO: 106 | AAAAKAKAR |
| SEQ ID NO: 107 | FLPNKAKAR |
| SEQ ID NO: 108 | KAKAR |
| SEQ ID NO: 109 | KGISSQY |
| SEQ ID NO: 110 | SSKYQL |
| SEQ ID NO: 111 | rvkvkvvvv-rrrrrrrr (IKD15800) |
| SEQ ID NO: 112 | RRRRRRRR-HHHHH |
| SEQ ID NO: 113 | RVKVK-RRRRRRRRR-HHHHHHHHHH |
| SEQ ID NO: 114 | rrrrrrrr |
| SEQ ID NO: 115 | RSKAKNPLY-RRRRRRRRRR (IK14900) |
| SEQ ID NO: 116 | RSKAKNPLY-RRRRRRRRR |
| SEQ ID NO: 117 | rskaknply (IKD94000) |
| SEQ ID NO: 118 | HHHH |
| SEQ ID NO: 119 | RRRR |
| SEQ ID NO: 120 | KKKK |
| SEQ ID NO: 121 | RRRRRRR |
| SEQ ID NO: 122 | RRRRRRRRRR |
| SEQ ID NO: 123 | RRRRRRRRRRRR |
| SEQ ID NO: 124 | RRRRRRRRRRRRRR |
| SEQ ID NO: 125 | HHHHH |

TABLE 2-continued

Table of Sequence Listings

Sequence ID Number  Amino acid sequence*

SEQ ID NO: 126   KKKKKKKK

SEQ ID NO: 127   RHHHHHHHHHH

SEQ ID NO: 128   RSKAKNPLYR-(2Adod)$_4$-NH$_2$

SEQ ID NO: 129   rskaknplyrrrrrrrrr (IKD14800)

SEQ ID NO: 130   RRRRRRRRRRRRRRRR

SEQ ID NO: 131   KKKKKK

SEQ ID NO: 132   RKKKKKKKKHHHHHHHHH

SEQ ID NO: 133   RRRRRRRRRHHHHHHHHHHHHHH

SEQ ID NO: 134   RHRHRHRHRHRHRHRHRHH

SEQ ID NO: 135   HRHRHRHRHRHRHRHRHH

SEQ ID NO: 136   RSKAKNPLYRRRRRRRRR

*Lowercase indicates dextrorotatory ("dextro") amino acids;
2Adod indicates 2-amino-dodecanoic acid (e.g. (S)-2-aminododecanoic acid);
12Adod indicates 12-amino-dodecanoic acid (e.g. (S)-12-aminododecanoic acid);
—OH indicates non-amidated.

The term "amino acid sequence(s)" as used in the present specification refers to molecules composed of amino acid monomers, typically linked by amide bonds. The term includes a 'pro-drug' of the sequences, charged and non-charged forms of the sequences, a pharmaceutically acceptable salt of the sequences, and any other variant, derivative or modification to the sequences, including modifications to the backbone and/or termini of the sequences, which retain functional activity in the methods and uses of the present disclosure.

The term "sequence", as used herein, should not be interpreted as implicitly specifying a maximum length of the number of amino acids that can form the molecule. In some embodiments, the maximum length is 10 amino acids. In some embodiments, the maximum length is 9 amino acids.

In some embodiments, the sequence is an isolated or purified sequence.

Methods of "isolation" and "purification" of a sequence produced by natural or recombinant techniques are known in the art for example in C-H Lee, *A Simple Outline of Methods for Protein Isolation and Purification*, Endocrinology and Metabolism; 2017, March; 32(1): 18. Further, the terms "isolated" or "purified" include synthesised and other artificially produced sequences. Methods for synthesising sequences are known in the art. Generally, sequences are chemically synthesized by the condensation reaction of the carboxyl group of one amino acid to the amino group of another. Chemical synthesis of sequences can be carried out using solution-phase techniques or solid-phase techniques. Synthetic techniques can allow for the production of sequences incorporating unnatural amino acid sequences, backbone modification and synthesis of D-isomers.

In some embodiments, the sequences of the invention are modified. In some embodiments, the modification may be a modification that alters the pharmacological properties of the sequences. In some embodiments, the modification increases the half-life of the composition or sequences of the invention. In some embodiments, the modification may increase the bioactivity of the sequences (and/or the composition of the invention). In some embodiments, the modification may be a modification that increases selectivity of the sequences or compositions of the invention.

In one embodiment, the modification is the addition of a protecting group. The protecting group may be an N-terminal protecting group, a C-terminal protecting group or a side-chain protecting group. The sequences of the present invention may have one or more of these protecting groups. The person skilled in the art is aware of suitable techniques to react amino acids with these protecting groups. These groups can be added by preparation methods known in the art. The groups may remain on the sequences or may be removed prior to use or administration. The protecting group may be added during synthesis.

The present inventors have demonstrated that amidating the Lck activating peptides described herein surprisingly increases the level of Lck activity. Accordingly, in one embodiment present invention provides a peptide as described herein, wherein the amino acid sequence is amidated at the C-terminal end of the Lck activating polypeptide moiety, or the cationic amino acid sequence.

In another embodiment the present invention provides a peptide as described herein, wherein the distal most fatty acid is amidated.

As used herein in context of a polypeptide sequence, "NH$_2$" indicates the polypeptide is amidated, for example at its C-terminus. For example, the C– terminal amino acid or the distal most fatty acid may be amidated.

All peptides used herein are amidated at the C-terminal end of the polypeptide moiety, unless otherwise indicated (e.g. by —OH) In another embodiment, the present invention provides a peptide as described herein, wherein the amino acid sequence is amidated at the C-terminal end of the Lck activating polypeptide moiety.

In some embodiments, the sequence is amidated at its C-terminus. Amidation refers to the process of N-oxidative cleavage of glycine-extended substrates by sequential endoand exoproteolysis. Methods are known in the art for producing amidated sequences in vitro, such as: enzymatic amidation; chemical modification of the C-terminus of recombinantly produced sequences and proteins; use of amide resins in solid-phase sequences synthesis; use of carboxypeptidase in the presence of ammonia; and conversion of the C-terminus of sequences to the methyl ester and addition of ammonia at low temperature. Examples of the disclosure of suitable techniques include D J Merkler, *C-terminal amidated sequences: production by the in vitro enzymatic amidation of glycine-extended sequences and the importance of the amide to bioactivity*; Enzyme Microbial technology, 1994, June; 16(6): 450-6 and V Čeřovský and M-R Kula *C-Terminal sequences Amidation Catalyzed by Orange Flavedo sequences Amidase*; Angewandte Chemie, 1998, August; 37(13-14): 1885.

Amidation of the C-terminus results in the C-terminal end being uncharged, so the modified sequences more closely mimic a native protein. This can have a series of advantages including an enhanced ability of the sequence to enter a cell; an improvement in the metabolic stability of the sequence in vivo; a decrease in the in vivo enzymatic degradation of the sequences by aminopeptidases, exopeptidases, and synthetases; and an improvement of the shelf-life of the sequences.

As described herein, the present inventors have identified that the Lck activating polypeptides described herein can comprise L or D amino acids and have biological activity. Accordingly, in one embodiment, the present invention describes a Lck activator as described herein wherein the amino acid sequence comprises L-arginine residues. In another embodiment, the present invention describes a Lck activator as described herein wherein the amino acid sequence comprises D-arginine residues.

As is known in the art, alpha amino acids include a chiral carbon at the alpha position. Consequently, all alpha amino acids, with the exclusion of glycine can exist in either of two enantiomers, being the L- or D-isomers. Generally, only L-amino acids are manufactured in mammalian cells and incorporated into proteins. D-amino acids can be artificially synthesised or may be found in bacterial proteins. The L and D convention is not used to directly refer to the stereochemistry of the amino acids, rather it is used in reference to amino acid configuration and does not refer to the optical activity of the amino acid itself, but rather to the optical activity of the isomer of glyceraldehyde from which that amino acid can be synthesized (D-glyceraldehyde is dextrorotatory; L-glyceraldehyde is levorotatory).

In at least some embodiments, an augmenting or other peptide (AP/P) of a Lck activator as described herein may comprise, or consist of, a peptide active selected from the group consisting of RSKAKNPLY (SEQ ID NO: 30), RSKAKNPLYR (SEQ ID NO: 31), RSRARNPLY (SEQ ID NO: 89), RARAKNPLY (SEQ ID NO: 90), KEKLKNPLF (SEQ ID NO: 91), KEKLKNPLFK (SEQ ID NO: 92), RVKVKVVVV (SEQ ID NO: 55), RAKAKAAAA (SEQ ID NO: 94), RAKAKNPLF (SEQ ID NO: 95), RSKAK (SEQ ID NO: 25), RAKAK (SEQ ID NO: 97) and RVKVK (SEQ ID NO: 98).

In other embodiments, the augmenting or other peptide (AP/P) may be selected from the group consisting of the inverted sequences YLPNKAKSR (SEQ ID NO: 87), RYLPNKAKSR (SEQ ID NO: 100), YLPNRARSR (SEQ ID NO: 101), YLPNKARAR (SEQ ID NO: 102), FLPNKLKEK (SEQ ID NO: 103), KFLPNKLKEK (SEQ ID NO: 104), VVVVKVKVR (SEQ ID NO: 105), AAAAKAKAR (SEQ ID NO: 106), FLPNKAKAR (SEQ ID NO: 107), KAKSR (SEQ ID NO: 88), KAKAR (SEQ ID NO: 108) and KVKVR (SEQ ID NO: 99).

Most typically, the augmenting or other peptide (AP/P) comprises, or consists of, RSKAKNPLY (SEQ ID NO: 30), YLPNKAKSR (SEQ ID NO: 87), RSKAK (SEQ ID NO: 25) or KAKSR (SEQ ID NO: 88).

The present inventors have demonstrated that the coupling of at least one fatty acid to a peptide as described herein can, surprisingly, confer on the peptide an increased ability to activate Lck.

Accordingly, in some embodiments, the peptide for activating Lck comprises one or more linked fatty acid moiety(ies). In some embodiments, the activator of Lck comprises four linked fatty acid moieties. This result is surprising since, on their own, fatty acid moieties comprising one to four linked fatty acids do not activate Lck. In some embodiments, the linked fatty acid moiety(ies) include at least one amino-dodecanoic acid moiety. In some embodiments, all of the fatty acid moieties are amino-dodecanoic acid.

In another preferred embodiment, more than one fatty acid is coupled at the C-terminal end of the polypeptide moiety of Formula I. For example, 2, 3, 4, 5, 6, 7, 8, 9, or 10 or more fatty acids are coupled to the polypeptide moiety of Formula I.

The at least one fatty acid may be provided by coupling together fatty acids by consecutively forming a respective amide bond between the amino group substituent of one fatty acid chain and the terminal carboxyl group of the next fatty acid to thereby provide coupled fatty acids.

Accordingly, fatty acids having an amino group ($NH_2$) substituent on the α or β carbon of the fatty acids are particularly suitable for coupling.

In one preferred embodiment, the present invention provides a peptide for activating Lck as described herein wherein at least four fatty acids are coupled to the C-terminal end of the activator.

In another preferred embodiment, the present invention provides a peptide for activating Lck as described herein, wherein the distal most fatty acid is amidated.

The coupling of the fatty acids may be linear and/or branched. In one embodiment the present invention provides a peptide for activating Lck as described herein, wherein the coupling of the at least four fatty acids is linear. In another embodiment the present invention provides a peptide for activating Lck as described herein, wherein the coupling of the at least four fatty acids is branched.

As discussed above, fatty acid moiety(ies) can be coupled to the peptide for activating Lck at any position to form a lipopeptide. However, in a preferred embodiment the fatty acid moiety(ies) is/are coupled at the C-terminal end of the peptide for activating Lck. The fatty acid moiety(ies) coupled to the amino acid sequence can be branched fatty acids or linear fatty acids.

In some embodiments, at least one, two three or four of the fatty acid moiety(ies) is/are linear. For example, when the coupling of the at least one fatty acid is linear, in one embodiment at least one fatty acid is coupled to the C-terminal end of the peptide for activating Lck via an amide bond.

As used herein, the term 'linear' refers to the hydrocarbon chain of the fatty acid being incorporated into the backbone of the peptide for activating Lck. For example, the fatty acid can comprise an amino group substituent at the omega carbon. In one embodiment 12 amino lauric fatty acid amides (e.g. 12-aminododecanoic acid; 'Adod') are used, and therefore an amide bond can be formed between the amino substituent at carbon 12 and another group (e.g. a carboxyl group).

Accordingly, in another embodiment, when the coupling of the at least one fatty acid is linear, a first fatty acid is coupled to the C-terminal end of the peptide for activating Lck via an amide bond, and a further fatty acid is coupled to the fatty acid by forming an amide bond between the terminal carboxyl group of the fatty acid and an amino group substituent of the further fatty acid (e.g. amino-dodecanoic acid). In another embodiment, a third fatty acid is coupled to the further acid by forming an amide bond between the terminal carboxyl group of the further fatty acid and an amino group substituent of the third fatty acid. In another embodiment, a fourth fatty acid is coupled to the third acid by forming an amide bond between the terminal carboxyl group of the third fatty acid and an amino group substituent of the fourth fatty acid.

Any number of fatty acids can be coupled to the C terminal end of the peptide for activating Lck by forming—from fatty acid monomers—a linear polymeric chain of fatty acids by forming an amide bond between the terminal carboxyl group of one fatty acid and an amino group substituent of another fatty acid, to be coupled to the peptide for activating Lck.

In other embodiments, the hydrocarbon chain of the fatty acid is not 'linear', for example, all or part of the hydrocarbon chain of the fatty acid is not part of the backbone of the peptide for activating Lck (e.g. is 'perpendicular' to the backbone of the peptide for activating Lck). For example, the fatty acid can comprise an amino group substituent at the alpha or beta carbon of the fatty acid. For example, in one embodiment 2-amino lauric fatty acid amides (e.g. 2-aminododecanoic acid; 'Adod') are used, and therefore an amide bond can be formed between the amino substituent at carbon 2 and another group (e.g. a carboxyl group of a peptide of Formula I, or a polycationic peptide).

As used herein the term Adod refers to aminododecanoic acid, and "2Adod" refers to 2-amino dodecanoic acid; "12Adod" refers to 12-aminododecanoic acid, etc. Where more than one fatty acid is coupled the number of fatty acids coupled is denoted by a subscript. For example, "(2Adod)$_2$" denotes two 2-aminododecanoic acids. Thus, a single unit of a polyamide moiety as described herein, corresponds to one 2-amino dodecanoic acid residue (also referred to herein as "(2Adod)$_1$". Two units of a polyamide moiety as described herein, corresponds to two 2-amino dodecanoic acid residues (also referred to herein as "(2Adod)$_2$". Three units of a polyamide moiety as described herein, corresponds to three 2-amino dodecanoic acid residues "(2Adod)$_3$". Four units of a polyamide moiety as described herein, corresponds to four 2-amino dodecanoic acid residues "(2Adod)$_4$".

In other embodiments, the fatty acid can comprise an amino group substituent at another carbon of the fatty acid.

In other embodiments, wherein the amino fatty acid is chiral, with one chiral centre, there will be two possible enantiomers (e.g. R and S). Accordingly, in one embodiment, a peptide for activating Lck of the present invention can comprise one enantiomer or the other enantiomer of an amino fatty acid, or one or more enantiomers of one or more amino fatty acids.

Accordingly, the present invention provides peptides for activating Lck comprising fatty acids coupled in a linear and/or non-linear (e.g. in a branched manner).

As used herein the term "branched" includes more than one fatty acid being coupled to an amino acid residue, or to a first fatty acid, so as to not be 'linear' or 'perpendicular' to the backbone of the peptide for activating Lck.

In one embodiment, the at least one fatty acid is a long-chain fatty acid, which contain 13-21 carbon atoms, a medium chain fatty acid, which contain 6 to 12 carbon atoms, or short chain fatty acids, which have fewer than 6 carbon atoms. In a preferred embodiment, the fatty acid comprises about 6 to 16 carbon atoms in length. For example, the fatty acid comprises from 6 to 16 carbons, 8 to 14 carbons or from 10 to 12 carbons.

In one embodiment, the fatty acid comprises 6 carbons, and is caproic acid or hexanoic acid. For example, in one embodiment the fatty acid is an aminohexanoic acid.

In another embodiment, the fatty acid comprises 8 carbons, and is caprylic acid or octanoic acid. For example, in one embodiment the fatty acid is an aminooctanoic acid.

In another embodiment, the fatty acid comprises 10 carbons, and is capric acid or decanoic acid. For example, in one embodiment the fatty acid is an aminodecanoic acid.

In another embodiment, the fatty acid comprises 12 carbons, and is lauric acid or dodecanoic acid. For example, in one embodiment the fatty acid is an aminododecanoic acid (e.g. (S)-2-aminododecanoic acid). The fatty acid may be saturated or unsaturated with one or more double bonds. Preferably, the fatty acid is saturated.

In one embodiment the present invention provides a peptide for activating Lck, wherein the peptide further comprises a compound coupled to the N-terminal or C-terminal end of the Lck activating polypeptide moiety, wherein the compound is at least one fatty acid.

In one embodiment the present invention provides a peptide for activating Lck as described herein wherein at least four fatty acids are coupled to the C-terminal end of the Lck activating polypeptide moiety.

In one embodiment the present invention provides a peptide for activating Lck as described herein, wherein the coupling of more than one fatty acids is linear.

In one embodiment the present invention provides a peptide for activating Lck as described herein, wherein the coupling of more than one fatty acids is branched.

In one embodiment the present invention provides a peptide for activating Lck as described herein, wherein the fatty acid is saturated.

In one embodiment the present invention provides a peptide for activating Lck as described herein, wherein the fatty acid is selected from the group consisting of caproic acid, caprylic acid, capric acid (decanoic acid), and lauric acid (dodecanoic acid).

In one embodiment the present invention provides a peptide for activating Lck as described herein, wherein the distal most fatty acid is amidated.

In one embodiment the present invention provides a peptide for activating Lck as described herein, wherein the amino acid sequence is amidated at the C-terminal end of the Lck activating polypeptide moiety.

In particularly preferred embodiments, the cell compound may comprise a saturated or unsaturated aliphatic, fatty acid, polyamide or other backbone of up to 20 atoms or more in length, which may have one or more side chains. Typically, the backbone chain will have a length in a range of from about 6 to 20 atoms in length (i.e., 6, 7, 8, 9, 10, 11, 12, 13, 14, 15, 16, 17, 18, 19 or 20 atoms), and may include one or more heteroatoms (e.g., independently selected from N, O, S and P). When branched, the backbone chain will generally have 1 to 5 side chains (e.g., 1, 2, 3, 4 or 5 side chains) each of which is independently up to 18 atoms in length (i.e., 1, 2, 3, 4, 5, 6, 7, 8, 9, 10, 11, 12, 13, 14, 15, 16, 17 or 18 atoms in length. Typically, each side chain is independently a saturated or unsaturated aliphatic carbon chain (e.g., a $C_1$ to $C_{18}$ chain). Most typically, the facilitator moiety has an aliphatic or polyamide backbone.

In at least some embodiments, the compound is a polyamide with from 3 to 5 repeating units, each repeating unit independently being from 3 to 9 atoms in length (i.e., a length of 3, 4, 5, 6, 7, 8 or 9 atoms) and having either no side chain or a single side chain. Typically, each repeating unit is from 3 to 6 atoms in length and more typically from 3 to 6, 3 to 5, or 3 to 4 atoms in length and most typically, is 3 atoms in length. The length of the side chain of each repeating unit is typically independently from 4 to 18 carbon atoms in length (i.e., $C_4$-$C_{18}$), e.g., 4, 5, 6, 7, 8, 9, 10, 11, 12, 13, 14, 15, 16, 17 or 18 carbon atoms and more usually, is from 8 to 18, 8 to 16, 8 to 14, 8 to 12 or 8 to 10 carbon atoms in length. The side chain of each repeating unit will typically independently extend from an α or β carbon atom of the repeating unit.

Typically, the compound to be coupled in accordance with embodiments of the invention comprises a compound of Formula II as follows:

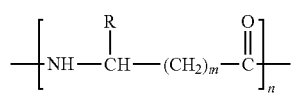

Formula II wherein:
n is the number of monomer units of the compound and is an integer of from 1 to 5;
each m is independently an integer of from 0 to 18; and
each R group is independently H or a $C_1$ to $C_{18}$ side chain.
Typically, the length of the R side chain of a monomer unit is substantially inversely proportional to the value of m of that monomer unit. Generally, each R will be 18−m carbon atoms in length wherein m has a value of from 0 to 17. For example, if m is 0, R will be a $C_{18}$ side chain, if m is 2, R will be a $C_{16}$ side chain, if m is 4, R will be a $C_{14}$ side chain, and so on.

Typically, n is 2 to 5 in a compound of Formula II; each m is independently 0, 1, 2 or 3; and each R is independently a carbon chain.

Typically, each R is independently a carbon chain of from 4 to 18 carbon atoms in length. Thus, in at least some embodiments, the compound of a Lck activator in accordance with the invention is a polyamide moiety (PM) of Formula IIa as follows:

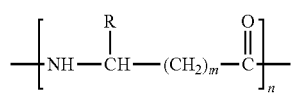

Formula IIa wherein:
n is the number of monomer units of the compound and is an integer of from 3 to 5;
each m is independently 0, 1, 2 or 3; and
each R group is independently a carbon chain of from 4 to 18 carbon atoms in length.

Typically, in a compound of Formula II or Formula IIa, each m is independently 0, 1 or 2. More typically, m is 0 or 1. Most typically, m is 0.

As will be understood, a monomer unit of a compound of Formula II as described herein can differ from one or more of the other monomer units of the compound.

A compound/polyamide moiety of Formula II or Formula IIa can, for example, be provided by coupling together fatty acids of the formula R—$CHNH_2$—$(CH_2)_m$—COOH which have an amino group substituent as shown, and R and m are as described above, by consecutively forming a respective amide bond between the amino group substituent of one fatty acid chain and the terminal carboxyl group of the next fatty acid to thereby provide a polyamide backbone from which the R group of each fatty acid extends as a side chain. That is, the R group side chain of each monomer unit of the resulting polyamide moiety is the remainder of the respective fatty acid from which the backbone of the polyamide moiety is formed.

Fatty acids having an amino group ($NH_2$) substituent on the α or β carbon of the fatty acids are particularly suitable for use in the synthesis of the polyamide moiety (PM), whereby the resulting polyamide moiety has an α or β polyamide backbone. Most typically, in a compound of Formula II, m of each monomer unit is 0. Hence, the polyamide moiety can be formed from fatty acids in which the α carbon atom of each of the fatty acids is substituted with an amino group.

In embodiments of the present invention, each fatty acid moiety comprises from 6 to 16 carbons, from 8 to 14 carbons, or from 10 to 12 carbons. In some embodiment at least one fatty acid moiety is saturated, unsaturated or polyunsaturated. In a preferred embodiment, one, two, three or four of the fatty acids are saturated. In some embodiments, the fatty acid is selected from the group consisting of: caproic acid (hexanoic acid), caprylic acid (octanoic acid), capric acid (decanoic acid), and lauric acid (dodecanoic acid). In a preferred embodiment, the fatty acid is dodecanoic acid (aminododecanoic acids/adod).

In embodiments of a Lck activator utilised in a method in accordance with the invention, the carbon chain of each R group of a compound of Formula II may independently be linear or branched, and may be saturated or unsaturated with one or more double bonds. Typically, each R group is a saturated carbon chain.

Typically, each R group of a compound of Formula II is independently a carbon chain of from 8 to 18, 8 to 16, more preferably 8 to 14 and most preferably, 8 to 12 carbon atoms in length. Most typically, each R group is independently a carbon chain of from 8 to 10 carbon atoms in length.

Thus, for example, 2-amino-capric and lauric fatty acids (respectively being 10 and 12 carbon atoms in length) are particularly suitable for use in the provision of a compound of Formula II as described herein. As will be understood, in the case of capric fatty acid, the R group of a monomer unit of the resulting compound of Formula II is 8 carbon atoms in length given carbons 1 and 2 (the α carbon) of the capric fatty acid chain are incorporated into the backbone of the compound. Likewise, in the case of lauric fatty acid, the R group of a monomer unit (n=1) of the resulting compound is 10 carbon atoms in length.

The length of the carbon chain of the R groups of a compound of Formula II can independently vary from one monomer unit of the compound to the next. Typically, the carbon chains of the R groups of a compound of Formula II are the same length as one another. The use of 2-amino lauric fatty acid amides in the provision of a compound of Formula II is particularly preferred. Hence, the R group of each monomer unit of the compound in this instance is 10 carbon atoms in length.

Typically, in a compound of Formula II, n is 3, 4 or 5, more typically n is 3 or 4 and most typically, n is 4.

However, all variations of a compound of Formula II of a Lck activator as described herein in are expressly encompassed.

Typically, the compound of Formula IIa of a Lck activator as described herein terminates in an amino group (NH$_2$) as illustrated below in Scheme 1.

Scheme 1: Compound of Formula II

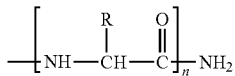

In other embodiments, a compound of Formula II which terminates in a hydrogen atom or terminal group other than NH$_2$ (as in Scheme 1) may also be employed, and the invention expressly extends to the use of therapeutic agents comprising all suitable, physiologically acceptable such compounds, including physiologically acceptable salts thereof.

A compound of Formula II utilised in accordance with the invention may, for instance, have an end terminal group selected from e.g., NH$_2$, H, COOH, OH, halo (e.g., F, Cl, Br, I), SH, alkyl, lower alkyl, alkenyl, lower alkenyl, OR, NHR' and NR'R", wherein the lower alkyl group, lower alkenyl group, OR, NHR' and NR'R" is optionally substituted, and R, R' and R" are each independently an optionally substituted lower alkyl or lower alkenyl.

Optional substituent(s) of the lower alkyl, lower alkenyl, OR, NHR' and NR'R" groups may be selected from, for example, OH, halo (e.g. F, Cl, Br I), C$_1$-C$_3$ alkyl (e.g., methyl), COOH etc.

By "lower alkyl" is meant a C$_1$-C$_6$ alkyl (e.g., methyl, ethyl, or propyl group etc. which may be linear or branched).

Likewise, by "lower alkenyl" is meant a C$_2$-C$_6$ alkenyl group including one or more double bonds in its longest chain.

Typically, however, a compound of Formula II will terminate in a NH$_2$ or COOH group.

Typically, a polycationic peptide (PP) as described herein which itself is a Lck activator in accordance with the invention will comprise at least 6 contiguous cationic amino acids. Likewise, a polycationic peptide as described herein comprising less than 6 contiguous cationic amino acids in length will typically be coupled to a an augmenting or other peptide (AP/P) of Formula I or a compound (C) or Formula II.

Amino acid differences between a modified or variant form of an augmenting or other peptide (AP/P) and the wild type or parent peptide (e.g., RSKAKNPLY, SEQ ID NO: 30) are typically conservative amino acid changes. By conservative amino acid substitution is meant replacing an amino acid residue with another amino acid having similar stereochemical properties (e.g., structure, charge, acidity or basicity characteristics) and which does not substantially effect conformation or the desired aspect or aspects of characteristic biological function. For example, an acidic amino acid such as aspartic acid (D) may be replaced by a glutamic acid residue (E), a polar amino acid such as serine (S) may be replaced by another polar amino acid such as threonine (T) or asparagine (N), and so on.

The sequence identity between amino acid sequences as described herein can be determined by comparing amino acids at each position in the sequences when the sequences are optimally aligned for the purpose of comparison. Alignment of sequences can be performed using any suitable program or algorithm such as for instance, by the Needleman and Wunsch algorithm (Needleman and Wunsch, 1970). Computer assisted sequence alignment can be conveniently performed using standard software programs such as GAP which is part of the Wisconsin Package Version 10.1 (Genetics Computer Group, Madison, Wisconsin, United States) using the default scoring matrix with a gap creation penalty of 50 and a gap extension penalty of 3. Other methods of alignment of amino acid sequences for comparison are also well known such as, but not limited to, the algorithms of Smith and Waterman, (1981) and Pearson and Lipman (1988), computerized implementation of such algorithms (e.g., BESTFIT, FASTA and BLAST), and by manual alignment and inspection of the sequences.

In embodiments as described herein, the Lck activator may comprise an augmenting or other peptide (AP/P) of Formula I as described above coupled to the N-terminal or C-terminal end of the polycationic peptide (PP) as illustrated below in Formula III and Formula IV.

In other embodiments, a compound such as a compound of Formula II can be coupled to the N-terminal end or C-terminal end of a polycationic peptide (PP) as exemplified in Formula V and Formula VI below.

In still other embodiments in which an augmenting or other peptide of Formula I, or other peptide moiety as described above, is coupled to the N-terminal end or C-terminal end of the polycationic peptide (PP), a compound (C) of Formula II can be coupled to the other of the N-terminal or C-terminal end of the polycationic peptide (PP) as exemplified below in Formula VII and Formula VIII.

AP/P-PP Formula III
PP-AP/P Formula IV
C-PP Formula V
PP-C Formula VI
AP/P-PP-C Formula VII
C-PP-AP/P Formula VIII The components, e.g., the polycationic peptide (PP), compound (C), and/or the augmenting peptide or other peptide (AP/P) of a Lck activator as described herein are normally coupled directly to one another as the case may be by a respective peptide bond or other suitable (e.g., covalent or ionic) bond. In other embodiments, the polycationic peptide (PP) may be coupled to the augmenting peptide or other peptide (AP/P) and/or compound (C) via a respective linker group (LG). The linker groups may be the same or different to one another. A linker group may, for instance, comprise or consist of a length of from 1 to 10 atoms or more (i.e., 1, 2, 3, 4, 5, 6, 7, 8, 9 or 10 atoms), wherein the linking atom or one or more of the atoms may be a non-carbon e.g., independently selected from N, S and O. However, any suitable linkage system may be employed.

From the above, at least some embodiments of Lck activators as described herein are, or comprise, lipopeptides.

It will be also understood that the augmenting peptide or other peptide (AP/P) in any of Formula III to Formula VIII can be an inverted sequence of an augmenting peptide of Formula I.

In still further embodiments, a Lck activator in accordance with the invention may be coupled to a linker moiety (LM) for coupling the Lck activator to a targeting moiety for targeted delivery of the Lck activator to target cells and/or to one or more other Lck activators as described herein. The linker group can, for example, be coupled to the polycationic peptide (PP) or an augmenting peptide or other peptide (AP/P) of a Lck activator of any of Formulae III to VIII as illustrated below in Formulae IX to XI.

LM-AP/P-PP Formula IX
PP-AP/PA-LM Formula X
C-PP-LM Formula XI
LM-PP-C Formula XII
LM-AP/P-PP-C Formula XIII
C-PP-AP/P-LM Formula XIV
AP/P-PP-LM Formula X
AP/P-PP-C-LM Formula XI In some embodiments, the linker moiety can couple the Lck activator directly to a targeting moiety.

In other embodiments, the linker moiety can comprise a bridging moiety for coupling a pair of Lck activators together, wherein the Lck activators are the same or different to one another.

The linker moiety (LM) can optionally include or consist of an amino acid sequence coding for one or more enzyme cleavage sites as exemplified below for being enzymatically cleaved at the surface of the target cells or intracellularly within the target cells to release the Lck activator(s).

Typically, the linker moiety comprises a coupling moiety for coupling of the linker moiety to a targeting moiety.

The coupling moiety can comprise any suitable amino acid or amino acid sequence for linkage to the targeting moiety, such as a cysteine (C) amino acid residue (for formation of a disulphide bridge with a terminal cysteine residue provided by the targeting moiety), a lysine residue (K), or a spacer amino acid sequence selected from the group consisting of e.g., KAA, CAA for spacing the lysine (K) or cysteine (C) residue from enzyme cleavage sites (when present) of the linker moiety, wherein A is an alanine amino acid residue. The spacer amino acid sequence can further act as a marker for determination of attachment to the selected targeting moiety. In particularly preferred embodiments, the coupling moiety will comprise one or more p amino acids (e.g., in the case of KAA and CAA the alanine residues can be p amino acids).

In one embodiment, the coupling moiety is an azide moiety.

In another embodiment, the coupling moiety (e.g. azide moiety) is coupled to dibenzocyclooctyne (DBCO).

The one or more enzyme cleavage sites of a linker moiety (LM) may be selected from the group consisting of cathepsin cleavage sites e.g., GFLGFK (SEQ ID NO: 68, e.g., see Orban et al., Amino Acids, 2011, 41(2):469-483), matrix metalloproteinase (MMP) cleavage sites examples of which include the cleavage sites for MMP-9 and MMP-2 such as GPLGIAGQ (SEQ ID NO: 69), PAGLLGC (SEQ ID NO: 70) and GPLGLWAQ (SEQ ID NO: 71, e.g., see Kratz F. et al., Bioorg Med Chem Letters, 2001, 11:2001-2006), prostate specific antigen (PSA) cleavage sites such as KGISSQY (SEQ ID NO: 73) and SSKYQL (SEQ ID NO 74, Kumar S K et al., Bioorg Med Chem, 2008, 16(6): 2764-2768; Niemela P et al., Clin Chem, 2002, 48(8):1257-1264) and a di-sulfide bridge (—S—S—) cleavable by an intracellular enzyme such as glutathione-s-transferase, the use of all of which is expressly encompassed herein.

Thus, the linker moiety (LM) can, for example, comprise or consist of various combinations of coupling moieties and/or enzymatic cleavage sites as described herein, as may be selected from the group consisting of GFLGFK (SEQ ID NO: 68 or 75), KAAGFLGFK (SEQ ID NO: 76), CAAGFLGFK (SEQ ID NO: 77), GPLGIAGQ (SEQ ID NO: 69), KAAGPLGIAGQ (SEQ ID NO: 79), CAAGPLGIAGQ (SEQ ID NO: 80), PAGLLGC (SEQ ID NO: 70), KAAPAGLLGC (SEQ ID NO: 82), CAAPAGLLGC (SEQ ID NO: 83), GPLGLWAQ (SEQ ID NO: 71), KAAGPLGLWAQ (SEQ ID NO: 85) and CAAGPLGLWAQ (SEQ ID NO: 86), amongst others. In at least some embodiments, a linker moiety (LM) as described herein may comprise more than one enzymatic cleavage site.

Importantly, the present inventors have demonstrated that the peptides described herein are not cleaved by MMP9 (data not shown).

An example of a pair of Lck activators coupled together by a linker moiety (LM) in accordance with an embodiment as described herein is illustrated in Scheme II below.

Scheme II. Example of a dimer Lck activator

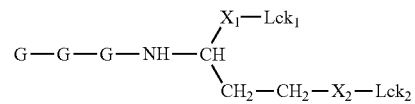

The dimer Lck activator shown in Scheme II comprises Lck activators Lck1 and Lck2 coupled together by a bridging moiety. In this instance, the bridging moiety comprises enzymatic cleavage sites $X_1$ and $X_2$ (e.g., PSA and/or MMP amino acid cleavage sequences) linked via a glutamic acid (Glu) moiety to a sequence of three glycine (G) amino acid residues ($Gly^3$) forming a coupling moiety for coupling the Lck activators to a targeting moiety by Sortase A-mediated ligation as described further below. The enzymatic cleavage sites $X_1$ and $X_2$ may be the same or different to one another. Lck1 and Lck 2 can, for example, each independently be a Lck activator selected from any one of Formulae III to VIII above wherein the bridging moiety is coupled e.g., to the end of a respective polycationic peptide (PP), augmenting moiety or other peptide (AP/P), or to a compound (C) of a respective Lck activator of the dimer.

Coupling moieties other than $Gly^3$ can also be employed in embodiments of the invention. For instance, the coupling moiety may comprise a sequence of from 3 to 5 glycine amino acid residues, another amino acid sequence (e.g., 3 to 5 amino acids long), or other suitable linker chain.

In still other embodiments, a Lck activator, dimer or other multimer of Lck activators as described herein may be coupled to one or more other individual Lck activators or Lck activator multimers by dendrimer or other suitable physiologically acceptable scaffolding/framework.

The entry of a Lck activator as described herein into a cell can occur via a number of mechanisms, including via diffusion across an outer cell membrane or by e.g., receptor mediated transport or internalisation, including via lysosomes which are rich in cathepsin enzyme.

The targeting moiety for the targeting of Lck activator(s) as described herein may be achieved by the use of a targeting moiety such as a ligand, a binding peptide, an antibody or binding fragment thereof (such as Fab and F(ab)$_2$ fragments), or a single-chain variable fragment (scFv), that binds to a receptor or other molecule expressed on the surface of the cells or in the tissue environment of target cells. Examples of antibody targeting moieties include anti-CD3 and anti-CD4 antibodies (e.g., TRX1, Ng C H et al, Pharmaceutical Research, 2006, doi: 10.1007/s11095-005-8814-3), and BT-061 (Humblet-Baron S & Baron F, Immunology & Cell Biology, 2015, doi:10.1038/icb.2014.120). Targeting moieties that may be utilised also include transferrin, biotin, folic acid, and hyaluronic acid amongst others, see for instance, Ojima I. et al., *Future Med Chem,* 2012, 4(1):33-50, the entire contents of which is incorporated herein by cross-reference.

HIV (e.g., HIV-1), for example, binds to CD4 expressed on T-lymphocytes via viral envelope protein gp120 for entry into the T-cells. The resulting conformational change in the gp120 protein following binding to CD4 enables the virus to bind to co-receptor CCR5 and/or CXCR4 of the lymphocyte enabling fusion of the virus with the cell. CD4, CCR5 and CXCR4 are examples of cell surface receptors that may be targeted in accordance with embodiments of the invention for delivery of therapeutic agent(s) in accordance with the invention to lymphocytes. Other examples of cell surface receptors or surface expressed molecules on target cells that may be targeted in accordance with the invention include CD2, CD3, CD8, CD28 and CD45 (e.g., CD45RA, CD45RB and CD45RO isoforms).

Examples of further molecules which may be targeted for delivery of therapeutic agent(s) to target cells in accordance with embodiments of the invention include members of the integrin family and subunits thereof, intercellular adhesion molecules (ICAMs) hormone receptors, neurotransmitter receptors, receptor tyrosine kinase receptors, G-protein linked receptors, growth factor receptors, transmembrane protease receptors, cell-surface proteoglycans, CD44, CD55, Fcγ receptors, carcinoembryonic antigen (CEA), hyaluronate receptors, transferrin receptors, folate receptors, prostate specific membrane antigen, vascular cell adhesion molecules, matrix proteins such as fibronectin, collagen vitronectin and laminin.

The chemotherapeutic Ibalizumab (formerly TNX-355) (Bruno C J and Jacobson J M, J Antimicrobial Chemotherapy, 2010, doi: 10.1093/jac/dkq261) targets CD4 and may be employed as a targeting moiety for delivery of Lck activator(s) to target cells in accordance with the invention, as may other drugs for the treatment of a cancer or other disease or condition in accordance with the invention. Likewise antibodies or antibody binding fragments thereof that bind to CD4 (e.g., OKT4) or CXCR4 may also be utilised.

In some embodiments the Lck activator may be administered either separately together with a therapeutic targeting antibody or conjugated to the targeting antibody as an antibody-drug conjugate (ADC). For example, an antibody against the Programmed death ligand-1 (PD-1) receptor or the Cytotoxic T-lymphocyte-associated protein 4 (CTLA4) receptor expressed on tumour-specific T cells that inhibits the inhibitory effect of these receptors on T cell activation and IL-2 production such as tremelimumab/ipilimumab (Yervoy) or MSB0010718C, respectively, may be conjugated to a Lck activator described herein to form an ADC for use in the treatment of cancers targeted by such antibodies such as melanoma, renal cancer and lung cancer (Ott P A, OncLive, published online Feb. 21, 2014). The conversion of the CTLA-4 receptor from an inhibitor to an activator of T cells has also previously been described using a bispecific tandem scFv ligand that mediates its effect via Lck activation (Madrenas J et al, J Immunol, 2004, 172: 5948-5956 and Teft W A et al, BMC Immunology, 2009; doi: 10.1186/1471-2172-10-23, Teft W A et al, BMC Immunology, 2009; doi: 10.1186/1471-2172-10-23). Hence, the conjugation of the scFv to a Lck activator as described herein may further promote T cell activation in accordance with an embodiment of the invention. As a further example, bi-specific antibodies known to those in the art may be used to link e.g., PEG-conjugated Lck activators as described herein to antibodies against cell surface receptors e.g., such as CD28.

Antibodies or binding fragments thereof (such as Fab, F(ab)$_2$ and Fv fragments) used as targeting moieties in embodiments of the invention will desirably be specific for the selected target molecule and so will generally comprise monoclonal antibodies or binding fragments thereof. The production of monoclonal antibodies and binding fragments thereof is well known. Chimeric and humanised monoclonal antibodies, and binding fragments of same, are particularly preferred. Chimeric antibodies may, for instance, be provided by substituting the Fc region of a non-human antibody specific for the target molecule with the Fc region of a human antibody. A humanised antibody can be provided by splicing the complementary determining regions (CDRs) in the variable regions of an Fab fragment of a non-human (e.g., mouse, rat, sheep or goat) monoclonal antibody into a human antibody scaffold using recombinant DNA techniques as is also known in the art.

As above, single-chain variable fragment (scFv) and multimeric forms thereof, e.g., bivalent scFvs (e.g., tandem scFvs and diabodies), trivalent scFvs (triabodies) and tetravalent scFvs (tetrabodies), may also be utilised as targeting moieties in embodiments of the invention, with the use of diabodies being particularly preferred. scFvs useful in embodiments in the invention may comprise humanised or native antibody heavy ($V_H$) and light ($V_L$) chains joined together by an amino acid linker sequence (AAL) in either of the two possible orientations $V_L$-AAL-$V_H$ or $V_H$-AAL-$V_L$. The length of the linker sequence can vary depending on whether monomeric scFVs, diabodies, triabodies or tetrabodies are to be formed. The linker sequence (AAL) of a scFv will generally be of a length in a range of from about 5 to about 30 amino acids and more generally, in a range of from 5 to 25 amino acids. For formation of diabodies, the linker sequence will generally be about 5 amino acids in length whereby the scFvs are thereby caused to dimerise. For triabodies, the linker sequence may be only 1 or 2 amino acids in length. The design of scFvs, including diabodies, for use in in vivo imaging and therapy is, for example, described in Todorovska A. et al., *J Immunol Methods,* 2001, Feb. 1; 248 (1-2):47-66, Wörn A. and Plückthun A., *J. Mol. Biol.,* 2001, 305, 989-1010, and Ahmed Z. A. et al., *Clinical and Developmental Immunology,* Vol. 2012, Article ID 980250, Hindawi Pub. Corp., the contents of all of which are incorporated herein in entirety by cross-reference.

When a scFv is employed as the targeting moiety, a respective Lck activator as described herein can be coupled to a free end of its $V_H$ and/or $V_L$ chain via a linker moiety comprising one or more enzymatic cleavage sites as described herein. That is, two Lck activators as described herein may be coupled to the scFv, one of the Lck activators being coupled to the free end of the $V_H$ chain and the other being coupled to the free end of the $V_L$ chain, wherein the Lck activators can be the same or different.

Likewise, a Lck activator as described herein can be coupled to an antibody, binding fragment(s) thereof, or other targeting moiety via a linker moiety typically comprising one or more enzyme cleavage sites as described above in any suitable manner.

In yet other embodiments, a Lck activator as described herein can be provided incorporated into the targeting moiety itself (e.g., an antibody, antibody binding fragment, or scFv) utilising recombinant DNA techniques. In such embodiments, the Lck activator can be coupled to the targeting moiety by a respective coupling moiety comprising enzymatic cleavage site(s) (e.g., a cathepsin cleavage site) at each end of the Lck activator, which join the Lck activator at each end to the targeting moiety. In such embodiments, the Lck activator may be incorporated at any suitable location in the targeting moiety which does not compromise the binding or targeting function of the targeting moiety and which allows for cleavage of the enzymatic cleavage sites in use. For example, a respective Lck activator as described herein may be inserted into one or both of the $V_H$ and $V_L$ chains of an scFv in the manner described above with retention of the binding or targeting function of the scFv, wherein e.g., the Lck activator is flanked by enzyme cleavage sequences selected from MMP and PSA cleavage sequences. A 17 mer peptide (i.e., VPNLRGDLQV-LAQKVA, SEQ ID NO: 72) that targets the β6 integrin subunit specifically and not by other αV-associated β integrin subunits has, for instance, been inserted into the CDR H3 loop of MFE-23, a murine scFv reactive with carcinoembryonic antigen (CEA).

Bi-specific targeting protocols employing more than one targeting moiety for targeting different sites on target tissue or a target cell surface, or as a means to recruit immune effector cells to target cells, is expressly encompassed by the present invention (e.g., bi-specific antibody targeting has recently been review by Weidle U H. et al., *Cancer Genomics & Proteomics,* 2013, 10: 1-18). That is, a single Lck activator as described herein may incorporate two different targeting moieties for targeting different target molecules to one another. As an example, a bi-specific tandem bi-scFv for targeting two different target molecules such as HER2 and CD4 may be provided e.g., with one or more enzyme (e.g., MMP and/or PSA) cleavage sequence(s) between the respective pairs of $V_H$ and $V_L$ chains.

Lck activators in the form of chimeric proteins (i.e., fusion proteins) including a polycationic peptide and optionally an augmenting peptide or other peptide (AP/P) as described herein, and with or without a targeting moiety and/or coupling moiety as described herein, are expressly encompassed as is their use in methods of the invention.

It is, for example, well recognised that cellular immune responses decrease with aging. In particular, lymphocyte proliferation has been shown to be significantly decreased in T lymphocytes from elderly patients and that this is associated with a significant reduction of Lck activity (Fulop T Jr et al, Experimental Gerontology, 1999, 34(2): 197-216). Hence, prophylactic administration of a specific Lck activator may be particularly beneficial in preventing or reducing the prevalence or severity of debilitating infections in the elderly. Moreover, loss of an appropriate T-cell immune response is a side effect of cancer chemotherapy highlighting the need for combinatorial use of Lck activators to overcome immune-suppression associated with cancer therapy that targets multiple tyrosine kinases. Beside a potential role for Lck activation in overcoming drug resistance to anti-cancer drugs as well as inhibition of cell cycle progression in acute leukemia and non-Hodgkin's lymphoma, Lck activation is also relevant in the management of a broad range of pathogenic infections (viral, bacterial, fungal, protozoal and parasitic) as well as various disorders associated with Lck deficiency.

T lymphocyte cells of the immune system are produced by the thymus, and can circulate and reside in specific tissues such as the skin, lymph nodes, and mucosal tissues such as those of the mouth, lung airway, intestine, and vagina. Intraepithelial T cells play pivotal roles in homeostasis and protection from malignancy. Epithelial tissues such as skin, intestine, lung are under constant environmental exposure and form the first line defence against invading microorganisms. The absence of intraepithelial T cells (which are known to express Lck) in mice causes defects in tumour rejection. In particular, the presence of such T cells within epithelia is required for down-regulation of epithelial malignancies including melanoma (Girardi M et al, Science, 2001, 294(5542): 605-9; Schon M P et al, J Invest Dermatology, 2003, 121: 951-962). The maturation of such tissue-specific T cells within the thymus is Lck dependent, and the cells contribute to protection from pathogenic infections and their pathological effects (e.g., of malaria) (Inoue S-I et al, PNAS USA, 2012, 109: 12129-12134). Moreover, gamma-delta (γ/δ) T cells play important roles in immune responses against infections by protozoan parasites, bacteria and viruses. Tissue-specific localisation of such T cells is a requirement for immune surveillance in the skin (Jamieson J M et al, Frontiers in Bioscience, 2004, 9: 2640-2651; Schon M P et al, J Invest Dermatology, 2003, 121: 951-962.

In several T cell lines activated Lck protein has been shown to stimulate interleukin-2 (IL-2) production, a hallmark of T cell activation, in the absence of antigenic stimulation (Luo K, and Sefton B M, Mol Cell Biol, 1992, 12(10): 4724-4732.

Regulatory T cells (Tregs) are a different subset of T cells to gamma/delta T cells and play a critical role in supressing the immune response to cancer. Tregs comprise 5-10% of the peripheral CD4+ T cell pool, recognised by constitutive expression of IL-2R alpha and the transcription factor FOXP3.

The presence of FoxP3 Tregs within tumour-infiltrating lymphocytes is known to correlate with a poor prognosis in various types of human cancer and IL-21 promotes antitumour immunity due to its ability to promote T cell responses and counteract Treg-mediated suppressive effects on the immune system (Kannappan V et al, Cancer Immunol Immunother, 2017, 66(5): 637-645).

The present inventors have demonstrated the Lck activating polypeptides of the present invention increase IL-21 secretion from cells (e.g. FIG. 28). Accordingly, the Lck activating polypeptides described herein have potential for the reduction of numbers of Tregs either ex vivo or in vivo. Indeed, the present inventors have demonstrated that the Lck activting polypeptides described herein reduce Tregs in vitro.

Importantly, the present inventors have surprisingly demonstrated the peptides for activating Lck described herein selectively activate Lck, and do not activate other Src family kinases. For example, FIG. 2 demonstrates Blk, cSrc, Fgr, Fyn, Hck, Lyn and Yes are not activated by the peptides for activating Lck described herein.

Accordingly, in one embodiment, the present invention provides a method of increasing an activity of Lck kinase, the method comprising contacting a Lck kinase with a composition comprising a peptide as described herein.

In one embodiment the peptide or a pharmaceutical composition comprising the peptide is administered to a subject to increase an activity of Lck in vivo As used herein the term "increasing an activity" and "activates" generally refer to an increase of an activity of a kinase, such as phosphotransferase activity (e.g. increasing Y394 phosphorylation of Lck kinase). For example, activation of an enzymatic activity of a kinase refers to any increase in activity of a kinase in the presence of an activator compared to the same activity in the absence of the activator. The term activates a protein kinase also includes an increase of autophosphorylation, an increase of movement from one intracellular location to another upon activation, increase of binding to or release from one or more proteins that anchor a kinase in a given location, or other activity or function of a protein kinase. This increase can be caused by any means including (but not limited to) increasing the probability that a complex forms between a protein kinase and a binding partner of the protein kinase, or an increase the activity of the kinase once bound to its target. Such activation may take place either in vivo or in vitro.

An enzymatic activity of a kinase can be monitored by a variety of methods known to those skilled in the art, e.g., the methods disclosed in Parker, Law, et al., (2000), Development of high throughput screening assays using fluorescence polarization: nuclear receptor-ligand-binding and kinase/phosphatase assays, J. Biomolec. Screening 5(2): 77-88; Bader et al. (2001), Journal of Biomolecular Screening 6(4): 255-64); Liu, F., X. H. Ma, et al. (2001). "Regulation of cyclin-dependent kinase 5 and casein kinase 1 by metabotropic glutamate receptors." Proceedings of the National Academy of Sciences of the United States of America 98(20): 11062-8; Evans, D. B., K. B. Rank, et al. (2002). "A scintillation proximity assay for studying inhibitors of human Tau protein kinase II/Cdk5 using a 96-well format." Journal of Biochemical & Biophysical Methods 50(2-3): 151-61.

Using such standard methods, samples containing the kinase of interest are exposed under the appropriate conditions to radioactive ATP and a synthetic peptide substrate of the appropriate composition to provide a site for phosphorylation. The radioactive phosphate newly associated with the peptide is then measured. Addition of a chemical moiety, such as biotin covalently linked to the substrate peptide, allows binding of the substrate peptide by a streptavidin-coated bead. Bead-bound peptide can be isolated and associated radioactivity measured, or, preferably, radioactivity associated with the substrate peptide can be measured directly using a bead suitable for scintillation proximity assays.

Phosphorylation of a peptide substrate can also be detected via direct binding of phosphospecific antibodies or by measuring displacement of a phosphospecific antibody from a competitor phosphopeptide (see, e.g., Parker, Law et al., 2000, Development of high throughput screening assays using fluorescence polarization: nuclear receptor-ligand binding and kinase/phosphatase assays, J. Biomolec. Screening 5(2): 77-88). Fluorescence methods such as fluorescence resonance energy transfer (FRET) or fluorescence polarization (FP) can be used to detect the specific phosphopeptide-antibody complexes. These methods have the advantage that they employ "homogeneous" detection that is not dependent on isolation of the bound species, but rather depends on changes in fluorescence that occur owing to specific binding in solution.

Methods of producing phosphospecific antibodies are well known in the art. In one embodiment, the methods disclosed in U.S. patent application Ser. No. 09/419,379, by Bibb et al., entitled "Methods of Identifying Agents That Regulate Phosphorylation/Dephosphorylation in Dopamine Signalling," filed Oct. 15, 1999, and Ser. No. 09/687,959, by Bibb et al., entitled "Methods of Identifying Agents That Regulate Phosphorylation/Dephosphorylation in Dopamine Signalling," filed Oct. 13, 2000, (each of which is incorporated herein by reference in its entirety) are used to produce phosphorylation state-specific antibodies having specificity for phosphorylated targets.

Phosphorylation state-specific antibodies against phosphoserine, phosphothreonine, or phosphotyrosine are commercially available. These antibodies are useful for determining whether proteins are phosphorylated in general, and on which residue. Such antibodies are available from commercial sources, (see, e.g., Smith, The Scientist 15[4]:24, Feb. 19, 2001 for list of commercial sources, including Santa Cruz Biotechnology Inc., Sigma RBI, Stratagene, Upstate Biotechnology and Zymed).

Fluorescence resonance energy transfer, or FRET, is widely used for homogeneous assays capable of detecting specific binding of macromolecules. FRET depends on the ability of excited "donor" fluorescent molecules (fluorophores) to transfer their energy to nearby "acceptor" fluorophores rather than emitting light. Thus, when the two fluorophores are brought together in space by binding to a substrate target, fluorescence emitted at the normal donor wavelength is reduced and fluorescence emitted by the acceptor fluorophore increases. Either the decrease in donor fluorescence or the increase in acceptor fluorescence can be used to measure the binding event.

Suitable methods for assessing kinase activity include, the methods disclosed in Bader et al. (2001, A cGMP-dependent protein kinase assay for high throughput screening based on time-resolved fluorescence resonance energy transfer, Journal of Biomolecular Screening 6(4): 255-64) are used to determine activity of e.g., a phosphodiesterase, kinase or protein phosphatase. Bader et al. discloses a cGMP-dependent protein kinase assay for high throughput screening based on time-resolved fluorescence resonance energy transfer ("FRET"), which, as, would be appreciated by one of skill in the art, may be adapted for assays of a phosphodiesterase or protein phosphatase. Samples containing the kinase of interest are exposed to ATP and a synthetic peptide substrate with a kinase-specific phosphorylation site and an amino-terminal biotin moiety. Phosphorylated peptide is detected using allophycocyanin-labelled strepavidin, a phosphopeptide specific antibody, and a Europium-chelate-labelled secondary antibody. Simultaneous binding of the streptavidin and the phosphospecific antibody to a phosphorylated substrate molecule brings the Europium chelate "donor" on the secondary antibody close enough to the allophycocyanin fluorophore "acceptor" for fluorescence resonance energy transfer to occur, measurable as a decrease in Europium emission at 615 nm and an increase in allophycocyanin emission at 665 nm wavelength. The Europium-allophycocyanin donor-acceptor pair is commonly used in order to take advantage of the long fluorescence lifetime of excited Europium, thus the signal is "time-resolved".

Other pairs of fluorophores, such as coumarin and fluorescein isothiocyanate, can be used. Pairs of such molecules that can engage in fluorescence resonance energy transfer (FRET) are termed FRET pairs. In order for energy transfer to occur, the donor and acceptor molecules must typically be in close proximity (up to 70 to 100 Å (Clegg, 1992, Methods Enzymol. 211:353-388; Selvin, 1995, Methods Enzymol. 246: 300-334). The efficiency of energy transfer falls off rapidly with the distance between the donor and acceptor molecules. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Fluorescence polarization measurements can also be used for measuring the activity of a phosphodiesterase, protein kinase or a phosphatase (see, e.g., Parker, Law et al., 2000, Development of high throughput screening assays using fluorescence polarization: nuclear receptor-ligand-binding and kinase/phosphatase assays, J. Biomolec. Screening 5(2): 77-88; Turek et al., 2001, Anal. Biochem. 299: 45-53). Binding of a large specific antibody to a fluorescent small phosphopeptide slows its tumbling rate and increases the fluorescence polarization signal. Accordingly, fluorescence polarization is proportional to the amount of bound fluorescent phosphopeptide. This assay can be used in a competitive mode, in which a fixed concentration of fluorescent peptide and antibody are added to a biological sample, and the presence of non-fluorescent phosphoprotein or phosphopeptide is recorded as a decrease in signal. It can also be used in a direct binding mode, in which phosphate addition (by e.g., a kinase) or removal by e.g., a phosphatase) modulates antibody binding and therefore polarization signal. In a specific embodiment, a fluorescence polarization assay is performed using the methods of Turek et al. (2001, Anal. Biochem. 299: 45-53), in which a product-specific and anti-phosphorylated peptide-specific (e.g., anti-phospho-serine) antibody is used.

Other suitable methods for assessing kinase activity include cell-based assays for phosphorylation. For example, signal transduction based on protein phosphorylation is visualized in vivo, e.g., in single living cells using fluorescent indicators, using methods such as those disclosed in Sato et al. (2002, Fluorescent indicators for imaging protein phosphorylation in single living cells, Nature Biotechnology 20(3): 287-94). Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

Lck Gene Abnormalities and Disease

A number of human diseases are caused by abnormalities at the Lck locus and one example is T-cell acute lymphoblastic leukemia (Converse P J, 2003 Sep. 24. Lymphocyte-specific protein-tyrosine kinase; Lck. Online Mendelian Inheritance in Man., http://www.ncbi.nlm.nih.gov/entrez/dispomim.cgi?id=153390.in). In addition, most DNA changes related to AML occur during a person's lifetime, rather than having been inherited before birth. Some of these acquired changes may have outside causes like radiation or cancer-causing chemicals, but in most cases the reason they occur is not known (http://www.cancer.org/cancer/leukemia-acutemyeloidaml/detailedguide/leukemia-acute-my-eloid-myelogenous-what-causes).

The IL-2/IL-2R Alpha (CD25) Axis in the Immune Response

In chronic infections and cancer, T cells are exposed to persistent antigen and/or inflammatory signals. This scenario is often associated with the deterioration of T cell function: a state called "exhaustion" (Wherry E J & Kurachi M, Nature Reviews Immunology, 2015, 15: 486-499). Exhausted T cells lose robust effector function, express multiple inhibitory receptors at signalling checkpoints such as PD-1, LAG3, CD160, or 2B4 and are defined by an altered transcriptional programme. However, revitalisation of exhausted T cells can re-invigorate immunity that offers new therapeutic targets for persisting infections such as HIV-1, Hepatitis C virus, and for cancer (Wherry & Kurachi, vide supra).

Upon initial activation CD8+ T cells produce a burst of IL-2 but then enter a transient refractory phase during which they maintain some effector functions but lose their capacity to produce IL-2. During this period the CD8+ T cells are dependent upon extrinsic IL-2 provided by CD4+ T cells for their continued proliferation and restoration of full functional capacity (reviewed in Cox M A et al, Trends Immunol, 2001, 32(4): 180-186). IL-2 signals through a trimeric receptor comprised of CD24 (IL-2Ra), CD122 (IL-2Rβ) and the gamma subunit. CD25 is not constitutively expressed but is upregulated following exposure to inflammatory cytokines such as IL-12 and IL-2 itself that regulate the amount and duration of CD25 expression which in turn controls the ability of the responding cells to receive IL-2 dependent signals thereby influencing the formation of effector and memory pools of T cells (Cox et al, vide supra).

CD4+ T cells are principle producers of IL-2 and cooperate with CD8+ T cells to promote the initial expansion of the response as well as the formation of durable memory cells that can elicit protective secondary responses. Importantly, the secretion of IL-2 by CD4+ T cells both upregulates CD25 expression by the responding CD8+ T cells and also provides a source of IL-2 which increases the proliferation of CD25+CD8+ T cells (Cox et al, vide supra, Obar J J et al, PNAS USA, 2010, 107(1): 193-198). Moreover, it has been demonstrated that IL-2 leads to a dose-dependent expression of the alpha chain of the IL-2 receptor on CD25-negative T lymphocytes in the absence of exogenous stimulation (Sereti I et al, Clin Immunol, 2000, 97(3): 266-76). Consequently, the absence of CD4+ T cells or CD25 expression on CD8+ T cells restricts the expansion phase of the pathogenic-specific response. Hence, regulation of cytokine receptor expression such as CD25 is likely to be a rate-limiting step in effector cell generation with higher expression of CD25 allowing the cell to receive stronger IL-2 signals (Cox et al, vide supra).

Besides the importance of CD25 expression in regulating effector and memory cell function in response to chronic sepsis and cancer, CD25-expressing CD8+ T cells have also been found to be potent memory cells in old age and accumulation of these cells in elderly persons appears to be a prerequisite of intact immune responsiveness in the absence of naive T cells in old age (Herndler-Brandstetter D et al, J Immunology, 2005, 175: 1566-1574). This finding has raised the suggestion of new vaccination approaches aimed at supporting the long-term survival of Immune-competent CD8+CD25+ memory T cells in the elderly population (Herndler-Brandstetter et al, vide supra).

The present inventors have demonstrated that the peptides described herein increase IL-12Rβ2 expression on human PBMCs and CD4+ T cells (Example 15, FIG. 17) and CD8+ T cells (Example 28, FIG. 25). Accordingly, the Lck activating peptides described herein can be used to enhance the physiological effects of IL-12R and IL-12 described herein.

Accordingly, in one embodiment, the present invention provides a method of increasing IL-12 secretion from a cell or a population of cells, the method comprising contacting a cell or a population of cells with a composition comprising a Lck activating peptide as described herein.

In one embodiment, the level of IL-12 secretion from a cell or a population of cells is increased when the level of IL-12 secretion from a cell or a population of cells contacted with a composition comprising a Lck activating peptide described herein is compared to the level of IL-12 secretion from a cell or a population of cells not contacted with a Lck activating peptide as described herein (e.g. a control), or a comparison of levels before and after contacting with a composition comprising a Lck activating peptide described herein.

In another embodiment, the present invention provides a method of increasing IL-12R expression on a cell or in a population of cells, the method comprising contacting a cell or a population of cells with a composition comprising a Lck activating peptide as described herein.

In one embodiment, the level of IL-12R expression on a cell or a population of cells is increased when the level of IL-12R expression on a cell or a population of cells contacted with a composition comprising a Lck activating peptide described herein is increased when compared to the level of IL-12R on a cell or a population of cells not contacted with a Lck activating peptide as described herein (e.g. a control), or a comparison of levels before and after contacting with a composition comprising a Lck activating peptide described herein.

In one embodiment, the IL-12R is IL-12Rβ1 and/or IL-12Rβ2.

In another embodiment, the present invention provides a method for increasing IL-12 responsiveness of a cell, the method comprising contacting a cell or a population of cells with a composition comprising a Lck activating peptide as described herein.

In one embodiment, the level of responsiveness of a cell or a population of cells to IL-12 is increased when the level of responsiveness of a cell or a population of cells contacted with a composition comprising a Lck activating peptide described herein to IL-12 is compared to the level of responsiveness of a cell or a population of cells to IL-12 not contacted with a Lck activating peptide as described herein (e.g. a control), or a comparison of levels before and after contacting with a composition comprising a Lck activating peptide described herein.

In a preferred embodiment, the cell is a CD4+ T cell, CD8+ T cell or an NK cell.

As discussed above, the methods described herein can be performed on a cell of a population of cells, either in vivo (e.g. in a subject) or in vitro (e.g. ex vivo).

During chronic viral infection or a tumour-bearing state, T cell memory formation and function becomes substantially altered due to a step-wise impairment of effector function and proliferative capacity of responding antigen-specific T cells that ultimately affects the ability to confer host protection (Jin H-T et al, BMB Reports, 2011, 44(4): 217-231). In the tumour environment CD8+ tumour-infiltrating lymphocytes (TILs) show low levels of CD25 (IL-2R alpha) expression and thus are refractory to IL-2 signalling, indicating that they are unable to proliferate, produce effector cytokines and differentiate into functional memory cells (Mumprecht S et al, Blood, 2009, 114: 1528-1536). For example, CML-specific CD8+ T cells exhibit decreased production of effector cytokines such as IFN-γ, TNFα and IL-2 in a retroviral-induced murine CML model (Mumprecht et al, vide supra).

CD25 expression is positively correlated with the cytotoxic activity of NK cells. The present inventors have demonstrated the Lck activating polypeptide RSKAKNPLY-RRRRRRRRR (SEQ ID NO: 24, IK14800) also increases the relative expression of CD25 on NK cells in splenocytes in Lewis Lung Cancer mice (data not shown).

Accordingly, in one aspect the present invention provides a method of enhancing a cytotoxic cell function, the method comprising contacting a cytotoxic cell or a population of cytotoxic cells with a composition comprising a Lck activating peptide as described herein.

In one embodiment, the present invention provides a method of reducing exhaustion of a T cell, the method comprising contacting a T cell with a composition comprising a Lck activating peptide as described herein.

The term "exhaustion" refers to T cell exhaustion as a state of T cell dysfunction that arises from sustained TCR signalling that occurs during many chronic infections and cancer. It is distinguished from anergy in that it arises not through incomplete or deficient signalling, but from sustained signalling. It is defined by poor effector function, sustained expression of inhibitory receptors and a transcriptional state distinct from that of functional effector or memory T cells. Exhaustion prevents optimal control of infection and tumours. Exhaustion can result from both extrinsic negative regulatory pathways (e.g., immunoregulatory cytokines) as well as cell intrinsic negative regulatory (costimulatory) pathways (PD-1, B7-H3, B7-H4, etc.). In one embodiment, the level of reduction of exhaustion is as least 10%, alternatively 20%, 30%, 40%, 50%, 60%, 70%, 30%, 90%. The manner of measuring exhaustion is known to one of ordinary skill in the art.

In one embodiment, the level of exhaustion of a T cell or a population of T cells is reduced when the level of a T cell function of a T cell or a population of T cells contacted with a composition comprising a Lck activating peptide described herein is compared to the level of a T cell function of a T cell or a population of T cells not contacted with a Lck activating peptide as described herein (e.g. a control), or a comparison of levels before and after contacting with a composition comprising a Lck activating peptide described herein.

In the setting of acute infection, where antigen and/or inflammation is cleared, the effector CD8+ T cells further differentiate into functional memory CD8+ T cells that can produce multiple cytokines (IFN-γ, TNFα and IL-2) and mount robust recall responses upon secondary infection. By contrast, during chronic infections, antigen and inflammation persist after the effector phase. As infection continues and T cell stimulation continues, T cells lose effector function in a hierarchical manner and become exhausted. Typically, functions such as IL-2 production and cytokine polyfunctionality, as well as high proliferative capacity, are lost early. This is followed by defects in IFN-γ and TNFα production. T cell exhaustion is also accompanied by a progressive increase in the amount and diversity of inhibitory receptors indicated above which, upon binding to their respective ligands, results in dysfunctional T cells.

Given that co-expression of multiple inhibitory receptors is a cardinal feature of T cell exhaustion simultaneous targeting of these receptors has been shown to result in synergistic reversal of T cell exhaustion (Wherry & Kurachi, vide supra). For example, in chronic LCMV infection simultaneous blockade of IL-10 and the Programmed Death Receptor 1 (PD-1) pathway in mice leads to synergistic reversal of CD8+ T cell exhaustion and enhances viral control, as has combining IL-2 treatment with blockade of the PD-1 pathway (Wherry & Kurachi, vide supra). In addition, in a LCMV mouse model, CD25-competent CD8+ T cells have been shown to expand to 5-fold higher numbers than CD25-deficient T cells after infection with LMCV (Bachmann M F et al, Eur J Immunol, 2007, 37:1502-1512). Moreover, these investigators showed that in contrast to acute/resolved infection where induction and maintenance of CD8+ T cells was largely independent of CD25 signalling, CD25 signalling was crucial for the for the maintenance of virus-specific CD8+ T cells during persistent viral infection.

Another inhibitory receptor, CTLA-4 is selectively upregulated in chronic HIV infection in CD4+ T cells but not in CD8+ T cells and this correlates with decreased ability of the T cells to produce IL-2 in response to viral antigen indicating a reversible immune-regulatory pathway selectively associated with CD4+ T cell dysfunction (Kaufmann D E et al, Nature Immunology, 2007, 8: 1246-1254). Hierarchical loss of T cell function is associated with duration of antigenic exposure, inflammation and increased expression of inhibitory molecules (PD-1, CD160, 2B4) (Wherry J et al, Nature Immunology, 2011). In turn, secretion of cytokines by CD4+/CD8+ T cells decreases (e.g., IL-2, TNFα and IFN-γ). In parallel, in conditions of chronic sepsis such as chronically infected HIV-1 patients the phenotype of HIV-specific CD8+ T cells reveals an accumulation of checkpoint molecules (e.g., PD-1, CD160).

T cell exhaustion is likely to be a significant factor in failed pathogen clearance during chronic HIV infection and is, in part, regulated by negative regulatory pathways (reviewed in Porichis F & Kaufamm D E, Curr Opin HIV AIDS, 2011, 6(3): 174-180). For example, the CTLA-4 inhibitory immune-regulatory receptor as well as the programmed cell death receptor-1 (PD-1) are up-regulated in CD4+ T cells but not CD8+ T cells in HIV-infected subjects (Kaufmann D E et al, Nature Immunol, 2007, 8: 1264-1254). This correlates with the inability of CD4+ T cells to produce IL-2 in response to viral antigen. T cells from HIV patients are impaired in their capacity to produce IL-2 and proliferative responses to recall antigens are disturbed early in HIV infection and can be restored in vitro by IL-2 (Fauer A S & Panteleo G (Eds), Immunopathogenesis of HIV infection, Springer, doi: 10.1007/978-3-642-60867-4, pp 41-42).

Hence, suppression of proliferation of HIV-specific CD4+ T cells in the context of high levels of antigen may be a mechanism by which the precursor frequency of virus-specific CD4+ T cells is limited (McNeil A C et al, PNAS USA, 2001, 98: 13878-3883). Moreover, blockade of the PD-1 pathway with PD-L1 blocking antibody increases HIV-specific CD4+ T cell proliferation (Porichis & Kaufmann, vide supra).

But not only CD4+ T cells become exhausted and ineffective upon subsequent antigen challenge, so do CD8+ T cells. In HIV infection loss of CD4+ T cells is associated with increasing exhaustion of CD8+ T cells and disease progression and the impact of changes in CD4+ T cell response on CD8+ T cell exhaustion is highly relevant (Wherry E J & Kurachi M, Nature Reviews, 2015, 15: 486-499). Exhausted CD8+ T cell also have high expression of PD-1 whereas senescent cells do not (reviewed in Wherry & Kurachi, vide supra). Moreover, combining IL-2 treatment with blockade of the PD-1 mediated inhibitory pathway has been shown to have striking synergistic effects for re-invigorating exhausted CD8+ T cells and decreasing the viral load (Wherry & Kurachi, vide supra). Ex vivo proliferation of HIV-1 specific CD8+ T cells critically depends on IL-2 (Lichterfield M et al, JEM, 2004, 200: 701-712). Taken together, a loss of HIV-specific CD8+ T cell function can be restored in chronic infection by augmentation of HIV-specific CD4+ T cell helper function.

Another phenotypic marker of T cell exhaustion is Tim-3 expression on CD8+ T cells that has led to the suggestion that targeting both Tim-3 and PD-1 might be the most effective means by which to overcome CD8 T cell dysfunction in chronic viral infections (Jin H T et al, PNAS USA, 2010, 107(33): 14733-8). Moreover, recent literature reports emphasise the potential importance of Lck in relation to Tim-3 in CD8+ T cell exhaustion. For example, galectin-9, a physiological ligand for Tim-3 binds to the receptor phosphatase CD45 which, when present at high levels, dephosphorylates Y394 on Lck, thereby, decreasing Lck activity (Clayton K L et al, J Immunol, 2014, 192(2): 782-791).

Furthermore, galectin-9 is able to increase levels of Tim-3 as well as CD45 within CD3 signalling rafts and high concentration of this phosphatase at the synapse has been suggested as a means whereby Lck is negatively regulated leading to dampening of TCR signalling (Clayton K L et al, J Immunol, 2014, 192(2): 782-791). In addition, analysis of cell lysates from T cells activated through ligation of the TCR with anti-CD3/CD28 leads to recruitment of Lck to Tim-3 and it has also been proposed that sequestration of Lck by Tim-3 depletes the intracellular pool of Lck resulting in incomplete activation of the TCR by prohibiting phosphorylation of the ITAM motifs on the TCR chains (Tomkowicz B et al, Plos One, 2015, 10(10): e0140694 (doi: 10.1371/journal.pone.0140694).

In cancer it is now clear that tumours co-opt certain immune-checkpoint pathways as a major mechanism of immune resistance, particularly against T cells that are specific for tumour antigens and clinical trials with antibody blockers of Cytotoxic T-lymphocyte associated antigen 4 (CTLA-4) and Programmed Cell Death Protein1 (PD-1) have demonstrated enhanced anti-tumour immunity with the potential to produce durable clinical responses (Pardoll D M, Nature Reviews Cancer, 2012, 12: 252-264).

Even though CTLA-4 is expressed by activated CD8+ effector T cells, the major physiological role of CTLA-4 seems to be through distinct effects on the two major subsets of CD4+ T cells: down-modulation of helper T cell activity and enhancement of regulatory T (Treg) cell immunosuppressive activity (reviewed in Pardoll, vide supra). However, blockade of the PD-1 pathway in cancer immunotherapy may also enhance immune responses by diminishing the number and/or suppressive activity of intra-tumoural Treg cells (Pardoll, vide supra). Moreover, PD-1 blockade not only enhances the activity of effector T cells in tissues and in the tumour micro-environment but also likely enhances natural killer cell activity in tumours and antibody production through direct effect on PD-1 B cells (Pardoll, vide supra). In cancer, the major PD-1 ligand expressed is PD-L1 and high expression of PD-L1 has been found in nearly all cancer types (Pardoll, vide supra). Hence, treatments that target one or more inhibitory checkpoints either alone or in combination are considered to hold great potential for the systemic control of cancer (Allison J P, JAMA, 2015, 314(11): 1113-1114; Creelan B C, cancer Control, 2014, 21(1): 80-9).

The present inventors have demonstrated that the peptides described herein activate Lck, as shown in FIGS. 1, 2, 4, 5 and 6, and increase Lck phosphorylation at Y394, as shown in FIG. 3 and FIG. 40.

Accordingly, the Lck activating peptides described herein can be used to increase the physiological effects of Lck described herein.

In one embodiment, the present invention provides a method of increasing an activity of Lck, the method comprising contacting a Lck kinase with a composition comprising a Lck activating peptide as described herein. The present invention also provides a method of increasing Y394 phosphorylation of Lck kinase, the method comprising contacting a Lck kinase with a composition comprising a Lck activating peptide as described herein.

In one embodiment, the activity of Lck contacted with a Lck activating peptide as described herein is increased when the level of Lck activity when contacted with a composition comprising a Lck activating peptide described herein is compared to the activity of Lck not contacted with a Lck activating peptide as described herein (e.g. a control), or a comparison of levels before and after contacting with a composition comprising a Lck activating peptide described herein. Similarly, the level of Y394 phosphorylation of Lck kinase is increased when the level of Y394 phosphorylation of Lck kinase contacted with a Lck activating peptide as described herein is compared to the level of Y394 phosphorylation of Lck kinase not contacted with a Lck activating peptide as described herein (e.g. a control), or a comparison of levels before and after contacting with a composition comprising a Lck activating peptide described herein.

Activities of Lck, including downstream effects of Lck activation, are described herein.

As used herein the term "contacting" refers to the bringing together of indicated moieties (e.g. a Lck activating peptide as described herein and Lck kinase) in an in vitro system or an in vivo system. For example, "contacting" a protein kinase with an activator as described herein includes the administration of a compound of the present invention to an individual or patient, such as a human, having the kinase, as well as, for example, introducing an activator as described herein into a sample containing a cellular or purified preparation containing the kinase.

The present inventors have also demonstrated that the peptides described herein increase IL-2 secretion from human T cells (FIG. 7, FIG. 8, FIG. 9, FIG. 29, FIG. 33, FIG. 34, FIG. 35, and FIG. 37). Importantly, pre-treatment of cells with the Lck activating peptides described herein increases IL-2 secretion when T cells are subsequently stimulated (e.g. see FIG. 29).

Accordingly, the Lck activating peptides described herein can be used to increase the physiological effects of IL-2 described herein.

In one embodiment, the present invention provides a method of increasing IL-2 secretion from a cell or a population of cells, the method comprising contacting a cell with a composition comprising a Lck activating peptide as described herein.

In one embodiment, the level of IL-2 secretion from a cell or a population of cells is increased when the level of IL-2 secretion from a cell or a population of cells contacted with a composition comprising a Lck activating peptide described herein is compared to the level of IL-2 secretion from a cell or a population of cells not contacted with a Lck activating peptide described herein (e.g. a control), or a comparison of levels before and after contacting with a composition comprising a Lck activating peptide described herein.

In one embodiment, the cell is a T cell.

The present invention provides methods of inducing proliferation of a cell, the methods comprising contacting a cell with a composition comprising a Lck activating peptide as described herein.

As used herein, the term proliferation includes an increase in a number of cells, or an increase in the number of cell divisions of a cell or a population of cells, and is used interchangeably with the term expansion. In one embodiment, the level of cell proliferation of a cell or a population of cells is increased when the level of proliferation of a cell or a population of cells contacted with a Lck activating peptide as described herein is compared to the level of cell proliferation of a cell or a population of cells not contacted with a Lck activating peptide as described herein (e.g. a control), or a comparison of levels before and after contacting with a composition comprising a Lck activating peptide described herein.

In another embodiment, the present invention provides methods of increasing the proliferation of a population of cells, the methods comprising contacting a population of cells with a composition comprising a Lck activating peptide as described herein.

In one embodiment the cell is, or the population of cells comprises, a cell selected from the group consisting of a CD4+ T cell, a CD8+ T cell, a NK cell, or a dendritic cell.

In another embodiment, the cell is, or the population of cells comprises, a naïve cell.

In a preferred embodiment, the methods are performed on a cell or a population of cells in vivo or in vitro. In another preferred embodiment, the method is performed on a cell or a population of cells ex vivo.

In another embodiment, the present invention provides methods of increasing proliferation of a cell or a population of cells in an animal, the methods comprising administering to an animal a composition comprising a Lck activating peptide as described herein.

A composition comprising a Lck activating peptide as described herein is typically administered in an effective amount. By the term "effective amount" (for example a "therapeutically effective amount" or a "pharmaceutically effective amount") as used herein refers to an amount of a Lck activating peptide as described herein that allows activation of a Lck kinase activity, or increases or decreases the molecular or cellular response. Said "effective amount" will vary from subject to subject, depending on the age and general condition of the individual and with the factors such as the particular condition being treated or prevented, the duration of the treatment, previous treatments and the nature and pre-existing duration of the condition.

In some embodiments, a Lck activating peptide as described herein is typically administered in an effective amount to a subject without a symptom of a disease or a condition to activate Lck, for example, to healthy individuals of any age.

Specifically, an effective amount of an activator defines an amount of a Lck activating peptide that can be administered to a subject without excessive or non-tolerable toxicity, irritation, allergic response, or other problem or complication, commensurate with a reasonable benefit/risk ratio, but one that is sufficient to provide the desired effect as assessed by an appropriate technique such as those disclosed throughout this specification. Thus, while it is not possible to specify an exact effective amount, those skilled in the art will be able to determine an appropriate "effective" amount in any individual case using routine experimentation and background general knowledge. A therapeutic result in this context includes eradication or lessening of symptom. A therapeutic result need not be a complete amelioration of the condition (i.e. a cure).

In another embodiment, the present invention provides a cell or a population of cells derived from a cell or population of cells contacted with a composition comprising a Lck activating peptide as described herein. For example, a T cell, a NK cell or a dendritic cell, or a population thereof, derived from a cell or population of cells derived from the methods described herein (e.g. following contacting, in vivo or in vitro, a cell or a population of cells with a composition comprising a Lck activating peptide as described herein). In another aspect the present invention provides methods and uses of the cells or cell populations described herein, for example, for adoptive cell transfer.

The present inventors have also demonstrated the Lck activating peptides described herein increase IL-2Ra (CD25) expression on a T cell line (FIG. 10 and FIG. 12), CD4+ and CD8+ T cells within PBMCs (FIG. 13), and exhausted CD4+ T cells (FIG. 11).

Accordingly, the Lck activating peptides described herein can be used to increase the physiological effects of IL2R (e.g. responsiveness to IL-2) described herein. In one embodiment, the present invention provides a method of increasing IL-2 responsiveness of a cell or in population of cells, the method comprising contacting a cell or a population of cells with a composition comprising a Lck activating peptide as described herein.

In one embodiment, the level of responsiveness of a cell or a population of cells to IL-2 is increased when the level of responsiveness of a cell or a population of cells contacted with a composition comprising a Lck activating peptide described herein to IL-2 is compared to the level of responsiveness of a cell or a population of cells to IL-2 not contacted with a Lck activating peptide as described herein (e.g. a control), or a comparison of levels before and after contacting with a composition comprising a Lck activating peptide described herein.

In one embodiment, the present invention provides a method of increasing IL-2Ra (CD25) expression on a cell or in a population of cells, the method comprising contacting a cell or a population of cells with a composition comprising a Lck activating peptide as described herein.

In one embodiment, the present invention provides a method of increasing CD25 expression in the presence of a checkpoint inhibitor, the method comprising contacting a cell or a population of cells with a composition comprising a Lck activating peptide as described herein.

In one embodiment, the present invention provides a method of increasing IL-2RB (CD122) expression on a cell or in a population of cells, the method comprising contacting a cell or a population of cells with a composition comprising a Lck activating peptide as described herein.

In one embodiment, the level of IL-2Ra or IL-2RB expression on a cell or a population of cells is increased when the level of IL-2Ra or IL-2RB expression on a cell or a population of cells contacted with a Lck activating peptide as described herein is compared to the level of IL-2Ra or IL-2RB expression on a cell or a population of cells not contacted with a Lck activating peptide as described herein (e.g. a control), or a comparison of levels before and after contacting with a composition comprising a Lck activating peptide described herein.

In one embodiment the cell is, or the population of cells comprises, a naïve cell.

In one embodiment, the cell is a T cell. In a preferred embodiment, the T cell is a CD4+ T cell or a CD8+ T cell.

As discussed above, the methods described herein can be performed on a cell of a population of cells, either in vivo (e.g. in a subject) or in vitro (e.g. ex vivo). As is also discussed above, the present invention provides cells and populations of cells derived from the methods described herein, and methods and uses of the cells or cell populations described herein.

The peptides described herein increase the proliferation of CD8+ T cells (FIG. 20, FIG. 21, and FIG. 27) and the proliferation of CD28+ CD8+ T cells (FIG. 24).

Accordingly, the Lck activating peptides described herein can be used to increase the physiological effects of CD28+ T cells described herein.

In one embodiment, the present invention provides a method of increasing CD28 expression on a cell or in a population of cells, the method comprising contacting a cell or a population of cells with a composition comprising a Lck activating peptide as described herein.

In one embodiment, the level of CD28 expression on a cell or a population of cells is increased when the level of CD28 expression on a cell or a population contacted with a Lck activating peptide as described herein is compared to the level of CD28 expression on a cell or a population of cells not contacted with a Lck activating peptide as described herein (e.g. a control), or a comparison of levels before and after contacting with a composition comprising a Lck activating peptide described herein.

In one embodiment, the present invention provides a method of increasing proliferation of a T cell, the method comprising contacting a T cell with a composition comprising a Lck activating peptide as described herein. In a preferred embodiment, the T cell is a CD8+ T cell.

Demographic evolution represents a challenge for public health. Global population, especially in the developed countries is aging and the proportion of the population above 60 years will increase from 8% in 1950 to an expected 21% by 2050 (reviewed in Compte N et al, PLOS One, 2013, doi: 10.1371/journal.pone.0065325). Decline in immune function is the hallmark of aging and older people present increasing rates and severity of bacterial and viral infections, cancer and reduced vaccine responses (Compte et al, vide supra).

The human immune system progressively deteriorates with age and this defect is manifested in a reduced capacity to induce immunological memory to vaccines and infections. Protection from pathogens and tumour development depends on the generation and maintenance of a diverse TCR repertoire and at older ages TCR diversity is markedly reduced thus making it difficult to combat new pathogens and mount vigorous recall responses to recurrent infections (reviewed in Moro-Garcia M A et al, Front Immunol, 2013, doi.org/10.3389/fimmu.2013.00107).

The reduced ability to fight against pathogens and respond to vaccination are reflected in the observed changes in CD4+ and CD8+ T cells during aging and it has been proposed that preventing the deterioration of the adaptive immune response in aging could be achieved by "rejuvenation" of the CD4+ T cell population (Moro-Garcia M A et al, Front Immunol, 2013, doi.org/10.3389/fimmu.2013.00107).

Loss of CD28 expression is a hallmark of the age-associated decline of CD4+ T cell function. CD28 plays a pivotal role during T cell activation, such as inducing cytokine production (IL-2) and promoting cell proliferation, so the lack of this co-stimulatory signal during activation results in only partial activation or even an anergic state of T cells (Godlove J et al, Exp Gerontol, 2007, 42(5): 412-5). In this way, the accumulation of CD28-negative T cells is associated with a reduced overall immune response to pathogens and vaccines in the elderly (Sauerwein-Teissl M et al, J Immunol, 2002, 168: 5893-5899) and CD4+/CD28−T cells can comprise up to 50% of the total CD4+ T cell compartment in some individuals older than 65 years (Vallejo An et al, J Immunol, 2000, 165: 6301-6307).

During aging in mammals there is a gradual decline in thymus integrity and function and thymic involution is considered an important factor in immune senescence (Li L et al, J Immunol. 2004, 172(5): 2909-2916). Murine studies have shown accelerated thymic involution in IL-12 knockout mice and IL-12 has been shown to provide a strong synergistic effect to augment IL-2 induced thymocyte proliferation both in aged wild type and IL-12 knockout mice (Li et al, vide supra).

The present inventors have demonstrated the Lck activating peptides described herein increase CD28 expression on CD8+ and CD4+ T cells (Example 21, FIG. 22, FIG. 30, and FIG. 31).

In another embodiment the present invention provides a method of treating and/or preventing age related immune dysfunction in a subject, the method comprising administering to the subject a composition comprising a Lck activating peptide as described herein.

In one embodiment the disease or condition characterised by inhibition or down-regulation of Lck or Lck activity is selected from the group consisting of pathogenic infections, sepsis (e.g., chronic sepsis) from pathogenic infections, immune deficiency disorders, reduced immune response, lowered T cell count, T cell abnormalities, T-cell exhaustion, and T cell checkpoint blockade.

In a preferred embodiment, the disease or condition is cancer.

As used herein, the term "age related immune dysfunction" includes the age-related immune changes discussed above.

In another embodiment the present invention provides a method of treating and/or preventing at least one symptom associated with a disease or condition characterised by inhibition or down-regulation of Lck or Lck activity, comprising administering to a subject a composition comprising a peptide as described herein.

As used herein the term "treatment" includes therapeutic treatment as well as prophylactic treatment (either preventing the onset of a disorder or a symptom of a disorder (including an age related change) altogether or delaying the onset of a symptom of a disorder (including an age related change), or a preclinically evident stage of a disorder in an individual).

The term "prevention" includes either preventing the onset of a disorder or a symptom of a disorder altogether or delaying the onset of disorder or a symptom of a disorder, or a preclinically evident stage of a disorder in an individual. This includes prophylactic treatment of those at risk of developing a disease, such as a cancer, for example. "Prophylaxis" is another term for prevention.

In addition, compromised IFN gamma production in the elderly contributes to the immune risk phenotype and the reduced capacity to produce this cytokine in the elderly on stimulation with bacterial products or viral antigens also contributes to disease susceptibility with aging (Ouyang Q et al, Eur Cytokine Netw, 2002, 13(4): 392-4). Notably, aged mice exhibit a diminished CD8+ cytotoxic T lymphocyte (CTL) response to influenza virus thought to be due, in part, to reduced IL-18 receptor (IL-18R) mRNA expression and both IL-12 and IL-18 can significantly increase IFN gamma production in aged mice thereby reversing the CD8+ CTL deficiency associated with aging (Zhang Y et al, J Interferon & Cytokine Res, 2004, doi.org/10. 1089/107999001753238097).

The present inventors have demonstrated the Lck activating peptides described herein increase IFNg production by CD4+ T cells (FIG. 18) and CD8+ T cells (FIG. 19).

Accordingly, the Lck activating peptides described herein can be used to increase the physiological effects of IFNg described herein.

In one embodiment, the present invention provides a method of increasing cytokine secretion from a cell or a population of cells, the method comprising contacting a cell or a population of cells with a composition comprising a Lck activating peptide as described herein.

In a preferred embodiment, the cytokine is IFNg.

In one embodiment, the level of cytokine (e.g. IFNg) secretion from a cell or a population of cells is increased when the level of cytokine (e.g. IFNg) secretion from a cell or a population of cells contacted with a composition comprising a Lck activating peptide described herein is increased compared to the level of cytokine (e.g. IFNg) secretion from a cell or a population of cells not contacted with a Lck activating peptide as described herein (e.g. a control) or a comparison of levels before and after contacting with a composition comprising a Lck activating peptide described herein.

Natural Killer (NK) cells also play an important role in immunity against infection and cancer. Age-related functional NK cell deficiency is well documented in humans and mice and injection of soluble IL-15/IL-15Ralpha complexes into aged mice has been shown to completely reverse age-related NK cell deficiency (Chiu B-C et al, J Immunol, 2013, doi: 10.4049/jimmunol.1301625). Moreover, IL-15 plays a critical role in the immune response to early infection and has been shown to increase the cytolytic properties of CD4+CD28−T cells and enhance their antigen-specific responses (Alonso-Arias R et al, Aging Cell, 2011, 10: 844-852).

IL-15 promotes the development, function and survival of NK and CD8+ T cells, and signalling by IL-15 occurs via the CD215 (IL-15R) receptor. The present inventors have demonstrated the Lck activating peptides described herein increase IL-15 secretion (FIG. 23) and CD215 expression on CD4+ and CD8+ T cells (FIG. 23, Example 22). Accordingly, the Lck activating peptides described herein can be used to enhance the physiological effects of IL-15R and IL-15 described herein.

Accordingly, in one embodiment, the present invention provides a method of increasing IL-15 secretion from a cell or a population of cells, the method comprising contacting a cell or a population of cells with a composition comprising a Lck activating peptide as described herein.

In one embodiment, the level of IL-15 secretion from a cell or a population of cells is increased when the level of IL-15 secretion from a cell or a population of cells contacted with a composition comprising a Lck activating peptide described herein is increased compared to the level of IL-15 secretion from a cell or a population of cells not contacted with a Lck activating peptide described herein (e.g. a control), or a comparison of levels before and after contacting with a composition comprising a Lck activating peptide described herein.

In one embodiment, the present invention provides a method of increasing IL-15R (CD215) expression on a cell, the method comprising contacting a cell with a composition comprising a Lck activating peptide as described herein.

In one embodiment, the level of IL-15R expression on a cell or a population of cells is increased when the level of IL-15R expression on a cell or a population of cells from a cell or a population of cells contacted with a composition comprising a Lck activating peptide described herein is increased when compared to the level of IL-15R on a cell or a population of cells not contacted with a Lck activating peptide as described herein (e.g. a control), or a comparison of levels before and after contacting with a composition comprising a Lck activating peptide described herein In another embodiment, the present invention provides a method for increasing IL-15 responsiveness of an NK cell, the method comprising contacting an NK cell with a composition comprising a Lck activating peptide as described herein.

In one embodiment, the level of responsiveness of a cell or a population of cells to IL-15 is increased when the level of responsiveness of a cell or a population of cells contacted with a composition comprising a Lck activating peptide described herein to IL-15 is increased compared to the level of responsiveness of a cell or a population of cells to IL-15 not contacted with a Lck activating peptide as described herein (e.g. a control), or a comparison of levels before and after contacting with a composition comprising a Lck activating peptide described herein.

In a preferred embodiment, the cell is a CD4+ T cell or a CD8+ T cell.

Without wishing to be bound by theory, increased responsiveness to IL-15 is expected to modulate the development, function and survival of NK and CD8+ T cells.

The present inventors have also demonstrated the Lck activating peptides described herein increase expression of pSTAT4 on CD4+ and CD8+ T cells (Example 25), and NK cells (FIG. 32).

Accordingly, the Lck activating peptides described herein can be used to enhance the physiological effects of pSTAT4 described herein.

For example, T helper type 1 (TH1) cell development involves interferon-γ (IFN-γ) signalling through signal transducer and activator of transcription 1 (STAT1) and interleukin-12 (IL-12) signalling through STAT4 activation.

Accordingly, in one embodiment, the present invention provides a method for increasing expression of pSTAT4 in a CD4+ T cell, a CD8+ T cell or an NK cell, the method comprising contacting a CD4+ T cell, a CD8+ T cell or an NK cell with a composition comprising a Lck activating peptide as described herein.

Interleukin-2 (IL-2) is a growth-promoting cytokine that is produced primarily by helper T cells and regulates growth and function of various cells that are involved in cellular and humoral immunity. The expression of IL-2 decreases with age and this decline has been shown to parallel the age-related decrease in immunologic function (Pahlavani M A & Richardson A, Mech Ageing Dev, 1996, 89(3): 125-54). Moreover, IL-21 administration to aged mice has been shown to rejuvenate their peripheral T cell pool by triggering de novo thymopoiesis (A l-Chami E et al, Aging Cell, 2016, 15(2): 349-60). For example, stimulation of T cells derived from rIL-21-treated aged mice displayed enhanced activation of Lck kinase which ultimately boosted their IL-2 production, CD25 expression, and proliferation capabilities in comparison with T cells derived from control aged mice (Al-Chami et al, vide supra).

The present inventors have demonstrated the Lck activating peptides described herein increase IL-2Ra (CD25) expression on a T cell line (FIG. 10), CD4+ T cells (FIG. 11), CD4+ and CD8+ cells within PBMCs (FIG. 13), and increase the proliferation of CD8+ T cells (FIG. 20, FIG. 21, FIG. 27), and the proliferation of NK cells (Example 20) Accordingly, the Lck activating peptides described herein can be used to increase the physiological effects of IL-2Ra described herein.

The Lck activating peptides described herein can be used to increase the physiological effects of CD8+ T cells described herein.

The Lck activating peptides described herein can be used to increase the physiological effects of CD4+ T cells described herein.

The Lck activating peptides described herein can be used to increase the physiological effects of NK cells described herein.

In one embodiment, the present invention provides a method of increasing IL-2Ra (CD25) expression on a T cell, the method comprising contacting a T cell with a composition comprising a Lck activating peptide as described herein. In another embodiment, the present invention provides a method for increasing IL-2 responsiveness of a T cell, the method comprising contacting a T cell with a composition comprising a Lck activating peptide as described herein. In a preferred embodiment, the T cell is a CD4+ T cell or a CD8+ T cell.

In another embodiment, the present invention provides a method of inducing proliferation of a cell, the method comprising contacting a cell with a composition comprising a Lck activating peptide as described herein. In a preferred embodiment, the cell is a CD8+ T cell or a NK cell.

In another embodiment, the present invention provides a method of increasing the proliferation of a population of cells, the method comprising contacting a population of cells with a composition comprising a Lck activating peptide as described herein. In a preferred embodiment, the cell population is a population of CD4+ T cells, CD8+ T cells or a NK cells. As indicated above, the methods can be performed on a cell or a population of cells in vivo or in vitro. In another preferred embodiment, the method is performed on a cell or a population of cells ex vivo.

In another embodiment, the present invention provides a population of cells derived from a cell or population of cells contacted with a composition comprising a Lck activating peptide as described herein. For example, a T cell, a NK cell or a dendritic cell, or a population thereof, derived from a cell or population of cells contacted with a composition comprising a Lck activating peptide as described herein.

In one aspect the present invention provides methods and uses of the cells or cell populations described herein. For example, the cells or cell populations described herein can be used for adoptive cell therapies, including CAR T cell therapies.

The cytokine IL-21 has been shown to be critical for the development of an optimal vaccine-induced primary response against rabies infections and, in combination with IL-7, to possess potent adjuvant efficacy in whole cell cancer vaccines (Dorfmeier C L et al, PLoS Negl Trop Di, 2013, doi: 10.1371/journal.pntd.0002129; Gu Y-Z et al, Scientific Reports, 2016, doi: 10.1038/srep32351).

The present inventors have demonstrated the Lck activating peptides described herein increase IL-21 production by T cells (FIG. 28).

Accordingly, the Lck activating peptides described herein can be used to increase the physiological effects of IL-21 described herein.

In one embodiment, the present invention provides a method of increasing IL-21 secretion from a cell or a population of cells, the method comprising contacting a cell or a population of cells with a composition comprising a Lck activating peptide as described herein.

In one embodiment, the level of IL-21 secretion from a cell or a population of cells is increased when the level of IL-21 secretion from a cell or a population of cells contacted with a composition comprising a Lck activating peptide described herein is increased compared to the level of IL-21 secretion from a cell or a population of cells not contacted with a Lck activating peptide described herein (e.g. a control), or a comparison of levels before and after contacting with a composition comprising a Lck activating peptide described herein.

In one embodiment, the present invention provides a method of inducing an immune response in a subject, comprising administering to the subject a composition comprising a Lck activating peptide as described herein.

In one embodiment, the present invention provides a method of vaccinating a subject in need thereof, comprising administering to a subject a composition comprising a Lck activating peptide as described herein simultaneously or sequentially with a vaccine. The present invention also provides a composition comprising a Lck activating peptide as described herein formulated with a vaccine (e.g. vaccine antigen).

The present inventors have demonstrated that the Lck activating polypeptides of the described herein can rescue CD25 expression in the presence of the checkpoint inhibitor PD-L1 (Example 11).

Accordingly, in one embodiment, the present invention provides a method of treating cancer in a subject, comprising administering to the subject a composition comprising a Lck activating peptide as described herein. In another embodiment, the present invention provides a method of treating cancer in a subject, comprising administering to the subject a composition comprising a Lck activating peptide as described herein sequentially or simultaneously with a checkpoint inhibitor.

Exemplary cancers are referred to herein.

In another embodiment, the present invention provides a method of activating an immune response in a subject, comprising administering to the subject a composition comprising a Lck activating peptide as described herein.

The present inventors have also demonstrated that the Lck activating polypeptides described herein decrease the proportion of Treg cells (Example 26).

Accordingly, the Lck activating peptides described herein can be used to enhance the physiological effects of decreasing the proportion of Treg cells described herein.

In one embodiment, the present invention provides a method of decreasing the proportion of Treg cells in a cell population, the method comprising contacting a Treg containing cell population with a composition comprising a Lck activating peptide as described herein.

In one embodiment, the proportion of Tregs in a cell population is decreased when the proportion of Tregs in a cell population contacted with a composition comprising a Lck activating peptide described herein is decreased compared to the proportion of Tregs in a cell population not contacted with a Lck activating peptide described herein (e.g. a control), or a comparison of before and after contacting with a composition comprising a Lck activating peptide described herein.

In one embodiment, the present invention provides a method of decreasing the proportion of Treg cells in a subject, the method comprising administering to the subject a composition comprising a Lck activating peptide as described herein.

In one embodiment, the Treg cells are Foxp3+ Treg cells.

In another embodiment, the present invention provides a method of decreasing immunosuppression in a subject, the method comprising administering to the subject a composition comprising a Lck activating peptide as described herein.

Rescue of exhausted CD8+ T cells by PD-1 targeted therapies is CD28-dependent. The present inventors have demonstrated that the Lck activating polypeptides described herein increase expression of CD28 in CD4+ and CD8+ T cells.

Accordingly, in one embodiment, the present invention provides a method of reducing exhaustion of a T cell in a subject, comprising administering to a subject a composition comprising a Lck activating peptide as described herein. In another embodiment, the composition comprising a Lck activating peptide as described herein is administered sequentially or simultaneously with a checkpoint inhibitor.

Cancer

Decreased cellular immunity is associated with many cancers and elevated levels of prostaglandin E2 (PGE2). It has been shown that CD4+ cells in Hodgkins lymphoma show similar regulation of genes that are altered in vitro by PGE2 in T cells from healthy individuals, which includes inactivation of Lck and reduced phosphorylation of ZAP70 (Chemnitz J M et al, Cancer Research, 2006, 66: 1114).

In Hodgkin's lymphoma and other tumours there is decreased cellular immunity because of impaired CD4+ T cell activation and it has been suggested that the elevated levels of PGE2 associated with Hodgkin's lymphoma inhibit CD4+ T cell function by inactivating Lck (Chemnitz J M et al, 2006, Cancer Res, 66(2), <http://www.ncbi.nlm.nih.gov/entrez/query.fcgi?cmd=Retrieve&db=pubmed&dopt=Abstract&list_uids=16424048&query_hl=5&itool=pubmed_docsum>). Lck also plays a key role in drug resistance, and it has been shown T cells that are Lck deficient are resistant to anti-cancer drugs (Samraj A K et al, 2006, Oncogene, 25: 186-197, <http://www.ncbi.nlm.nih.gov/entrez/query.fcgi?cmd=Retrieve&db=pubmed&dopt=Abstract&list_uids=16116473&query_hl=18&itool=pubmed_docsum>).

Cytarabine is one of the most effective chemotherapeutic agents used in the treatment of acute myelogenous leukemia (Frei E et al, Cancer Res, 1969, 29: 1325-1332). The serine/threonine kinase p34cdc2 kinase complexes with cyclins A and B and p34cdc2 activity is required for the initiation of cell division. Hence, p34cdc2 represents a mitotic checkpoint that monitors for completion of DNA synthesis and the presence of DNA damage (Nurse P, Nature, 1990, 344: 503-507). However, whilst the state of DNA replication is dependent on serine/threonine activity of p34cdc2 this is regulated by phosphorylation of p34cdc2 on Tyr15 in vivo (Atherton-Fessler S et al, Mol Cell Biol, 1993, 13: 1675-1685), and serine/threonine activity of p34cdc2 has been shown to be inhibited by phosphorylation of Tyr15 in the catalytic subunit of p34cdc2 (Gould K & Nurse P, Nature, 1989, 342: 39-44). Lck kinase has been shown to phosphorylate Tyr15 of p34cdc2 (Draetta G et al, Nature, 1988, 336: 738-744) suggesting a potential role for activators of Lck in the treatment of leukemias and other solid cancers.

The targeting of γ/δ T lymphocytes for cancer immunotherapy by ex-vivo or in vivo stimulation of peripheral blood lymphocytes with a combination of zoledronate and IL-2 has previously been described (Gomes A Q et al, Cancer Res, 2010, doi: 10.1158/0008-5472.CAN-10-3236; Dieli F et al, Cancer Res, 2007, 67(15): 7450-7; Wilhelm M et al, Blood, 2003, 102(1): 200-6), and Lck activators as described herein may serve as an alternative to the use of IL-2 for either generating gamma/delta T cells ex vivo and have application to therapeutic administration for patients with malignancies ranging from breast cancer, prostate cancer to lymphoid malignancies (Dieli F et al, vide supra; Wilhem M et al vide supra; Capietto A H et al, J Immunol, 2011, 187(2): 1031-8). In addition, γ/δ T cell cytotoxicity against tumour cells has been shown to be enhanced in combination regimes that include rituximab and trastuzumab (Tokuyama H et al, Int J Cancer, 2008, 122(11): 2526-343; Capietto A H vide supra), and the invention extends to the use of Lck activators as described herein in combination treatments with anti-cancer drugs as described above, and/or other with other drugs for the treatment of cancer or other diseases or conditions in accordance with the invention.

The present inventors have demonstrated that treatment of exhausted CD4+ cells with peptides of the present invention induces CD25 expression (FIG. 11).

Accordingly, in one embodiment, the present invention provides a method of reducing exhaustion of a T cell, the method comprising contacting a T cell with a composition comprising a Lck activating peptide as described herein.

The present inventors have demonstrated the Lck activating polypeptides described herein increase cytotoxicity in specific cytotoxicity of Calcein-AM stained K562 cells in a PBMC co-culture (Example 44).

Accordingly, in one embodiment the present invention provides a method of enhancing a cytotoxic cell function, the method comprising contacting a cytotoxic cell or a population of cytotoxic cells with a Lck activating peptide as described herein.

In one embodiment, the level of a cytotoxic cell function of a cell or a population of cells is enhanced when the level of a cytotoxic cell function of a cell or a population of cells contacted with a Lck activating peptide as described herein is increased compared to the level of the cytotoxic cell function of a cell or a population of cells not contacted with a Lck activating peptide as described herein (e.g. a control), or a comparison of levels before and after contacting with a composition comprising a Lck activating peptide described herein.

In another embodiment the present invention provides a method of enhancing a T cell function, the method comprising contacting a T cell or a population of T cells with a composition comprising a Lck activating peptide as described herein.

As used herein "enhancing a T-cell function" means to induce, cause or stimulate a T-cell to have a sustained or amplified biological function, or renew or reactivate exhausted or inactive T-cells. Examples of enhancing T-cell function include: increased secretion of IFNg from CD8+ T-cells, increased proliferation, increased antigen responsiveness (e.g., viral, pathogen, or tumour clearance) relative to such levels before the intervention. In one embodiment, the level of enhancement s as least 50%, alternatively 60%, 70%, 80%, 90%, 100%, 1 20%, 150%, 200%. The manner of measuring this enhancement is known to one of ordinary skill in the art. In one embodiment, the level of a T cell function of a cell or a population of cells is enhanced when the level of a T cell function of a cell or a population of cells contacted with a Lck activating peptide as described herein is increased compared to the level of the T cell function of a cell or a population of cells not contacted with a Lck activating peptide as described herein (e.g. a control), or a comparison of levels before and after contacting with a composition comprising a Lck activating peptide described herein.

Exemplary cytotoxic cell functions and T cell functions are discussed herein.

As discussed above, the methods described herein can be performed on a cell of a population of cells, either in vivo (e.g. in a subject) or in vitro (e.g. ex vivo).

Aging

T cells play a central role in cell immunity and the incidence of age-related diseases, many of which are influenced by dysregulation of the immune system, is increasing. There is a large body of evidence suggesting that the immune response, mainly the T cell response, is dysregulated in aging (Fulop T et al, Longevity & Healthspan, 2012, 1:6). Several alterations in the signalling pathways of T cells associated with the aging process have been described and it has been proposed that phospholipid structures within the plasma membrane (lipid rafts) serve to assemble the components of the TCR cascade (reviewed in Fulop et al, vide supra). Further, the recruitment of Lck and its activated form to lipid rafts has been shown to be decreased in activated T cells from aged individuals (Larbi A et al, J Leukoc Biol, 2004, 75(2): 373-381).

Age-associated alterations in T cell activation pathways have been observed in experimental animal models and in humans, and the most important changes occur in CD4+ T cells resulting in decreased production of the cytokine interleukin-2 (IL-2) and clonal expansion (reviewed in Fulop et al, vide supra).

In the IL-2 system, intracellular signal transduction is triggered by the beta chain of the IL-2 receptor and as a result of the association between specific sites in the catalytic domain of Lck and the cytoplasmic domain of the IL-2R receptor, the IL-2R beta receptor is phosphorylated by phosphorylated Lck (Hatakeyama M et al, Science, 1991, 252: 152308). Lck is the only Src family kinase that has been shown to be activated upon IL-2 stimulation of T cells (Brockdorff J et al, Eur Cytokine Netw, 2000, 11(2): 225-31), and activated Lck protein has been shown to stimulate IL-2 production in the absence of antigenic stimulation (Luo K & Sefton B M, Mol Cell Biol, 1992, 12(10): 4724-45732).

Impaired T cell activation and proliferation are key changes in immune function loss during aging (NASA-T-cell activation in aging, Report 2016; http://www.nasa.gov/mission_pagres/station/research/wexperiments/857/html), and information gained from comparing spaceflight and ground controls provides insight into understanding and identifying specific factors that play a role in this. Spaceflight and simulated microgravity are known to cause a significant reduction of key gene expression in early T cell activation, and numerous spaceflight missions have demonstrated a significant reduction in interleukin-2 (IL-2), interleukin-2 receptor alpha (IL-2Ra or CD25), interferon gamma (IFNγ) and tumour necrosis factor-alpha (TNFα) (Reviewed in Martinez E M et al, *Am J Physiol Regul Integr Comp Physiol,* 2015, 308: R480-R488).

Such is the concern about suppressed immunity during spaceflight that it has been questioned whether spaceflight-associated immune system weakening may preclude the expansion of human presence beyond Earth's orbit (Gueguinou N et al, *J Leukocyte Biology,* 2009, doi: 10.1189/jib.0309167). As described herein, in at least some embodiments, expression of the aforementioned cytokines as well as proliferation of CD4+ and CD8+ T cells may be induced by compounds utilised in methods as described herein in both normal and exhausted T cells. Accordingly, methods of the invention expressly extend to use in low- and microgravity environments.

Immunosuppression

A significant unwanted side effect of many novel anti-cancer drugs is immunosuppression leading to overwhelming sepsis. For example, Sorafenib a drug for metastatic renal cancer has been reported to cause an irrecoverable inhibition of T cell proliferation at a dosage of more than 10 μM even after drug withdrawal (Zhao W et al, Leukemia, 2008, 22: 1226-1233). Increasing Lck up-regulation has, for example, been proposed as a feasible option for re-stimulating the immune response in chronic myeloid leukemia patients undergoing tyrosine kinase inhibitor treatment (Wang G et al, BioMed Research International, 2014, doi.org/10.1155/2014/682010). Moreover, for instance, the BCR-ABL kinases inhibitor imatinib (Gleevec, ST1571) is highly effective in the treatment of chronic myeloid leukemia. However, long-term treatment with this drug induces immunosuppression which is mainly due to T cell dysfunction associated with inhibition of tyrosine kinases such as Lck and Zap70 (Wang G et al, vide supra). In addition, glucocorticoids act as potent immunosuppressant agents that block signalling events required for TCR activation and the inhibition of Lck by dexamethasone has been shown to down-regulate inositol-phosphate 3 receptors, thereby suppressing the immune response by weakening the strength of the TCR signal (Harr M W et al, JBC, 2009, 284: 31860-31871). With the development and use of tyrosine kinase inhibitors in cancer rapidly expanding, potential side effects of these drugs are of considerable clinical importance. Besides imatinib, nilotinib and dasatinib have, for instance, also been reported to suppress T cell function which has been attributed to Lck inhibition.

Cancer therapy may, therefore, benefit from combinatorial treatment with immune-enhancing drugs such as bacterial superantigens. However, bacterial superantigens are a class of antigens that cause non-specific activation of T cells and a massive cytokine release leading to severe life-threatening symptoms including toxic shock and multiple organ failure. Staphylococcal enterotoxin A (SEA) is a concern in the clinical setting as it is a common cause of antibiotic-associated diarrhoea. Notwithstanding the potential morbidity caused by SEA it has been proposed that SEA be used for the prevention of imatinib-mediated T cell immunosuppression in chronic myeloid leukemia given that Lck is activated by SEA (Wang G et al, BioMed Research International, 2014, 2014: Article ID 682010) and the prior lack of selective Lck activators.

These reports highlight the importance of Lck for T cell development and activation and hence, for adaptive immune responses (Stirnweiss A et al, 2013, Sci Signal, 6(263):ra13. Doi: 10.1126/scisignal.2003607). Dendritic Cell (DC)-mediated activation of Lck leads to "TCR licensing", a process that dramatically increases the sensitivity and magnitude of the TCR response to cognate peptide-MHC class II antigen complexes (Meraner P et al, 2007, J Immunol, 178(4): 2262-2271). However imatinib, for example, reduces TCR-induced proliferation and activation through inhibition of Lck activity (Seggewiss R et al, 2005, Blood, 105: 2473-2479). This has implications for induction of opportunistic infections and graft-versus-host or graft-versus-leukemia reactions after stem cell transplantation (Seggewiss R et al, 2005, Blood, 105: 2473-2479).

As discussed above, the present inventors have demonstrated that the peptides described herein increase Lck activity as shown in FIGS. 1, 2, 3, 4, 5 and 6, and increase Lck phosphorylation at Y394, as shown in FIG. 3 and FIG. 40, as well as increase the proliferation of CD8+ T cells (e.g. FIG. 20, FIG. 21, FIG. 27).

The present inventors have also demonstrated that the Lck activating peptides described herein;
    reduce tumour area in a Lewis Lung Cancer (LCC) model (FIG. 36);
    increase the proportion of CD4+ and CD8+ T cells expressing CD28 and CD215 in splenocytes removed from peptide treated Lewis Lung Cancer mice (FIG. 30, FIG. 31); and
    Increase expression of pSTAT4 on NK cells in splenocytes removed from peptide treated Lewis Lung Cancer mice (FIG. 32).

Accordingly, in one embodiment, the present invention provides a method of treating lung cancer in a subject, comprising administering to the subject a composition comprising a Lck activating peptide as described herein.

Accordingly, in one embodiment, the present invention provides a method of preventing or delaying progression lung cancer in a subject, comprising administering to the subject a composition comprising a Lck activating peptide as described herein.

Multiple Myeloma/Leukaemias/Lymphoma

Simultaneous targeting of IL-2 and IL-12 to Hodgkin's lymphoma enhances activation of resting NK cells and tumour cell lysis (Hombach A et al, Int J Cancer, 2005, doi.org/10.1002/ijc.20829).

The present inventors have demonstrated that the peptides described herein increase IL-12Rβ2 expression on NK cells (FIG. 17) and CD4+ T cells (Example 15, Example 28) and CD8+ T cells (Example 28, FIG. 25).

The present inventors have also demonstrated the Lck activating peptides described herein increase IL-2 secretion by T cells (FIG. 7), including CD4+ and CD8+ T cells (FIG. 8, FIG. 9), and a T cell line (Example 44).

In acute myeloid leukemia multiple aspects of deranged T cell function are operative at the time of diagnosis with exhaustion and senescence being the dominant processes (Knaus H A et al, JCI Insight, 2018, doi: 10.1172/jci.insight.120974). Indeed, T cells in patients with acute and chronic leukemia express exhaustion markers such as PD-1 or TIM-3 and can be poorly responsive, eg, impaired proliferation and reduced production of IL-2 and IFNg (Siska P J et al, Blood, 2014, 124: 4121).

The present inventors have demonstrated that treatment of exhausted CD4+ cells with peptides of the present invention induces CD25 expression (FIG. 10, FIG. 11 and FIG. 12), and that the peptides described herein induce IFNg secretion in PBMCs (Example 17) and CD4+ and CD8+ T cells (Example 18).

The present inventors have also demonstrated that the peptides described herein increase IL-2 secretion from human T cells (FIG. 7, FIG. 8, FIG. 9, FIG. 37).

Multiple myeloma (MM) is a progressive B-lineage neoplasia characterised by clonal proliferation of malignant plasma cells. T cells in multiple myeloma also display features of exhaustion and senescence at the tumour site and the number and function of T cell subsets are aberrant in patients with MM; for example, the CD4:CD8 ratio is inverted, the helper T cell type 1 to type 2 (Th1:Th2) ratio among CD4 cells is abnormal, levels of CD28 expression required for T cell activation are downregulated in T cells, and circulating dendritic cells from MM patients are dysfunctional (reviewed in Sharabi A & Haran-Ghera N, Bone Marrow Res, 2011, Article ID 269519). The present inventors have demonstrated the Lck activating peptides described herein increase CD28 expression on CD8+ and CD4+ T cells (FIG. 22, FIG. 30, FIG. 31).

Importantly, pre-treatment of cells with the Lck activating peptides described herein increase IL-2 secretion from human T cells upon subsequent antigenic stimulation (e.g. FIG. 29).

As used herein, antigenic stimulation includes the exposure or contacting of a cell or a population of cells with antigen, or with antibodies such as CD3 or CD28 antibodies.

As used herein a naïve cell includes a cell that has not been exposed to or contacted with antigen.

Accordingly, the present invention provides methods and uses wherein an Lck activating peptide as described herein is administered prophylactically, for example, prior to onset of a symptom of a disease, prior to antigenic stimulation, prior to exposure to a pathogen etc.

In addition, CD8+ T cells from myeloma tumour sites fail to produce IFNg after CD3/CD28 in vitro stimulation and display a reduced ability to degranulate in response to T cell stimuli (Zelle-Rieser C et al, J Haematology & Oncology, 2016, doi.org/10.1186/s13045-016-0345-30). The impaired immune response in MM is further accentuated by increases in functionally active immunosuppressive Tregs in the peripheral blood of MM patients (reviewed in Dosani T et al, Blood Cancer Journal, 2015, 5: e306).

The present inventors have also demonstrated that the Lck activating polypeptides described herein decrease the proportion of immunosuppressive Treg cells (Example 26).

The presence of Foxp3+ Treg cells in tumour-infiltrating lymphocytes correlates with a poor prognosis in various types of human cancers. The present inventors have demonstrated that the Lck activating polypeptides described herein decrease Foxp3+ Treg cells (Example 26).

Accordingly, the present invention provides methods of reducing the proportion of Fop3+ Treg cells in a cell population, the method comprising contacting a cell population with a composition comprising a Lck activating peptide as described herein.

IL-21 inhibits immunosuppressive Tregs. The present inventors have demonstrated that the Lck activating polypeptides described herein increase IL-21 production by T cells (FIG. 28).

Adoptive Cell Therapy (ACT)

A surrogate for vaccination against refractory or advanced cancer is Adoptive T-cell therapy (ACT), ie, the administration of ex vivo processed T cells (Kaartinen T et al, Cytotherapy, 2017, 19(6): 689-702). Furthermore, it has also become clear from murine studies that the conditioning of T cells during ex vivo expansion prior to ACT is also a critical parameter affecting in vivo efficacy (Rubinstein M P et al, Cancer Immunol Immunother, 2015, 64(5): 539-549). The adoptive transfer of T cells can mediate potent anti-tumour and anti-viral immunity in patients and such therapy may depend on the transfer of genetic information including T-cell receptors, chimeric antigen receptors (CARs) or other effector molecules (reviewed in Andrijauskaite K et al, Cancer Gene Ther, 2015, 22(7): 360-367).

Interleukins have been successfully employed to enhance T cell functionality when incorporated into medium during ex vivo expansion of T cells. For example, IL-12-conditioning improves retrovirally-mediated transduction efficiency of CD8+ T cells (Andrijauskaite K et al, vide supra); the addition of IL-21 has been shown to induce greater expansion of lymphocytes in culture and increased yield of CD8+ T central-memory cells (Zoon C K et al, Int J Mol Sci, 2015, 16: 8744-8760); and, the adoptive transfer of CAR+ T cells cultured with IL-21 has been shown to improve control of CD19+B-cell malignancy in mice (Singh H et al, Cancer Res, 2011, 71 (10: 3516-3527).

In adoptive immunotherapy, IL-12- and IL-18-cultured tumour-draining lymph node cells (TDLN) have been shown to eradicate pulmonary metastases more efficiently than T cell generated with IL-12 or IL-18 alone (Li Q et al, Cancer Res, 2005, 65(3): 1063-70). This shows that IL-12 and IL-18 can be used to generate potent CD4+ and CD8+ anti-tumour effector cells by synergistically polarising antibody-activated TDLN cells towards a Th1 phenotype (Li et al, vide supra). The Lck activating peptides described herein be used to generate potent CD4+ and CD8+ anti-tumour effector cells.

The present inventors have demonstrated the Lck activating peptides described herein increase expression of IL-18R.

In one embodiment, the level of IL-18R expression on a cell or a population of cells is increased when the level of IL-18R expression on a cell or a population of cells from a cell or a population of cells contacted with a composition comprising a Lck activating peptide described herein is increased when compared to the level of IL-18R on a cell or a population of cells not contacted with a Lck activating peptide as described herein (e.g. a control), or a comparison of levels before and after contacting with a composition comprising a Lck activating peptide described herein.

In another embodiment, the present invention provides a method for increasing IL-18 responsiveness of an NK cell, the method comprising contacting an NK cell with a composition comprising a Lck activating peptide as described herein.

In one embodiment, the level of responsiveness of a cell or a population of cells to IL-18 is increased when the level of responsiveness of a cell or a population of cells contacted with a composition comprising a Lck activating peptide described herein to IL-18 is increased compared to the level of responsiveness of a cell or a population of cells to IL-18 not contacted with a Lck activating peptide as described herein (e.g. a control), or a comparison of levels before and after contacting with a composition comprising a Lck activating peptide described herein.

In a preferred embodiment, the T cell is a CD4+ T cell or a CD8+ T cell.

As discussed above, the peptides described herein increase the proliferation of CD8+ T cells (FIG. 20, FIG. 21, and FIG. 27) and the proliferation of CD28+CD8+ T cells (FIG. 24). Accordingly, the Lck activating peptides described herein can be used to induce proliferation of cells and populations of cells in vivo and in vitro, for example, for adoptive cell therapies.

IL-12 receptor expression correlates with IL-12 binding and induction of a Th1 immune response. The present inventors have demonstrated that the Lck activing peptides described herein promote expression of IL-12R on PBMCs (FIG. 17), and T cells (FIG. 25).

Accordingly, in one embodiment, the present invention provides a method of inducing a Th1 response in a subject, the method comprising administering to the subject a composition comprising composition comprising a Lck activating peptide as described herein.

T cells can be expanded in vitro/ex vivo for adoptive cell therapy using IL-21. The present inventors have demonstrated that the Lck activing peptides described herein promote expression of IL-21 (FIG. 28).

Oxidative Stress

The ability of agents that block various steps of the lipid peroxidation process and, thereby, enhance the immune response has been known for nearly 40 years (Terrell Hoffeld J, Eur J Immunology, 1981, doi.org/10.1002/eji.1830110505).

In addition, scavengers of phospholipid hydroperoxides are vital for survival and expansion of recently activated T cells in the presence of pathogenic infections (Matsushita M et al, JEM, 2015, doi.10.1084/jem.20140857).

Immune suppressor cells such as myeloid-derived suppressor cells (MDSCs) expand with aging and this expansion of MDSCs also contributes to suppression of T-cell responses, due in large part, to the generation of oxygen species that include peroxynitrite—one of the most powerful oxidants in the body (Gabrilovich D I & Nagaraj S, Nat Rev Immunol, 2009, 9(3): 162-174; Bueno V et al, Age (Dordr), 2014, 36(6): 9729).

The reaction between nitric oxide and superoxygen radicals (that leads to peroxynitrite formation) induces lipid peroxidation of polyunsaturated fatty acids present in biomembranes and lipoproteins and UVB irradiation produces high levels of peroxynitrite that results in oxidative injury and cell death (Radi R, PNAS, 2018, doi.10.1073/pnas.1904932115; Wu S et al, Photochem Photobiol, 2010, 86(2): 389-396; Bartesaghi S & Radi R, Redox Biol, 2018, 14: 618-625).

Moreover, cigarette smoke-induced oxidative stress has also been shown to suppress generation of IL-12 production by CD40L-matured dendritic cells (DC) (Kroening P R et al, J Immunol, 2008, 181(2): 1536) and this cytokine is required for an active Th1 immune response.

The present inventors have demonstrated the Lck activating polypeptide RSKAKNPLY-RRRRRRRRR (SEQ ID NO: 24) not only induces CD40L-mediated production of IL-12 by DCs but also inhibits lipid peroxidation in cell membranes (e.g. FIG. 39).

Accordingly, in one embodiment, the present invention provides a method of treating oxidative damage, the method comprising contacting a cell or a population of cells population with a composition comprising a Lck activating peptide as described herein. In a preferred embodiment, the cell is a Treg cell or a population of cells comprising Treg cells.

In one embodiment, the level of oxidative damage is decreased when the level of oxidative damage in a cell or population of cells contacted with a composition comprising a Lck activating peptide described herein is decreased compared to the level of oxidative damage in a cell or a population of cells not contacted with a Lck activating peptide as described herein (e.g. a control) or a comparison of levels before and after contacting with a composition comprising a Lck activating peptide described herein.

In one embodiment, the level of reduction is as least 10%, alternatively 20%, 30%, 40%, 50%, 60%, 70%, 80%, or 90%. The manner of measuring such reductions is known to one of ordinary skill in the art.

The Lck activating polypeptides RVKVKVVVV-RRRRRRRRR (SEQ ID NO: 58, IK15800) and RSKAKNPLY-RRRRRRRRR (SEQ ID NO: 24, IK14800) increased the population of CD14 negative Dendritic Cells (data not shown).

Accordingly, in one embodiment the present invention provides a method of inducing proliferation of a dendritic cell or a population of dendritic cells, the method comprising contacting a cell or a population of cells with a composition comprising a peptide described herein. In another embodiment the present invention provides a method of increasing proliferation of a population of dendritic cells, the method comprising contacting a population of cells with a composition comprising a peptide described herein.

Alzheimer's Disease (AD)

Alzheimer's disease is a leading cause of dementia and is characterised by degeneration and loss of neurons as well as formation of senile plaques and neurofibrillary tangles.

A PD-1/PD-L1 pathway checkpoint inhibitor has recently been reported to ameliorate AD in transgenic mouse models by triggering an IFNγ-dependent increase in the monocyte-derived macrophage population in the brain leading to clearance of cerebral amyloid and improvement in cognitive defects (Baruch K et al, Nature Med, 2016, 22: 135-37). As described herein, in at least some embodiments compounds utilised in the invention may rescue immune response suppressed by the PD-1/PD-L1 interaction.

Further, Lck is involved in the regulation of neurite outgrowth and clinical reports have described down-regulated levels of Lck in the hippocampus of AD patients (Hata R et al, BBRC, 2001, 284: 310-316). Indeed the human Lck gene has been located in the Alzheimer's diseases-associated genetic linkage region 1p34-36 (Blacker D et al, *Hum Mol Genet*, 2003, 12: 23-32). A recent in vitro and in vivo functional characterisation of Lck in mammalian brains further suggests that Lck is a critical mediator of the acquisition and maintenance of memory which are the most salient processes impaired in AD (Kim E-J et al, Cell Mol Life Sci, 2012, doi: 10.1007/s00018-102-1168-1).

The present inventors have demonstrated that the Lck activating polypeptides of the described herein can rescue IL-2Ra expression on a T cell line in the presence of the checkpoint inhibitor PD-L1 (FIG. 12, Example 11).

HIV Infection

Although Lck is associated with both CD4 and CD8, Lck activity is higher when it is associated with CD4 (Delves P J and Roitt I M, editors. 1998. Encyclopaedia of Immunology, Second Edition. San Diego: Academic Press). HIV is characterised by a depletion of CD4+ cells and HIV strains that lack Nef do not progress to AIDS (Olszewski A et al, 2004, PNAS. USA, 101(39): http://www.pnas.org/cgi/content/full/101/39/14079). The important role of Lck in HIV infection is well recognised. For example, cells expressing inactive Lck show accelerated viral replication, whereas, cells expressing Lck with normal or elevated enzymatic activity show a delay in virus replication proportional to the initial endogenous Lck enzyme activity (Yousefi S et al, 2003, Clinical & Experimental Immunology, 133(1): 78-90)

The Nef gene is unique to primate lentiviruses (human immunodeficiency type 1) HIV-1), HIV-2, and simian immunodeficiency virus (SIV), and encodes a myristoylated membrane-associated protein of approximately 25 Kd (Greenway A L et al, 1999, J Virol., 73(7): 6152-6158). At the cellular level, Nef reduces the level of cell surface receptors including CD4, interleukin-2 receptor, MHC class I, interferes with T-cell signalling, and impairs specific cytokine production (Reviewed in Greenway A L et al, 1999, vide supra).

Nef interacts directly with the T-cell restricted Lck tyrosine kinase (lymphocyte protein-tyrosine kinase) and decreases Lck kinase activity both in vitro and in intact cells thereby resulting in impairment of both proximal and distal Lck-mediated signalling events (Collette Y et al, 1996, JBC, 271: 6333-6341. Lck binding to Nef does not require other virion or cellular proteins since inhibition of the catalytic activity of Lck has been shown to occur by binding between purified Lck and HIV-1 Nef or SIV proteins, illustrating the complexity of Nef mediated pathogenesis.

Specifically, Nef binds to the SH3 domain of Lck resulting in inhibition of Lck catalytic activity (Collette Y et al, 1996, JBC, 271: 6333-6341; Greenway A et al, 1996, J Virol, 70(10): 6701-6708; Greenway A L et al, 1999, J Virol, 73(7): 6152-6158), and the development of activators of Lck may complement development of anti-retroviral therapeutics.

Lck is the only Src family kinase activated upon Interleukin-2 (IL-2) stimulation in T cells (Brockdorff J et al, 2000, Eur Cytokine Netw., 11(2): 225-231) and although earlier studies suggested that IL-2 therapy in patients with HIV infection added no clinical benefit above use of anti-retroviral therapy alone a substantial and sustained increase in CD4+ cell counts was observed (The INSIGHT-ESPRIT Study Group and SILCAAT Scientific Committee, N Eng J Med, 2009, 361: 1548-1559). However, more recent data suggest that IL-2 administration as an adjuvant with HIV DNA or protein vaccines should be considered in future HIV vaccine study designs (Baden L R et al, 2011, J Infect Dis, 204(10): 1541-1549) and IL-2 does in fact inhibit HIV-1 replication in some infected cell lines (Raphael M O et al, 2013, JBC, doi: 10.1074/jbc.M113.468975).

These reports highlight the importance of Lck for T cell development and activation and, hence, for adaptive immune responses (Stirnweiss A et al, 2013, Sci Signal, 6(263):ra13. Doi: 10.1126/scisignal.2003607).

In one embodiment, the present invention provides a method of treating HIV infection in a subject, comprising administering to the subject a composition comprising a Lck activating peptide as described herein.

Other Pathogenic Infections

An adequate immune response to resist infections caused by viruses, bacteria, protozoa and parasites may be compromised by lack of specific kinase activity, facilitating replication and entry of microorganisms into cells and/or inhibiting effective immune responses.

Many bacterial pathogens, for example, associate intimately with host cells. Whilst some remain attached to the surface of the cell, others are internalised. γ/δ intra-epithelial T cells within the intestinal mucosa can detect the presence of invading bacteria through cross-talk with neighbouring epithelial cells and are an essential component of the hierarchy of immune defences that maintain homeostasis with the intestinal microflora (Ismail A S et al, PNAS, 2011, 108: 8743-8748).

A highly conserved evolutionary means by which bacteria have been able to establish their life cycles inside cells following invasion is via bacterially-produced UDP-sugar hydrolases. These are bi-functional enzymes with UDP-sugar hydrolase and 5 prime nucleotidase activities. For example, E coli can produce a UDP-sugar hydrolase, the products of which significantly inhibit Lck activity (Berger S A et al, JBC, 1996, 271: 23431-23437). Specifically, following infection of HeLa cells by E coli this relatively non-specific nucleotidase results in the accumulation of adenosine which is directly responsible for Lck inhibition. Moreover, over-expression of UDP-sugar hydrolase has been shown to enhance bacterial survival once inside HeLa cells. Loss of ATP within the cells is not responsible of Lck inhibition: rather it is the accumulation of ADP, AMP and adenosine (Berger et al, vide supra) and it has been proposed by those investigators that other pathogens may also employ this enzyme during infectious situations. Indeed, Candida Albicans cultures contain adenosine which has been shown to be responsible for inhibiting neutrophil function (Smail E H et al, J Immunol, 1992, 148: 3588-3595).

Shigella flexneri, the causative agent of bacillary dysentery, has also been shown to invade activated CD4+ T cells in vitro, inhibit T cell migration towards a chemoattractant stimulus, and also impair T cell dynamics in vivo within the site of adaptive immunity priming, i.e., the lymph node, thereby, preventing the induction of an efficient immune response to bacteria (reviewed in Nothelfer K et al, J Exp Med, 2014, 211(6): 1215; Salgado-Pabon W et al, PNAS, 2013, 110: 4458-4463). Moreover, in a mouse model of shigellosis treatment with Unc119 supresses Shigella infection (Vepachedu R et al, PLOS one, 2009, doi: 10.1371/journal.pone.0005211). Conversely, Unc119 knockdown was shown to enhance bacterial invasion and lethality. Similarly, enhanced infectivity of Mycobacterium bovis BCG infection of THP-1 cells has been reported following Unc119 knockdown indicating that the action of Unc119 is not specific to Shigella (Vepachedu et al, vide supra). The inhibitory effect of Unc119 was attributed to its interaction with the AbN family kinases and not mediation by the Src family kinases, which were not investigated. Further, Unc119 knockdown was found to double Shigella infection in the cell line employed. It is believed that until the present invention no selective Lck activator has previously been described. (Bae O-N et al, J. Neuroscience, 2012, 32(21): 7278-7286). Although recently reported data suggests that Unc119 can activate Lck in T cells, both Unc119 and its SH3 peptide motif have been shown to activate not just Lck but also Hck, Lyn and Fyn kinase members within the Src kinase family (Cen O et al, JBC, 2003, 278: 8837-8845; Gorska M M et al, J Exp Med, 2004, 199 (3): 369-379). Hence, Lck activators as described herein may act as surrogate antibiotics or serve as complimentary therapy to traditional antibiotic therapies, and the invention extends to all such use.

Malaria is a highly prevalent disease caused by Plasmodium species that infect hepatocytes and erythrocytes. CD4+ T cells protect against chronic blood-stage malaria and depletion of CD8+ T cells delays the clearance of the parasite, implicating these cells in protection against chronic disease (reviewed in Wykes M N et al, Cell Reports, 2013, 5: 1204-1213). Moreover, just as signalling through the programmed cell death-1 receptor (PD-1) is thought to "exhaust" HIV-specific CD4+ and CD8+ T cells, PD-1 has been shown to mediate loss and exhaustion of malarial parasite-specific CD8+ T cells and to a lesser extent the function of CD4+ T cells (Wykes et al, vide supra). Importantly, it has recently been demonstrated in PD-1 knockout mice that enhanced IFNγ secretion by CD8+ T cells is linked to protection against malarial infection leading to the proposal that future malaria vaccines consider boosting the responsiveness of CD8+ T cells (Wykes M N et al, Scientific Reports, 2016, 6: 26210). As described herein, in at least some embodiments compounds utilised in accordance with methods of the invention can enhance IFNγ secretion in e.g., exhausted murine CD4+ T cells, human peripheral blood mononuclear cells and for instance CD8+ expressing Jurkat cells, thereby further indicating a role in the treatment of malaria, and the use of compounds as described herein for this is expressly encompassed.

T-lymphotropic viruses, e.g., herpesvirus, are particular targets for Lck activators and methods embodied by the invention given that, for instance, the Herpesvirus saimiri tyrosine kinase interacting protein (Tip) physically interacts with Lck and inhibits Lck activity in stably expressing cell lines (Isakov N and Biesinger B, Eur J Biochem, 2000, 267(12): 3413-21).

Further, filoviruses, represented by the genera Ebolavirus and Marburgvirus, cause a lethal haemorrhagic fever in humans and in non-human primates. This virus attacks the immune system by decreasing the numbers of B lymphocytes and T lymphocytes. B cells and T-cells such as CD4 and CD8 lymphocytes are necessary to produce cytokines as immune regulators and patients who die within a couple of days have been shown to have a decrease in B cell and T cell numbers due to apoptosis. T cells need to be activated for the destruction of virus infected cells (Wauquier N et al, Public Library of Science, 2010, 4(10): 837-847) and exposure of human blood peripheral mononuclear cells to inactivated Ebola Zaire virus has been shown to result in decreased IL-2 production (Yaddanapudi K et al, The FASEB journal, 2006, 20: 2519-2530). The use of Lck activators as described herein therefore have application to stimulating T-cell activation and IL-2 production against these diseases.

Moreover, the use of Lck activators as described herein may also have a role in other infections such as tuberculosis. For example, most individuals require CD4+ and CD8+ T cells to control *Mycobacterium tuberculosis* (MTB) yet fail to eradicate MTB. Amongst the molecular mechanisms used by MTB to evade recognition by CD4+ T cells is signalling by the glycolipid, ManLAM, one of the most abundant glycolipids in the MTB wall which interferes with TCR signalling by inhibiting Lck phosphorylation but not phosphorylation on Tyr 505 (Mahon R N et al, 2012, Cell Immunol. 275(1-2): 98-105; Mahon R N III, PhD Dissertation, 2010, http://rave.ohiolink.edu/etdc/view?acc_num=case1275668686.

It is known that IL12RB1 is essential for human resistance to *Mycobacterium tuberculosis* infection. The present inventors have demonstrated a Lck activating peptide described herein induces IL12RB1 expression in CD4+ and CD8+ T cells (e.g. Example 28, FIG. 25, Example 15, FIG. 17).

Accordingly, in one embodiment, the present invention provides a method of treating *Mycobacterium tuberculosis* in a subject, comprising administering to the subject a composition comprising a Lck activating peptide as described herein.

Other infections that may be inhibited or treated in accordance with the invention by up-regulating Lck activity include the plague and hepatitis viruses (e.g., hepatitis B virus and hepatitis C virus). Hepatitis B is the most prevalent virus that leads to liver injury and inflammation and like hepatitis C virus, is associated with T cell exhaustion (Ye B et al, Cell Death & Disease, 2015, 6, e1694). A key virulence factor for the aetiological agent of plague *Yersinia pestis*, is the tyrosine phosphatase YopH. The bacterium injects YopH into host cells and Lck has been shown to be dephosphorylated at its positive regulatory site Tyr 394 in cells containing active YopH. By turning off Lck, YopH blocks T cell antigen receptor signalling at its very first step, effectively preventing the development of a protective immune response against this lethal disease (Alonso A et al, 2003, JBC, 279: 4922-4928). In hepatitis C, the hepatitis C virus core protein binds to T cells and inhibits Lck activation suggesting that the core protein inhibits the very early events of T-cell activation (Yao S Q et al, 2004, J Virol, 78(12): 6409-6419).

The hazards of a blood transfusion in terms of susceptibility to either a general infection, a post-operative infection or even cancer recurrence have been known since 1973 and a recent meta-analysis reconfirms this risk of health care-associated infection after red blood cell transfusion (Rhode J M et al, JAMA, 2014, 311(13): 1317-1326; Blumberg N et al, Transfusion, 2007, 47(4): 573-81; Fergusson D et al, Can J Anaesth, 2004, 51(5): 417-24). While the proposed mechanisms of transfusion-induced immuno-modulation remain unclear, documented changes considered to play a role include decreased CD4/CD8 ratios and decreased IL-2 secretion (Kirkley S A, Clinical and Diagnostic Laboratory Immunology, 1999, 6(5): 652-657). Hence, administration of a Lck activator in association with a blood transfusion may ameliorate the risk of one or more of these conditions.

Moreover, in vitro IL-2 treatment of syngeneic spleen cells to generate lymphokine-activated killer cells has been shown to enhance IL-2 prevention of sepsis-related death in a murine model of thermal injury and activated Lck has been shown to stimulate IL-2 production in the absence of antigenic stimulation (Mendez M V et al, J Surg Res, 1993, 54(6): 565-70; Luo K and Sefton B M, Mol Cell Biol, 1992, 12(10): 4724-4732). Furthermore, prostaglandin E2 (PGE2) is known to play a significant role in T cell suppression during sepsis and in a neonatal Sprague-Dawley rat model of T cell suppression during sepsis, has been shown to be accompanied by a decrease in IL-2 production. Such suppressions were ameliorated with a COX-2 inhibitor thereby implicating PGE2 in this process. Given this and since exposure of T cells to PGE2 leads to inactivation of Lck and reduced phosphorylation of ZAP70 (Dallal O et al, Biol Neponate, 2003, 83(3): 201-7; Chemnitz J M et al, Cancer Res, 2006, 66: 1114), treatment with a Lck activator in accordance with the invention may also have application to stimulation of the immune response during sepsis via stimulation of T-cell activity, and stimulation of IL-2 production.

A Lck activator as described herein therefore finds broad use in a range of applications. Diseases and conditions that may be treated by a Lck activator as described herein and/or in accordance with a method embodied by the invention include but are not limited to diseases and conditions characterised by less than optimal expression of Lck or inhibition of Lck or down-regulation of Lck or Lck activity, disorders relating to intraepithelial and intramucosal resident T cell dysfunction and/or the requirement for T cell activation in response to pathogenic infections (e.g., including chronic infections), sepsis (e.g., chronic sepsis) from pathogenic infections and blood transfusion related sepsis, cancers and cutaneous and epithelial malignancies; the prophylaxis or treatment of cancers in general (e.g., breast, colon, colorectal, and prostate cancers), including lymphomas, Hodgkin's Disease and leukemias; immune suppression caused by therapies that suppress T cell function (e.g., therapies for cancer and non-cancer conditions); immune-deficiency disorders including but not limited to Severe Combined Immune Deficiency Syndrome (SCID). conditions requiring survival of CD4/CD8 T cells and conditions or disorders that cause a lowering of the T cell count (e.g., infections such as pneumonia, influenza, herpes infections); pathogenic infections by viruses, bacteria, fungi, and parasites; T cell exhaustion (e.g., associated with cancer or non-cancer conditions (such as sepsis (e.g., chronic sepsis) from pathogenic infection) and/or treatments for cancer or non-cancer conditions), and checkpoint blockade in T cells (e.g., associated with cancer or chronic sepsis), and age associated alterations in T cell activation pathways.

Various ligand-receptor interactions are known to contribute to checkpoint signalling inhibition (e.g., see Pardoll D M, Nature Reviews Cancer, 2012, 12:252-264), and in at least some embodiments of the invention, T cell function may be restored by inhibiting one or more of these interactions (e.g., the PD-1/PD-L1 interaction). Accordingly, in at least some embodiments, the invention expressly extends to the administration of a Lck activator as described herein for overcoming checkpoint blockade/inhibition of T cell signalling in exhausted T cells.

Further examples of pathogens and pathogenic infections include viral infections such as by poxviruses, other T-lymphotropic viruses besides herpesviruses, myxoviruses, reoviruses, enteroviruses, coxsackieviruses, echoviruses, foot and mouth viruses, hepatitis causing viruses (e.g., hepatitis A virus, hepatitis B virus and hepatitis C virus), encephalitis and choriomeningitis, Simian immunodeficiency viruses, SARS, coronavirus, dengue fever virus, influenza viruses, Yellow fever virus, West Nile virus, arenovirus, vesicular stomatitis virus, rhinovirus, human papilloma virus (HPV), respiratory syncytial virus, human cytomegalovirus, and varicella-zoster virus (VZV); bacterial infections such as by other mycobacteria infections besides tuberculosis (e.g., leprosy), diseases caused by Gram positive and Gram negative bacteria such as Gram positive cocci and Gram negative cocci, and Gram negative bacilli and cocco-bacilli, haemolytic streptococci, enterococci, and toxin producing bacteria such as tetanus, diphtheria, and chlostridial and botulism infections; protozoan infections such as by amebiasis, malaria (the causative agent of which is *P. falciparum*), leishmaniasis, trypanosomiasis, toxoplamosis and giardiasis; and helminth infections such as by intestinal nematodes, filariasis, cestodes (tapeworms) and echinococcal infections.

Besides use of Lck activators as described herein in prophylaxis or treatment of disease or conditions as described above, in other embodiments of the invention Lck activators in accordance with the invention can further have application to stem cell therapy, embryonal stem cell self-renewal, and maintenance of pluripotency of embryonic stem cells (e.g., of the blastocyst embryo), and all such uses are expressly encompassed by the invention.

In particular, induced pluripotent cells are adult cells that have been genetically reprogrammed to an embryonic stem cell-like state by being forced to express genes and factors important for maintaining the defining properties of embryonic stem cells.

Only once adult cells have been programmed to become stem cells can they then be induced to differentiate into the desired germ cell layer. Whilst members of the Src-family tyrosine kinases are essential for differentiation of human embryonic stem cells, Lck expression levels drop dramatically as a function of embryonic stem cell differentiation (Zhang X et al, Stem Cell Res, 2014, 13 (3 Pt A):379-389).

Leukemia inhibitory factor (LIF) is one of the key extrinsic factors used for the cultivation and derivation of mouse embryonic and induced pluripotent stem cells and activates "signal transducer and activator of transcription 3" (STAT3), an important regulator of mouse embryonic stem cell self-renewal (Dang-Nguyen T Q et al, Molecular Reproduction and Development, 2014, 81:230). In turn, STAT3 is known to inhibit differentiation into both mesoderm and endoderm lineages by preventing the activation of lineage-specific differentiation programs (Graf U et al, Genes, 2011, 2(1): 280-297). Hence, STAT3 is essential for the maintenance of an undifferentiated embryonic stem cell phenotype (Raz R et al, PNAS USA, 1999, Cell Biology, 96: 2846-2851).

Importantly, activation of STAT3 is a limiting factor for the induction of pluripotency and its over-expression eliminates the requirement for additional factors to establish pluripotency (Yang J et al, Cell Stem Cell, 2010, 7(3): 319-328). As such, STAT3 signalling is considered one of the master reprogramming factors that dominantly instructs naive pluripotentiality because STAT3 promotes the expression of self-renewal factors (Li Y-Q, Cellular Reprogramming, 2010, 12(1): 3-13). Lck has been shown to directly activate STAT3 and the activation of STAT3 by exogenous Lck is attenuated by the Lck-specific inhibitor PP1 (Lund T C et al, Cell Signal, 1999, 11(11): 789-796). Thus, Lck activators in accordance with the invention may serve to upregulate STAT3 activity via stimulation of Lck activity, and so have application to the promotion and maintenance of stem cell self-renewal.

Further, Lck activators as described herein have particular application to T cells, boosting immunity and immune responses including cell mediated immunity, rescuing cellular immunity, up-regulating T cell receptor signalling, up-regulating production of one of more cytokines (e.g., selected from IL-2, IFN-γ and TNF-α), reinvigoration of T-cells, revitalisation of T-cell immune response(s), and as an adjuvant (e.g., in a vaccine composition or for administration separately to an individual to stimulate an immune response to antigen).

Accordingly, there is further provided herein a vaccine composition for vaccination of an individual, comprising one or more Lck activators embodied by the invention together with a pharmaceutically acceptable carrier. The vaccine may comprise any suitable antigen(s) against which the immune response is to be generated by administration of the vaccine and optionally, any additional adjuvant for stimulating an immune response to the antigen(s).

In at least some embodiments, stimulation of the T cell receptor (TCR) may be required to achieve T cell physiological outcomes (e.g., increased IL-2 cytokine production, up-regulated T cell signalling etc.) stemming from treatment with Lck activators as described herein. That is, rather than basally activating T cells, the Lck activator may act to enhance the physiological outcomes of T cell receptor stimulation. Accordingly, in at least some embodiments of methods described herein, the T cells treated by the administered Lck activator are stimulated T cells.

T cell populations responsive to Lck activators in accordance with one or more embodiments of the invention may, for example, be selected from the group consisting of intraepithelial T cells, intramucosal T cells, γ/δ T-cells, dendritic epidermal T cells, CD4+ T cells, CD8+ T cells, cytotoxic T cells, regulatory T cells (Tregs), and combinations of the foregoing cell populations.

A Lck activator as described herein or component(s) thereof (e.g., a polycationic peptide (PP), augmenting peptide (AP/P) and/or a compound of Formula II) can be provided by synthetic or recombinant techniques well known to the skilled addressee. Further, the polycationic peptide and/or the augmenting peptide or other peptide (AP/P) as described herein of a Lck activator in accordance with the invention can incorporate an amino acid or amino acids not encoded by the genetic code, or amino acid analog(s).

For example, one or more D-amino acids, beta-amino acids, and/or homo amino acids may be utilised rather than L-amino acids. Indeed, a polycationic peptide (PP) and/or augmenting peptide of a Lck activator as described herein may consist partly or entirely of D amino acids or combinations of e.g., one or more of D-amino acid(s), beta-amino acid(s), homo amino acid(s), beta-homo amino acid(s), L-amino acid(s), and L- or D-homo amino acids. Examples of beta amino acids include beta-alanine ($NH_2$—$CH_2$—$CH_2$—COOH), beta-phenylalanine, beta-tryptophan, beta-tyrosine, beta-leucine and the like, including beta variant forms of cationic amino acids. Examples of homo variant forms of amino acids include homo-cysteine having an additional $CH_2$ group compared standard L-cysteine. Thus, in some embodiments, the polycationic peptide (PP) and/or an augmenting or other peptide of a Lck activator as described herein may, for example, include L-amino acids, D-amino acids or a mixture of L-, D-amino acids and/or other amino acid types as described above. The use of peptide(s) including D-amino acids can, for instance, inhibit peptidase activity (e.g., endopeptidases) and thereby enhance stability and increase the half-life of the peptide and thereby the Lck activator in vivo.

A peptide or fusion protein as described herein may be constrained in a 3-dimensional conformation for use in a method as described herein. For instance, it may be synthesised with side chain structures or otherwise be incorporated into a molecule with a known stable structure in vivo, or be cyclised to provide enhanced rigidity and thereby stability in vivo. Various methods for cyclising peptides, fusion proteins or the like are known. A peptide may be cyclised via four different routes, namely head to tail (C-terminal end to N-terminal end), head to side chain, side chain to tail, or side chain to side chain. For example, a peptide of fusion protein may be provided with two cysteine residues distanced from each other along the peptide or fusion protein and be cyclised by the oxidation of the thiol groups of the residues to form a disulfide bridge between them. Cyclisation may also be achieved by the formation of a peptide bond between N-terminal and C-terminal amino acids of a peptide or for instance, through the formation of a bond between the positively charged amino group on the side chain of a lysine residue and the negatively charged carboxyl group on the side chain of a glutamine acid residue. The formation of direct chemical bonds between amino acids or the use of any suitable linker to achieve cyclisation is also well within the scope of the skilled addressee. A particularly preferred method for achieving cyclisation in accordance with the invention comprises the formation of a lactam group and the use of lactamisation to form cyclised forms of peptides and/or Lck activators as described herein is expressly encompassed. Methods for achieving cyclisation including suitable lactamisation methods are, for example, described in White C J and Yudin A K., Contemporary strategies for peptide macrocyclization. Nature Chemistry, June 2011, pp. 509, the entire contents of which is incorporated herein by cross-reference.

A peptide or fusion protein (e.g., a polycationic peptide-augmenting peptide moiety) comprising a Lck activator as described herein may also include post-translational or post-synthesis modification such as the attachment of carbohydrate moieties or chemical reaction(s) resulting in alkylation or acetylation of amino acid residues or other changes involving the formation of chemical bonds.

The use of peptidomimetics of peptide(s) comprising a Lck activator in accordance with the invention is also contemplated and is expressly encompassed herein. A peptidomimetic may, for example, comprise the substitution of one or more of the amino acids of the peptide with an amino acid analogue wherein the amino acid analogue(s) essentially do not diminish the activity of the parent peptide as may be assessed by conventional activity, cell toxicity and/or other suitable assays.

Lck activators and components thereof as described herein can be chemically synthesised or produced using conventional recombinant techniques. A nucleic acid encoding a fusion protein may, for instance, be provided by joining separate cDNA fragments encoding peptides having the desired amino acid sequence(s) by employing blunt-ended termini and oligonucleotide linkers, digestion to provide staggered termini as appropriate, and ligation of cohesive ends. Alternatively, PCR amplification of DNA fragments can be utilised employing primers which give rise to amplicons with complementary termini which can be subsequently ligated together.

Peptides and fusion proteins as described herein may be expressed in vitro and purified from cell culture for administration to the mammalian subject or for being coupled to a compound of Formula II to provide a Lck activator for use in a method embodied by the invention utilising any suitable techniques.

Solid-phase peptide synthesis (SPPS), click chemistry and Staphylococcal Sortase A mediated peptide-peptide fusion protocols, or combinations of the foregoing, may also be utilised in the provision of a Lck activator as described herein, such as for coupling peptide components together and/or for coupling to a targeting moiety e.g., a scFv etc. Various protocols for such synthesis methods are well known and any suitable such methods may be employed.

SPPS methods employing Fmoc or t-Boc or protecting groups for synthesis of a therapeutic agent are particularly preferred. Such synthesis methods are well known and comprise repeated coupling and deprotection cycles with wash steps before and after the deprotection step. In at least some embodiments described herein the entire therapeutic agent can be synthesised on a solid support by SPSS. For synthesis of e.g., a polyamide moiety of Formula II, pseudo fatty acid building blocks with e.g., an Fmoc protected 2-amino group can be sequentially coupled together to form a polyamide backbone of the moiety having from 3 to 5 repeating units each of which has an R group side chain as described above. Likewise, the peptide component(s) of the Lck activator can then be sequentially coupled to the polyamide moiety (PM) to extend the activator in the C-terminal to N-terminal direction prior to release and collection of the synthesised Lck activator from the solid support.

Sortase A (Srt A) is a bacterial enzyme first described in *Staphylococcus aureus* which cleaves between threonine and glycine in the cleavage sequence LPXTG generating an acyl-enzyme intermediate which can then react with an N-terminal glycine residue to release the enzyme and fuse the glycine and LPXTG tagged components together by a peptide bond, see Levary, D. A et al., "Protein-protein fusion catalysed by sortase A". *PLoS ONE*, April 2011, Vol. 6(4): 1-6, e18342. See also e.g., Witte, M. D., "Production of unnaturally linked chimeric proteins using a combination of sortase-catalysed transpeptidation and click chemistry". *Nat. Protoc.* September 2013, 8(9): 1808-1819, and Bently M L. et al., J. Biol Chem, 2008, 283:14762-14771, and Mazmanian S K. et al., 1999, *Science,* 285:760-763. Recombinant HER1 and HER2 targeted antibodies linked to fluorescent tags or toxins via Sortase A-mediated protein ligation have, for example, been described, see e.g., Madej M P et al., *Biotechnology and Bioengineering,* 2012, 109:1461-1470, and Kornberger P. and Skeria A., 2014, mAbs 6(2): 354-366, the contents of all of all of the foregoing being incorporated herein in their entirety by cross-reference.

Click chemistry is another high yield method suitable for coupling components together in the provision of Lck activators as described herein such as by a metal catalysed (e.g., Cu(I)) azide-alkyne cycloaddition reaction between a terminal azide group on one component and azide group on the other component whereby the components are coupled together by a 1,2,3 triazole bond rather than a peptide bond. 1,2,3 triazole bonds act as a bioisostere to a conventional peptide bond and have the advantage that they are resistant to hydrolysis, see e.g., Li et al., Click chemistry in peptide-based drug design, Molecules, 2013, 18, pp:9797-9817; doi:10.3390/molecules18089797. Cyclooctynes such as dibenzo-bicyclo-octyne (DBCO) are likewise highly reactive with azides and offer alternative forms of click chemistry reactions to azide-alkyne cycloadditions as described above, or may be used in combination with azide-alkyne cycloadditions, to provide Lck activators embodied by the invention. Cyclooctyne based click synthesis reactions have the advantage in that they can be carried out without a copper or other metal catalyst.

A targeting moiety such as an scFv, antibody or antibody fragment can, for example, be coupled to a linker moiety (LM) of a Lck activator as described above by firstly preparing cysteine derivatives of the two components, which are cleaved and purified as HCl salts then coupled to the respective click reagents employing maleimide coupling, exploiting the free sulfhydryl of cysteine in solution phase. The targeting moiety is subsequently derivatized with either the azide or alkyne (or e.g., DBCO) reagent, and click conjugation occurs via the complimentary reagent coupled to the linker moiety (LM).

In other embodiments, target cells of a mammalian subject may be transfected with nucleic acid encoding a fusion protein (i.e., a chimeric protein) Lck activator as described herein (e.g., comprising a polycationic peptide (PP) and augmenting peptide or other peptide (AP/P) as described herein) for in vivo expression of the nucleic acid utilising the cellular transcription elements and translation ribosomal complexes of the host cell(s) for effecting therapeutic treatment (e.g., prophylaxis or treatment of a pathogenic infection) in accordance with the invention.

For expression of nucleic acid encoding a Lck activator component(s) thereof (e.g., a peptide active and augmenting peptide) as described herein, the nucleic acid will typically first be introduced into a cloning vector and amplified in host cells, prior to the nucleic acid being excised and incorporated into a suitable expression vector(s) for transfection of cells. The expression vector may be designed for expression of the nucleic acid insert independently of genomic DNA of the host cell, or for site directed, homologous, or heterologous recombination into genomic DNA of the host cell for subsequent expression of the nucleic acid insert in the host cells.

Typical cloning vectors (e.g., cosmids) incorporate an origin of replication (on) for permitting efficient replication of the vector, a reporter or marker gene for enabling selection of host cells transformed with the vector, and restriction enzyme cleavage sites for facilitating the insertion and subsequent excision of the nucleic acid sequence of interest. Preferably, the cloning vector has a polylinker sequence incorporating an array of restriction sites. The marker gene may be drug-resistance gene (e.g., $Amp^r$ for ampicillin resistance), a gene encoding an enzyme such as chloramphenicol acetyltransferase (CAT), 3-lactamase, adenosine deaminase (ADA), aminoglycoside phosphotransferase (APH), dihydrofolate reductase (DHFR), hygromycin-B-phosphotransferase (HPH), thymidine kinase (TK), or for instance β-galactosidase encoded by the *E. coli* lacZ gene (LacZ). Yeast reporter genes include imidazole glycerolphosphate dehydratase (HIS3), N-(5'-phosphoribosyl)-anthranilate isomerase (TRP1) and β-isopropylmalate dehydrogenase (LEU2). An expression vector may also incorporate such marker genes. Cloning vectors that may be used include cloning vectors for mammalian, yeast and insect cells. Particular vectors that may find application include pBR322 based vectors and pUC vectors such as pUC118 and pUC119.

Suitable expression vectors include plasmids capable of expression of a DNA (e.g., genomic DNA or cDNA) insert. An expression vector will typically include transcriptional regulatory control sequences to which the inserted nucleic acid sequence is operably linked. By "operably linked" is meant the nucleic acid insert is linked to the transcriptional regulatory control sequences for permitting transcription of the inserted sequence without a shift in the reading frame of the insert. Such transcriptional regulatory control sequences include promoters for facilitating binding of RNA polymerase to initiate transcription, expression control elements for enabling binding of ribosomes to transcribed mRNA, and enhancers for modulating promoter activity. A promoter may be a tissue specific promoter which facilitates transcription of the nucleic acid insert only in specific cell lineages and not in other cell types or only to a relatively low level in such other cell types. The design of an expression vector will depend on the host cell to be transfected, the mode of transfection, and the desired level of transcription of the nucleic acid insert.

Numerous expression vectors suitable for transfection of prokaryotic (e.g., bacterial) or eukaryotic (e.g., yeast, insect or mammalian cells) are known in the art. Expression vectors suitable for transfection of eukaryotic cells include pSV2neo, pEF.PGK.puro, pTk2, pRc/CNV, pcDNAI/neo, non-replicating adenoviral shuttle vectors incorporating the polyadenylation site and elongation factor 1-α promoter and pAdEasy based expression vectors most preferably incorporating a cytomegalovirus (CMV) promoter. For expression in insect cells, baculovirus expression vectors may be utilised examples of which include pVL based vectors such as pVL1392, and pVL941, and pAcUW based vectors such as pAcUW1. Preferred expression vectors for expression of a nucleic acid insert in mammalian cells in accordance with embodiments of the invention include plasmids with a CMV or elongation factor 1a promoter such as pEF.PGK.puro (Huang, David C. S. et al., Oncogene (1997) 14:405-414). The pEF.PGK.puro plasmid contains an SV40 origin, EF-1α promoter, polycloning sites and a polyA region, and is particularly preferred for expression of a nucleic acid insert encoding a peptide or chimeric protein as described herein.

Various forms of expression vectors are known in the art and any suitable such expression construct may be used for the intended purpose. Viral transfer methods can also be used for achieving the introduction of nucleic acids encoding a Lck activator as described herein into a target cell either in vitro or in vivo. Suitable virus into which expression vectors may be packaged for delivery to target cells include adenovirus, vaccinia virus, retroviruses of avian, murine and human origin, herpes viruses including Herpes Simplex Virus (HSV) and EBV, papovaviruses such as SV40, and adeno-associated virus. Particularly preferred viruses useful in methods described herein include replication deficient recombinant adenovirus or other virus. Recombinant virus may be administered locally or systemically to achieve delivery of nucleic acid encoding a peptide or fusion protein into a target cell. Nucleic acid encoding a peptide or fusion protein as described herein may also be intracellularly delivered in vitro using conventional cold or heat shock techniques or for instance, calcium phosphate co-precipitation or electroporation protocols as are known in the art.

Transfected cells can be screened to identify cultures or cell lines that exhibit stable, reproducible expression of the nucleic acid insert and concomitant production of the encoded peptide or fusion protein. Stable integration and expression of nucleic acids within a variety of host cells are well known in the art. Host cells that can be used for expression of peptides or fusion proteins as described herein include bacteria and probiotic bacteria such as *E. coli, B. subtilis, Lactococcus lactis, Streptomyces* and *Pseudomonas, Brevibacterium* and particularly B. linens bacterial strains, yeast such as *Saccharomyces* and *Pichia*, insect cells, avian cells and mammalian cells such as Chinese Hamster Ovary cells (CHO), COS, HeLa, HaRas, WI38, SW480, and NIH3T3 cells. The use of *E. Coli* for recombinant protein production is well known, and suitable promoters for use in such expression systems include T7, trc and IacUV5 (Tegel H et al, FEBS Journal, 2011, 278: 729-739). The host cells are cultured in a suitable culture medium under conditions for facilitating expression of the introduced nucleic acid prior to purification of the expressed product from the host cells, and/or supernatants as the case may be using standard purification techniques. Moreover, the expressed products may include a histidine tag for quantitation by ELISA within the host cell (e.g., bacterial cells such as *E. coli*) from which targeted minicell preparations as described below may be made (MacDiarmid J et al, Cancer Cell, 2007, 11: 431-445).

In particular, minicells (e.g., De Boer P A, et al., A division inhibitor and topological specific factor coded for by the minicell locus determine proper placement of the division septum in *E. coli. Cell,* 56; 641-649, 1989), liposomes, ghost bacterial cells, caveospheres, synthetic polymer agents, ultracentrifuged nanoparticles and other anucleate nanoparticles may be loaded with Lck activators, nucleic acids or expression vectors (e.g., plasmids) in as described herein for targeted delivery of the cargo to target cells. Such shuttles may be formulated for injection, or oral consumption for passage through the acid environment of the stomach for release and uptake of the cargo via the small intestine.

Minicells are nano-sized cells that can be produced by mutations in gene(s) that control normal cell division and contain the cytoplasm and thereby cytoplasmic components for protein expression of the parent cell, but which are achromosonal and incapable of self-replication. The generation of minicells by depressing (or upregulating) genes that control cell division has been shown to offer a solution to drug delivery to tumours at doses far less than would normally be used during intravenous infusion (MacDiarmid, J. A. et al., J C (2007), *Cancer Cell;* 11; 431-445). A minicell in the context of the present invention can be any achromosomal cell produced by aberrant cell division of the parent cell, as may result from pertubation or disturbance of the cell division process (e.g., binary fission) such as by genetic mutation(s) and/or inhibition of cellular components involved. Minicells for use in a method as described herein can be prepared by any conventionally known method such as described in International patent application No. WO 03/033519, U.S. Pat. No. 7,183,105, and MacDiarmid, J. A., et al., 2007, the contents of all of which are expressly incorporated herein in their entirety by cross-reference. The inactivation of bacterial genes that control cell division to generate bacterial minicells is, for instance, further described in De Boer, P. A., et al., "A division inhibitor and a topological specificity factor coded for by the minicell locus determine placement of the division septum in *E. coli". Cell* 56, 1989, pp. 641-649. Methods for the purification of intact minicells utilising density gradient centrifugation (e.g., OptiPrep™, Axis-Shield PLC, Dundee, Scotland) and cross-flow filtration are described in U.S. Pat. Nos. 7,611,885 and 8,003,091, the contents of both of which are also expressly incorporated herein in their entirety by cross-reference.

Examples of bacterial cells from which minicells useful herein may be derived include bacteria such as *Escherichia coli (E. coli)* (e.g., with mutations in MinA, MinB, cya, crp, MukA1, or MukeE, or which overexpress minB, minE, flsZ, sdi), *Bacillus subtilis* spp. (e.g., with mutations in minC, minD, ripX, or has smc mutations or OriC deletions), *Lactobacillus* spp., and *Pseudomonas* spp. Bacteria may be Gram-positive (e.g., *L. monocytogenes*) or Gram-negative (e.g., *P. aeruginosa*). Minicells that have segregated from bacteria with porins in their outer membrane (i.e., normally Gram-negative bacteria although some Gram-positive bacteria also have porins) are particularly preferred for facilitating loading of the minicells with a nucleic acid, expression vector or Lck activator as described herein to be delivered to the target cells. Minicells may also be derived from archeabacteria or eukaryotic cells, e.g., see U.S. Pat. No. 7,183,105. Typically, however, bacterial derived minicells that is, minicells derived from bacterial parent cells, will be utilised.

The targeting of minicells to cells for effecting treatment in accordance with the invention may be obtained by the use of any suitable targeting moiety (e.g., via bispecific antibodies, scFv(s) targeting peptides or the like on the minicell or liposome etc.). The targeting moiety can be expressed on the surface of the minicell or, for example, minicells can be tagged or labelled with one or more selected targeting moieties. In particularly preferred embodiments, the targeting of minicells to tumour cells may be achieved using a targeting moiety in the form of a bi-specific antibody complex that recognizes the 0-antigen component of minicell surface lipopolysaccharide and a cell surface receptor specific for the mammalian cell to be targeted (e.g., EFGR), the two antibodies of the complex being linked together via their Fc regions with the use of protein A/G (see MacDiarmid, J. A., et al., J C (2007), *Cancer Cell;* 11; 431-445, and WO 03/033519. However, the invention is not limited thereto and other targeting moieties may be employed as described above.

Lck activator(s) as described herein may be carried within, or on, minicells to target cells or tissues. For example, the Lck activator(s) may be loaded into the minicells, expressed in the membrane of a minicell, or be carried on the membrane of the minicell e.g., by charge association.

Minicells may be loaded with a Lck activator or nucleic acid (e.g., expression vector) as described herein by passive diffusion via incubation of the minicells in an incubation medium containing the Lck activator or nucleic acid. To assist loading, the minicells may be rendered permeable to the Lck activator(s) or nucleic acid(s) (e.g., by perforating the minicells) or the permeability of the minicells to the agent may otherwise be increased or enhanced such as by conventionally known techniques.

In particular, the entry of Lck activators and nucleic acids as described herein through the membrane of bacterial minicells may be facilitated by the use of various known reversible and irreversible methods. These include electroporation (Miller L. et al, *Technology in Cancer Research & Treatment,* 2005, 4: 1-7), exposure to digitonin (Melo R F. et al, *Cell Biochemistry and Function,* 1998, 16: 99-105), NSAIDS (Mizushima T, *Inflammation and Regeneration,* 2008, 28: 100-105), Triton-X100 (van de Ven A L. et al, *J Biomedical Optics,* 2009, 14(2): 1-10), plant saponins (Bachran C. et al, *Mini-Reviews in Medicinal Chemistry,* 2008, 8: 575-584), lactic acid (Alakomi H L et al., Appl Environ Microbiol, 2000, 66(5): 2001-5), and such-like.

Alternatively, bacterial or other cells from which minicells can be produced may be transfected with an expression vector of expression of a Lck activator as described herein, wherein the minicells when produced are thereby loaded with the expressed Lck activator.

Entry of the contents or cargo of the minicells into target cells may be by translocation of the minicells into the target cells by phagocytosis (e.g., by neutrophils and macrophages) arising from interaction of the minicells with cell surface receptors expressed on the target cells or by endocytosis (either clathrin mediated or clathrin independent endocytosis), and subsequent degradation of the minicells and release of the contents of the minicells into the cytoplasm of the target cells (e.g., from intracellular compartments e.g., endosomes and/or lysosomes).

To assist loading of minicells, a peptide component of an embodiment of a Lck activators as described herein can be linked to a carbohydrate moiety e.g., glucose (D or L isomers) for the purpose of facilitating transport through LamB porins present on bacterial derived minicells. The porin superfamily contains a number of homotrimeric, transmembrane proteins that form water-filled pores across the outer cell membranes of Gram negative bacteria. Most porins form general, non-specific channels that are regulated by environmental changes. Maltoporin (LamB porin), is responsible for the guided diffusion of maltose and maltodextrins into *E. coli* cells. In particular, LamB protein can also facilitate the diffusion of glucose (von Meyerburg K and Nikaido H, *Biochem Biophys Res*. Vol. 78: pp 1100-1107, (1977)) and glucose has been found to have the fastest rate of diffusion across LamB protein in vitro from a large range of sugars tested (Luckey M and Nikaido H, *Proc. Natl. Acad. Sci.* USA Vol. 77: pp167-171, (1980). Lck activators, fusion proteins and peptide components thereof as described herein can be purified from cell culture by sonication or disruption of cell membranes using detergents, centrifugation to remove membrane and solid fragments, and purification from solution or supernatant as applicable by affinity or immunoaffinity chromatography by methods known in the art. Suitable such solid substrates and supports that may be used include, but are not limited to agarose, sepharose and other commercially available supports (e.g., beads of latex, polystyrene, or dextran etc. Antibodies, binding fragments thereof or other suitable binding molecules for immobilizing the peptide or fusion protein of the invention on the solid support for subsequent elution and concentration therefrom can be bound to the solid substrate covalently utilizing commonly employed amide or ester linkers, or by adsorption.

Further, nanoparticles such as albumin, gelatine, phospholipids suitable for use in liposomes, polymers, solid metal-containing nanoparticles and the like may also be utilised for delivery of Lck activators as described herein (e.g., see De Jong W H & Borm P J A, Int J Nanomedicine, 2008, 3(2):133-149). The technique of external coating of nanoparticles with antibodies to various ligands or receptors of target cells is also well-recognised and can be employed in embodiments of the invention.

In particular, lipid delivery of Lck activators in accordance with the invention includes by liposomes, solid lipid nanoparticles, inverse lipid micelles, lipid microtubules and lipid microcylinders (reviewed in Swaminatham J & Ehrhardt C, Expert Opin Drug Deliv, 2012, 9(12): 1489-1503). Liposome containing peptide cargoes have, for example, been proposed for transdermal delivery, as nebulisers, for intranasal, ocular and buccal routes and for oral, parenteral and pulmonary routes (reviewed in Swaminatham J & Ehrhardt C, Expert Opin Drug Deliv, 2012, 9(12): 1489-1503). Liposomes have been widely studied as drug and gene delivery vehicles and more recently as peptide delivery vehicles (PCT Pub. No. WO2013033838 A1, Pharmagap Inc, filing date Aug. 21, 2012, Inventors; Sokoli K & Chabot J M) and pegylated liposomal formulations comprise a mixture of neutral lipids and anionic lipids in most instances.

A number of clinically proven liposome-based drug therapies are available, and targeted liposomes compared with non-targeted liposomes achieve enhanced intracellular drug delivery in tumour tissues (Kirpotin D B et al, Cancer Res, 2006, 66: 6732). Moreover, successful liposomal-mediated gene delivery across the blood brain barrier for treatment of gliomas has recently been reported (Yue P-J et al, Molecular Cancer, 2014, 13: 191). A combination of liposomal-based cell-targeting and cell-internalisation approaches are available to deliver Lck activators to cells in accordance with methods of the invention (e.g., to T cells to boost the immune system/immune responses such as to pathogens or cancer cells, etc).

A method for improving delivery of Lck activators as described herein to target cells (e.g., immune cells) may comprise functionalization of the surface of liposomes with targeting ligands that recognise receptors expressed selectively by immune cells such as CD3 or the humanised anti-CD4 antibody (TNX-355, now known as Ibalizumab, TMB-355) described by Zhang X-Q et al, Antimicrobial Agents and Chemotherapy, 2006, 50(6): pp 2231-2233). Ibalizumab is a non-immunosuppressive monoclonal antibody that binds CD4, the primary receptor for HIV, and inhibits the viral entry process (Ibalizumab (TMB-355): TaiMed Biologics. 2009-09-09). PEGylation on the outer surface of liposomes also facilitates use of bi-specific antibodies or derivatives thereof that simultaneously target PEG units and a receptor on either immune or cancer cells. By targeting cancer cells with a Lck activator linked to an MMP9/2 cleavage sequence, that cleaves off the Lck activating polypeptides described herein Lck, this can augment tumour infiltrating lymphocyte anti-cancer activity. The inventors have demonstrated that MMP9/2 does not cleave the Lck activator polypeptides descried herein. Hence, Lck activators as described herein may be encapsulated within liposomes that are targeted to surface antigens expressed on target cells (e.g., cancer cells or immune cells) such as HER1, HER2, PSMA (prostate-specific membrane antigen) or another antigen.

Lck activators, peptides, fusion proteins, engineered antibody and other binding moieties (e.g., scFvs) as described herein can, for example, be expressed in host cells with a tag as is known in the art (e.g., c-myc and poly-His tags) for aiding their purification and/or evaluation of their binding ability to cell lines. Where such a tag is utilised the encoded Lck activator, peptide or the like may further include suitable amino acid sequence that facilitates removal of the tag using endopeptidases). Likewise, nucleic acid encoding a Lck activator, peptide, fusion protein or the like as described herein may further include a signal peptide sequence for facilitating secretion of the translated product from a host cell for purification by affinity chromatography as described above. Protocols for the preparation of solid substrates for immunoaffinity chromatography and affinity chromatography protocols are for instance described in Current Protocols in Molecular Biology—Ausubel F M. et al, Wiley-Interscience, 1988 and subsequent updates thereof.

Lck activators, peptide components thereof, fusion proteins, and nucleic acids as described herein can be provided in isolated or purified form. The term "purified" as used herein encompasses partial purification e.g., to a level of 80% purity or more, or at least 85%, or at least 90%, or at least 95%, or at least 96%, or at least 97%, or at least 98%, or more (e.g., 99% or greater) as may be evaluated by electrophoretic and/or other techniques.

In still further embodiments, free terminal end(s) of peptide component(s) of a Lck activator as described herein may be e.g., methylated, acetylated, or pegylated with a plurality of ethylene glycol monomer units to render it less resistant to degradation by proteases in vivo or to inhibit clearance of the Lck activator from the circulation via the kidneys. Methods for pegylation of polypeptides/peptides are well known in the art and all such methods are expressly encompassed. Typically, a pegylated peptide used in a method embodied by the invention will be coupled to 2 or more monomer units of polyethylene glycol (PEG) and generally, from about 2 to about 11 monomers of PEG (i.e., (PEG)n where n equals from 2 to 11). Most usually, n will be 2. Moreover, a peptide comprising a Lck activator embodied by the invention may be cyclised to provide enhanced rigidity and thereby stability in vivo, and various such methods are known in the art.

Whilst a Lck activator as described herein may be administered to a subject as the sole drug for prophylaxis or treatment of the applicable disease or condition in accordance with the invention, in at least some embodiments the therapeutic agent may be administered in combination with one or more other drugs for treatment (i.e., prophylactic or therapeutic) of the disease or condition. Any suitable drugs conventionally used for the treatment of the particular disease or condition may be utilised with therapeutic agent(s) as described herein in the combination therapy, such as checkpoint blockers.

Conventional antiviral drugs that may be used in a combination therapy in accordance with the invention may, for instance, be selected from retroviral drugs, protease inhibitors, integrase inhibitors, cell entry inhibitors, and neuraminidase inhibitors. Examples include nucleoside reverse transcriptase inhibitors such as zidovudine (AZT), Abacavir, lamivudine, emtricitabine, and Acyclovir, nucleotide reverse transcriptase inhibitors such as Tenofovir, non-nucleoside reverse transcriptase inhibitors such as nevirapine and efavirenz, cell entry inhibitors such as maraviroc, and enfuvirtide, integrase inhibitors such as Raltegravir, Elvitegravir, and Dolutegravir, protease inhibitors such as Darunavir, Atazanavir, Indinavir, Lopinavir, Nelfinavir, Amprenavir, and Ritonavir, and neuraminidase inhibitors such as zanamivir, and oseltamivir.

In at least some embodiments a Lck activator as described herein may be included in conventional combination therapies for treatment of HIV or other retroviral infection such as may be selected from the group consisting of combivir (zidovudine and lamivudine), Trizivir (abacavir, zidovudine and lamivudine), Kaletra (lopinavir and ritonavir) Epzicom (abacavir and lamivudine), Truvada (tenofovir and emtricitabine), Atripla (efavirenz, tenofovir and emtricitabine), Stribild (elvitegravir, cobicistat, tenofovir and emtricitabine) and triumeq (dolutegravir, abacavir and lamivudine).

Conventional antibacterial drugs that may be used in a combination therapy in accordance with the invention may, for example, be selected from the group consisting of antibiotics such as penicillins, cephalosporins, carbapenems, aminoglycosides, sulfonamides, quinolones, and oxazolidinones.

Conventional anti-protozoan drugs that may be used in a combination therapy in accordance with a method of the invention may, for example, be selected from the group consisting of metronidazole, ornidazole, eflornithine, furazolidone, melarsoprol, tinidazole and pyrimethamine.

Conventional anti-helminth drugs that may be used in a combination therapy as described herein include benzimidazoles such as albendazole, mebebdazole, triclabendazole, flubendazole, and fenbendazole.

A Lck activator as described herein may also be used for treatment of opportunistic infections arising from treatment with a conventional drug for another disease or condition. For example, the drug Gleevec (imatinib, ST1571), commonly used in the treatment of chronic myelogenous leukemia, is a potent inhibitor of tyrosine kinases and reduces TCR-induced proliferation and activation through inhibition of Lck activity (Seggewiss R et al, 2005, Blood, 105: 2473-2479), which has implications for induction of opportunistic infections. This also applies equally to the amelioration of side effects from other tyrosine kinase inhibitors such as imatinib, nilotinib or dasatinib. For example, notwithstanding the potential morbidity caused by immune-enhancing drugs such as bacterial superantigens (e.g., staphylococcal enterotoxin A (SEA)), it has been proposed that SEA be used for the prevention of imatinib mediated T cell immunosuppression in chronic myeloid leukemia given that Lck is activated by SEA and the lack of selective Lck activators (Wang G et al, BioMed Research International, 2014, Article ID 682010).

In some embodiments, a conventional drug for prophylaxis or treatment of a pathogenic infection or other disease or condition as described herein may be complexed with a Lck activator in accordance with the invention by, for example, a covalent bond, by charge attraction, or with the use of a suitable linker. Suitable linkers for linking the drug to the Lck activator include e.g., linkers of from 1 to 10 atoms in length, sulfhydryl linkers and/or an amino acid or amino acid sequence preferably defining one or more enzyme cleavage sites (e.g., an MMP cleavage site) for release of the drug at, or within, target cells or tissues. As an example, the drug may be coupled to a compound (e.g., a polyamide moiety of Formula II) of the Lck activator (e.g., via a terminal $NH_2$ group or other suitable terminal group of the polyamide moiety), or to e.g., the terminal end of a polycationic peptide (PP) or augmenting peptide or other peptide (AP/P) of the Lck activator, either directly or indirectly using a suitable linker system as described above.

The activity and/or cell toxicity profile of a Lck activator as described herein on cells may be determined by various conventionally known assays such as one or more of evaluation of cell morphology, trypan-blue exclusion, assessment of apoptosis, cell proliferation studies (e.g., cell counts, $^3$H-thymidine uptake and MTT assay), kinase activity assays, Western blot and immunofluorescence studies.

A Lck activator as described herein can be administered to the mammal in accordance with a method of the invention or cells can be contacted with the Lck activator in vitro. Likewise, the invention provides for ex vivo treatment where cells are treated with the Lck activator externally of the mammal prior to return, administration to, or implantation of the cells in, the mammal.

A Lck activator, vector (e.g., expression vector) or nucleic acid as described herein can be provided in a pharmaceutical composition comprising a pharmaceutically acceptable diluent, carrier and/or excipient for administration to the intended subject. The Lck activator or nucleic acid can be administered orally, intranasally, via inhalation (e.g., by aerosol spray), intravenously, parenterally, rectally, subcutaneously, by infusion, topically, intramuscularly, intraperitoneally, intranasally, intraspinally, intraocularly, or via any other route deemed appropriate.

The rectum and/or colon provides a route for enhancing drug absorption of peptides using various absorption enhancers coupled to the peptides such as enamines (phenylalanine and phenylglycine), 5-amino or -methoxysalicylate, chelating agents, medium chain fatty acids, cyclodextrins, pH sensitive polymer coated drugs, azo-polymeric prodrugs and suchlike (e.g., see Tiwari G et al, International J Drug Delivery, 2010, 2:01-11; Kolte B P et al, Asian J Biomedical & Pharmaceutical Sciences, 2012, 2(14): 21-28; Philip A K et al, O M J, 2010, 25: 70-78; and Lakshmi P J et al. 2012, Asian J Res Pharm Sci, 2(4): 143-149), and such modes of administration and forms of Lck activators as described herein are also expressly encompassed herein.

A pharmaceutical composition can, for example, be in the form of a liquid, suspension, emulsion, syrup, cream, ingestible tablet, capsule, pill, suppository, powder, troche, elixir, or other form that is appropriate for the selected route of administration.

Pharmaceutical compositions useful in methods in accordance with the invention include aqueous pharmaceutical solutions. Injectable compositions will be fluid to the extent that syringability exists and typically, will normally be stable for a predetermined period to provide for storage after manufacture. Moreover, a pharmaceutically acceptable carrier may include any suitable conventionally known solvents, dispersion media, water, physiological saline and isotonic preparations or solutions, surfactants, and any suitable pharmaceutically acceptable carrier (e.g., orally or topically acceptable carriers) may be utilised. Suitable dispersion media can for example contain one or more of ethanol, polyols (e.g., glycerol, propylene glycol, liquid polyethylene glycol and the like), vegetable oils and mixtures thereof. In particular, the Lck activator or nucleic acid can, for example, be formulated with an inert diluent, an assimilable edible carrier and/or it may be enclosed in a hard or soft shell gelatin capsule.

A pharmaceutical composition as described herein can also incorporate one or more preservatives suitable for in vivo and/or topical administration such as parabens, chlorobutanol, phenol, sorbic acid, and thimerosal. In addition, prolonged absorption of the composition may be brought about by the use in the compositions of agents for delaying absorption such as aluminium monosterate and gelatin. Tablets, troches, pills, capsules and the like containing a Lck activator or nucleic acid as described herein can also contain one or more of the following: a binder such as gum tragacanth, acacia, corn starch or gelatin; a disintegrating agent such as corn starch, potato starch or alginic acid; a lubricant such as magnesium stearate; a sweetening agent such as sucrose, lactose or saccharin; and a flavouring agent.

The use of ingredients and media as described above in pharmaceutical compositions is well known. Except insofar as any conventional media or ingredient is incompatible with a Lck activator as described herein, use thereof in therapeutic and prophylactic pharmaceutical compositions as described herein is included.

By "combination therapy" as used herein is meant prior, simultaneous or sequential administration of the Lck activator or nucleic acid in accordance with the invention in the same or different formulations to the other drug(s) by the same or different routes whereby the Lck activator(s) and and/or nucleic acid(s) exert their effect(s) in over overlapping therapeutic windows.

It is particularly preferred to formulate parenteral compositions in dosage unit form for ease of administration and uniformity of dosage. Dosage unit form as used herein is to be taken to mean a physically discrete unit suited as a unitary dosages for the subject to be treated, each unit containing a predetermined quantity of at least one Lck activator or nucleic acid in accordance with the invention calculated to produce the desired therapeutic or prophylactic effect in association with the relevant carrier and/or excipient used. When the dosage unit form is for example, a capsule, tablet or pill, various ingredients may be used as coatings (e.g., shellac, sugars or both) to otherwise modify the physical form of the dosage unit or to facilitate administration to the subject.

A pharmaceutical composition will generally contain at least about 1% by weight of a Lck activator as described herein. The percentage may be varied and can conveniently be between about 5% to about 80% w/w of the composition or preparation. Again, the amount of a Lck activator or nucleic acid in accordance with the invention will be such that a suitable effective dosage will be delivered to the subject taking into account the proposed route of administration. Preferred oral pharmaceutical compositions will contain between about 0.1 µg and 15 g of the Lck activator.

The dosage of the Lck activator or nucleic acid in accordance with the invention will depend on a number of factors including whether the Lck activator or nucleic acid is to be administered for prophylactic or therapeutic use, the disease, condition or purpose for which the agent is intended to be administered, the severity of the disease or condition, the age of the subject, and related factors including weight and general health of the subject as may be determined by the physician or attendant in accordance with accepted principles. For instance, a low dosage may initially be given which is subsequently increased at each administration following evaluation of the subject's response. Similarly, the frequency of administration may be determined in the same way that is, by continuously monitoring the subject's response between each dosage and if necessary, increasing the frequency of administration or alternatively, reducing the frequency of administration.

Typically, a Lck activator as described herein will be administered in accordance with a method embodied by the invention to provide a dosage of the Lck activator of up to about 100 mg/kg body weight of the individual, more usually in a range up to about 50 mg/kg body weight, and most usually in a range of about 5 mg/kg to 40 mg/kg body weight. In at least some embodiments, the Lck activator will be administered to provide a dosage of the Lck activator in a range of from about 5 to 25 mg/kg body weight, usually in a range of from about 5 mg/kg to about 20 mg/kg and more usually, in a range of from 10 mg/kg to about 20 mg/kg. When administered orally, up to about 20 g of the Lck activator may be administered per day, (e.g., 4 oral doses per day, each dose comprising 5 g of the Lck activator).

With respect to intravenous routes, particularly suitable routes are via injection for systemic distribution of the Lck activator or nucleic acid into blood vessels which supply tissue or particular organ(s) to be treated. Moreover, the Lck activator can be delivered by any suitable infusion or perfusion techniques. The Lck activator or nucleic acid (e.g., an expression vector loaded in bacterially-derived minicells) may also be delivered into cavities such for example the pleural or peritoneal cavity, or be injected directly into tissue to be treated.

Suitable cloning and expression vectors useful in methods described herein and methods for their preparation and delivery are described in manuals and handbooks well known to the skilled addressee, e.g., see Ausubel et al. (1994) Current Protocols in Molecular Biology, USA, Vol. 1 and 2, John Wiley & Sons, 1992; Sambrook et al (1998) Molecular cloning: A Laboratory Manual, Second Ed., Cold Spring Harbour Laboratory Press 1989, New York, and reprints and updates thereof, the contents of which are incorporated herein in their entirety by cross-reference. Likewise, suitable pharmaceutically acceptable carriers and formulations useful in compositions as described herein can for instance, be found in handbooks and texts well known to the skilled addressee, such as "Remington: The Science and Practice of Pharmacy (Mack Publishing Co., 1995)", and any reprints and updates thereof. Methods and protocols for the transfection of cells and expression of nucleic acid inserts in vivo are for example described in WO 200631996, WO 200631689, WO 200629981, WO 200629005, US 20060063731, and US 20060063924, the contents of all of the foregoing publications, manuals and handbooks listed above are incorporated herein in their entirety by cross-reference.

The mammal treated as described herein may be any mammal treatable in accordance with the invention. For instance, the mammal may be a member of the bovine, porcine, ovine or equine families, a laboratory test animal such as a mouse, rabbit, guinea pig, a cat or dog, or a primate or human. Typically, the mammal is a human.

In another aspect the present invention provides the use of a Lck activating polypeptide described herein in the manufacture of a medicament for use in treating and/or preventing the diseases and/or conditions (including age related changes) referred to herein/

In another aspect the present invention provides uses of a Lck activating polypeptide described herein for use in treating and/or preventing the diseases and/or conditions (including age related changes) referred to herein.

The invention is further described below by a way of a number of non-limiting Examples.

Examples

Example 1: Lymphocyte-Specific Protein tyrosine kinase (Lck) Activation by polyarginine polypeptides In Vitro The ability of polypeptides of the present invention to activate Lck was examined in vitro. Lck is member of the Src family of tyrosine kinases. In vitro Lck activation kinase studies were conducted by Eurofins Pharma Discovery Services UK Limited (Dundee Technology Park, Dundee, United Kingdom) using ATP concentrations within 15 μM of the apparent Km in the presence of peptide substrate (KVEKIGEGTYGVVYK, SEQ ID NO: 67) and test polypeptide in semi-log dose ranges. All results in are percentage Lck activity relative to control (100%).

Test polypeptides were assessed at a concentration of 1.0 μM.

FIG. 1 shows polypeptides comprising 4, 5, or 6 consecutive arginine residues SEQ ID NO: 119, 2, and 3, respectively) do not activate Lck at a concentration of the peptide of 1 μM.

No increase in Lck activity was observed when peptides comprising 10 consecutive histidine residues (SEQ ID NO: 14, deca-histidine peptide; 10His) were used at a concentration of the peptide of 1 μM.

Negligible Lck activity was observed when peptides comprising 10 consecutive ornithine residues (SEQ ID NO: 15, deca-ornithine peptide; 10 Orn) were used at a concentration of the peptide of 1 μM.

Surprisingly however, for example, polypeptides comprising 8 to 20 consecutive arginine residues are able to activate Lck. polypeptides comprising 8, 9, 10, 12, 14, 20 consecutive arginine residues activate Lck at a concentration of the peptide of 1 μM.

For example, the 12 mer arginine sequence (SEQ ID NO: 8, IK01200) activates Lck, resulting in 401% Lck activity relative to control.

FIG. 1 also shows that 10 consecutive lysine residues (SEQ ID NO: 13, deca-lysine peptide; 10Lys) was found to increase Lck activity by 161% a concentration of the peptide of 1 μM.

FIG. 1 shows peptides comprising consecutive D arginine residues activate Lck at a concentration of the peptide of 1 μM. For example, the 8 mer arginine sequence (SEQ ID NO: 5, IKD00800) activates Lck, resulting in 80% Lck activity relative to control. The 14 mer arginine sequence (SEQ ID NO: 10, IKD01400) activates Lck, resulting in 228% Lck activity relative to control.

FIG. 1 also demonstrates peptides comprising consecutive arginine residues and consecutive histidine residues activate Lck at a concentration of the peptide of 1 μM. For example, the 9 mer arginine sequence and 10 mer histidine sequence (SEQ ID NO: 20, IK00910) activates Lck, resulting in 348% Lck activity relative to control.

Importantly, FIG. 1 also demonstrates peptides comprising anionic residues do activate Lck. For example the 9 mer aspartate sequence (SEQ ID NO: 21, IKD9; DDDDDDDDD) does not activate Lck at a concentration of the peptide of 1 μM.

This data demonstrates that the peptides of the present invention activate Lymphocyte-specific protein tyrosine kinase (Lck).

Example 2: Selective Lymphocyte-Specific Protein Tyrosine Kinase (Lck) Activation by Polyarginine and Polylysine Polypeptides The ability of polypeptides of the present invention to activate Src family kinases was examined in vitro. Kinase activation studies utilising peptides were carried out as described in Example 1, and all kinase activity values are shown as percentage relative to control.

FIG. 2 shows that Lck is selectively activated by the polyarginine Lck activating polypeptides of FIG. 1; no Src family kinases (SFKs) other than Lck were activated by the polyarginine and polylysine peptides at a peptide concentration of 1 μM. Consistent with Example 1 and FIG. 1, the deca-histidine peptide (SEQ ID NO: 14, 10His) did not induce any activation of Lck at this concentration.

This data demonstrates that Lck activating peptides selectively activate Lck, and do not activate Blk, cSRC, Fgr, Fyn, Hck, Lyn or Yes.

Example 3: Lck Activating Polyarginine Polypeptides Increase Lck Phosphorylation and Lck Activating Polyarginine Polypeptides Increase Lck Phosphorylation at Y394

Phosphorylation of Tyr394 of Lck results in conformational opening of Lck that activates Lck kinase.

Western blot studies were performed by Eurofins Pharma Discovery Services UK Limited (Dundee, United Kingdom). In brief, Lck(h) was incubated in the presence of test peptide employing standard KinaseProfiler™ reaction conditions (Eurofins Pharma Discovery Services UK Limited) and an ATP concentration within 15 μM of the $K_m$. Reactions were allowed to proceed for 40 minutes at room temperature before being stopped by the addition of SDS-sample buffer. In each case the Lck enzyme was diluted to yield 20 ng per 25 μl reaction. Appropriate controls in the absence of compound and peptide were also run as well as an untreated sample of both the Lck(h) and Lck(h) activated kinases. The resulting samples were then subjected to SDS-PAGE and western blot analysis using the antibodies 4G10 (anti-phospho-tyrosine antibody) (see FIG. 3) and anti-pY394 Lck (R&D Systems MAB7500) (see FIG. 2). An additional blot using the secondary detection antibody (anti-mouse-HRP) was also performed. The membranes were stained by Ponceau S to verify sample loading and effective protein transfer. The 4G10 antibody is a general anti-phospho-tyrosine antibody and there are several tyrosine residues in Lck but only one auto-phosphorylating tyrosine residue, i.e., at position Y394. Hence, the anti-py394 antibody specifically detects autophosphorylation of Lck. Samples were as follows (numbers correspond to the lanes on the gel):
1. Molecular weight markers
2. Standard Lck
3. Standard Lck+peptide substrate+ATP (no test peptide)
4. Standard Lck−peptide substrate+ATP (no test peptide)
5. Standard Lck+ATP+10Arg peptide (SEQ ID NO: 7, IK00100; 1 µM) (no peptide substrate)
6. Standard Lck+ATP+10 Arg peptide (SEQ ID NO: 7, IK00100; 10 µM) (no peptide substrate)
7. Standard Lck+ATP+8 Arg peptide (SEQ ID NO: 4, IK00800; 1 µM) (no peptide substrate)
8. Standard Lck+ATP+8 Arg peptide (SEQ ID NO: 41K00800; 10 µM) (no peptide substrate)
9. 10 Arg (SEQ ID NO: 7, IK00100) (10 µM) (test peptide only)
10. 8 Arg (SEQ ID NO: 4, IK00800) (10 µM) (test peptide only)

The steps of the western blot protocol were as below:
SDS-PAGE gel: 50 minutes at 200V
Western blot transfer: 90 minutes at 25V
Membrane: Nitrocellulose Pre-Cut Blotting Membranes 0.2 µm pore size (LC2000 (Life Tech))
Ponceau stain: 0.1% Ponceau S (w/v) in 5% acetic acid
The membrane was blocked with 10 mL PBST and 10% BSA for 1 hour before application of primary and secondary antibodies.
Primary Antibodies:
1. Anti-4G10 (Millipore 05-777) 1/1000 in PBST with overnight incubation at 4° C. followed by washing with 4×20 mL PBST.
2. Anti-pY394 Lck (R&D Systems) 1/2500 in PBST with overnight incubation at 4° C. followed by washing with 4×20 mL PBST.
Secondary Antibody:
Anti-mouse-hrp (Sigma A5278) 1/5000 in PBST followed by washing with 4×20 mL PBST for 5 hours on a spiral shaker at room temperature. Detection was performed via SuperSignal ELISA Pico Chemiluminescent Substrate—37070 (Pierce).

Figure 3A:
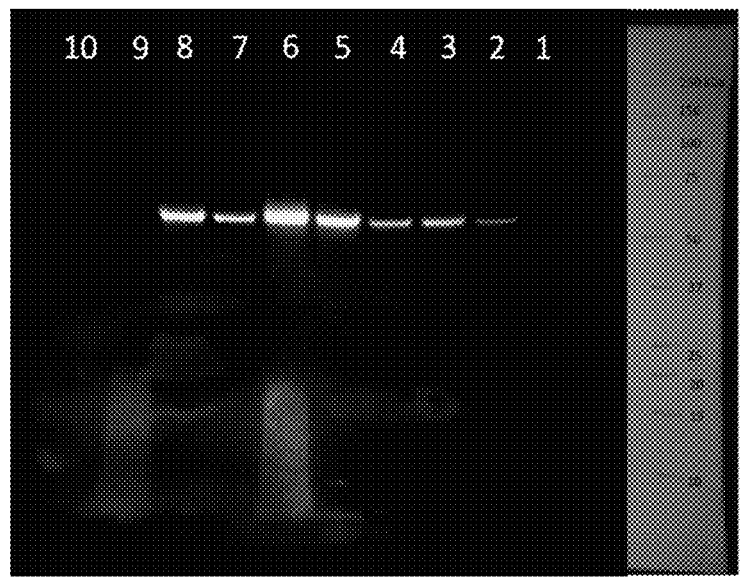
FIG. 3 shows Lck activating polyarginine polypeptides increase Lck phosphorylation and Lck activating polyarginine polypeptides increase Lck phosphorylation at Y394.

Probing with the anti-phospho tyrosine 4G10 antibody resulted in bands in all of lanes 2-8 as shown in FIG. 3A. That standard Lck in lane 1 yielded a faint band suggests some endogenous Lck phosphorylation. Incubation in the presence of ATP resulted in an increase in the intensity of the band consistant with autophosphorylation, whilst the presence of the peptide substrate KVEKIGEGTYGVVYK (SEQ ID NO: 67) in the incubation did not appear to significantly influence the degree of autophosphorylation (see lanes 3-4). Incubation in the presence of the test peptide (8Arg: RRRRRRRR (SEQ ID NO: 4, IK00800); or 10Arg: RRRRRRRRRR (SEQ ID NO: 7, IK00100)) resulted in a significant increase in the level of phosphorylation observed on Lck. Moreover, the level of phosphorylation increased with increasing test peptide concentration (see lanes 5-8). No corresponding bands are shown in lanes 9 and 10 (test peptides only).

This data demonstrates that polyarginie polypeptides that selectively activate Lck enhance autophosphorylation of Lck. This data also demonstrates that polyarginie polypeptides enhance autophosphorylation of Lck in a dose dependent manner.

Figure 3B:
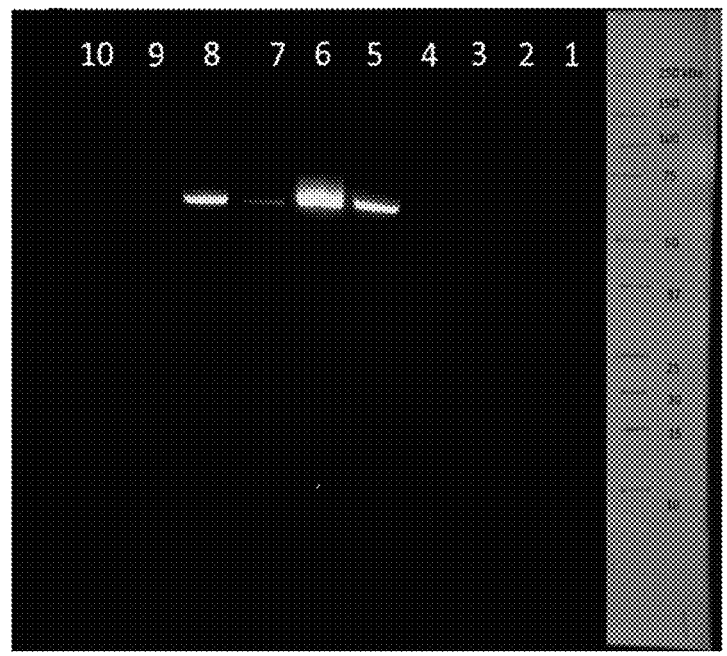

The developed western blot in FIG. 3B shows the results obtained for auto-phosphorylation of Lck at Y394 detected by the anti-pY394 antibody. As can be seen, the standard Lck lane (lane 2) does not show a band indicating that there is no endogenous Lck phosphorylation at the tyrosine Y394 site. Incubation in the presence of ATP either with or without peptide substrate KVEKIGEGTYGVVYK (SEQ ID NO: 67) did not result in an increase in the intensity of the band (lanes 3-4). Incubation in the presence of test peptide resulted in a significant increase in the level of phosphorylation detected at amino acid position Y394 of Lck. Again, the level of phosphorylation increased with increasing test peptide concentration (see lanes 5-8 of FIG. 3B). No corresponding bands are visible in either lanes 9 or 10 indicating no cross-reactivity with the test peptides 8 Arg (SEQ ID NO: 4, IK00800) and 10 Arg (SEQ ID NO: 7, IK00100).

This data demonstrates that polyarginie polypeptides that selectively activate Lck enhance phosphorylation of Lck at Y394. This data also demonstrates that polyarginie polypeptides enhance phosphorylation of Lck at Y394 in a dose dependent manner.

Example 4: Enhancement of Lck Activation by Polyarginine Polypeptides in Vitro

The ability of polypeptides comprising both lysine and arginine to activate Lck in vitro was examined. Lck activation studies utilising peptides were carried out as described in Example 1, and all kinase activity values are shown as percentage relative to control.

FIG. 4 shows that the polypeptides RSKAKNPLY (SEQ ID NO: 30, IK09400) and RSKAKNPLYR (SEQ ID NO: 31, IK14000) do not activate Lck at 1 uM. Similarly, shorter derivatives of this polypeptide show no or only negligible Lck activation.

For example, RSKAK (SEQ ID NO: 25) and RSKAK-RR (SEQ ID NO: 27) show an activation of only 5% Lck relative to control.

FIG. 4 shows that the when non-Lck activating polypeptides are fused to Lck activating polypeptides described in FIG. 1, the fusion is surprisingly able to not only activate Lck, an unexpected enhancement of Lck activation is observed. For example, when the non-Lck activating polypeptide RSKAKNPLY (SEQ ID NO: 30) is fused to a polypeptide comprising 9 consecutive arginine residues shown in FIG. 1 to selectively activate Lck (SEQ ID NO: 6, RRRRRRRRR; 325%), the resulting RSKAKNPLY-RRRRRRRRR (SEQ ID NO: 24) fusion shows increased Lck activation (496%).

As can be seen from FIG. 4, no or negligible Lck activation was observed for the peptide RSKAK (SEQ ID NO: 25) alone or when coupled from 1 to 4 arginine residues. Similarly, no Lck activation was observed for the peptides RSKAKNPLY (SEQ ID NO: 30) or RSKAKN-PLYR (SEQ ID NO: 31) alone, or when the peptide RSKAKNPLY (SEQ ID NO: 30) was coupled to a sequence of 4 arginine residues (SEQ ID NO: 32). However, when the peptide RSKAKNPLY (SEQ ID NO: 30) was coupled to 5 contiguous polyarginine residues (SEQ ID NO: 33, peptide IK14400) a modest level of Lck activation was observed (85%). Similar results were obtained by the peptide RSKAKNPLY-RRRRRR (SEQ ID NO: 34, IK 14500) (82%), and for the dextro-reverso peptide rskaknply-rrrrrr (SEQ ID NO: 35, ID94600) consisting entirely of D amino acids which induced a 60% increase in Lck activity.

Surprisingly, as also shown in FIG. 4, a substantial increase in Lck activity was obtained when the peptide RSKAKNPLY-RRRRR (SEQ ID NO: 33) was cyclised by the addition of a cysteine amino acid to each terminal end of the peptide (i.e., peptide C-RSKAKNPLY-RRRRR-C, SEQ ID NO: 36; IK4500C) (221%), or when longer polyarginine sequences were coupled to the peptides RSKAK (SEQ ID NO: 25) and RSKAKNPLY (SEQ ID NO: 30). Similar substantial increases in Lck activation were also obtained when a longer polyarginine sequence was coupled to reverso or dextro-reverso forms of the peptide RSKAKNPLY (SEQ ID NO: 30). See, for example, the peptide RSKAK-RRRRRRRRR (SEQ ID NO: 37, IK50900) for which a 531% increase in Lck activity was observed, RRRRRRRRR-YLPNKAKSR (SEQ ID NO: 43, IK9R94Y) for which an increase in Lck activity of 630% was obtained, and the peptides rskaknply-rrrrrrrrr (SEQ ID NO: 129, IKD14800) and rrrrrrrrr-ylpnkaksr (SEQ ID NO: 39, IKR81400) for which increases in Lck activity of 490% and 616% were obtained, respectively.

Furthermore, the peptide RRRRRRRRR-SKAKNPLYR (SEQ ID NO: 42, IK9R94S) a substantial increase in Lck activity of 542% was obtained. As also shown in FIG. 4, only modest increases in Lck activity were observed when the polycationic sequence KKKKKKKKK (SEQ ID NO: 126) or RHHHHHHHHH (SEQ ID NO: 127) was coupled to the peptide RSKAKNPLY (SEQ ID NO: 30; see peptides IK94K90, SEQ ID NO: 44, and IK14010, SEQ ID NO: 45) (49% and 30%, respectively), indicating that Lck activation/stimulation is enhanced to a greater degree by polyarginine sequences than polylysine and polyhistidine sequences.

Substantial increases in Lck activity were also obtained when the peptide RSKAKNPLY (SEQ ID NO: 30) was coupled to two or three contiguous polycationic sequences (i.e., each consisting of polyargine or polyhistidine sequences) or to a polycationic sequence comprising repeating RK amino acid couplets as shown in FIG. 4 and FIG. 5. Indeed, increases in Lck activity of 883% and 899% were obtained for the peptide IK11480 (SEQ ID NO: 50) and IK14810 (SEQ ID NO: 47), respectively. Substantially increased Lck activity was also retained in the branched peptide RSKAKNPLY-RRRRRRRRR-HHHHHHHHH (SEQ ID NO: 48, Br IK14810).

Furthermore, substantial increases in Lck activity were obtained by peptide RVKVKVVVV (SEQ ID NO: 55, IK95000) alone or when coupled to polyarginine sequences tested ranging from 5 to 9 contiguous arginine amino acid residues as can be seen in FIG. 5. As also shown in that table, a similar increase in Lck activity was obtained for the peptide RRRRRRRR-RVKVKVVVV-R (SEQ ID NO: 59, IK80150).

Results for the stimulation of Lck when the peptide RVKVKVVVV (SEQ ID NO: 55, IK95000) is coupled to a combination of polyarginine and polyhistidine sequences, or to a polycationic sequence comprising repeating arginine and histidine (RH) couplets, are also set out in FIG. 5. Again, substantial increases in Lck activity were observed, with an increase in Lck activity compared to control activity of 778% observed for peptide RVKVK-RRRRRRRRR-HHHHHHHHH (SEQ ID NO: 113, IK50810).

These results indicate that, surprisingly, non-Lck activating polypeptides (e.g. RSKAKNPLY, SEQ ID NO: 30) are able to enhance Lck activation by Lck activating polypeptides of the present invention, including Lck activating polyarginine polypeptides (e.g. RRRRRRRRR, SEQ ID NO: 6) at 1 uM.

Example 5: The Lck Activating Fusion Polypeptides RSKAKNPLY-RRRRRRRRR (SEQ ID NO: 24) and RSKAKNPLY-RRRRRRRRR-(2Adod)₄-NH₂ (SEQ ID NO: 65) Activates Lck in a Dose Dependent Manner FIG. 6 demonstrates the Lck activating polypeptides RSKAKNPLY-RRRRRRRRR (SEQ ID NO: 24, "IK14800") and RSKAKNPLY-RRRRRRRRR-(2Adod)₄-NH₂ (SEQ ID NO: 65, "IK14804") activate Lck in a dose dependent manner. "(2Adod)₄" denotes four 2-aminododecanoic acids.

Example 6: Lck Activating Polypeptides Increase IL-2 Secretion in a Human T Lymphocyte (Jurkat) Cell Line The ability of Lck activating polypeptides to alter IL-2 secretion was examined.

In brief, wild-type Jurkat cells (an immortalised line of human T lymphocyte cells) were stimulated by exposure to biotinylated anti-CD3 antibody in the presence of anti-CD28 antibody and avidin. During the culture period (48 hours or 72 hours) cells were exposed to test polypeptides. Cell supernatant was assayed for IL-2 at the end of 48 or 72 hours using a standard commercially available ELISA kit as described above.

Figure 7A:
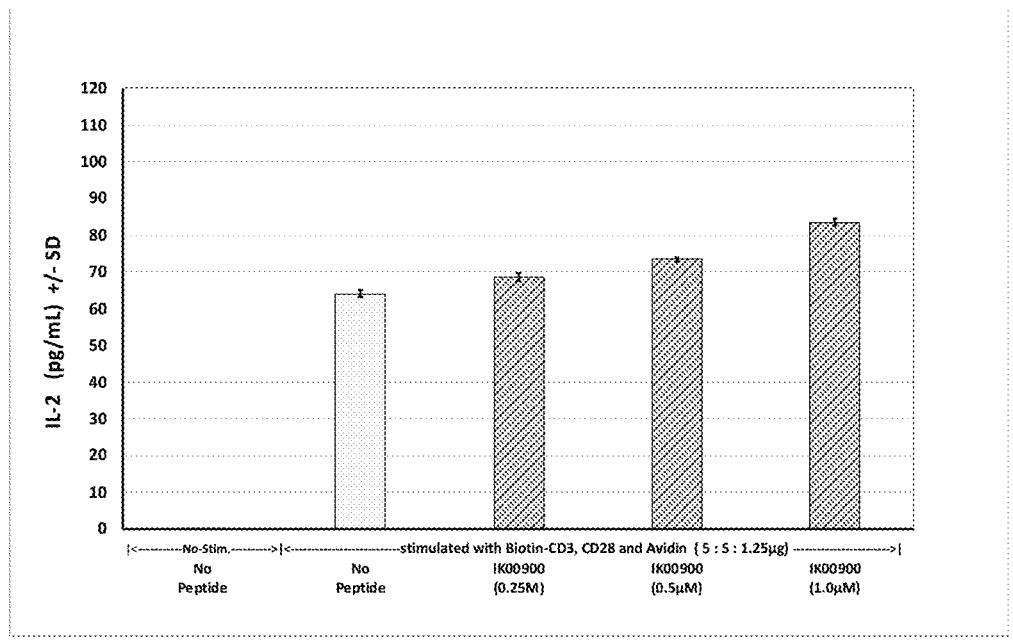

FIG. 7A shows that the Lck activating polypeptide "IK00900" RRRRRRRRR (SEQ ID NO: 6) induces IL-2 secretion relative to control in wild-type Jurkat cells following 48 h exposure.

Figure 7B:
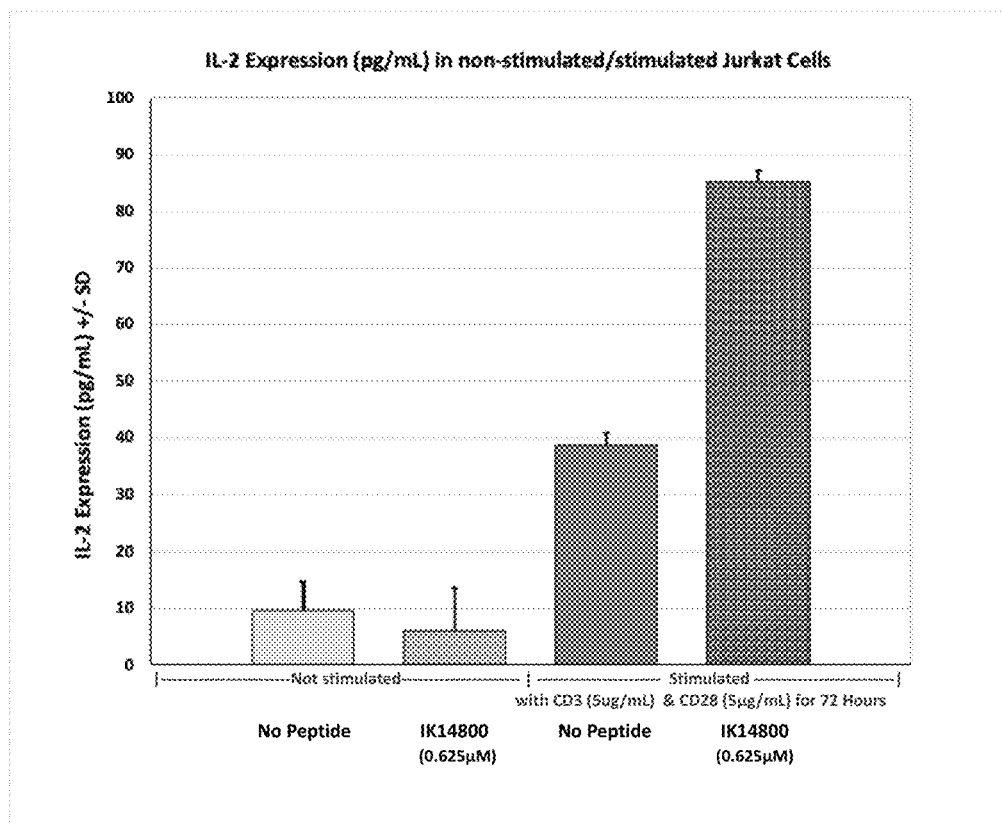

FIG. 7B shows that the Lck activating polypeptide "IK14800" RSKAKNPLY-RRRRRRRRR (SEQ ID NO: 24) induces IL-2 secretion relative to control in wild-type Jurkat cells following 72 h exposure.

These data demonstrate that a Lck activating polypeptide of the present invention is able to induce IL-2 secretion in a human T cell line, and that no IL-2 secretion is induced in non-stimulated Jurkat cells.

Example 7: Lck Activating Polypeptides Increase IL-2 Secretion from Isolated Human CD4+ and CD8+ T Cells The effect of Lck activating polypeptides on IL-2 secretion from isolated human CD4+ and CD8+ T cells was examined.

In brief, CD4+ and CD8+ T cells were isolated and immuno-magnetically separated from healthy human PBMCs. Levels of IL-2 were examined following anti-CD3 and anti-CD28 stimulation for 48 hours in the presence the Lck activating fusion polypeptide RSKAKNPLY-RRRRRRRRR (SEQ ID NO: 24).

FIG. 8 shows that the Lck activating polypeptide RSKAKNPLY-RRRRRRRRR (SEQ ID NO: 24, "IK14800") induces IL-2 secretion relative to control in isolated human CD4+ and CD8+ T cells.

Example 8: Lck Activating Polypeptides Increase IL-2 Secretion from Isolated Human CD3+ T Cells The effect of Lck activating polypeptides on IL-2 secretion from isolated T cells (CD3+ T cells) was examined.

In brief, isolated T cells (CD3+) were stimulated with anti-CD3 anti-CD28 Dynabeads™ and cultured together the Lck activating polypeptides RSKAKNPLY-RRRRRRRRR (SEQ ID NO: 24, "IK14800"), RVKVKVVVV-RRRRRRRRR (SEQ ID NO: 58, "IK15800"), and RVKVKVVVV-RRRRRRRRR (SEQ ID NO: 24) comprising only D amino acids (i.e. rvkvkvvvv-rrrrrrrrr; SEQ ID NO: 129, "IKD15800"), over a 5-concentration range plus vehicle control (0-1.25 µM) for 72 hours after which supernatants were collected and assessed for IL-2 by ELISA.

FIG. 9 shows that the Lck activating polypeptides RSKAKNPLY-RRRRRRRRR (SEQ ID NO: 24), RVKVKVVVV-RRRRRRRRR (SEQ ID NO: 58), and RVKVKVVVV-RRRRRRRRR (SEQ ID NO: 24) comprising only D amino acids (i.e. rvkvkvvvv-rrrrrrrrr, SEQ ID NO: 129), induce IL-2 secretion relative to control in isolated human T cells.

The effect of Lck activating polypeptides on IL-2 secretion from CD4+ T cells in a stimulated CD4+ T cell assay was also examined. In brief, Isolated CD4+ T cells were stimulated with anti-CD3 anti-CD28 Dynabeads™ and cultured together with the Lck activating polypeptides RRRRRRRRR (SEQ ID NO: 6, "IK00900") and RSKAKNPLY-RRRRRRRRR (SEQ ID NO: 24, "IK14800"), over a 5-concentration range plus vehicle control (0-1.25 µM) for 24 hours after which supernatants were assessed for IL-2 and IFN-γ by ELISA. The Lck activating polypeptides RRRRRRRRR (SEQ ID NO: 6) and RSKAKNPLY-RRRRRRRRR (SEQ ID NO: 24) induce IL-2 secretion relative to control in human CD4+ T cells in a stimulated T cell assay (data not shown). These data indicate that Lck activating polypeptides of the present invention are able to induce IL-2 secretion from stimulated human CD4+ T cells (data not shown).

Example 9: Lck Activating Polypeptides Increase IL2Ra (CD25) Expression in a Human T Lymphocyte (Jurkat) Cell Line The effect of Lck activating polypeptides on IL2Ra (CD25) expression on a T cell line was examined.

In brief, wild-type Jurkat cells ($1 \times 10^6$ cells) were cultured in standard RPMI medium and 10% foetal calf serum as above and either not stimulated or stimulated with PMA (50 ng/ml) and ionomycin for a period of 96 hours. Cells were exposed to the test peptides (2.5 µM conc.) listed in FIG. 10 for the entire 96 hour culture period, and IL-2R alpha levels were determined in cell lysates using a standard commercial ELISA format as described above.

FIG. 10 shows IL-2R alpha (CD25) expression was increased when stimulated cells were exposed to peptides RSKAKNPLY-RRRRRRRRR (SEQ ID NO: 115, IK14900), HHHHH-RSKAKNPLY-RRRRRRRRR (SEQ ID NO: 50, IK11480), RSKAKNPLY-RRRRRRRRR-HHHHHHHHHHHH (SEQ ID NO: 49, IK14820) and in particular, the peptide RSKAKNPLY-RRRRRRRRR (SEQ ID NO: 24, IK14800).

This data indicates that Lck activating polypeptides of the present invention are able to induce IL-2Ra expression on a human T cell line.

Example 10: Lck Activating Polypeptides Increase IL2Ra (CD25) Expression on Exhausted CD4+ Cells on Restimulation T-cell exhaustion is characterized by the stepwise and progressive loss of T-cell functions and can culminate in the physical deletion of the responding cells. Interleukin-2 (IL-2) production is one of the first effector activities to be extinguished, followed by tumour necrosis factor-α (TNF-α) production, whereas the ability to produce interferon-γ (IFN-γ) is more resistant to inactivation.

The effect of the peptide IK14000 (RSKAKNPLYR) which does not activate Lck at 1 uM, and the Lck activating fusion polypeptides IK14800 (RSKAKNPLY-RRRRRRRRR, SEQ ID NO: 24) and IKD14800 (rskaknply-rrrrrrrrr, SEQ ID NO: 129) on IL2Ra expression was examined.

A CD4+ T cell exhaustion assay using a murine model (Tg4 Ly5.1 (MBP-Tracker Mouse), B10PIxC57BL/6) was used whereby CD4+ T cell receptor transgenic T cells are stimulated with wild-type myelin basic protein peptide (WT-MBP) to produce fully responsive effector T cells or altered peptide ligand peptide MBP (APL-MBP) to produce exhausted T cells. These are rested in IL-2 and then a secondary stimulation with APC, a dose of APL-MBP peptide along with any treatments under investigation.

Cell Culture Procedure

Spleens from the aforementioned mice were removed and processed to generate a single cell suspension of splenocytes. MBP-Tracker splenocytes were resuspended at $3 \times 10^6$/mL and stimulated with WT-MBP (control, non-exhausted cells) or APL-MBP (to generate exhausted cells). Cells were stimulated for 72 hr. Following stimulation, T cells were purified by Ficoll density gradient, and subsequently re-plated at $2 \times 10^6$/mL in 20 U/mL IL-2 for four days. At the end of this rest period, cells were resuspended ($4 \times 10^5$/mL, final $2 \times 10^4$ per well) and restimulated using irradiated APC (from B10PLxC57BL/6 mice, $4 \times 10^6$/mL, final concentration of $2 \times 10^5$ cells per well), a single dose of APL-MBP peptide and test peptide across a range of concentrations. Following 48-72b hours of culture the cells were assessed by flow cytometry for markers of IL-2Ra and proliferation (CD25 and Ki-67, respectively) and supernatant was collected for assessment of cytokine production (IFN-γ and TNF-α) by ELISA or multiplexed immunoassays.

Cells were stained for flow cytometry after 72 hours in culture to assess CD25 (MFI, top, to indicate level of expression and frequency, bottom). From within the viable population, cells were gated to focus on CD4+ cells which were then gated on CD25+ populations.

FIG. 11 demonstrates that expression of CD25 is increased in exhausted CD4+ T cells upon restimulation with the Lck activating fusion polypeptides IK14800 (RSKAKNPLY-RRRRRRRRR, SEQ ID NO: 24) and IKD14800 (rskaknply-rrrrrrrrr, SEQ ID NO: 129). This data demonstrates that the Lck-activating polypeptides are able to enhance physiologically-controlled outcomes (e.g., IL-2Ra expression) in exhausted T cells that have been restimulated.

Example 11: Lck Activating Polypeptides Rescue a Human T Cell Line from Checkpoint Blockade To prevent over-activation of the immune system, the programmed death 1 (PD-1) pathway works as a checkpoint to control T cell activation. The pathway is activated when the ligands PD-L1 and PD-L2 bind to the PD-1 receptor, resulting in T cell "exhaustion," a reversible inhibition of T cell activation and proliferation. The ability of a Lck activating fusion polypeptide of the present invention was examined for the ability to rescue human T cells from checkpoint blockade induced by PD-L1.

In brief, Jurkat cells were activated by means of exposure to culture dish adhered anti-CD3 antibody to induce cell surface expression of programmed cell death receptor 1 (PD-1), and where cultured for 48 hours in the absence of additives or with the peptide RSKAKNPLY-RRRRRRRRR-NH$_2$ (SEQ ID NO: 24, IK14800 at 2.5 µM) alone, 5 µg/ml recombinant PD-L1 (the ligand for PD-1) alone to induce checkpoint blockade in the cells, or with the IK14800 peptide (SEQ ID NO: 24) plus recombinant PD-L1. IL-2R alpha (CD25) was measured in cell lysates by means of a standard commercially available ELISA kit as described above.

Consistent with the data shown above, FIG. 12 shows CD3-stimulated cells (in the absence of PD-L1), when treated with a Lck Activation fusion polypeptide of the present invention, have increased levels of CD25 expression.

Importantly, FIG. 12 shows the addition of RSKAKN-PLY-RRRRRRRRR-NH$_2$ (SEQ IS NO: 24) rescued suppression of IL-2Ralpha induced by the PD-1/PD-L1 interaction.

This data demonstrates a Lck activating polypeptide of the present invention is able to rescue human T cells from checkpoint blockade induced by PD-L1.

Example 12: Lck Activating Polypeptides Increase IL2Ra (CD25) Expression on Anti-CD3 Stimulated CD4+ Cells and CD8+ Cells The effect of Lck activating polypeptides on IL2Ra (CD25) expression on CD4+ and CD8+ T cells from anti-CD3 stimulated PBMCs was examined. Freshly isolated PBMCs were stimulated with or without (−aCD3) anti-CD3 (1 μg/mL) for 24 hours in the presence of a Lck activating polypeptide according to the present invention; RSKAKN-PLY-RRRRRRRRR-NH$_2$ (SEQ ID NO: 24, "IK14800") at indicated concentrations (μM).

FIG. 13 demonstrates that expression of IL2Ra (CD25) is increased in CD4+ and CD8+ T cells when stimulated with anti-CD3.

This data demonstrates that Lck-activating peptides enhance IL-2Ra expression in CD4+ and CD8+ T cells.

Example 13: Lck Activating Polypeptides Increase IL-12 Secretion in a Human T Lymphocyte (Jurkat) Cell Line The ability of Lck activating polypeptides to alter IL-12 secretion was examined. In brief, wild-type Jurkat cells (an immortalised line of human T lymphocyte cells) were stimulated by exposure to biotinylated anti-CD3 antibody in the presence of anti-CD28 antibody and avidin. During the culture period (48 hours) cells were exposed to test polypeptides. Cell supernatant was assayed for IL-12 at the end of 48 hours using a standard commercially available ELISA kit as described above.

FIG. 14A shows that the Lck activating fusion polypeptide RSKAKNPLY-RRRRRRRRR (SEQ ID NO: 24) induces IL-12 secretion relative to control in wild-type Jurkat cells following 48 h exposure. The Lck activating polyarginine polypeptide RRRRRRRRR (SEQ ID NO: 6) also induced IL-12 secretion relative to control in wild-type Jurkat cells following 48 h exposure (data not shown). This data indicates that a Lck activating polypeptide of the present invention is able to induce IL-12 secretion in a human T cell line.

The role of Lck in the ability of Lck activating polypeptides to alter IL-12 secretion was also examined. In brief, Jurkat cells deficient for Lck (J.Cam 1.6) were stimulated by exposure to biotinylated anti-CD3 antibody in the presence of anti-CD28 antibody and avidin. During the culture period (48 hours) cells were exposed to test polypeptide. Cell supernatant was assayed for IL-12 at the end of 48 hours using a standard commercially available ELISA kit as described above.

FIG. 14B shows that the ability of the Lck activating polypeptide RSKAKNPLY-RRRRRRRRR (SEQ ID NO: 24, IK14800) to induce IL-12 secretion in Jurkat cells relative to control, is enhanced by the presence of Lck. These data demonstrates that IL-12 secretion in a human T cell line by the Lck activating fusion polypeptide RSKAKN-PLY-RRRRRRRRR (SEQ ID NO: 24) is enhanced by the presence of Lck.

Example 14: Lck Activating Polypeptides Increase IL-12 Secretion in Stimulated PBMCs The ability of Lck activating polypeptides to alter IL-12 (IL-12p70) secretion was examined further. In brief, anti-CD3 stimulated PBMCs were cultured together with the Lck activating polypeptides RVKVKVVVV-RRRRRRRRR (SEQ ID NO: 58, "IK15800"), RSKAKNPLY-RRRRRRRRR (SEQ ID NO: 24, "IK14800"), and RVKVKVVVV-RRRRRRRRR (SEQ ID NO: 58) and RSKAKNPLY-RRRRRRRRR (SEQ ID NO: 24) comprising only D amino acids (SEQ ID NO: 111, "IKD15800", and SEQ ID NO: 129, "IKD14800", respectively), in the presence and absence of anti-CD40L blocking antibody for 24 hours. Supernatants were assessed for IL-12p70 levels by ELISA.

FIG. 15 shows that the Lck activating polypeptides RVKVKVVVV-RRRRRRRRR (SEQ ID NO: 58) and RSKAKNPLY-RRRRRRRRR (SEQ ID NO: 24), and RSKAKNPLY-RRRRRRRRR (SEQ ID NO: 24) and RVKVKVVVV-RRRRRRRRR (SEQ ID NO: 58) comprising only D amino acids (SEQ ID NO: 129, "IKD14800" and SEQ ID NO: 111, "IKD15800", respectively) induce IL-12 secretion in anti-CD3 stimulated PBMCs, relative to anti-CD3 stimulated PBMCs in the presence of anti-CD40L blocking antibody, which inhibits the production of IL-12.

These data also indicate that Lck activating polypeptides of the present invention are able to induce IL-12p70 secretion in PBMCs.

The ability of Lck activating polypeptides to alter IL-12 (IL-12p70) secretion was examined relative to no peptide. In brief, PBMCs were cultured together with anti-CD3 (1 ug/ml) and the Lck activating polypeptide RSKAKNPLY-RRRRRRRRR (SEQ ID NO: 24) or RVKVKVVVV-RRRRRRRRR (SEQ ID NO: 58) for 24 or 72 hours. Supernatants were assessed for IL-12p70 levels by ELISA.

FIG. 16 shows that the Lck activating polypeptide RSKAKNPLY-RRRRRRRRR (SEQ ID NO: 24, IK14800) induced IL-12p70 secretion relative to no peptide at 24 hours (and at 72 hours; data not shown). The Lck activating polypeptide RVKVKVVVV-RRRRRRRRR (SEQ ID NO: 58, IK15800) induced IL-12p70 secretion relative to no peptide control at 72 hours (data not shown).

Example 15: Lck Activating Polypeptides Increase IL-12Rβ2 Secretion in stimulated PBMCs The ability of Lck activating polypeptides to alter IL-12 receptor subunit beta 2 (IL-12Rβ2) expression was examined.

Anti-CD3 stimulated PBMCs were cultured together with the Lck activating polypeptide RSKAKNPLY-RRRRRRRRR (SEQ ID NO: 24, IK14800) plus vehicle control for 72 hours after which CD4+ T cells and NK cells (CD3$^{neg}$ CD56+ cells) were assessed for IL-12Rβ2 expression by flow cytometry.

FIG. 17 shows the Lck activating polypeptide RSKAKN-PLY-RRRRRRRRR (SEQ ID NO: 24) induces IL-12Rβ2 expression in a population of NK cells (CD3$^{neg}$ CD56+ cells). The Lck activating polypeptide RSKAKNPLY-RRRRRRRRR (SEQ ID NO: 24) also induced IL-12Rβ2 expression in a population of CD4+ T cells (data not shown).

Example 16: Lck Activating Polypeptides do not Increase IL-21R Expression in Stimulated CD4+ T Cells The effect of Lck activating polypeptides on IL-21R (CD360) expression on CD4+ T cells in a stimulated CD4+ T cell assay was examined. In brief, Isolated CD4+ T cells were stimulated with anti-CD3 anti-CD28 Dynabeads™ and cultured together with the Lck activating polypeptides RRRRRRRRR (SEQ ID NO: 6) and RSKAKNPLY-RRRRRRRRR (SEQ ID NO: 24), after which cells were assessed for IL-21R expression by flow cytometry. The Lck activating polypeptides RRRRRRRRR (SEQ ID NO: 6, IK00900) and RSKAKNPLY-RRRRRRRRR (SEQ ID NO: 24, IK14800) do not increase IL-21R expression in human stimulated CD4+ T cells (data not shown).

Example 17: Lck Activating Polypeptides Induce IFN-γ Secretion

The ability of Lck activating polypeptides to alter IFN-γ secretion by human PBMCs was examined. In brief, anti-CD3 stimulated PBMCs were cultured together with the Lck activating polypeptides RRRRRRRRR (SEQ ID NO: 6), RVKVKVVVV-RRRRRRRRR (SEQ ID NO: 58) and RSKAKNPLY-RRRRRRRRR (SEQ ID NO: 24) for 48 hours after which supernatants were collected and assessed for IFN-γ by ELISA. The Lck activating polypeptides RRRRRRRRR (SEQ ID NO: 6), RVKVKVVVV-RRRRRRRRR (SEQ ID NO: 58) and RSKAKNPLY-RRRRRRRRR (SEQ ID NO: 24) induce IFN-γ secretion relative to no peptide control (data not shown).

The ability of Lck activating polypeptides to alter IFN-γ secretion by isolated human CD4+ T cells in a stimulated CD4+ T cell assay was also examined. In brief, Isolated CD4+ T cells were stimulated with anti-CD3 anti-CD28 Dynabeads™ and cultured together with the Lck activating polypeptides RRRRRRRRR (SEQ ID NO: 6, IK00900) and RSKAKNPLY-RRRRRRRRR (SEQ ID NO: 24, IK14800) for 24 hours after which supernatants were assessed for IFN-γ by ELISA. FIG. 18 shows that the Lck activating polypeptide RSKAKNPLY-RRRRRRRRR (SEQ ID NO: 24) induces IFN-γ secretion relative to no peptide control The Lck activating polypeptide RRRRRRRRR (SEQ ID NO: 6) induced IFN-γ secretion relative to no peptide control (data not shown).

The ability of Lck activating polypeptides to alter IFN-γ secretion by isolated human CD8+ T cells in a stimulated CD8+ T cell assay was examined. In brief, Isolated CD8+ T cells were stimulated with anti-CD3 anti-CD28 Dynabeads™ and cultured together with the Lck activating polypeptides RRRRRRRRR (SEQ ID NO: 6, IK00900) and RSKAKNPLY-RRRRRRRRR (SEQ ID NO: 24, IK14800) for 24 hours after which supernatants were assessed for IFN-γ by ELISA. The Lck activating polypeptides RRRRRRRRR (SEQ ID NO: 6) and RSKAKNPLY-RRRRRRRRR (SEQ ID NO: 24) induced IFN-γ secretion relative no peptide control (data not shown). This data demonstrates that Lck activating polypeptides of the present invention are able to induce IFN-γ secretion by stimulated human CD8+ T cells.

Example 18: Lck Activating Polypeptides Comprising D Amino Acids Induce IFN-γ Secretion by Stimulated Human CD4+ and CD8+ T Cells The ability of Lck activating polypeptides comprising D amino acids to alter IFN-γ secretion by isolated human CD8+ T cells in a stimulated CD8+ T cell assay was examined.

In brief, Isolated CD8+ T cells were stimulated with anti-CD3 anti-CD28 Dynabeads™ and cultured together with the Lck activating polypeptide RSKAKNPLY-RRRRRRRRR (SEQ ID NO: 24), comprising only D amino acids (SEQ ID NO: 129, IKD14800), for 24 hours after which supernatants were assessed for IFN-γ by ELISA. FIG. 19 shows that the Lck activating polypeptide RSKAKNPLY-RRRRRRRRR (SEQ ID NO: 24, IK14800), comprising only D amino acids (SEQ ID NO: 129, IKD14800), induces IFN-γ secretion by stimulated human CD8+ T cells, relative to no peptide control.

The ability of Lck activating polypeptides comprising D amino acids to alter IFN-γ secretion by isolated human CD4+ T cells in a stimulated CD4+ T cell assay was also examined. In brief, Isolated CD4+ T cells were stimulated with anti-CD3 anti-CD28 Dynabeads™ and cultured together with the Lck activating polypeptide RSKAKNPLY-RRRRRRRRR (SEQ ID NO: 24, IK14800), or the Lck activating polypeptide RSKAKNPLY-RRRRRRRRR (SEQ ID NO: 24) comprising only D amino acids (SEQ ID NO: 129, IKD14800), for 24 hours after which supernatants were assessed for IFN-γ by ELISA. The Lck activating polypeptide RSKAKNPLY-RRRRRRRRR (SEQ ID NO: 24) comprising only D amino acids (SEQ ID NO: 129), like RSKAKNPLY-RRRRRRRRR comprising only L amino acids (SEQ ID NO: 24), induces IFN-γ secretion by stimulated human CD4+ T cells, relative no peptide control (data not shown).

Example 19: Lck Activating Polypeptides Increase Proliferation of CD8+ T Cells in a Stimulated CD8+ T Cell Assay The ability of Lck activating polypeptides to induce proliferation of isolated human CD8+ T cells in a stimulated CD8+ T cell assay was examined. In brief, isolated CD8+ T cells were stimulated with anti-CD3 anti-CD28 Dynabeads and cultured together with the Lck activating polypeptide RSKAKNPLY-RRRRRRRRR (SEQ ID NO: 24) for 24 hours after which CD8+ T cells were assessed for Ki67 expression by flow cytometry. Ki67 is a proliferation marker used to determine the growth fraction of a given cell population, in this case CD8+ cells. FIG. 20 shows that the Lck activating polypeptide RSKAKNPLY-RRRRRRRRR (SEQ ID NO: 24, IK14800) increases the proliferating population of human CD8+ T cells.

Example 20: Lck Activating Polypeptides Increase Proliferation of CD8+ T Cells and CD3$^{neg}$ CD56$^+$ NK Cells within PBMCs The ability of Lck activating polypeptides to induce proliferation of isolated human CD8+ T cells within PBMCs was examined. In brief, anti-CD3 stimulated PBMCs were cultured together with the Lck activating polypeptides RRRRRRRRR (SEQ ID NO: 6, IK00900) and RVKVKVVVV-RRRRRRRRR (SEQ ID NO: 58, IK15800) for 72 hours after which CD8+ T cells were assessed for Ki67 expression by flow cytometry. Ki67 is a proliferation marker used to determine the growth fraction of a given cell population, in this case CD8+ cells. FIG. 21 shows that the Lck activating polypeptide RVKVKVVVV-RRRRRRRRR (SEQ ID NO: 58, IK15800) increases the proliferating population of human CD8+ T cells.

The ability of Lck activating polypeptides to induce proliferation of isolated human CD3$^{neg}$ CD56$^+$ NK cells within PBMCs was examined. In brief, anti-CD3 stimulated PBMCs were cultured together with the Lck activating polypeptide rvkvkvvvv-rrrrrrrrr (SEQ ID NO: 111, IKD15800) for 72 hours after which CD3$^{neg}$ CD56$^+$ NK cells were assessed for Ki67 expression by flow cytometry. Ki67 is a proliferation marker used to determine the growth fraction of a given cell population, in this case CD3$^{neg}$ CD56$^+$ NK cells. The Lck activating polypeptide rvkvkvvvv-rrrrrrrrr (SEQ ID NO: 111, IKD15800) increased the proliferating population of human CD3$^{neg}$ CD56$^+$ NK cells (data not shown).

The Lck activating polypeptide rvkvkvvvv-rrrrrrrrr (SEQ ID NO: 111, IKD15800) also increased the population of human CD3$^{neg}$ CD56$^+$ NK cells that were CD25 positive, the population of human CD3$^{neg}$ CD56$^+$ NK cells that were CD215 positive, and the population of human CD3$^{neg}$ CD56$^+$ NK cells that were CD360 positive (data not shown).

Example 21: Lck Activating Polypeptides Increase CD28 Expression in CD8+ and CD4+ T Cells The ability of Lck activating polypeptides to alter CD28 expression was examined. In brief, anti-CD3 stimulated PBMCs were cultured together with the Lck activating polypeptides RVKVKVVVV-RRRRRRRRR (SEQ ID NO: 58) and RSKAKNPLY-RRRRRRRRR (SEQ ID NO: 24) for 72 hours after which cells were assessed for expression of CD28 by flow cytometry.

Figure 22A:
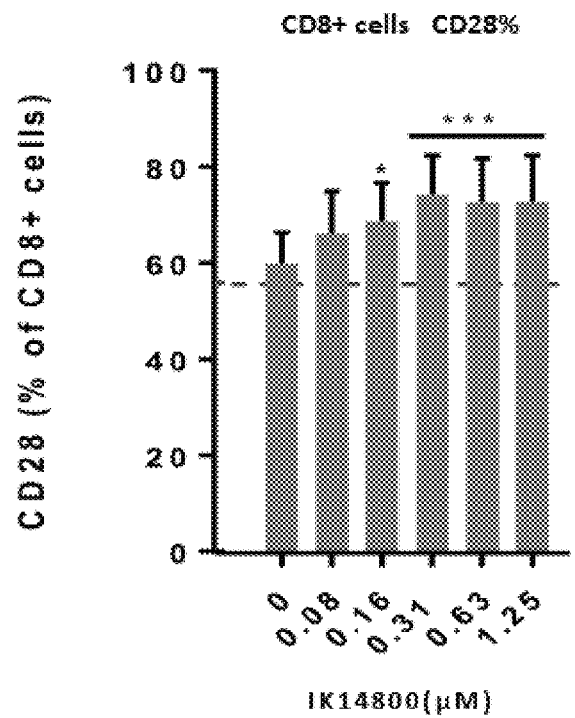

FIG. 22A shows that the Lck activating polypeptide RSKAKNPLY-RRRRRRRRR (SEQ ID NO: 24, IK14800) induces CD28 expression in CD8+ T cells relative to no peptide control.

Figure 22B:
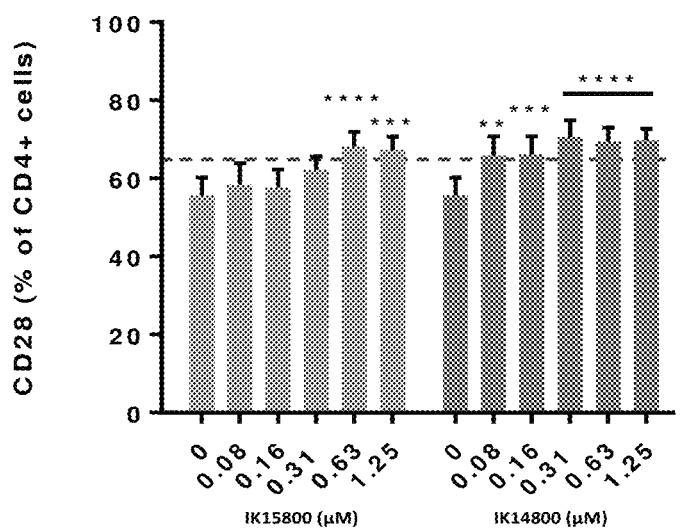

FIG. 22B shows that the Lck activating polypeptides RVKVKVVVV-RRRRRRRRR (SEQ ID NO: 58, IK15800) and RSKAKNPLY-RRRRRRRRR (SEQ ID NO: 24, IK14800) induce CD28 expression in CD4+ T cells relative to no peptide control.

Example 22: Lck Activating Polypeptides Increase IL-15R Expression on and IL-15 Secretion from PBMCs The effect of Lck activating polypeptides on CD215 (IL-15R) expression on CD4+ T cells in PBMCs was examined. In brief, PBMCs were cultured together with anti-CD3 (1 μg/ml) stimulation and RSKAKNPLY-RRRRRRRRR (SEQ ID NO: 24, IK14800) and RVKVKVVVV-RRRRRRRRR (SEQ ID NO: 58) over a 5-concentration range (0-1.25 μM) for 72 hrs after which cells were assessed for expression of CD215 (IL-15R) by flow cytometry. The Lck activating polypeptide RSKAKNPLY-RRRRRRRRR (SEQ ID NO: 24) increased IL-15R expression on human stimulated CD4+ T cells (data not shown).

The effect of Lck activating polypeptides on IL-15R expression on and IL-15 secretion from CD8+ T cells in a stimulated CD8+ T cell assay was also examined. In brief, PBMCs were cultured together with anti-CD3 (1 μg/ml) stimulation Lck activating polypeptides RVKVKVVVV-RRRRRRRRR (SEQ ID NO: 58, IK15800) and RSKAKNPLY-RRRRRRRRR (SEQ ID NO: 24, IK14800) over a 5-concentration range (0-1.25 μM). Supernatants were collected and assessed for IL-15 by ELISA. FIG. 23A shows that the Lck activating polypeptide RSKAKNPLY-RRRRRRRRR (SEQ ID NO: 24, IK14800) increases IL-15R expression on CD8+ T cells and FIG. 23B shows that the Lck activating polypeptide RVKVKVVVV-RRRRRRRRR (SEQ ID NO: 58, IK15800) increases IL-15 secretion from CD8+ T cells. FIG. 23C shows the Lck activating polypeptide RVKVKVVVV-RRRRRRRRR (SEQ ID NO: 58, IK15800) also increased IL-15R expression on human stimulated CD8+ T cells.

Example 23: Lck Activating Polypeptides Increase Proliferation of CD28+CD8+ T Cells within PBMCs The ability of Lck activating polypeptides to induce proliferation of PBMCs was examined. In brief, anti-CD3 stimulated PBMCs were cultured together with the Lck activating polypeptides RVKVKVVVV-RRRRRRRRR (SEQ ID NO: 58) and RSKAKNPLY-RRRRRRRRR (SEQ ID NO: 24) for 72 hours after which cells were assessed for Ki67 expression by flow cytometry. Ki67 is a proliferation marker used to determine the growth fraction of a given cell population, in this case CD28+/CD8+ cells.

FIG. 24 shows that the Lck activating polypeptides RVKVKVVVV-RRRRRRRRR (SEQ ID NO: 58, IK15800) and RSKAKNPLY-RRRRRRRRR (SEQ ID NO: 24, IK14800) increase the proliferating population of human CD28+/CD8+ T cells.

Example 24: Lck Activating Polypeptides Increase IL-18Ra Expression on CD4+ and CD8+ T Cells The effect of Lck activating polypeptides on IL-18Ra expression on CD4+ and CD8+ T cells in stimulated CD4+ and CD8+ T cell assays was examined. In brief, isolated CD8+ T cells were stimulated with anti-CD3 anti-CD28 Dynabeads™ and cultured together with the Lck activating polypeptides RSKAKNPLY-RRRRRRRRR (SEQ ID NO: 24), and RSKAKNPLY-RRRRRRRRR (SEQ ID NO: 24) comprising only D amino acids (SEQ ID NO: 129), for 24 hours after which cells were assessed for IL-18Ra expression by flow cytometry. The Lck activating polypeptides RSKAKNPLY-RRRRRRRRR (SEQ ID NO: 24, IK14800), and RSKAKNPLY-RRRRRRRRR (SEQ ID NO: 24) comprising only D amino acids (SEQ ID NO: 129, IKD14800), increase IL-18Ra expression on human stimulated CD8+ T cells (data not shown).

Isolated CD4+ T cells were stimulated with anti-CD3 anti-CD28 Dynabeads™ and cultured together with the Lck activating polypeptides RSKAKNPLY-RRRRRRRRR (SEQ ID NO: 24), and RSKAKNPLY-RRRRRRRRR (SEQ ID NO: 24) comprising only D amino acids (SEQ ID NO: 129), for 24 hours after which cells were assessed for IL-18Ra expression by flow cytometry. The Lck activating polypeptides RSKAKNPLY-RRRRRRRRR (SEQ ID NO: 24, IK14800), and RSKAKNPLY-RRRRRRRRR (SEQ ID NO: 24) comprising only D amino acids (SEQ ID NO: 129, IKD14800), increase IL-18Ra expression on human stimulated CD4+ T cells (data not shown).

Example 25: Lck Activating Polypeptides Alter pSTAT4 Expression in CD4+ and CD8+ T Cells The effect of Lck activating polypeptides on intracellular pSTAT4 expression in CD4+ and CD8+ T cells in a stimulated T cell assay was examined. In brief, isolated T cells (CD3+) were stimulated with anti-CD3 anti-CD28 Dynabeads™ and cultured together with the Lck activating polypeptides RSKAKNPLY-RRRRRRRRR (SEQ ID NO: 24), RVKVKVVVV-RRRRRRRRR (SEQ ID NO: 58) and RVKVKVVVV-RRRRRRRRR (SEQ ID NO: 58) comprising only D amino acids (SEQ ID NO: 111), over a 5-concentration range plus vehicle control (0-1.25 µM) for 72 hours after which supernatants were collected and assessed for p-STAT4 expression by flow cytometry.

The Lck activating polypeptides RSKAKNPLY-RRRRRRRRR (SEQ ID NO: 24, IK14800), RVKVKVVVV-RRRRRRRRR (SEQ ID NO: 58, IK15800), and RVKVKVVVV-RRRRRRRRR (SEQ ID NO: 58) comprising only D amino acids (SEQ ID NO: 111, IKD15800), increase p-STAT4 expression on human stimulated CD4+ T cells (data not shown).

Example 26: Lck Activating Polypeptides Decrease the Percentage of Regulatory T Cells within Human PBMCs The effect of Lck activating polypeptides on regulatory T cell numbers within human PBMCs was examined. In brief, anti-CD3 stimulated PBMCs were cultured together with the Lck activating polypeptides RVKVKVVVV-RRRRRRRRR (SEQ ID NO: 58) and RSKAKNPLY-RRRRRRRRR (SEQ ID NO: 24) for 48 hours after which Treg populations were determined by measuring Foxp3+ proportion of cells within CD4+CD25+ CD127$^{low}$ population. The Lck activating polypeptides RVKVKVVVV-RRRRRRRRR (SEQ ID NO: 58, IK15800), and RSKAKNPLY-RRRRRRRRR (SEQ ID NO: 24, IK14800), decreased the proportion of Tregs (Foxp3+) (data not shown).

Example 27: CD40L Enhances the CD14$^{neg}$ CD11c$^+$ Dendritic Cell Phenotype

The effect of CD40L on dendritic cell phenotype (CD14 expression) in isolated immature DC cell cultures was examined. In brief, immature monocyte derived DCs (iMoDCs) were derived from isolated CD14+ monocytes cultured for 7 days in MoDC differentiation media. iMoDCs were cultured for 72 hours in the presence of CD40L (5 ug/mL) and anti-CD3 (1 ug/mL). After 72 hours, cells were assessed for CD14 and CD11c expression by flow cytometry to determine DC cell phenotype. CD40L increased the proportion of CD14 negative CD11c+ dendritic cells (data not shown).

Effect of test peptides on dendritic cell (DC) phenotype (CD14 expression) in isolated immature DC cultures was also examined.

In brief, immature monocyte derived DCs (iMoDCs) were derived from isolated CD14+ monocytes cultured for 7 days in Mo-DC differentiation media. iMoDCs were cultured for 72 hrs in the presence of test peptides over a 5-point concentration curve plus vehicle (0-1.25 µM) and anti-CD3 (1 µg/mL). After 72 hrs, cells were assessed for CD14 and CD11c expression by flow cytometry to determine DC cell phenotype. Data presented indicates the mean respective CD14 positive or negative cell populations (%) within CD11c positive population in response to peptide treatment, +/- SEM, n=4. Data were analysed by RM two-way ANOVA with Dunnett's post-test comparing each peptide concentration with vehicle, *p<0.05, p<0.01, *p<0.001.

The Lck activating polypeptides RVKVKVVVV-RRRRRRRRR (SEQ ID NO: 58, IK15800) and RSKAKNPLY-RRRRRRRRR (SEQ ID NO: 24, IK14800) increased the population of CD14 negative Dendritic Cells (data not shown).

Example 28: Lck Activating Polypeptides Increase IL-12Rβ2 Expression on cd4+ and CD8+ T cells in a stimulated T cell assay The ability of Lck activating polypeptides to alter IL-12 receptor subunit beta 2 (IL-12Rβ2) expression on T cells was examined.

In brief, isolated T cells (CD3+) were stimulated with anti-CD3 anti-CD28 Dynabeads™ and cultured together with RVKVKVVVV-RRRRRRRRR (SEQ ID NO: 58) over a 5-concentration range plus vehicle control (0-1.25 µM) for 72 hrs after which CD4+ and CD8+ T cells were assessed for IL-12Rβ2 expression by flow cytometry.

FIG. 25 shows the Lck activating polypeptide RVKVKVVVV-RRRRRRRRR (SEQ ID NO: 58, IK15800) induces IL-12Rβ2 expression in CD4+ and CD8+ T cells.

Example 29: Lck Activating Polypeptides Increase IL-2Rβ (CD122) Expression on NK Cells in a Stimulated PBMC Assay The ability of Lck activating polypeptides to alter IL-2 receptor subunit beta 2 (IL-2Rβ) expression on NK cells was examined.

In brief, PBMCs from healthy donors were stimulated with anti-CD3 (1 µg/mL) for 72 hrs in the presence of test peptides (0.08-1.25 µM) or vehicle control. At the end of the culture period, cells were collected and assessed for IL-2Rβ (CD122) expression within CD3$^{neg}$CD564$^{+/dim}$ NK cells by flow cytometry.

FIG. 26 shows the Lck activating polypeptides RVKVKVVVV-RRRRRRRRR (SEQ ID NO: 58, IK15800) and RSKAKNPLY-RRRRRRRRR (SEQ ID NO: 24, IK14800) induce IL-2Rβ expression in CD3$^{neg}$CD564$^{+/dim}$ NK cells.

Example 30: Lck Activating Polypeptides Cause Expansion of CD8+ Cell Populations The ability of Lck activating polypeptides to cause expansion of CD8+ cell populations within PBMCs was examined.

In brief, PBMC or isolated CD8+ T cells from healthy donors were stimulated via TCR +IL-2 for 10 days in the presence of RVKVKVVVV-RRRRRRRRR (SEQ ID NO: 58; 0.08-1.25 µM) or vehicle control. At the end of the culture period, cells were collected and assessed for CD8+ cell proportions by flow cytometry.

FIG. 27 shows the Lck activating polypeptide RVKVKVVVV-RRRRRRRRR (SEQ ID NO: 58, IK15800) induces expansion of CD8+ cell populations within PBMCs.

Example 31: Lck Activating Polypeptides Induce IL-21 Production by CD4+ T-Cells

The ability of Lck activating polypeptides to induce IL-21 production by CD4+ T cells was examined.

In brief, CD4+ T cells were isolated and cultured in the presence of anti-CD3 anti-CD28 stimulation and RSKAKN-PLY-RRRRRRRRR (SEQ ID NO: 24) for 24 hr or 48 hr. At the end of culture, supernatants were assessed for IL-21 by ELISA.

FIG. 28 shows the Lck activating polypeptide RSKAKN-PLY-RRRRRRRRR (SEQ ID NO: 24, IK14800) induces IL-21 production by CD4+ T-cells.

Example 32: Lck Activating Polypeptides Provided Prior to Antigenic Stimulation Induce IL-2 Secretion in a Human T Lymphocyte (Jurkat) Cell Line The ability of Lck activating polypeptides to induce IL-2 production by a human T lymphocyte (Jurkat) cell line was examined.

In brief, 5 million cells seeded in T25 flasks and treated with varying concentrations of RSKAKNPLY-RRRRRRRRR (SEQ ID NO: 24, IK14800) as indicated in the above table for 1 hour, after which the cell suspensions were centrifuged and washed twice with fresh media. A mixture of Biotin-anti-CD3 and Avidin (5: 1.25 ug) in 500 uL of media was added into the wells of a 12 well plate. After 10 minutes the cells were seeded at 1 million per well and the cell suspension made up to 2 mL volume with media. The samples were subsequently further stimulated with aniti-CD28 (5 ug/mL), incubated for 48 hours at 37° C. and the supernatant (100 uL, n=3), was then analyzed for IL-2 content by ELISA.

FIG. 29 shows the Lck activating polypeptide RSKAKN-PLY-RRRRRRRRR (SEQ ID NO: 24, IK14800) induces IL-2 production by a human T cell line upon subsequent stimulation, when administered prior to antigenic stimulation.

Example 33: Lck Activating Polypeptides Administered to Mice Induce CD4+CD28+ T Cells in Lewis Lung Cancer Mice (Metastatic Model)

The ability of Lck activating polypeptides to induce CD4+CD28+ T cells in mice was examined.

In brief, Lewis Lung Cancer cells sourced from ATCC and were grown to 70% confluence in DMEM, detached and washed in PBS. On Day 0 each mouse received $0.5 \times 10^6$ LLC cells by intravenous injection into the tail vein. Treatments (IK14800, SEQ ID NO: 24, at a dose of 250 µg in 200 µl water) were administered I.P. twice weekly (Days 1, 4, 8 and 11 post cell transfer). Fifteen days after cell inoculation the mice were euthanased and the spleens removed to produce single cell suspensions as detailed in the protocol above (italics). Isolated splenocyte cell suspensions were then assessed by flow cytometry for expression of CD4, CD8, NK1.1, CD28, CD215 and pSTAT4.

FIG. 30 shows the Lck activating polypeptide RSKAKN-PLY-RRRRRRRRR (SEQ ID NO: 24, IK14800) increases the percentage of CD4+ T Cells expressing CD28 and the relative expression of CD28 on CD4+ T Cells in splenocytes in Lewis Lung Cancer mice.

The Lck activating polypeptide RSKAKNPLY-RRRRRRRRR (SEQ ID NO: 24, IK14800) also increases the relative expression of CD25 on NK cells in splenocytes in Lewis Lung Cancer mice (data not shown).

The present inventors have also demonstrated that the Lck activating polypeptide RSKAKNPLY-RRRRRRRRR (SEQ ID NO: 24, IK14800) induces CD25 expression in CD57+ NK cells isolated from human lung cancer tumour infiltrating lymphocytes (TILs) as measured by CD25+ MFI and CD25+CD57+ MFI of TILs. In brief, RSKAKNPLY-RRRRRRRRR (SEQ ID NO: 24, IK14800) increased CD25 expression upon treatment at 1.25 um.

Example 34: Lck Activating Polypeptides Administered to Lewis Lung Cancer Mice (Metastatic Model) Induce CD8+ T Cells Expressing CD28 and CD215 in Splenocytes The ability of Lck activating polypeptides to induce CD8+ T cells expressing CD28 and CD215 in mice was examined.

Lewis Lung Cancer cells sourced from ATCC and were grown to 70% confluence in DMEM, detached and washed in PBS. On Day 0 each mouse received $0.5 \times 10^6$ LLC cells by intravenous injection into the tail vein. Treatments (IK14800 at a dose of 250 µg in 200 µl water) were administered I.P. twice weekly (Days 1, 4, 8 and 11 post cell transfer). Fifteen days after cell inoculation the mice were euthanased and the spleens removed to produce single cell suspensions as detailed in the protocol above (italics). Isolated splenocyte cell suspensions were then assessed by flow cytometry for expression of CD4, CD8, NK1.1, CD28, CD215 and pSTAT4.

In brief, splenocytes from Lewis Lung Cancer mice treated with RSKAKNPLY-RRRRRRRRR (SEQ ID NO: 24) were isolated and the proportion of CD28+CD8+ cells of treated Lewis Lung Cancer Mice was examined.

FIG. 31 shows the Lck activating polypeptide RSKAKN-PLY-RRRRRRRRR (SEQ ID NO: 24, IK14800) increases the percentage of CD8+ T cells expressing CD215 (IL-15R) and CD28 on CD4+ cells in splenocytes in Lewis Lung Cancer mice.

Example 35: Lck Activating Polypeptides Administered to Mice Increase the Expression of pSTAT4 on NK Cells The ability of Lck activating polypeptides to induce pSTAT4 expression in mice was examined.

Lewis Lung Cancer cells sourced from ATCC and were grown to 70% confluence in DMEM, detached and washed in PBS. On Day 0 each mouse received $0.5 \times 10^6$ LLC cells by intravenous injection into the tail vein. Treatments (IK14800, SEQ ID NO: 24, at a dose of 250 µg in 200 µl water) were administered I.P. twice weekly (Days 1, 4, 8 and 11 post cell transfer). Fifteen days after cell inoculation the mice were euthanased and the spleens removed to produce single cell suspensions as detailed in the protocol above (italics). Isolated splenocyte cell suspensions were then assessed by flow cytometry for expression of CD4, CD8, NK1.1, CD28, CD215 and pSTAT4.

In brief, splenocytes from Lewis Lung Cancer mice treated with RSKAKNPLY-RRRRRRRRR (SEQ ID NO: 24) were isolated and the expression of pSTAT4 on NK cells of treated Lewis Lung Cancer Mice was examined.

FIG. 32 shows the Lck activating polypeptide RSKAKN-PLY-RRRRRRRRR (SEQ ID NO: 24, IK14800) increases the expression of pSTAT4 on NK Cells in splenocytes from Lewis Lung Cancer mice.

Example 36: Polypeptides Comprising Anionic Residues do not Activate Lck

The ability of peptides comprising anionic residues to activate Lck was examined. FIG. 33 shows the polypeptide DDDDDDDDD (SEQ ID NO: 21) does not increase the activity of Lck.

Example 37: Lck Activating Polypeptides Increase IL-2 Secretion in a Human T Lymphocyte (Jurkat) Cell Line The role of Lck in the ability of Lck activating polypeptides to alter IL-2 secretion was also examined.

In brief, 12 well plates were coated with anti-CD3 (5 µg/mL) solution made up in PBS (200 µL) and incubated at 37° C. overnight. The next day the anti-CD3 solution was aspirated and wells gently washed twice with media (1 mL, 10 minutes). Jurkat cells (WT and Lck Deficient) were seeded at 1 million per well in anti-CD3 coated 12 well plates, further stimulated with anti-CD28 (5 mg/mL) and at time zero treated with IK14800 (2.5 µM). Cells were incubated for 24 hours and supernatants were then analysed for IL-2 by ELISA.

FIG. 34 shows that the ability of the Lck activating polypeptide RSKAKNPLY-RRRRRRRRR (SEQ ID NO: 24, IK14800) to induce IL-2 secretion in Jurkat cells relative to control, is dependent on Lck. This data demonstrates that IL-2 secretion in a human T cell line by the Lck activating fusion polypeptide RSKAKNPLY-RRRRRRRRR (SEQ ID NO: 24) is dependent on Lck.

Example 38: Lck Activating Polypeptides Increase IL-2 Secretion in a Human T Lymphocyte (Jurkat) Cell Line Only when Stimulated The ability of Lck activating polypeptides to induce IL-2 production by a human T lymphocyte (Jurkat) cell line in the presence or absence of stimulation was examined.

In brief, 12 well plates were coated with anti-CD3 (5 µg/mL) solution made up in PBS (200 µL) and incubated at 37° C. overnight. The anti-CD3 solution was then aspirated and wells gently washed twice with media (1 mL, 10 minutes). Jurkat cells were seeded at 1 million per well, further stimulated with anti-CD28 (5 µg/mL) and then treated with RSKAKNPLY-RRRRRRRRR (SEQ ID NO: 24, IK14800) (2.5 µM) at time zero. Cells were incubated for 72 hours and the supernatants were then analysed for IL-2 by ELISA.

FIG. 35 shows the increase in IL-2 production by treatment with Lck activating polypeptide RSKAKNPLY-RRRRRRRRR (SEQ ID NO: 24, IK14800) does not occur in the absence of antigenic stimulation.

Example 39: Suppression of Tumour Mass in Lewis Lung Cancer Mice (Xenograft Model) by a Lck Activating Polypeptide The ability of a Lck activating polypeptide to decrease tumour mass in Lewis Lung Cancer (LLC) mice was examined.

The Lewis Lung Carcinoma cell line was cultured to approximately 70% confluency before cells were collected, counted and resuspended at $5 \times 10^6$/mL in sterile HBSS. C57BL/6 were injected subcutaneously with $1 \times 10^6$ cells (100 µl) into the right flank. Mice were randomly assigned to treatment groups 5 days after tumour cell implantation such that the average tumour size was approximately equal between the two groups. RVKVKVVVV-RRRRRRRRR (SEQ ID NO: 58; 200 ugs in 200 uls water) or vehicle (water) were administered twice weekly (Monday and Thursday) via intraperitoneal (i.p) injections, from day 10 post tumour cell implantation, until the tumours reached an average of 10 mm in diameter in the vehicle treated group. Tumours were measured three times each week using digital callipers (Monday, Wednesday and Friday) by a scientist who was blinded to treatment groups. Once the mean tumour size for the vehicle group reached 10 mm in diameter, mice were sacrificed by cervical dislocation and tumour and spleens collected.

Tumours were placed in 2 mL RPMI-1640 containing Collagenase D (2 mg/mL, Roche Lot #28960126) and DNase 1 (100 µg/mL, Sigma Lot #SLBV1446) and mechanically digested before being incubated at 37° C., in a shaking incubator at 80 rpm for 30 minutes. Digested tumour samples were passed through a 70 µm strainer and washed twice with ice cold RPMI-10. Samples were centrifuged and red blood cell lysis was carried out, before being washed and resuspended in RPMI-10. The tumour cells were enumerated by trypan blue exclusion and stained for the immune cell marker CD45 (AF700).

FIG. 36 demonstrates that when administered intraperitoneally, RVKVKVVVV-RRRRRRRRR (SEQ ID NO: 58, IK15800) decreases the mean area of tumour mass relative to control.

Example 40: Lck Activating Polypeptides Coupled to Fatty Acids Increase IL-2 Secretion from a Human T Lymphocyte (Jurkat) Cell Line The ability of Lck activating polypeptides coupled to fatty acids to alter IL-2 secretion was examined.

In brief, cells were seeded at 1 million cells per well (12 well plate, 2 mL volume) and stimulated with Biotin-CD3, CD28, and avidin (5:5:1.25 µg). The cells were then treated with IK14804, and then incubated for 48 hours at 37° C. The supernatant (100 uL, n=3), was then analyzed for IL-2 content.

FIG. 37 shows that the Lck activating polypeptides RSKAKNPLY-RRRRRRRRR-(2Adod)$_4$-NH$_2$ (SEQ ID NO: 65, IK14804) induces IL-2 secretion relative to control in wild-type Jurkat cells following 48 h exposure.

These data demonstrate that a Lck activating polypeptide coupled to fatty acids of the present invention is able to induce IL-2 secretion in a human T cell line.

Example 41: Lck Activating Polypeptides Increase IL-12 Secretion in a Human T Lymphocyte (Jurkat) Cell Line The ability of Lck activating polypeptides coupled to fatty acids to alter IL-12 secretion was examined.

In brief, cells were seeded at 1 million cells per well (12 well plate, 2 mL volume) and stimulated with Biotin-CD3, CD28, and avidin (5:5:1.25 µg). The cells were then treated with IK14800 (SEQ ID NO: 24), IK15800 (SEQ ID NO: 58), IK14804 (SEQ ID NO: 65) and IK15804 (SEQ ID NO: 66). The cells were then incubated for 48 hours at 37° C. The supernatants (100 uL, n=3), were then analyzed for IL-12 content.

FIG. 38 shows that the Lck activating polypeptides RSKAKNPLY-RRRRRRRRR (SEQ ID NO: 24, IK14800), RVKVKVVVV-RRRRRRRRR (SEQ ID NO: 58, IK15800), RSKAKNPLY-RRRRRRRRR-(2Adod)$_4$-NH$_2$ (SEQ ID NO: 65, IK14804) and RVKVKVVVV-RRRRRRRRR-(2Adod)$_4$-NH$_2$ (SEQ ID NO: 66, IK15804) induce IL-2 secretion relative to control in wild-type Jurkat cells following 48 h exposure.

Example 42: Lck Activating Polypeptides Inhibit UVB Lipid Peroxidation in Cell Membranes The ability of Lck activating polypeptides to alter lipid peroxidation in cell membranes was examined.

In brief, oxidising agents can alter lipid structure, creating lipid peroxides that result in the formation of malondialdehyde which can be measured as thiobarbituric acid-reactive substances (TBARS).

After irradiation or sham-irradiation of dermal fibroblasts and/or keratinocytes, test peptides are added and incubated for 90 minutes, following which supernatants (900 µL) are collected. 90 µL of butylated hydroxytoluene (2% w/w in ethanol) are added and samples kept frozen (−20° C.) until the TBARS assay. Petri dishes are washed twice with 1 mL of HBSS, cells scraped in 600 µL of water and 60 µL of 0.5% aqueous Triton X100 added to this solution, for protein determination carried out by the Lowry method (Lowry O H et al, J. Biol. Chem., 1951, 193:265-275). TBARS are fluorometrically assayed as described (Morlière P et al, Biochim. Biophys. Acta, 1991, 1084:261-268). Briefly, for thawing samples are heated in the presence of thiobarbituric acid in acidic conditions, and TBARS extracted with 1-butanol and fluorometrically quantified (λexc=515 nm and λem=550 nm). Tetraethoxypropane, which quantitatively yields the malondialdehyde-thiobarbituric acid adduct in the assay conditions, is used for calibration. TBARS values, expressed in malondialdehyde (MDA) equivalents, are normalized to the cell protein for each Petri dish. Each TBARS determination is done in triplicate (e.g., with three Petri dishes per data point).

FIG. 39 shows that RSKAKNPLY-RRRRRRRRR (SEQ ID NO: 24, IK14800) reduces the % TRS in a dose dependent manner.

Example 43: RSKAKNPLY-RRRRRRRRR (SEQ ID NO: 24) Increases Phosphorylation of Lck at Y394

As discussed above, phosphorylation of Tyr394 of Lck results in conformational opening of Lck that activates Lck kinase.

Western blot studies were performed as follows:
Cell type: Jurkat wild type
Cell number: 5×10⁵/1 ml
Medium: RPMI-1640 MEDIUM (Sigma, R8758), 1× Penicillin-Streptomycin (Sigma, 100×, P0781), 10% FBS
Peptide: IK14800 (RSKAKNPLY-RRRRRRRRR, SEQ ID NO: 24)
Peptide Conc: 1 uM
Peptide exposure time: 2 hours
Cell lysis solution:
(100 ul/well/30 min on ice)
RIPA Buffer (Sigma, R0278): 97 ul
Protease Inhibitor Cocktail (P8340): 1.5 ul
Phosphatase Inhibitor Cocktail 2 (Sigma, P5726): 1.5 ul
Protein Assay: Pierce™ BCA Protein Assay Kit (#23225)
Gel: NuPAGE® Novex® 4-12% Bis-Tris Gels (Life Technologies, NP0335BOX), Load 20 ug protein
Running Buffer (1×): NuPAGE® MOPS SDS Running Buffer (Life Technologies, NP0001)
Transfer Blot: iBlot® Transfer Stack, nitrocellulose, Novex, mini (Life Technologies, IB3010-32)
Blocking Solution: TBS Blotto B (Santa Cruz, SCZSC-2335)
Primary Antibody: p-Lck (Tyr 394), rabbit polyclonal antibody (Santa Cruz, sc-101728), 1/200 dilution, overnight at 4. Anti-Lck antibody [Y123], rabbit monoclonal antibody (Abcam, ab32149), 1/1000 dilution, overnight at 4C
Secondary Antibody: goat anti-rabbit IgG-HRP (sc-2004), 1/5000 dilution, 1 hour
ECL: Amersham ECL Prime Western Blotting Detection Reagent FIG. 40 shows RSKAKNPLY-RRRRRRRRR (SEQ ID NO: 24) increases phosphorylation of Lck at Y394 detected by the anti-pY394 antibody, relative to no peptide control, while levels of total Lck remained unchanged.

This data demonstrates that the Lck activating polypeptide RSKAKNPLY-RRRRRRRRR (SEQ ID NO: 24) selectively activates Lck enhance autophosphorylation of Lck.

Example 44: The Polypeptides RSKAKNPLYR (SEQ ID NO: 31) and RSKAKNPLY (SEQ ID NO: 30) Increase IL-2 Secretion in a Human T Lymphocyte (Jurkat) Cell Line, and Rskaknply, but not RSKAKNPLYR (SEQ ID NO: 31), Increase IL-12 Secretion in a Human T Lymphocyte (Jurkat) Cell Line The ability of the polypeptides RSKAKNPLYR (SEQ ID NO: 31, "14000"), RSKAKNPLY (SEQ ID NO: 30, "IK94000) and rskaknply (SEQ ID NO: 117, "IKD94000") to alter IL-2 and IL-12 secretion was examined.

In brief, wild-type Jurkat cells (am immortalised line of human T lymphocyte cells) were stimulated by exposure to biotinylated anti-CD3 antibody in the presence of anti-CD28 antibody and avidin. Cells were seeded at 1 million cells per well (12 well plate, 2 mL volume) and stimulated with Biotin-anti-CD3, anti-CD28, and avidin (5:5:1.25 µg). Cells were treated with the test peptides and then incubated for 48 hours at 37° C. The supernatants (100 ul, n=3), were then analysed for IL-2 and IL-12 content. During the culture period (48 hours) cells were exposed to test polypeptide RSKAKNPLYR-(2Adod)$_4$-NH$_2$ (SEQ ID NO: 128). Cell supernatant was assayed for IL-2 and IL-12 at the end of 48 hours using standard commercially available ELISA kit as described above.

FIG. 41A shows the polypeptides RSKAKNPLYR (SEQ ID NO: 31) and RSKAKNPLY (SEQ ID NO: 30) increase IL-2 secretion in a human T lymphocyte (Jurkat) cell line.

FIG. 41B shows rskaknply (SEQ ID NO: 117), but not RSKAKNPLYR (SEQ ID NO: 31), increase IL-12 secretion in a human T lymphocyte (Jurkat) cell line.

Although a number of embodiments of the invention have been described above it will be understood that various modifications and changes may be made thereto without departing from the scope of the invention. The above described embodiments are therefore only illustrative and are not to be taken as being restrictive.

Example 44: Lck Activating Polypeptides Increase the Percentage of Specific Cytotoxicity of Calcein-AM Stained K562 Cells in a PBMC Co-Culture The ability of the Lck activating polypeptides RSKAKN-PLY-RRRRRRRRR (SEQ ID NO: 24, IK14800), RVKVKVVVV-RRRRRRRRR (SEQ ID NO: 58, IK15800), RSKAKNPLY-RRRRRRRRR-(2Adod)$_4$-NH$_2$ (SEQ ID NO: 65, IK14804) and RVKVKVVVV-RRRRRRRRR-(2Adod)$_4$-NH$_2$ (SEQ ID NO: 66, IK15804) to induce a cytotoxic response was examined.

In brief, PBMC were incubated for 48 hrs then co-cultured together with Calcein AM stained K562 cells stimulated with or without human recombinant IFN-α 2A (5 ng/mL) for 4 hrs. Supernatants were assessed for Calcein green fluorescence intensity using the GloMax® Discover and percentage specific cytotoxicity was calculated. Data shown indicates mean percentage specific cytotoxicity +/− SEM, n=4. Data were analysed by paired t test in comparison to the vehicle control, *p<0.05.

PBMC were also pre-treated with or without the Lck activating polypeptides RSKAKNPLY-RRRRRRRRR (SEQ ID NO: 24, IK14800), RVKVKVVVV-RRRRRRRRR (SEQ ID NO: 58, IK15800), RSKAKNPLY-RRRRRRRRR-(2Adod)$_4$-NH$_2$ (SEQ ID NO: 65, IK14804) and RVKVKVVVV-RRRRRRRRR-(2Adod)$_4$-NH$_2$ (SEQ ID NO: 66, IK15804) (0.08-1.25 µM) for 48 hrs, then co-cultured with Calcein AM stained K562 cells at a 5:1 ratio and incubated for a further 4 hrs. Supernatants were assessed for Calcein green fluorescence intensity using the GloMax® Discover and percentage specific cytotoxicity was calculated. Data shown indicates mean percentage specific cytotoxicity +/− SEM, n=4. Data were analysed by repeated measures two-way ANOVA with Holm-Sidak's post-test comparing peptide treatment with vehicle control, *p<0.05, P<0.01, *P<0.001, ****p<0.0001.

The Lck activating polypeptides RSKAKNPLY-RRRRRRRR (SEQ ID NO: 24, IK14800), RVKVKVVVV-RRRRRRRRR (SEQ ID NO: 58, IK15800), RSKAKNPLY-RRRRRRRRR-(2Adod)$_4$-NH$_2$ (SEQ ID NO: 65, IK14804) and RVKVKVVVV-RRRRRRRRR-(2Adod)$_4$-NH$_2$ (SEQ ID NO: 66, IK15804) increased the percentage of specific cytotoxicity of Calcein-AM stained K562 cells in a PBMC co-culture, to a level greater than that observed with IFN-α 2A (data not shown).

---

The invention claimed is:

1. A peptide for activating Lck comprising a peptide amino acid sequence selected from RSKAKNPLYR-RRRRRRRR (SEQ ID NO: 24) or rskaknplyr-rrrrrrrr (SEQ ID NO: 129).

* * * * *

SEQUENCE LISTING

```
<160> NUMBER OF SEQ ID NOS: 136

<210> SEQ ID NO 1
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 1

Arg Arg Arg Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 2

Arg Arg Arg Arg Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Arg Arg Arg Arg Arg Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 4

Arg Arg Arg Arg Arg Arg Arg Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(8)
<223> OTHER INFORMATION: D amino acids

<400> SEQUENCE: 5
```

```
Arg Arg Arg Arg Arg Arg Arg Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Arg Arg Arg Arg Arg Arg Arg Arg Arg
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 7

Arg Arg Arg Arg Arg Arg Arg Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 8

Arg Arg Arg Arg Arg Arg Arg Arg Arg Arg Arg Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 9

Arg Arg Arg Arg Arg Arg Arg Arg Arg Arg Arg Arg Arg Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(14)
<223> OTHER INFORMATION: D amino acids

<400> SEQUENCE: 10

Arg Arg Arg Arg Arg Arg Arg Arg Arg Arg Arg Arg Arg Arg
1               5                   10

<210> SEQ ID NO 11
<211> LENGTH: 14
<212> TYPE: PRT
<213> ORGANISM: Artificial Sequence
<220> FEATURE:
```

```
<223> OTHER INFORMATION: Synthetic polypeptide

<400> SEQUENCE: 11

Arg Arg Arg Arg Arg Arg Arg Arg Arg Arg Arg Arg
1               5                   10

<210> SEQ ID NO 12
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 12

Arg Arg Arg Arg Arg Arg Arg Arg Arg Arg Arg Arg Arg Arg Arg
1               5                   10                  15

Arg Arg Arg Arg Arg
            20

<210> SEQ ID NO 13
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 13

Lys Lys Lys Lys Lys Lys Lys Lys Lys Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 14

His His His His His His His His His His
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(10)
<223> OTHER INFORMATION: Xaa is Orn

<400> SEQUENCE: 15

Xaa Xaa Xaa Xaa Xaa Xaa Xaa Xaa Xaa Xaa
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 16

His His His Arg Arg Arg Arg Arg Arg Arg Arg Arg His His His
1               5                   10                  15
```

```
<210> SEQ ID NO 17
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 17

His His His His His Arg Arg Arg Arg Arg Arg Arg Arg Arg His His
1               5                   10                  15

His His His

<210> SEQ ID NO 18
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 18

Lys Lys Lys Lys Lys Lys Lys Lys His His His His His His His His
1               5                   10                  15

His His

<210> SEQ ID NO 19
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 19

Arg Arg Arg Arg Arg Arg Arg Arg His His His His His His His His
1               5                   10                  15

His His

<210> SEQ ID NO 20
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 20

Arg Arg Arg Arg Arg Arg Arg Arg Arg His His His His His His His
1               5                   10                  15

His His His

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 21

Asp Asp Asp Asp Asp Asp Asp Asp Asp
1               5

<210> SEQ ID NO 22
<211> LENGTH: 9
<212> TYPE: PRT
<213> ORGANISM: Artificial Sequence
<220> FEATURE:
```

```
<223> OTHER INFORMATION: Synthetic polypeptide

<400> SEQUENCE: 22

Arg Arg Arg Arg Arg Arg Arg Arg Arg
1               5

<210> SEQ ID NO 23
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 23

Asp Ser Glu Ala Glu Asn Pro Leu Tyr Asp Asp Asp Asp Asp Asp
1               5                   10                  15

Asp Asp

<210> SEQ ID NO 24
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 24

Arg Ser Lys Ala Lys Asn Pro Leu Tyr Arg Arg Arg Arg Arg Arg
1               5                   10                  15

Arg Arg

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 25

Arg Ser Lys Ala Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 26

Arg Ser Lys Ala Lys Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 27

Arg Ser Lys Ala Lys Arg Arg
1               5

<210> SEQ ID NO 28
<211> LENGTH: 8
```

```
<212> TYPE: PRT
<213> ORGANISM: Artificial Sequence
<220> FEATURE:
<223> OTHER INFORMATION: Synthetic polypeptide

<400> SEQUENCE: 28

Arg Ser Lys Ala Lys Arg Arg Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 29

Arg Ser Lys Ala Lys Arg Arg Arg Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 30

Arg Ser Lys Ala Lys Asn Pro Leu Tyr
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

Arg Ser Lys Ala Lys Asn Pro Leu Tyr Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 32

Arg Ser Lys Ala Lys Asn Pro Leu Tyr Arg Arg Arg Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 33

Arg Ser Lys Ala Lys Asn Pro Leu Tyr Arg Arg Arg Arg Arg
1               5                   10

<210> SEQ ID NO 34
<211> LENGTH: 15
<212> TYPE: PRT
```

```
<213> ORGANISM: Artificial Sequence
<220> FEATURE:
<223> OTHER INFORMATION: Synthetic polypeptide

<400> SEQUENCE: 34

Arg Ser Lys Ala Lys Asn Pro Leu Tyr Arg Arg Arg Arg Arg Arg
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(15)
<223> OTHER INFORMATION: D amino acids

<400> SEQUENCE: 35

Arg Ser Lys Ala Lys Asn Pro Leu Tyr Arg Arg Arg Arg Arg Arg
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(17)
<223> OTHER INFORMATION: Cyclised

<400> SEQUENCE: 36

Cys Arg Ser Lys Ala Lys Asn Pro Leu Tyr Arg Arg Arg Arg Arg
1               5                   10                  15

Cys

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 37

Arg Ser Lys Ala Lys Arg Arg Arg Arg Arg Arg Arg Arg Arg
1               5                   10

<210> SEQ ID NO 38
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(19)
<223> OTHER INFORMATION: D amino acids

<400> SEQUENCE: 38

Arg Ser Lys Ala Lys Asn Pro Leu Tyr Arg Arg Arg Arg Arg Arg
1               5                   10                  15

Arg Arg Arg

<210> SEQ ID NO 39
```

```
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(18)
<223> OTHER INFORMATION: D amino acids

<400> SEQUENCE: 39

Arg Arg Arg Arg Arg Arg Arg Arg Arg Tyr Leu Pro Asn Lys Ala Lys
1               5                   10                  15

Ser Arg

<210> SEQ ID NO 40
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 40

Ile Ala Gly Gln Arg Ser Lys Ala Lys Asn Pro Leu Tyr Arg Arg Arg
1               5                   10                  15

Arg Arg Arg Arg Arg Arg
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 41

Arg Ser Lys Ala Lys Asn Pro Leu Tyr Arg Arg Arg Arg Arg Arg Arg
1               5                   10                  15

Arg Arg Gly Pro Leu Gly
            20

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Arg Arg Arg Arg Arg Arg Arg Arg Arg Ser Lys Ala Lys Asn Pro Leu
1               5                   10                  15

Tyr Arg

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 43

Arg Arg Arg Arg Arg Arg Arg Arg Arg Tyr Leu Pro Asn Lys Ala Lys
1               5                   10                  15

Ser Arg
```

```
<210> SEQ ID NO 44
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 44

Arg Ser Lys Ala Lys Asn Pro Leu Tyr Lys Lys Lys Lys Lys Lys
1               5                   10                  15

Lys Lys

<210> SEQ ID NO 45
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 45

Arg Ser Lys Ala Lys Asn Pro Leu Tyr Arg His His His His His
1               5                   10                  15

His His His His
            20

<210> SEQ ID NO 46
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 46

Arg Ser Lys Ala Lys Asn Pro Leu Tyr Arg Arg Arg Arg Arg Arg
1               5                   10                  15

Arg Arg His His His His His
            20

<210> SEQ ID NO 47
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 47

Arg Ser Lys Ala Lys Asn Pro Leu Tyr Arg Arg Arg Arg Arg Arg
1               5                   10                  15

Arg Arg His His His His His His His His His
            20                  25

<210> SEQ ID NO 48
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(28)
<223> OTHER INFORMATION: Branched

<400> SEQUENCE: 48

Arg Ser Lys Ala Lys Asn Pro Leu Tyr Arg Arg Arg Arg Arg Arg
1               5                   10                  15
```

Arg Arg His His His His His His His His His
        20                  25

<210> SEQ ID NO 49
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 49

Arg Ser Lys Ala Lys Asn Pro Leu Tyr Arg Arg Arg Arg Arg Arg
1               5                   10                  15

Arg Arg His His His His His His His His His His His
        20                  25                  30

<210> SEQ ID NO 50
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 50

His His His His His Arg Ser Lys Ala Lys Asn Pro Leu Tyr Arg Arg
1               5                   10                  15

Arg Arg Arg Arg Arg Arg Arg
            20

<210> SEQ ID NO 51
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 51

His His His His His Arg Arg Arg Arg Arg Arg Arg Arg His His
1               5                   10                  15

His His His Arg Ser Lys Ala Lys Asn Pro Leu Tyr Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 52

Arg Arg Arg Arg Arg Arg Arg Arg His His His His His His His
1               5                   10                  15

His His Arg Ser Lys Ala Lys Asn Pro Leu Tyr Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 53

His His His His His Arg Ser Lys Ala Lys Asn Pro Leu Tyr Arg Arg

```
                1               5                  10                  15
Arg Arg Arg Arg Arg Arg Arg His His His His His
                20                  25
```

<210> SEQ ID NO 54
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 54

```
Arg Ser Lys Ala Lys Asn Pro Leu Tyr Arg Lys Arg Lys Arg Lys Arg
1               5                   10                  15
Lys Arg Lys
```

<210> SEQ ID NO 55
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 55

```
Arg Val Lys Val Lys Val Val Val Val
1               5
```

<210> SEQ ID NO 56
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 56

```
Arg Val Lys Val Lys Val Val Val Val Arg Arg Arg Arg Arg
1               5                   10
```

<210> SEQ ID NO 57
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 57

```
Arg Val Lys Val Lys Val Val Val Val Arg Arg Arg Arg Arg Arg
1               5                   10                  15
Arg
```

<210> SEQ ID NO 58
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 58

```
Arg Val Lys Val Lys Val Val Val Val Arg Arg Arg Arg Arg Arg
1               5                   10                  15
Arg Arg
```

<210> SEQ ID NO 59
<211> LENGTH: 18

```
<212> TYPE: PRT
<213> ORGANISM: Artificial Sequence
<220> FEATURE:
<223> OTHER INFORMATION: Synthetic polypeptide

<400> SEQUENCE: 59

Arg Arg Arg Arg Arg Arg Arg Arg Val Lys Val Lys Val Val Val
1               5                   10                  15

Val Arg

<210> SEQ ID NO 60
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 60

Arg Val Lys Val Lys Val Val Val Arg Arg Arg Arg Arg Arg Arg
1               5                   10                  15

Arg Arg His His His His His His His His His His His
            20                  25

<210> SEQ ID NO 61
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 61

Arg Val Lys Val Lys Val Val Val Arg His Arg His Arg His Arg
1               5                   10                  15

His Arg His Arg His Arg His Arg His His His
            20                  25

<210> SEQ ID NO 62
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 62

Lys Glu Lys Leu Lys Asn Pro Leu Phe Lys Arg Arg Arg Arg Arg
1               5                   10                  15

Arg Arg His His His His His His His His His
            20                  25

<210> SEQ ID NO 63
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 63

Arg Val Lys Val Lys Val Val Val Val Arg His Arg His Arg His Arg
1               5                   10                  15

His Arg His Arg His Arg His Arg His
            20                  25

<210> SEQ ID NO 64
<211> LENGTH: 28
```

```
<212> TYPE: PRT
<213> ORGANISM: Artificial Sequence
<220> FEATURE:
<223> OTHER INFORMATION: Synthetic polypeptide

<400> SEQUENCE: 64

Lys Glu Lys Leu Lys Asn Pro Leu Phe Lys Arg Arg Arg Arg Arg
1               5                   10                  15

Arg Arg His His His His His His His His His
            20                  25

<210> SEQ ID NO 65
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: LIPID
<222> LOCATION: (18)..(18)
<223> OTHER INFORMATION: 2-amino-dodecanoic acid x 4
<220> FEATURE:
<221> NAME/KEY: MOD_RES
<222> LOCATION: (18)..(18)
<223> OTHER INFORMATION: AMIDATION

<400> SEQUENCE: 65

Arg Ser Lys Ala Lys Asn Pro Leu Tyr Arg Arg Arg Arg Arg Arg
1               5                   10                  15

Arg Arg

<210> SEQ ID NO 66
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: LIPID
<222> LOCATION: (18)..(18)
<223> OTHER INFORMATION: 2-amino-dodecanoic acid x 4
<220> FEATURE:
<221> NAME/KEY: MOD_RES
<222> LOCATION: (18)..(18)
<223> OTHER INFORMATION: AMIDATION

<400> SEQUENCE: 66

Arg Val Lys Val Lys Val Val Val Val Arg Arg Arg Arg Arg Arg
1               5                   10                  15

Arg Arg

<210> SEQ ID NO 67
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 67

Lys Val Glu Lys Ile Gly Glu Gly Thr Tyr Gly Val Val Tyr Lys
1               5                   10                  15

<210> SEQ ID NO 68
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 68

Gly Phe Leu Gly Phe Lys
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 69

Gly Pro Leu Gly Ile Ala Gly Gln
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 70

Pro Ala Gly Leu Leu Gly Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 71

Gly Pro Leu Gly Leu Trp Ala Gln
1               5

<210> SEQ ID NO 72
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 72

Val Pro Asn Leu Arg Gly Asp Leu Gln Val Leu Ala Gln Lys Val Ala
1               5                   10                  15

<210> SEQ ID NO 73
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 73

Lys Gly Ile Ser Ser Gln Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 74

Ser Ser Lys Tyr Gln Leu
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 75

Gly Phe Leu Gly Phe Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 76

Lys Ala Ala Gly Phe Leu Gly Phe Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 77

Cys Ala Ala Gly Phe Leu Gly Phe Lys
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 78

Gly Pro Leu Gly Ile Ala Gly Gln
1               5

<210> SEQ ID NO 79
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 79

Lys Ala Ala Gly Pro Leu Gly Ile Ala Gly Gln
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 80
```

Cys Ala Ala Gly Pro Leu Gly Gly Ile Ala Gly Gln
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 81

Pro Ala Gly Leu Leu Gly Cys
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 82

Lys Ala Ala Pro Ala Gly Leu Leu Gly Cys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 83

Cys Ala Ala Pro Ala Gly Leu Leu Gly Cys
1               5                   10

<210> SEQ ID NO 84
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 84

Gly Pro Leu Gly Leu Trp Ala Gln
1               5

<210> SEQ ID NO 85
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 85

Lys Ala Ala Gly Pro Leu Gly Leu Trp Ala Gln
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 86

```
Cys Ala Ala Gly Pro Leu Gly Leu Trp Ala Gln
1               5                   10
```

<210> SEQ ID NO 87
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 87

```
Tyr Leu Pro Asn Lys Ala Lys Ser Arg
1               5
```

<210> SEQ ID NO 88
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 88

```
Lys Ala Lys Ser Arg
1               5
```

<210> SEQ ID NO 89
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 89

```
Arg Ser Arg Ala Arg Asn Pro Leu Tyr
1               5
```

<210> SEQ ID NO 90
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 90

```
Arg Ala Arg Ala Lys Asn Pro Leu Tyr
1               5
```

<210> SEQ ID NO 91
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 91

```
Lys Glu Lys Leu Lys Asn Pro Leu Phe
1               5
```

<210> SEQ ID NO 92
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 92

```
Lys Glu Lys Leu Lys Asn Pro Leu Phe Lys
```

```
1               5               10
```

<210> SEQ ID NO 93
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 93

```
Arg Val Lys Val Lys Val Val Val Val
1               5
```

<210> SEQ ID NO 94
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 94

```
Arg Ala Lys Ala Lys Ala Ala Ala Ala
1               5
```

<210> SEQ ID NO 95
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 95

```
Arg Ala Lys Ala Lys Asn Pro Leu Phe
1               5
```

<210> SEQ ID NO 96
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 96

```
Arg Ser Lys Ala Lys
1               5
```

<210> SEQ ID NO 97
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 97

```
Arg Ala Lys Ala Lys
1               5
```

<210> SEQ ID NO 98
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 98

```
Arg Val Lys Val Lys
1               5
```

```
<210> SEQ ID NO 99
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 99

Lys Val Lys Val Arg
1               5

<210> SEQ ID NO 100
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 100

Arg Tyr Leu Pro Asn Lys Ala Lys Ser Arg
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 101

Tyr Leu Pro Asn Arg Ala Arg Ser Arg
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 102

Tyr Leu Pro Asn Lys Ala Arg Ala Arg
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 103

Phe Leu Pro Asn Lys Leu Lys Glu Lys
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 104

Lys Phe Leu Pro Asn Lys Leu Lys Glu Lys
1               5                   10
```

```
<210> SEQ ID NO 105
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 105

Val Val Val Val Lys Val Lys Val Arg
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 106

Ala Ala Ala Ala Lys Ala Lys Ala Arg
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 107

Phe Leu Pro Asn Lys Ala Lys Ala Arg
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 108

Lys Ala Lys Ala Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 109

Lys Gly Ile Ser Ser Gln Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 110

Ser Ser Lys Tyr Gln Leu
1               5
```

```
<210> SEQ ID NO 111
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(18)
<223> OTHER INFORMATION: D amino acids

<400> SEQUENCE: 111

Arg Val Lys Val Lys Val Val Val Arg Arg Arg Arg Arg Arg Arg
1               5                   10                  15

Arg Arg

<210> SEQ ID NO 112
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 112

Arg Arg Arg Arg Arg Arg Arg Arg Arg His His His His His
1               5                   10

<210> SEQ ID NO 113
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 113

Arg Val Lys Val Lys Arg Arg Arg Arg Arg Arg Arg Arg His His
1               5                   10                  15

His His His His His His His His
            20

<210> SEQ ID NO 114
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(9)
<223> OTHER INFORMATION: D amino acids

<400> SEQUENCE: 114

Arg Arg Arg Arg Arg Arg Arg Arg Arg
1               5

<210> SEQ ID NO 115
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 115

Arg Ser Lys Ala Lys Asn Pro Leu Tyr Arg Arg Arg Arg Arg Arg
1               5                   10                  15

Arg Arg Arg
```

```
<210> SEQ ID NO 116
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 116

Arg Ser Lys Ala Lys Asn Pro Leu Tyr Arg Arg Arg Arg Arg Arg
1               5                   10                  15

Arg Arg

<210> SEQ ID NO 117
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(9)
<223> OTHER INFORMATION: D amino acids

<400> SEQUENCE: 117

Arg Ser Lys Ala Lys Asn Pro Leu Tyr
1               5

<210> SEQ ID NO 118
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 118

His His His His
1

<210> SEQ ID NO 119
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 119

Arg Arg Arg Arg
1

<210> SEQ ID NO 120
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 120

Lys Lys Lys Lys
1

<210> SEQ ID NO 121
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 121

Arg Arg Arg Arg Arg Arg Arg
1               5

<210> SEQ ID NO 122
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 122

Arg Arg Arg Arg Arg Arg Arg Arg Arg Arg Arg
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 123

Arg Arg Arg Arg Arg Arg Arg Arg Arg Arg Arg Arg Arg
1               5                   10

<210> SEQ ID NO 124
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 124

Arg Arg Arg Arg Arg Arg Arg Arg Arg Arg Arg Arg Arg Arg Arg
1               5                   10                  15

<210> SEQ ID NO 125
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 125

His His His His His
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 126

Lys Lys Lys Lys Lys Lys Lys Lys Lys
1               5

<210> SEQ ID NO 127
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 127
```

Arg His His His His His His His His His
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: LIPID
<222> LOCATION: (10)..(10)
<223> OTHER INFORMATION: 2-amino-dodecanoic acid x 4
<220> FEATURE:
<221> NAME/KEY: MOD_RES
<222> LOCATION: (10)..(10)
<223> OTHER INFORMATION: AMIDATION

<400> SEQUENCE: 128

Arg Ser Lys Ala Lys Asn Pro Leu Tyr Arg
1               5                   10

<210> SEQ ID NO 129
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(18)
<223> OTHER INFORMATION: D amino acid

<400> SEQUENCE: 129

Arg Ser Lys Ala Lys Asn Pro Leu Tyr Arg Arg Arg Arg Arg Arg
1               5                   10                  15

Arg Arg

<210> SEQ ID NO 130
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 130

Arg Arg Arg Arg Arg Arg Arg Arg Arg Arg Arg Arg Arg Arg Arg Arg
1               5                   10                  15

<210> SEQ ID NO 131
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 131

Lys Lys Lys Lys Lys Lys
1               5

<210> SEQ ID NO 132
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 132

Arg Lys Lys Lys Lys Lys Lys Lys His His His His His His
1               5                   10                  15

His His His

<210> SEQ ID NO 133
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 133

Arg Arg Arg Arg Arg Arg Arg Arg Arg His His His His His His
1               5                   10                  15

His His His His His His His
            20

<210> SEQ ID NO 134
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 134

Arg His Arg His Arg His Arg His Arg His Arg His Arg His Arg His
1               5                   10                  15

Arg His His

<210> SEQ ID NO 135
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 135

His Arg His Arg His Arg His Arg His Arg His Arg His Arg His Arg
1               5                   10                  15

His His

<210> SEQ ID NO 136
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 136

Arg Ser Lys Ala Lys Asn Pro Leu Tyr Arg Arg Arg Arg Arg Arg
1               5                   10                  15

Arg Arg